(12) United States Patent
Ishibashi et al.

(10) Patent No.: US 10,172,547 B2
(45) Date of Patent: Jan. 8, 2019

(54) SYSTEM AND METHOD USING INFORMATION OF INVOLUNTARY BODY MOVEMENT DURING SLEEP, AND SLEEPING STATE DETECTION SYSTEM AND METHOD

(71) Applicants: C'STEC CORPORATION, Hokkaido (JP); Akira Ishibashi, Hokkaido (JP); Masahiro Yasutake, Tokyo (JP)

(72) Inventors: Akira Ishibashi, Hokkaido (JP); Masahiro Yasutake, Tokyo (JP); Fusao Ishibashi, Saga (JP)

(73) Assignees: C'Stec Corporation, Hokkaido (JP); Akira Ishibashi, Hokkaido (JP); Masahiro Yasutake, Tokyo (JP)

( * ) Notice: Subject to any disclaimer, the term of this patent is extended or adjusted under 35 U.S.C. 154(b) by 186 days.

(21) Appl. No.: 15/032,749

(22) PCT Filed: Oct. 28, 2014

(86) PCT No.: PCT/JP2014/078543
§ 371 (c)(1),
(2) Date: Apr. 28, 2016

(87) PCT Pub. No.: WO2015/064547
PCT Pub. Date: May 7, 2015

(65) Prior Publication Data
US 2016/0278696 A1     Sep. 29, 2016

(30) Foreign Application Priority Data

Oct. 29, 2013 (JP) .................................. 2013-223958
Jun. 4, 2014 (JP) .................................. 2014-115365

(51) Int. Cl.
*A61B 5/00*     (2006.01)
*A61B 5/11*     (2006.01)
(Continued)

(52) U.S. Cl.
CPC .......... *A61B 5/4812* (2013.01); *A61B 5/1126* (2013.01); *A61B 5/6889* (2013.01);
(Continued)

(58) Field of Classification Search
CPC ... A61B 5/4806–5/4818; A61B 5/1126; A61B 2560/0242
See application file for complete search history.

(56) References Cited

FOREIGN PATENT DOCUMENTS

| JP | 2006200111 | 8/2006 |
| JP | 2010264074 | 11/2010 |

(Continued)

OTHER PUBLICATIONS

A report on an investigation of the trend of technology of patent applications of 2013 (Summary) "Technology for analyzing big data" Feb. 2014 Japan Patent Office.

(Continued)

*Primary Examiner* — Sean Dougherty
(74) *Attorney, Agent, or Firm* — K&L Gates LLP

(57) ABSTRACT

Provided are a sleeping state detection system and method that can detect the sleeping state of a subject such as an inpatient or a tenant without causing the subject stress, and that can ascertain the health state of the subject from the detection results. The sleeping state detection system includes a room or closed space (201) in which the subject sleeps, and a dust counter (206) that measures the dust particles inside the room or closed space (201). In a state where the inside of the room or closed space (201) is kept cleaner than the outside of the room or closed space (201) by using a fan filter unit (208) disposed in the room or closed space (201), while the subject sleeps, the change over time in the number of dust particles inside the room or closed space (201) is measured using the dust counter (206), and thereby the sleeping state of the subject is detected. The (Continued)

inside of the room or closed space (201) is preferably kept at a cleanliness of US 209D Class100 or better.

20 Claims, 57 Drawing Sheets

(51) Int. Cl.
  *F24F 3/16* (2006.01)
  *F24F 7/08* (2006.01)
  *F24F 120/14* (2018.01)
(52) U.S. Cl.
  CPC ............ *A61B 5/7278* (2013.01); *F24F 3/161* (2013.01); *F24F 3/1607* (2013.01); *F24F 7/08* (2013.01); *A61B 2560/0242* (2013.01); *F24F 2120/14* (2018.01)

(56) References Cited

FOREIGN PATENT DOCUMENTS

| WO | 2008139777 | 11/2008 | |
|---|---|---|---|
| WO | 2012011547 | 1/2012 | |
| WO | WO-2012011547 A1 * | 1/2012 | ................ F24F 7/00 |

OTHER PUBLICATIONS

Japanese Journal of Clinical Ecology{vol. 9, No. 2, 2000) General remarks, "House and Human Body"—Viewpoint from engineering, Shuzo Murakami.

A. Ishibashi et al. Connected box-units-based compact highly clean environment for cross-disciplinary experiments platform, Electronics Letters, Jun. 23, 2005 vol. 41 No. 13.

Hideo Kaiju, Study of very low airborne particle count in clean-unit system platform, Laboratory of Quantum Electronics, Research Institute for Electronic Science, Hokkaido Unil'ersity Sapporo, Hokkaido 060-0812, Japan, Review of Scientific Instruments 76, 085111 (2005).

Nikkei Newspaper (Apr. 12, 2014) Front page: "Ratio of households of the aged exceeds 40%. 18,450,000 people live alone (estimated for 2035) ." Third page: "Today' s words. In Tokyo the number of members of one family will become less than two." Fifth page: "Number of solitary aged rapidly increases. Greatest, 44% in Tokyo and also serious in the country. Governments speed up measures."

Office Action received in JP Application 2015-516351, dated Sep. 4, 2015, 9 pages.

International Search Report received in PCT, dated Jan. 13, 2015, 1 page.

\* cited by examiner

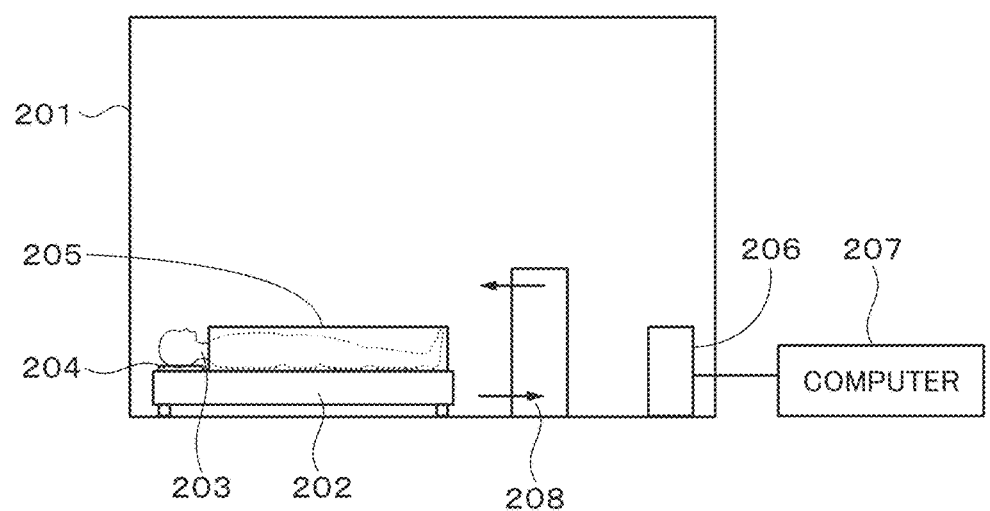

SYSTEM AND METHOD USING INFORMATION OF INVOLUNTARY BODY MOVEMENT DURING SLEEP, AND SLEEPING STATE DETECTION SYSTEM AND METHOD

CROSS REFERENCES TO RELATED APPLICATIONS

The present application is a national stage of International Application No. PCT/JP2014/078543 filed on Oct. 28, 2014 and claims priority to Japanese Patent Application No. 2013-223958 filed on Oct. 29, 2013, and Japanese Patent Application No. 2014-115365 filed on Jun. 4, 2014 the disclosure of which is incorporated herein by reference.

TECHNICAL FIELD

The invention relates, most broadly, to a system and method using information of involuntary body movement during sleep, which are suitable for the following applications. That is, for example, data with a new attribute that is obtained by information of involuntary body movement of a person during sleep is combined with data that is an object of existing what is called "Big Data" analysis to obtain a new space with a wide deep attribute. And ever-progressing Big Data analytical method is applied to the new space. As a result, for example, it becomes possible to confirm the safety of persons, support medical treatment, nursing and care in hospitals, institutions for the aged, general homes, etc., develop new industry and reduce social cost for watching solitary households, especially solitary households of the aged that will increase in the future. That is, individuals and the whole state, which are mutually counterparts, join hands to keep and develop sustainably and finally increase the true total value of human society. More specifically, the invention relates to, for example, a sleeping state detection system and method that are preferably applied to detect the sleeping state of a subject during sleep in, for example, hospitals, institutions for the aged, general homes, etc.

BACKGROUND ART

Big data are characterized by three "V" as Volume (bulk), Variety (diversity) and Velocity (high speed) (for example, see nonpatent literature 1). Recently, it has been widely recognized that extraction of information from mass data has the value. By communicating and cooperating data among different types of business and analyzing, it is possible to acquire new knowledge, create new business in a corporation and realize improvement of efficiency of the social system. These are data originated from persons and the total amount of data produced is of the order that is limited by the scale of a population. However, in the future, sensors and measuring instruments are massively introduced in the society as represented by M2M (Machine-to-Machine) service and mass various data are produced every moment from them. Therefore, it is necessary to make sure of appropriate data source among various data sources (for example, see nonpatent literature 1).

Weight percentage of substances that a person takes in a lifetime are substances inhaled (83%), drinks (8%) and food (7%) in descending order. Among substances inhaled, "air in his or her home" occupies mostly. It occupies 56% of the total weight of substances that a person takes in a lifetime and has a large effect on life. A house is exactly the second womb environment in this context, so we need to pay more attention to "air in his or her home" (for example, see nonpatent literature 2). Invasion of foreign bodies into the body of a person is blocked at the front by keratin of skin and mucous membranes of the throat and the intestines. And if they fail to block, the foreign bodies are eliminated by phagocytosis of neutrophil and macrophage. Clean air is important from the point of view of immunology regardless.

On the other hand, conventionally, as a method of detecting the sleeping state of inpatients in a general ward of a hospital, tenants in institutions for the aged (nursing care homes for the aged) or members of a general family and ascertaining the health state, known are a method of photographing an inpatient or a tenant with a video camera during sleep and a method of attaching a clinical thermometer, a pulsimeter, a pulse oximeter, etc. to them and measuring temperature, a pulse rate, oxygen saturation, etc. Developed also is a system that uses a sheet-like two-dimensional pressure sensor and obtains information when a person lowers his legs to the floor from a bed and information of posture on a bed during sleep.

PRIOR ART LITERATURE

Patent Literature

[PATENT LITERATURE 1] Laid-open publication No. 2006-200111

Nonpatent Literature

[NONPATENT LITERATURE 1] "Technology for analyzing big data", A report on an investigation of the trend of technology of patent applications of 2013 (Summary), February, 2014, Japan Patent Office
[NONPATENT LITERATURE 2] Shuzo Murakami, "House and Human Body", Japanese Journal of Clinical Ecology (Vol. 9, No. 2, 2000) pp. 49-62
[NONPATENT LITERATURE 3] A. Ishibashi, H. Kaiju, Y. Yamagata and N. Kawaguchi: Electron. Lett. 41, 735 (2005)
[NONPATENT LITERATURE 4] H. Kaiju, N. Kawaguchi and A. Ishibashi: Rev. Sci. Instrum. 76, 085111(2005)
[NONPATENT LITERATURE 5] Nikkei Newspaper (Apr. 12, 2014), front page "Ratio of households of the aged exceeds 40% and 18,450,000 people live alone" (estimated for 2035), third page "Today's words", fifth page "Number of solitary aged rapidly increases in cities. Local governments speed up measures."

SUMMARY OF INVENTION

Subjects to be Solved by Invention

However, in principle, almost all conventional data originating from persons relate to events resulting from decisions made by a person in the conscious state. Data from a large number of sensors and measuring instruments that are introduced into a society are information data of inanimate objects and machines. There is no doubt that the data are useful information. Nevertheless, if it is possible to further take data with other attributes, they will certainly become a data source that is very suitable to adopt a policy and make decisions in the future.

It is necessary for IoT (Internet of Things) business to easily take data from various devices. The structure of cloud computing that is strong and has scalability has been constructed in a global scale. In this situation, if data with new attributes (information taken without contact and noninvasively in the involuntary state) is combined with existing data space, it is possible to maximize the possibility to find points and opportunities that are important for business. In addition to this, it is possible to remarkably improve effect of present IT such as data visualization and data mining. Furthermore, it is possible to plan a higher IoT strategy.

The method of photographing an inpatient or a tenant with a video camera during sleep and the method of attaching a clinical thermometer, a pulsimeter, a pulse oximeter, etc. to them and measuring temperature, a pulse rate, oxygen saturation, etc. will possibly cause the inpatient or the tenant unnecessary stress. Furthermore, these methods have a difficulty that it is not easy to use them in general homes.

Therefore, a subject to be solved by the invention is, most broadly, to provide a system and method using information of involuntary body movement during sleep that can create new innovation and business value and come up with a solution for a trinity of increase of costs of medical treatment and nursing of the aged, increase of administrative costs and creation of new industry by recognizing the importance of IT infrastructure demanded in the cloud computing and big data age and introducing new elements into attributes of data in new age towed by cloud computing and big data.

Another subject to be solved by the invention is to provide a sleeping state detection system and method that can detect the sleeping state of a subject such as an inpatient or a tenant without causing the subject stress, and that can ascertain the health state of the subject from the detection results.

The above subjects and other subjects will be apparent from the following statement of this description referring to accompanying drawings.

Means for Solving the Subjects

In order to solve the above subjects, according to the invention, there is provided a system using information of involuntary body movement during sleep, comprising:

a room or closed space in which a subject sleeps; and a measurement device disposed inside the room or closed space for measuring information of involuntary body movement during sleep of the subject without contact and noninvasively with the subject, the state of the subject being examined by measuring the information of involuntary body movement during sleep by the measurement device while the subject sleeps.

In the invention, the subject includes not only a person but also an animal other than a person. The measurement device preferably includes a dust counter for measuring dust particles inside the room or closed space. And while the subject sleeps in a state where the inside of the room or closed space is kept cleaner than the outside of the room or closed space, the information of involuntary body movement during sleep is measured by measuring the change over time in the number of dust particles inside the room or closed space by the dust counter. It is possible to examine the state of the subject by the information of involuntary body movement during sleep thus measured.

In the broadest sense, the system using information of involuntary body movement during sleep according to the invention is a system of extracting information in living activity of the subject. The system using information of involuntary body movement during sleep is noninvasive and does not contact with the subject and detect the change appeared as a result of action including at least involuntary action of the living organisms. Here, the change can be detected by decreasing background, not enhancing detection sensitivity. The background has a harmful influence on the subject. The system can not only decrease the background having a harmful influence on the subject but also detect useful information at the same time. It is a case of killing two birds with one stone. Especially, it is possible to provide an environment in which the subject lives and extract information appeared from the environment surrounding the subject by interaction of the subject and the environment, which is hidden by the background noise and cannot be used without the system using information of involuntary body movement during sleep. And it is possible to extract health information, activity information, etc. of the subject by calculating the information. From the viewpoint of medical applications, the main target is a case where the subject is a person.

Typically, the background noise is airborne dust, i.e., dust particles, the measurement device that is an information extracting device is noncontact and noninvasive with the subject and information appeared from the environment surrounding the subject by the interaction of the subject and the environment is information of involuntary body movement when the subject sleeps, i.e., during sleep. Calculation executed is acquisition of one dimensional time series data and its correlation analysis. Information of involuntary body movement during sleep is preferably obtained under a clean environment.

The data extracted becomes data hysteresis for a person. By using the data as data when the person is health, it is possible to execute information analysis before the person is involved in a medical institution and develop QOL (Quality of Life) in a healthy condition. Furthermore, it is expected that the data extracted is shared among persons constituting a family and the safety is confirmed from a remote place and common recognition of illness of the family is given to lead a timely treatment. The data extracted may be data extracted for persons constituting families constituting self-governing bodies with various sizes, prefectures and a state. In the future, it will be realized that the safety of the aged living alone and residents living alone is confirmed, poor health is detected and thereby emergency dispatch, rushing and contact with the medical institution are carried out. As a result, it is possible to stop shift into a serious disease and a serious situation and reduce total cost.

It is possible to obtain a deep wide data space by combining (obtaining the direct product of) data with a new attribute never obtained before as "data measured without contact and noninvasively in an involuntary state of a subject" obtained by the system using information of involuntary body movement during sleep with a data space as an object of the existing big data analysis. And it is possible to obtain very useful information by carrying out big data analysis for the data space.

Furthermore, according to the invention, there is provided a method using information of involuntary body movement during sleep, comprising:

examining the state of a subject by measuring information of involuntary body movement of the subject during sleep without contact and noninvasively with the subject in a state where the inside of a room or closed space in which the subject sleeps is kept cleaner than the outside of the room or closed space, while the subject sleeps.

In the invention of the method using information of involuntary body movement during sleep, the explanation concerning the invention of the system using information of involuntary body movement during sleep comes into effect unless it is not contrary to its character.

A typical example of the system using information of involuntary body movement during sleep according to the invention is a sleeping state detection system described below. The following description comes into effect for the invention of the system using information of involuntary body movement during sleep unless it is not contrary to its character.

That is, according to the invention, there is provided a sleeping state detection system, comprising:

a room or closed space in which a subject sleeps;

a measurement device disposed inside the room or closed space for measuring environmental information and/or vital information of the subject without contact and noninvasively with the subject, the sleeping state of the subject being detected by measuring the environmental information and/or vital information by the measurement device while the subject sleeps.

Here, environmental information is, for example, the density of dust particles inside the room or closed space, temperature, humidity, wind speed (speed and direction of air flow), atmospheric pressure, odor (kind and concentration of chemical substance causing odor), kind and intensity of sound, the brightness (illuminance), etc. Vital information is, for example, body movement, heartbeats, pulse, respiration, body temperature and its distribution, etc. The environmental information and/or vital information is typically measured at least in temporal resolution of the order of a minute, but not limited to this.

In the sleeping state detection system, the measurement device is typically a dust counter that measures dust particles inside the room or closed space. And in a state where the inside of the room or closed space is kept cleaner than the outside of the room or closed space, the change over time in the number of dust particles inside the room or closed space is measured by the dust counter, while the subject sleeps and thereby the sleeping state of the subject is detected.

In the sleeping state detection system, cleanliness of the inside of the room or closed space is determined, for example, so that the number density of dust particles corresponding to the ultimate cleanliness of the room or closed space when the subject is at rest is smaller than the number density of dust particles emitted inside the room or closed space when the subject produces involuntary body movement during sleep, for example, the subject tosses about. The inside of the room or closed space is preferably kept at a cleanliness of US 209D Class100 or better. The sleeping state of the subject is preferably detected by executing an analysis of the characteristic of the change over time for a parameter, the number of dust particles inside the room or closed space. As the analysis of the characteristic of the change over time, autocorrelation function analysis and an analysis based on the fast Fourier transform (FFT) are exemplified, but not limited to these. For example, a mechanical learning, modeling in the era of Big Data, data mining and software are also exemplified. When the autocorrelation function analysis is used as the analysis of the characteristic of the change over time, the sleeping state detection system comprises further, for example, an arithmetic unit that obtains the autocorrelation by calculating the autocorrelation function from the result of measurement of the change over time in the number of dust particles measured by the dust counter. The change over time in the number of dust particles inside the room or closed space is typically measured at least in the temporal resolution of the order of a minute, but not limited to this. For example, the change over time in the number of dust particles depends on the timing of measuring the number of particles, so it is possible to measure in the temporal resolution of the order of a second.

At least a part of walls of the room or closed space, more strictly, partitions separating the outside and the inside of the closed space and defining the closed space is constituted by a membrane not passing through dust particles but passing through gas molecules, preferably a wall with an internal space capable of introducing outside air for a room, comprising: airways communicating the outside and the internal space on the edge of the wall, at least one of major surfaces forming the internal space of the wall being made of a membrane not passing through dust particles but passing through gas molecules. Preferably, the wall is in contact with the inside of the room or closed space via the membrane, and the area A of the membrane is set so as to satisfy at least $$A \geq \frac{BL}{D(\eta_0 - \eta)} \tag{16}$$

where B is the oxygen consumption rate inside the room or closed space, $\eta_0$ is the oxygen concentration in equilibrium state with the outside, L is the thickness of the membrane, D is the diffusion constant of oxygen in the membrane and $\eta$ ($\eta > 0.18$) is the target oxygen concentration inside the room.

For example, the closed space has a tent-like or a mosquito net-like structure as a whole in which at least one of the walls constituting the closed space, more strictly, partitions separating the outside and the inside of the closed space and defining the closed space is made of a membrane not passing through dust particles but passing through gas molecules, the closed space being configured so that there is no movement of air as an air current between the inside and the outside of the closed space, the closed space is provided inside with an opening for absorbing air inside the closed space and a blowing opening for returning again all of the absorbed air after cleaning inside the closed space as a pair, the area of the membrane being scaled by $\{(V/A)/(D/L)\}$ when the volume of the closed space is denoted as V, the area of the membrane is denoted as A, the thickness of the membrane is denoted as L and the diffusion constant of oxygen in the membrane is denoted as D, the area A of the membrane being set so as to satisfy at least $$A \geq \frac{BL}{D(\eta_0 - \eta)} \tag{16}$$

where B is the oxygen consumption rate inside the closed space, $\eta_0$ is the oxygen concentration in equilibrium state with the outside and $\eta$ ($\eta > 0.18$) is the target oxygen concentration inside the closed space.

For example, the closed space is configured so that at least one of the walls constituting the closed space, more strictly, partitions separating the outside and the inside of the closed space and defining the closed space is made of a membrane not passing through dust particles but passing through gas molecules, the membrane being attached to a curtain rail etc. to provide movability and capability of opening and closing of the closed space, the closed space with airtightness being formed when closing and the closed space being configured so that there is no movement of air as an air current between the inside and the outside of the closed space, the closed space being provided inside with an opening for absorbing air inside the closed space and a blowing opening for returning again all of the absorbed air after cleaning inside the closed space as a pair, the area of the membrane being scaled by $\{(V/A)/(D/L)\}$ when the volume of the closed space is denoted as V, the area of the membrane is denoted as A, the thickness of the membrane is denoted as L and the diffusion constant of oxygen in the membrane is denoted as D, the area A of the membrane being set so as to satisfy at least $$A \geqq \frac{BL}{D(\eta_0 - \eta)} \quad (16)$$

where B is the oxygen consumption rate inside the closed space, $\eta_0$ is the oxygen concentration in equilibrium state with the outside and $\eta$ ($\eta$>0.18) is the target oxygen concentration inside the closed space.

For example, the room comprises at least one room of a system of highly clean rooms, comprising:

at least one room, at least one of walls constituting the room being constituted of a wall with an internal space capable of introducing outside air for a room, airways communicating the outside and the internal space being provided on the edge of the wall, at least one of major surfaces forming the internal space being made of a membrane not passing through dust particles but passing through gas molecules, the room being configured so that the room is provided inside with a living space as a closed space, there is no movement of air as an air current between the inside and the outside of the living space, the room is provided with the first fan filter unit provided with a blow opening so as to supply gases inside the living space, at least one opening corresponding to an absorption opening of the first fan filter unit is provided in at least one of lateral walls of the room, and all of gases flowing inside the living space from the blow opening pass through the opening and a gas flow path airtightly communicating the absorption opening and the opening and are fed back to the first fan filter unit, the room being provided with doorways capable of moving in the living space.

For example, the room comprises at least one room of a system of highly clean rooms, comprising:

at least one room, at least one of walls constituting the room being constituted of a wall with an internal space capable of introducing outside air for a room, airways communicating the outside and the internal space being provided on the edge of the wall, at least one of major surfaces forming the internal space being made of a membrane not passing through dust particles but passing through gas molecules, the room being configured so that the room is provided inside with a living space as a closed space, and there is no movement of air as an air current between the inside and the outside of the living space, the room being provided inside with an opening for absorbing air inside the room and a blowing opening for returning again all of the absorbed air after cleaning inside the room as a pair.

For example, the gas flow path is provided in the internal space of the wall and at least a part of the wall is provided with at least one opening corresponding to the absorbing opening.

Preferably, when the volume of the living space is denoted as V, the diffusion constant of oxygen in the membrane of the wall is denoted as D and the thickness of the membrane is denoted as L, the room is designed so that the volume V and the area A of the membrane are scaled by $\{(V/A)/(D/L)\}$.

Preferably, when the volume of the living space is denoted as V, the oxygen consumption rate inside the living space is denoted as B, the volume of oxygen in equilibrium state with the outside and without oxygen consumption inside the living space is denoted as $V_{O_2}$, the diffusion constant of oxygen in the membrane of the wall is denoted as D, the thickness of the membrane is denoted as L and the target oxygen concentration inside the living space is denoted as $\eta$ ($\eta$>0.18), the area A of the membrane is set so as to satisfy at least $$A \geqq \frac{BL}{D\left(\frac{V_{O_2}}{V} - \eta\right)} \quad (15)$$

Preferably, directions of air flows flowing in the living space and the internal space of the wall separated by the wall are the same. The doorway may be a sliding door. In an example, the room further comprises an anteroom which is a closed space capable of moving formed by providing a partition so as to face with the doorway inside the living space, the partition is provided with a doorway and the subject can move between the living space and the anteroom through the doorway, there is no air current moving between the inside and the outside of the anteroom, the anteroom is provided with the second fan filter unit in which a blow opening is provided so as to send gases inside the anteroom, at least one opening corresponding to an absorption opening of the second fan filter unit is provided on the lower part of lateral walls of the anteroom, all of gases flowing inside the anteroom from the blow opening of the second fan filter unit pass through the opening and the second gas flow path communicating the absorption opening of the second fan filter unit and the opening airtightly and are fed back to the second fan filter unit, and the subject can move between the living space and the outside of the room by the doorway and the doorway provided in the partition.

For example, the doorway provided in the partition may be a sliding door. The doorway provided in the partition may be the sliding door with the membrane.

For example, the room is provided inside with a local exhaust device having the gas exchange function that exhausts inside air of the living space and the local exhaust device is constituted so that the inside air and the outside air come in contact with each other via at least one membrane, thereby the concentration of molecules constituting the inside air of the living space and the concentration of molecules constituting the outside air approach to the equilibrium state by concentration diffusion of molecules through the membrane and thereafter the inside air of the living space is fed back to the living space.

Preferably, the room is one room of a construction, comprising:

at least one room, at least one of walls constituting the room being constituted of a wall with an internal space capable of introducing outside air for a room, airways communicating the outside and the internal space being provided on the edge of the wall, at least one of major surfaces forming the internal space being made of a membrane not passing through dust particles but passing through gas molecules, the room being configured so that the room is provided inside with a living space as a closed space, there is no movement of air as an air current between the inside and the outside of the living space, outside air is introduced into the internal space of the wall from the outside space enclosing the room through the airway of the wall, the room is provided with the first fan filter unit provided with a blow opening so as to supply gases inside the living space, at least one opening corresponding to an absorption opening of the first fan filter unit is provided in at least one of lateral walls of the room, and all of gases flowing inside the living space from the blow opening pass through the opening and a gas flow path airtightly communicating the absorption opening and the opening and are fed back to the first fan filter unit, the room being provided with doorways capable of moving in the living space.

Preferably, the room further comprises an anteroom which is a closed space capable of moving formed by providing a partition so as to face with the doorway inside the living space, the partition is provided with a doorway and the subject can move between the living space and the anteroom through the doorway, there is no air current moving between the inside and the outside of the anteroom, the anteroom is provided inside with the second fan filter unit in which a blow opening is provided so as to send gases inside the anteroom, at least one opening corresponding to an absorption opening of the second fan filter unit is provided on the lower part of lateral walls of the anteroom, and all of gases flowing inside the anteroom from the blow opening of the second fan filter unit pass through the opening and the second gas flow path communicating the absorption opening of the second fan filter unit and the opening airtightly and are fed back to the second fan filter unit, and persons can move between the living space and the outside of the room by the doorway and the doorway provided in the partition.

For example, the room is one room of a system of highly clean rooms, comprising:

at least one room, at least one of walls constituting the room being constituted of a wall with an internal space capable of introducing outside air for a room, airways communicating the outside and the internal space being provided on the edge of the wall, at least one of major surfaces forming the internal space being made of a membrane not passing through dust particles but passing through gas molecules, the room being provided inside with an opening for absorbing air inside the room and a blowing opening for returning again all of the absorbed air after cleaning inside the room as a pair.

For example, the opening and the blow opening are connected to an air filtering device or an air cleaning device placed inside the room.

For example, the sleeping state detection system comprises the plural rooms, and the opening and the blow opening provided in the plural rooms respectively communicate with a central air filtering device or a central air cleaning device placed outside the room.

For example, the wall of the room is a wall with an internal space capable of introducing outside air for a room provided inside with a living space as a closed space, comprising:

airways communicating the outside and the internal space, provided on the edge of the wall, at least one of major surfaces forming the internal space of the wall being made of a membrane not passing through dust particles but passing through gas molecules, the membrane having the area A set by scaling of $\{(V/A)/(D/L)\}$ where V is the volume of the living space, A is the area of the membrane, L is the thickness of the membrane and D is the diffusion constant of oxygen in the membrane, the wall being in contact with the inside of the room via the membrane, the area A of the membrane being set so as to satisfy at least $$A \geqq \frac{BL}{D(\eta_0 - \eta)} \tag{16}$$

where B is the oxygen consumption rate inside the room, $\eta_0$ is the oxygen concentration in equilibrium state with the outside, L is the thickness of the membrane, D is the diffusion constant of oxygen in the membrane and $\eta$ ($\eta > 0.18$) is the target oxygen concentration inside the room.

For example, the room is one room of a system of highly clean rooms, comprising:

at least one room, at least one of walls constituting the room being constituted of a wall with an internal space capable of introducing outside air for a room, airways communicating the outside and the internal space being provided on the edge of the wall, at least one of major surfaces forming the internal space being made of a membrane not passing through dust particles but passing through gas molecules, the room being configured so that the room is provided inside with a living space as a closed space, there is no movement of air as an air current between the inside and the outside of the living space, outside air is introduced into the internal space of the wall from the outside space enclosing the room through the airway of the wall, the room is provided with the first fan filter unit provided with a blow opening so as to supply gases inside the living space, at least one opening corresponding to an absorption opening of the first fan filter unit is provided in at least one of lateral walls of the room, and all of gases flowing inside the living space from the blow opening pass through the opening and a gas flow path airtightly communicating the absorption opening and the opening and are fed back to the first fan filter unit, the room being provided with doorways capable of moving in the living space, the membrane having the area A set by scaling of $\{(V/A)/(D/L)\}$ where V is the volume of the living space, A is the area of the membrane, L is the thickness of the membrane and D is the diffusion constant of oxygen in the membrane, the area A of the membrane being set so as to satisfy at least $$A \geqq \frac{BL}{D\left(\frac{V_{O_2}}{V} - \eta\right)} \tag{15}$$

where V is the volume of the living space, B is the oxygen consumption rate inside the living space, $V_{O_2}$ is the volume of oxygen in equilibrium state with the outside and without oxygen consumption inside the living space, D is the diffusion constant of oxygen in the membrane of the wall, L is the thickness of the membrane and $\eta$ ($\eta > 0.18$) is the target oxygen concentration inside the living space.

For example, the room is one room of a system of highly clean rooms, comprising:

at least one room, at least one of walls constituting the room being constituted of a wall with an internal space capable of introducing outside air for a room, airways communicating the outside and the internal space being provided on the edge of the wall, at least one of major surfaces forming the internal space being made of a membrane not passing through dust particles but passing through gas molecules, the room being provided inside with a living space as a closed space, the room being provided inside with an opening for absorbing air inside the room and a blow opening for returning again all of the absorbed air after cleaning inside the room as a pair, the membrane having the area A set by scaling of $\{(V/A)/(D/L)\}$ where V is the volume of the living space, A is the area of the membrane, L is the thickness of the membrane and D is the diffusion constant of oxygen in the membrane, the area A of the membrane being set so as to satisfy at least $$A \geq \frac{BL}{D\left(\frac{V_{O_2}}{V} - \eta\right)} \quad (15)$$

where V is the volume of the living space, B is the oxygen consumption rate inside the living space, $V_{O_2}$ is the volume of oxygen in equilibrium state with the outside and without oxygen consumption inside the living space, D is the diffusion constant of oxygen in the membrane of the wall, L is the thickness of the membrane and $\eta$ ($\eta > 0.18$) is the target oxygen concentration inside the living space.

For example, the sleeping state detection system comprises the plural rooms, and the opening and the blow opening provided in the plural rooms respectively communicate with a central air filtering device or a central air cleaning device placed outside the room.

For example, the room is a tent in which a part or all of the side and the ceiling is occupied by a membrane not passing through dust particles but passing through gas molecules, the tent being in contact with the inside of the room, the area A of the membrane being set so as to satisfy at least $$A \geq \frac{BL}{D(\eta_0 - \eta)} \quad (16)$$

where B is the oxygen consumption rate inside the room, $\eta_0$ is the oxygen concentration in equilibrium state with the outside, L is the thickness of the membrane, D is the diffusion constant of oxygen in the membrane and $\eta$ ($\eta > 0.18$) is the target oxygen concentration inside the room.

According to the invention, there is also provided a sleeping state detection method, comprising:

detecting the sleeping state of a subject by measuring the change over time in the number of dust particles inside a room or closed space in which the subject sleeps by a dust counter in a state where the inside of the room or closed space is kept cleaner than the outside of the room or closed space, while the subject sleeps.

In the invention of the sleeping state detection method, the explanation concerning each invention of the sleeping state detection system and the system using information of involuntary body movement during sleep comes into effect unless it is contrary to its character.

In the sleeping state detection system or the sleeping state detection method, the room or closed space in which the subject sleeps is provided by a novel functional wall which was realized by the inventors for the first time and a system of highly clean rooms or a construction based on the wall in which persons can live and act comfortably and peacefully. The wall and the system of highly clean rooms or the construction will be described, though there may be description overlapped with the above description.

That is, the wall is a wall with an internal space capable of introducing outside air for a room, comprising:

airways communicating the outside and the internal space, provided on the edge of the wall, at least one of major surfaces forming the internal space being made of a membrane not passing through dust particles but passing through gas molecules.

Furthermore, the system of highly clean rooms, comprises:

at least one room, at least one of walls constituting the room being constituted of a wall with an internal space capable of introducing outside air for a room, airways communicating the outside and the internal space being provided on the edge of the wall, at least one of major surfaces forming the internal space being made of a membrane not passing through dust particles but passing through gas molecules, the room being configured so that the room is provided inside with a living space as a closed space, there is no movement of air as an air current between the inside and the outside of the living space, outside air is introduced into the internal space of the wall from the outside space enclosing the room through the airway of the wall, the room is provided with the first fan filter unit provided with a blow opening so as to supply gases inside the living space, at least one opening corresponding to an absorption opening of the first fan filter unit is provided in at least one of lateral walls of the room, and all of gases flowing inside the living space from the blowing opening pass through the opening and a gas flow path airtightly communicating the absorption opening and the opening and are fed back to the first fan filter unit, the room being provided with doorways capable of moving in the living space.

Furthermore, the construction comprises:

at least one room, at least one of walls constituting the room being constituted of a wall with an internal space capable of introducing outside air for a room, airways communicating the outside and the internal space being provided on the edge of the wall, at least one of major surfaces forming the internal space being made of a membrane not passing through dust particles but passing through gas molecules, the room being configured so that the room is provided inside with a living space as a closed space, there is no movement of air as an air current between the inside and the outside of the living space, outside air is introduced into the internal space of the wall from the outside space enclosing the room through the airway of the wall, the room is provided with the first fan filter unit provided with a blow opening so as to supply gases inside the living space, at least one opening corresponding to an absorption opening of the first fan filter unit is provided in at least one of lateral walls of the room, and all of gases flowing inside the living space from the blow opening pass through the opening and a gas flow path airtightly communicating the absorption opening and the opening and are fed back to the first fan filter unit, the room being provided with doorways capable of moving in the living space.

Furthermore, the system of highly clean rooms comprises:

at least one room, at least one of walls constituting the room being constituted of a wall with an internal space capable of introducing outside air for a room, airways communicating the outside and the internal space being provided on the edge of the wall, at least one of major surfaces forming the internal space being made of a membrane not passing through dust particles but passing through gas molecules, the room being provided inside with an opening for absorbing air inside the room and a blowing opening for returning again all of the absorbed air after cleaning inside the room as a pair.

Furthermore, a production method of a system of highly clean rooms uses:

at least one room, at least one of walls constituting the room being constituted of a wall with an internal space capable of introducing outside air for a room, airways communicating the outside and the internal space being provided on the edge of the wall, at least one of major surfaces forming the internal space being made of a membrane not passing through dust particles but passing through gas molecules, the room being configured so that the room is provided inside with a living space as a closed space, there is no movement of air as an air current between the inside and the outside of the living space, outside air is introduced into the internal space of the wall from the outside space enclosing the room through the airway of the wall, the room is provided with the first fan filter unit provided with a blowing opening so as to supply gases inside the living space, at least one opening corresponding to an absorption opening of the first fan filter unit is provided in at least one of lateral walls of the room, and all of gases flowing inside the living space from the blow opening pass through the opening and a gas flow path airtightly communicating the absorption opening and the opening and are fed back to the first fan filter unit, comprising:

designing the room by scaling the volume V of the living space and the area A of the membrane of $\{(V/A)/(D/L)\}$ where D is the diffusion constant of oxygen in the membrane of the wall and L is the thickness of the membrane and producing the room.

The room is constituted of an enclosure constituting a closed space and its specific example is a room of a construction etc. The construction may be all rooms supporting human activity such as, for example, detached houses, apartments, condominiums, buildings, hospitals, movie theaters, nursing institutions, schools, preschools, kindergartens, gyms, factories, paint rooms, lacquer rooms, etc. The room can be also applied to, for example, a room inside a mobile body with an internal space. The mobile body may be, for example, cars, especially ambulances, planes, passenger trains, passenger buses, sailboats, passenger boats, etc.

No movement of air as an air current between the inside and the outside of the room means, for example, that the incoming and outgoing air currents for the room are strictly zero during operation of the system of highly clean rooms. However, its meaning is not limited to this and it includes, for example, a case that moves a clean air current with the flow rate much smaller than the flow rate of air subjected to 100% circulation feedback in the highly clean room. That is, it is possible to prepare air with a cleanliness better than the cleanliness of the highly clean room attained by operation of the system of highly clean rooms by, for example, high performance filters etc. and supply the air to the highly clean room as the minimum fresh air demanded by the Building Standards Act etc. It is to be noted that the air introduced from the outside may contribute positively to the cleanliness attained by the 100% circulation feedback system to the negligibly small degree, but does not have a negative effect on the cleanliness. That is, the clean air from the outside does not improve the cleanliness inside the room practically but contributes to the room as a bystander that does not have a bad effect on the cleanliness of the air inside the room at least. When the same amount of air is exhausted outside the room in response to introduction of cleaner air into the room from the outside, the air may be exhausted via a highly grade fan filter unit. In this case, when a fan filter unit for introducing air into the room and a fan filter unit for exhausting air outside the room are the same, high symmetry can be obtained and it is possible to avoid a countercurrent, in other words, to stabilize the cleanliness of the air inside the room. Furthermore, no net air current between the inside and the outside of the room includes, for example, that pressure inside and outside the room are the same. It is to be noted that the condition of equal pressure is satisfied by the symmetrical arrangement of fan filter units with respect to introduction of air into the room and exhaustion of air outside the room by the same effect as the 100% circulation feedback when the outside air is introduced.

The doorway is not essentially limited as far as it has a structure capable of moving of persons etc. The doorway preferably has a structure capable of blocking the living space from the outside airtightly by opening and shutting it. Objects moving through the doorway are not limited to persons and they may be, specifically, small animals etc. Examples of the doorway are doors, specifically, hinged doors, sliding doors, sliding doors with pocket, glide-side doorways, folding doors, slide shutters, winding-up shutters, etc. The doorway may be automatic or manual. When the closed space is formed by the tent-like or mosquito-like structure in which a part or all of it is made of the gas exchange membrane, persons move by hauling the hem of the membrane as the same as the traditional mosquito net. Furthermore, when the closed space is airtightly formed by the two-dimensional body (curtain) having the gas exchange membrane occupying a part or all of it and having the movability by attaching to the curtain rail etc., persons move by opening the curtain along the curtain rail.

The wall is not essentially limited as for as it is a wall, a plate, etc. partitioning the closed space constituting the room and may be, for example, ceiling walls, lateral walls, floor walls, partitions, etc. The structure of the wall is not essentially limited and may be, for example, the single layer structure and multi-layered structure using the same materials, the multi-layered structure using different materials, etc. It is also possible to use a wall that increases the strength by inserting diagonal braces inside or by inserting metal materials having the cross section of U-shape, H-shape or C-shape inside. Materials constituting the wall have preferably rigidity to some extent when the wall is constituted of the materials and they are, for example, concrete, metals, bricks, woods, wood pulp, resin, plaster, glasses, composite materials, etc., but not limited to these. The wall may be, for example, vinyl sheet and tube composite body that can support the structure by sealing air into the body.

Partitions are not essentially limited as far as they are provided so as to partition the inside of the room and they are, for example, ceiling plates, partition walls, etc.

The living space is not limited as far as it is a space isolated from the outer space and it is preferably a space having the size in which living things can live. The living space has more preferably the size allowing persons to live in. The living things are, for example, animals, plants, etc. and specifically, persons, dogs and cats that are small animals, potted plants that are small plants, useful fungi, fungi for food (mushrooms), further, cultured cells or tissues, especially, iPS cells, tissues cultured based on iPS cells, cloned living things, etc. When the living space is used as, for example, a room for pets in which small animals live, it needs to have the enough volume allowing the small animals to live. In this case, the living space can be used as a small room in which even though small animals such as pets etc. live, there are no odor and floating germs, i.e., a small room that can be provided inside a living room for persons without a harmful influence. The performance of the gas exchange membrane forming a part of lateral walls of the room is set so that the oxygen concentration inside the living space not only always exceeds the value provided by the law so as to allow persons to live but also always keep preferably more than 18%, more preferably 19%. The living space can be constituted so as to have a main room and an anteroom that are independent rooms. The anteroom is a room that persons etc. enter before they enter the main room. The anteroom is a closed space capable of moving formed, for example, by providing a partition so as to face with the doorway inside the living space. The partition may be provided with a doorway and persons etc. can move between the living space that is the main room and the anteroom through the doorway. There is no air current moving between the inside and the outside of the anteroom. The anteroom may be provided with the second fan filter unit in which a blow opening is provided so as to send gases inside the anteroom. At least one opening corresponding to an absorption opening of the second fan filter unit is provided on the lower part of lateral walls of the anteroom. And all of gases flowing inside the anteroom from the blow opening of the second fan filter unit pass through the opening and the second gas flow path communicating the absorption opening of the second fan filter unit and the opening airtightly and are fed back to the second fan filter unit. By constituting like this, it is possible to move between the living space and the outside of the room by the doorway and the doorway provided in the partition. The doorway provided in the partition is not essentially limited and can be constituted as the same as the doorway described above. The doorway provided in the partition is preferably a sliding door and at last a part of the doorway is preferably constituted of a membrane not passing through dust particles but passing through gas molecules.

The internal space is not essentially limited as far as it is formed inside the wall. For example, the internal space may be a closed space of the single wall (panel) having the hollow structure, a closed space formed by sandwiching the outer wall of the room and the inner wall provided inside the room, etc. The internal space may be also formed by additionally providing partitions such as panels etc. inside the room or by using walls provided in the existing room. The wall constituting the internal space is, for example, a hollow wall. The hollow wall is not essentially limited as far as it has a hollow part in at least a part of the wall. For example, the hollow wall preferably has a hollow part capable of moving gases from the upper edge to the edge of the wall at least in a part of the inside of the wall. Or the hollow wall preferably has a duct capable of moving gases from the upper edge to the lower edge of the wall or a hollow part capable of carrying a structure having the function equivalent to the duct. For example, the hollow wall has preferably a piercing part communicating one lateral part of the wall to the other lateral part facing to it. The piercing part is not essentially limited as far as it is provided at least a part of the side of the wall. In cases where the hollow wall has, for example, a rectangular parallelepiped shape, the piercing part is preferably provided throughout the pair of sides facing each other of the wall. Specifically, the hollow wall is, for example, the one having a cylinder shape and its cross section is preferably rectangular. A wall with inserted braces or a wall enclosing a pillar provided with metal materials having the cross section of U-shape is preferably placed on the lateral walls other than the hollow wall. The hollow wall may be made of a single material or plural materials. In cases where the hollow wall is made of plural materials, for example, it is preferable to provide the outer wall and the inner wall facing each other a constant distance apart and use the space formed by the outer wall and the inner wall as the hollow part. By using the existing walls, it is possible to use the existing room as the system of highly clean rooms without narrowing the living space. These features are suitably applied to ambulances, private rooms of a long-distance train, private rooms of a long-distance buses, tube hotels, etc.

The fan filter unit is a dust filter having a ventilation power. Although the dust filter means a dust filter using filter materials itself, the fan filter unit specifically defines that a ventilation power accompanies the dust filter. More specifically, a ventilation fan is provided outside the dust filter as one body, or a ventilation fan is provided apart from the dust filter on the way of the gas flow path on which the dust filter is placed, which means that the dust filter has a ventilation power by the ventilation fan.

Hereafter, as necessary, an airtight gas flow path for introducing gases flowing from the dust filter into an absorption opening of the dust filter is referred as a feedback gas flow path. Gases flowing in the feedback gas flow path do not essentially generate a macroscopic mass flow passing through the membrane not passing through dust particles 100%. Therefore, it is possible to prevent dust particles from entering inside the room from the outside of the room and cleanliness inside the room does not deteriorate.

The membrane not passing through dust particles but passing through gas molecules is not essentially limited as far as it does not pass through dust particles but pass through gas molecules between spaces separated by the membrane. For example, the membrane not passing through dust particles but passing through gas molecules is preferably possible to exchange gas molecules through the membrane when the pressure difference between spaces separated by the membrane is zero but there is a difference of partial pressure of gas constituents constituting air on both sides of the membrane. From this, the membrane not passing through dust particles but passing through gas molecules may be, for example, a partition not passing through dust particles but passing through gas molecules. Here, "not passing through dust particles" includes not only the case where dust particles cannot pass through completely (100%) but also the case where dust particles cannot pass through strictly 100% (hereafter the same). More specifically, although the blocking rate (passing rate) is not 100% (0%), the blocking rate of particles having a particle size of 10 μm or above is at least equal to or larger than 90% (equal to or less than 10%), preferably equal to or smaller than 99% (1%). More specifically, the membrane not passing through dust particles but passing through gas molecules may be, for example, a gas exchange membrane, a planar structure having the two-dimensional structure obtained by interweaving the gas exchange membrane, etc. The gas exchange membrane may be preferably, for example, filter materials of a dust filter, shoji paper, nonwoven fabric, shoji paper-like membrane having the gas exchange ability or bellows structure obtained by folding these membranes valley-shape or mountain-shape. Materials constituting the gas exchange membrane are preferably made of many network structures, for example, and further they are preferably many piercing holes, cavities, closed spaces coexisting. If there is a difference of the concentration of constituent molecules of gases occupying spaces on the both sides separated by the gas exchange membrane, there occurs concentration diffusion so that the concentration on the both sides becomes equal. More specifically, as materials constituting the gas exchange membrane, for example, synthetic fibers such as polyester, acryl, etc., cellulose fibers such as pulp, rayon, etc. can be used. Based on the above action, the gas exchange membrane can make the concentration of constituent molecules of gases inside the room converge to almost the same value of that of outside gases through the membrane even though gases do not move as a mass. These breathable materials have breathability (permeability) of 1~100 [l/(m²·s)], typically 30~70 [l/(m²·s)]. Its detail will be described later. The two-dimensional structure is not essentially limited as far as it is a structure having a two-dimensional expanse as a whole. The two-dimensional structure is, for example, a structure having a surface expansion structure microscopically and a planar structure as a whole, a structure having a surface expansion structure as a multiple nesting structure such as a zigzag structure etc., etc.

The system of highly clean rooms is not essentially limited as far as it has at least one closed space capable of closing. The system of highly clean rooms has the enough volume that living things and living organisms that use the closed space and live can act or multiply. For example, the system of highly clean rooms has preferably the volume allowing small animals to live, more preferably the volume allowing persons to live. The system of highly clean rooms may have the compact size for cell culture, formation of tissues and cloning based on iPS cells, etc. For example, in order to always keep cleanliness, the system of highly clean rooms has preferably at least two closed spaces capable of closing and, for example, the system is constituted of an anteroom and a main room. The anteroom is, for example, a room that persons etc. directly move from the outside. The main room is provided, for example, adjacent to the anteroom and is a room that persons etc. can move only through the anteroom. The anteroom and the main room are respectively constituted as a closed space capable of closing as a room. The anteroom and the main room are provided with a fan filter unit and a feedback flow path. The fan filter unit and the feedback flow path are preferably provided independently in each closed space.

With respect to the highly clean rooms, when the density of dust particles inside the room is denoted as n(t), the desorption rate of dust particles per unit area and unit time is denoted as σ and the dust collection efficiency of a HEPA filter is denoted as γ, in cases where the flow inside the closed space is not uniform and it has a location dependence, the density of dust particles n(t) is a function of location and the desorption rate of dust particles per unit area and unit time σ is also considered to be a function of location most generally. In this time, inside the closed space V concerned, dust does not generate or disappear. The density of dust particles $n(x_0, t)$ at time t in the position vector $x_0$ inside the closed space V changes depending on propagation of the influence of the inside of the closed space, i.e., inner walls of the room and satisfy the following differential equation:

$$\frac{dn(\vec{x}, t)}{dt} = \int_V G(\vec{x}, \vec{x}', t)\sigma(\vec{x}')\delta(\vec{x} - \vec{x}'_s)d^3\vec{x}' + \quad (1)$$
$$\int_V G(\vec{x}, \vec{x}', t)[-n(\vec{x}', t)]f_{in}\delta(\vec{x} - \vec{x}'_{inlet})d^3\vec{x}' +$$
$$\int_V G(\vec{x}, \vec{x}', t)[(1-\gamma)n(\vec{x}', t)]f_{out}\delta(\vec{x} - \vec{x}'_{outlet})d^3\vec{x}'$$

Here, the vector $x'_s$ is a position vector corresponding to the inner surface of the closed space. Similarly, the position vector corresponding to apart that is the absorption opening of the fan filter unit is denoted as $x'_{inlet}$ and the position vector corresponding to a part that is the exhaust opening of the fan filter unit is denoted as $x'_{outlet}$. G(x, x', t) is a propagation function showing that generation or disappearance of dust at the position x' has an influence on the position x mainly with propagation by flow of gases and propagation by diffusion. $f_{in}$ denotes the wind velocity at the absorption opening of the fan filter unit and $f_{out}$ denotes the wind velocity at the exhaust opening of the fan filter unit.

The volume of the clean space, i.e., the closed space inside the room is denoted as V, the inner area of the closed space is denoted as S, the dust density of the installation environment (i.e., the outside air) the system of highly clean rooms is denoted as $N_0$ and the wind velocity is denoted as F. In cases where air flow inside the closed space V caused by the fan filter unit is uniform throughout and it does not have a location dependence, each term of the equation (1) converges respectively to $$G \to \frac{1}{V}, \int_V \sigma(\vec{x}')\delta(\vec{x} - \vec{x}'_s)d^3\vec{x}' \to \sigma S, \quad (2)$$
$$\int_V [-n(\vec{x}', t)]f_{in}\delta(\vec{x} - \vec{x}'_{inlet})d^3\vec{x}' \to -nF,$$
$$\int_V [(1-\gamma)n(\vec{x}', t)]f_{out}\delta(\vec{x} - \vec{x}'_{outlet})d^3\vec{x}' \to (1-\gamma)nF$$

And the equation (1) becomes the following function of only time.

$$V\frac{dn(t)}{dt} = S\sigma - n(t)F + n(t)F(1-\gamma) = S\sigma - \gamma F n(t) \quad (3)$$

Here the solution of the equation is:

$$n(t) = \frac{S\sigma}{\gamma F} + \left(N_0 - \frac{S\sigma}{\gamma F}\right)\exp\left(-\frac{\gamma F}{V}t\right) \quad (4)$$

Therefore, when enough time has passed (t>10V/γF), in the closed circulation system, regardless of the installation environment of the closed circulation system, the following ultimate cleanliness can be obtained, which was shown by the inventor in nonpatent literatures 3, 4 etc.

$$n = \frac{S\sigma}{\gamma F} \quad (5)$$

On the other hand, in a conventional clean room, the circulating air flow $F_1$ is filtered every circulation and the air flow $F_2$ introduced as fresh air from the outside is doubly filtered and introduced inside (For simplicity, suppose that the dust collection efficiency is the same and air flow inside the space V is uniform throughout and it does not have a location dependence). Then, $$V\frac{dn(t)}{dt} = S\sigma - n(t)(F_1 + F_2) + (1-\gamma)nF_1 + \quad (6)$$
$$N_0 F_2 (1-\gamma)^2$$
$$= S\sigma - n(t)(\gamma F_1 + F_2) + N_0 F_2 (1-\gamma)^2$$

is the equation describing time change in the number density of inside dust.

The solution of the equation is as follows:

$$n(t) = \left\{\frac{S\sigma}{\gamma F_1 + F_2} + \frac{N_0 F_2}{\gamma F_1 + F_2}(1-\gamma^2)\right\} + \quad (7)$$
$$\left[N_0 - \left\{\frac{S\sigma}{\gamma F_1 + F_2} + \frac{N_0 F_2}{\gamma F_1 + F_2}(1-\gamma^2)\right\}\right] \exp\left(-\frac{\gamma F_1 + F_2}{V}t\right)$$

When the air flow flowing from the chamber concerned is denoted as F ($=F_1+F_2$), the density of dust n after enough time has passed can be expressed in good approximation as follows because $\gamma \sim 1$.

$$n = \frac{S\sigma}{F} + N_0(1-\gamma)^2 \frac{F_2}{F} \quad (8)$$

Comparing the equation (5) and the equation (8), it is understood that parameters dominating cleanliness in the invention are completely different from those of the conventional clean unit. The most important element with respect to the performance of the conventional clean unit is the particle collection efficiency γ of the filter from the equation (8) and γ is desired to be near 1 possibly. This is also apparent from that in a general clean unit, a HEPA filter is preferred than a medium performance filter and an ULPA filter is preferred than the HEPA filter, for example.

As described above, in the existing system, because the removing ability of a filter has a direct influence on the performance of a clean unit, an expensive high performance filter such as ULPA filters, HEPA filters, etc. are used. Because one side of the filter is always in contact with the outside air, the filter is choked. Furthermore, the filter is more easy to be choked in a high dust environment as the performance of the filter is high and the air supply efficiency reduces seriously, the filter is generally exchanged in about 2~3 years. In order to avoid such choking, a prefilter may be placed in the front stage of the filter, but the number of filters increases. Increase of the number of filters not only falls on cost, maintenance, etc. but also increase pressure loss on the absorption side and causes new problems such as increase of power consumption etc.

On the other hand, in the system of highly clean rooms according to the invention, the particle collection efficiency of a filter is not so dominant and generation of rubbish and dust inside the system of highly clean rooms is rather important. Attainable cleanliness inside the system of highly clean rooms of the invention is dominated by only the inside environment of the room and not influenced at all by the installation environment of the system of highly clean rooms as understood from that the density of dust $N_0$ of the outside air does not appear in the equation (5), which is very preferable characteristic. This is an advantage widely different from the conventional clean room and super clean room. That is, the system of highly clean rooms can be applied in any place as far as rain and wind can be blocked such as manufacturing lines, laboratories and general living spaces. Furthermore, as understood from the equation (5), it is a distinctive characteristic that cleanliness hardly deteriorates even though the dust collection efficiency γ is not near to 1. Therefore, it is possible to attain good cleanliness even though cheap filters or filters having the photocatalytic function and realize the high performance.

FIG. 19 is a schematic view showing the change in the number of dust particles inside the system of highly clean rooms using a medium performance filter (γ=0.95) as the dust filter. As shown in FIG. 19, after five minutes from the start of operation the number of dust particles inside the room (living space) rapidly decreases below 100 and after about forty minutes from the start of operation the number of dust particles inside the room (living space) decreases below 10. As described above, it was demonstrated that even though a filter not having the dust collection efficiency γ near to 1 without limit such as 3 nines, 5 nines filter, etc. represented by HEPA or ULPA is used as the dust filter of the system of highly clean rooms of the invention, cleanliness hardly deteriorates.

It is now considered the case where persons etc. act inside the living space at the oxygen consumption rate B. For simplicity, supposing that air is stirred quickly enough inside the living space and the internal space and gas molecules constituting air inside the both spaces equalize quickly enough, it is possible to neglect space coordinate dependence inside the living space and the internal space. Here, when the volume of oxygen inside the room at time t is denoted as $V_{O_2}(t)$, the volume of oxygen when the inside of the room is in an equilibrium state with the outer space and there is no oxygen consumption inside the room is denoted as $V_{O_2}$, the Avogadro number is denoted as $N_0$, the volume of gases per litter at a pressure (~1 atm) that the system is installed is denoted as C, the area of the partition is denoted as A, and the flux of oxygen entering inside the enclosure through the partition is denoted as j, the following equation is satisfied.

$$V_{O_2}(t+\delta t) = V_{O_2}(t) - B\delta t + \frac{CAj}{N_0}\delta t \quad (9)$$

Here, j is given as follows:

$$j = D\nabla\varphi \quad (10)$$

Here, φ denotes the number of oxygen molecules per unit volume inside the enclosure and D denotes the diffusion constant of oxygen in the gas exchange membrane. Supposing that the direction perpendicular to the gas exchange membrane is the x axis, $\nabla$ is a differential operator in the direction of the x axis. In this case, the enclosure means a room or the internal space of the wall. When the volume of the living space is denoted as V and the thickness of the gas exchange membrane is denoted as L, L is smaller than the size of the living space and the thickness of the internal space by about three orders of magnitude or more and presumed to be very thin. Therefore, the equation (9) can be approximated with good accuracy as follows:

$$V_{O_2}(t+\delta t) = V_{O_2}(t) - B\delta t + AD \cdot \frac{\frac{V_{O_2}}{V} - \frac{V_{O_2}(t)}{V}}{L} \cdot \delta t \quad (11)$$

It is to be noted that $V_{O_2}(t)/V$ is the oxygen concentration at time t and $V_{O_2}/V = \eta_0$ is the oxygen concentration when the inside of the room is in an equilibrium state with the outside and there is no oxygen consumption inside the room.

From this, the differential equation $$\frac{dv_{O_2}(t)}{dt} = -B + AD \cdot \frac{\frac{V_{O_2}}{V} - \frac{V_{O_2}(t)}{V}}{L} \quad (12)$$

is derived. Although the exact solution of the equation (12) can be obtained immediately, here interest is directed to the solution corresponding to the stationary state after enough time has passed. Therefore, setting the left side=0, the oxygen concentration at time t can be obtained as follows:

$$\frac{V_{O_2}(t)}{V} = \frac{V_{O_2}}{V} - \frac{BL}{AD} \quad (13)$$

Here, when the oxygen concentration inside the room (living space) is requested to be larger than a constant value $\eta$, $$\frac{V_{O_2}}{V} - \frac{BL}{AD} \geq \eta \quad (14)$$

From this, the necessary area A is requested as:

$$A \geq \frac{BL}{D\left(\frac{V_{O_2}}{V} - \eta\right)} \quad (15)$$

When the oxygen concentration of the outer space is denoted as $\eta_0$, the equation (15) can also be expressed as follows:

$$A \geq \frac{BL}{D(\eta_0 - \eta)} \quad (16)$$

With this, it can be understood that there is a lower limit of A to be satisfied as a function of the oxygen concentration $\eta$ to be satisfied. From the equation (16), obtained is the guideline that A may be small as the consumption quantity of oxygen is small, the gas exchange membrane is thin and the diffusion constant of gas molecules is large.

Generally, given a two-dimensional membrane, permeability is defined as the volume of gases passing through the membrane per unit time and unit area when a constant pressure difference (difference of partial pressure) is given between both sides of the membrane and is actually measured. With this, the above constant D can be obtained. For example, permeability of filter cloth, an example of the gas exchange membrane, is known to be 3 [l/(dm$^2$·min)]~several tenths [l/(dm$^2$·min)] for the pressure difference of 196 Pa (~200 Pa) (Here, l is a unit of volume, litter).

A membrane having permeability of about 70 [l/(m$^2$·s)] for the pressure difference of 196 Pa was reported as the membrane having high permeability (For example, see patent literature 1). In Japan, the target oxygen concentration is requested by law to be always above about 18% and is desired to be near 20.9% possibly. Shoji paper is considered to have permeability of the same order as the above although its permeability may be different depending on methods of papermaking etc. (More strictly, permeability is measured by JISL1096 permeability A method (Frazir type method), KES permeability testing machine, etc.). And using the above analytical equation, it is possible to determine the area of the membrane not passing through dust particles bus passing through gas molecules that constitutes at least a part of the internal space adjacent to the living space, for example, the gas exchange membrane based on the consumption quantity of oxygen inside the living space and the target oxygen concentration according to the equation (16).

The conventional clean room is passive because dust generated inside the clean room is only pushed out outside. On the other hand, the highly clean room of the invention can recover cleanliness by actively removing dust generated inside in a short time (for example, within a time of several times of V/γF at most) with the 100% circulation feedback system and keep cleanliness of the living space inside the highly clean room stably. From this, by applying the highly clean room of the invention to a general living space etc. in which generation of dust cannot be avoided in daily life, it is possible to obtain stable high cleanliness inside the living space and realize a system of highly clean rooms with very low running cost.

As a filter used in the fan filter unit, a filter combining a filter with the photocatalytic function with the dust filter or a multi-function filter with the plural functions obtained by adding a function by photocatalyst to the dust filter is effective.

In realizing the multi-function filter, by noting a flow of gases inside the feedback gas flow path and placing decomposition mechanism of organic matter by photocatalyst in the upper stream of the dust filter, it is possible to receive enough irradiation of light and prevent photocatalytic materials from flowing in the clean space.

That is, by using further a multi-function filter having both the dust removing function and the photocatalytic function in a system configured so that it is provided with a feedback gas flow path of the invention and all of gases flowing out flow into the entrance of the dust filter through the gas flow path (hereafter, referred to 100% circulation feedback system), it is possible to reduce the concentration of chemical substances to the utmost limit. This is true because convergence from the equation (1) to the equation (3) for dust, germs, etc. is valid and an equation obtained by replacing n, σ and γ of the equation (3) with the concentration of chemical substances in gases, the generation rate of chemical substances and the decomposition efficiency of chemical substances by photocatalyst, respectively is also valid.

On the other hand, when the photocatalytic function is added to a usual system, air is taken in through a filter from the outside space and emitted to the outside space. Therefore, taken in air passes through the filter only once or several times at most and decomposition of chemical substances etc. by the photocatalytic effect is carried out only by each passage.

In contrast to this, according to the invention, air passes through photocatalytic mechanism repeatedly after taking in by the 100% circulation feedback system, so that it is possible to markedly increase the decomposition efficiency of chemical substances etc. by the photocatalytic effect compared with the conventional example.

When the photocatalytic function is simply added to a dust filter in an air cleaning system provided in a conventional clean room, especially in an air cleaning system provided with a dust filter always being in contact with high dust atmosphere directly, there occurs serious choking in the surface of the dust collection filter on the side being in contact with the high dust atmosphere. The choking of the dust filter hinders enough irradiation of light to the photocatalyst or the choking hinders contact of the photocatalyst with substances to be decomposed essentially, so that the efficiency of photocatalytic action is seriously reduced.

In the 100% circulation feedback system of the invention, because the dust filter is placed in a place separated from the outside space, the dust filter is never in contact with the outside air directly. Furthermore, by incorporating the dust filter into the 100% circulation feedback system, it is possible to make use of a characteristics capable of reducing the number of dust by several orders of magnitude by the circulation corresponding to essentially infinite times, which is a characteristic of the 100% circulation feedback system, and reduce the rate of choking of the dust filter below 1/(several thousands to ten thousand) compared with the prior art. At the same time, this can also solve the problem that the function of decomposition of chemical substances etc. by photocatalyst deteriorates by choking of the filter.

Furthermore, by utilizing that the dust collection efficiency $\gamma$ is not necessarily quite near to 1, which is a characteristic of the invention, it is possible to avoid choking of the dust filter by reducing the value of the dust collection efficiency $\gamma$, or it is possible to use materials having the high functions such as the photocatalytic ability but having difficulty in making the collection efficiency $\gamma$ approach to 1 as the sufficiently high function dust filter in the circulation feedback system of the invention. Therefore, it is possible to obtain both high cleanliness and the decomposition efficiency of chemical substances etc.

Because the condition of the collection efficiency $\gamma$ is loosened, it is possible to realize a low dust environment integrating the decomposition function of chemical substances etc. by the photocatalyst and the dust removing function. The photocatalyst is, for example, titanium oxide, platinum, palladium, etc. The photocatalytic filter is, for example, a paper filter carrying the above photocatalyst, a resin filter carrying the above photocatalyst, a porous photocatalytic ceramic filter made of tungsten oxide etc., etc. Specifically, the photocatalytic filter is a high density filter made of nonwoven fabric (made of polyester, modaacryl, etc.) with penetrated photocatalytic materials such as titania, tungsten oxide, etc. The porous photocatalytic ceramic filter can realize both low harmful chemical substances environment by the photocatalyst and the super clean environment by the dust filter. As described above, it is not necessary to use the tandem arrangement of a HEPA filter and a photocatalytic filter. Therefore, it is possible to make compact the system. Furthermore, it is possible to reduce pressure loss by the filter, improve the efficiency widely, reduce the load of ventilation power and contribute to save of energy.

According to the present system, gases inside the closed space are actively passed through the filter having both the dust removing function and the photocatalytic function, it is possible to markedly improve the decomposition efficiency of contamination compared with the case where the photocatalyst is simply used for walls etc. Furthermore, by adding the photocatalytic function to the surface of the dust filter, it is possible to decompose germs, dust, etc. captured by the dust filter into carbon dioxide and water. Therefore, it is not necessary to clean and exchange the dust filter and it is possible to realize the ultimate system in which the dust filter can be used semipermanently. Especially, according to the highly clean room of the invention, it is possible to realize a germ-free, dust-free and harmful gas-free environment anywhere, for example, in the middle of a city. Therefore, by placing plants such as balmy trees, herb, etc. inside the room, it is possible to realize a forest bath and a rich natural highland air environment at home. Furthermore, it is possible to produce the relaxation effect by introducing aroma intentionally, etc. With these, it is possible to realize an environment contributing to alleviation of symptoms of asthma and treatment of asthma.

The multi-function filter is preferably made by combining the photocatalytic function filter to the dust filter, or by adding the photocatalytic function to the dust filter to obtain a filter having the plural functions. When the photocatalytic function filter is combined with the dust filter, for example, the photocatalytic function filter is preferably provided inside the gas flow path in series with the dust filter. It is also possible to constitute the multi-function filter with only photocatalyst. For example, it is possible to constitute $TiO_2$ made of porous body as a multi-function filter. When realizing the multi-function filter, it is preferable to note a flow of gases inside the feedback gas flow path and constitute the multi-function filter so as to irradiate the photocatalyst provided on the multi-function filter by enough light and prevent photocatalytic materials from flowing in the clean space. More specifically, for example, by placing a photocatalytic function filter in the upper stream of the dust filter, it is possible to obtain the decomposition function of organic matter by receiving enough irradiation of light and prevent photocatalytic materials from flowing in the clean space.

The room or tent-like structure may be provided with a local exhaust device having the gas exchange function that exhausts inside air of the living space. The constitution of the local exhaust device is not essentially limited. For example, the local exhaust device is preferably constituted so that the direction of the air current inside the local exhaust device is designed to make the inside air and the outside air of the living space have the common direction of movement. Furthermore, the local exhaust device is preferably constituted so that the inside air and the outside air come in contact with each other via at least one membrane not passing through dust particles but passing through gas molecules, thereby the concentration of molecules constituting the inside air of the living space and the concentration of molecules constituting the outside air approach to the equilibrium state by concentration diffusion of molecules through the membrane not passing through dust particles but passing through gas molecules and thereafter the inside air of the living space is fed back to the living space. The local exhaust device constituted above is preferable, for example, for reducing a stench and removing harmful smell in sickrooms and nursing rooms, and can realize reduction of the concentration of organic solvent in air in painting factories etc., while the density of dust is suppressed to be very low.

It is also possible to combine a heat pump type air conditioner provided with a heat exchanger with the feedback gas flow path. Furthermore, by placing, for example, ion emission type air cleaning devices inside the highly clean room of the invention, it is possible to heighten drastically the extinction effect of virus etc. by ions such as OH radicals. Conventionally, when the air cleaning device is placed in an environment that is in contact with the outside air having very low cleanliness, generated ions are taken in by large dust, so that it is not possible to show the effect of decomposing small dust, virus, etc. by ions to its abilities. In contrast to this, inside the highly clean room of the invention, the size of existing dust is very small and the quantity of the existing dust is also small. Furthermore, because new dust is not supplied from the outside air inside the highly clean room of the invention, it is possible to show the effect of decomposing small dust, virus, etc. by ions to its abilities. It is also possible to extend the lifetime, etc. of the filter provided inside the ion emission type air cleaning device.

Effect of the Invention

According to the invention of the system and method using information of involuntary body movement during sleep, it is possible to carryout analysis and prediction, which relied before on intuition and experience of specialists, quantitatively, objectively and with high accuracy from past facts based on the information of involuntary body movement during sleep. Furthermore, for example, in financial service business, enormous data concerning past activities on the market are accumulated to verify a complicated model newly developed by data scientists called Quants. In this connection, by applying its medical treatment and nursing version to the whole data space including time series data of body movement during sleep (involuntary state) as a subspace and using, it is possible to keep health or recover health condition from the condition in which a person is likely to become ill.

According to the invention of the sleeping state detection system and method, the sleeping state of the subject is detected by measuring environmental information and/or vital information by measurement devices that measure environmental information and/or vital information of the subject without contact and noninvasively with the subject, while the subject sleeps. Therefore, it is possible to detect the sleeping state without causing the subject stress. As a result, it is possible to ascertain the health state of the subject. Especially, when the sleeping state of the subject is detected by measuring the change overtime in the number of dust particles inside the room or closed space by a dust counter, which is noncontact and noninvasive with the subject, while the subject sleeps, it is possible to detect the sleeping state without causing the subject stress and therefore it is possible to ascertain the health state of the subject based on, for example, frequency of tossing about.

Furthermore, especially, when the system of highly clean rooms or the construction is used as the room or closed space in which the subject sleeps, the following advantages can be obtained. That is, it is possible to realize a daily living space itself as a clean space of class 100 or higher looking like just a common room in appearance within, for example, thirty minutes, essentially in ten minutes without increasing a load of space and structure in the building structure. Furthermore, for example, it is possible to realize US209D Class1 after ten hours from the start of operation of the system. In addition, the system does not suffer the problem that the pressure difference results between a room of a house and parts of the house other than the room, which is caused by using conventional clean room technology and cleanliness of the room can be improved. By actively collecting dust generated inside by the fan filter unit attached to the room, it is possible to save "a situation such that generated dust is scattered outside of the room and people living outside of the room are troubled". It is possible to provide a system of highly clean rooms capable of always keeping the high air cleaning ability of, for example, class 1 or higher of a room in which people in Japan and the world live, act and are subjected to treatment and nursing without changing parameters of the pressure difference of living customs of conventional houses, and capable of living and acting comfortably and peacefully inside. As described above, while the density of dust particles in the stationary state of the conventional clean room depends on the density of dust particles $N_0$ in the environment and therefore a high quality filter having the dust collection efficiency $\gamma$ that is near to 1 possibly, according to the invention, the density of dust particles n(t) in the stationary state does not depend on $N_0$ (therefore the installation environment is not limited) and $\gamma$ is included in the denomination of the equation of n(t) (therefore it is not important that $\gamma$ is near 1) and therefore it is possible to realize very high cleanliness using a cheap dust filter. Furthermore, according to the invention, because gas constituent inside the room and gas constituent of the installation environment are efficiently exchanged, it is possible to realize a completely closed environment with respect to dust particles and an environment capable of exchanging gas constituent by diffusion.

BRIEF DESCRIPTION OF THE DRAWINGS

FIG. 1 A schematic view showing a sleeping state detection system according to a first embodiment.

FIG. 39B is incorporated into a room of the system of highly clean rooms.

MODES FOR CARRYING OUT THE INVENTION

Figure 2A:
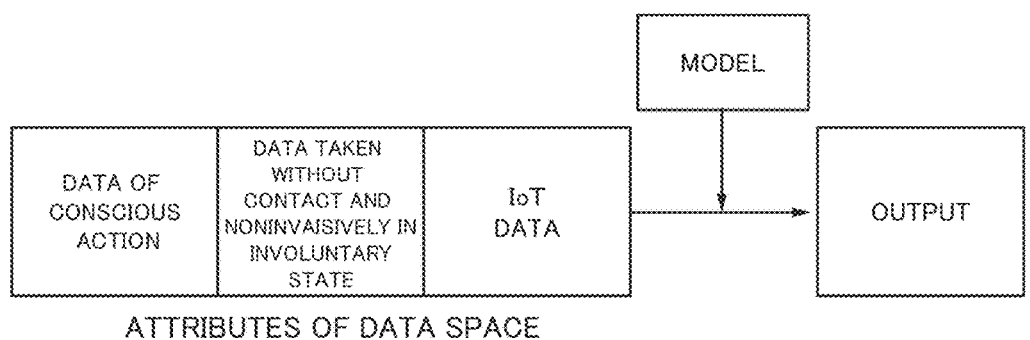
FIG. 2A A block diagram showing a method of analyzing big data using data space with a new attribute constituted by information of involuntary body movement during sleep that is taken by the sleeping state detection system according to the first embodiment.

Modes for carrying out the invention (hereafter referred as "embodiments") will now be explained below.

1. The First Embodiment

[Sleeping State Detection System]

FIG. 1 shows a sleeping state detection system according to the first embodiment. As shown in FIG. 1, in the sleeping state detection system, a bed 202 is placed on the floor of a room or closed space 201. A subject 203 can sleep on the bed 202 in a supine position or a recumbent position. There is no movement of air as an air current between the inside and the outside of the room or closed space 201. The room or closed space 201 is provided inside with an opening (not shown) for absorbing air inside the room or closed space 201 and a blow opening (not shown) for returning again all of the absorbed air after cleaning inside the room or closed space 201 as a pair. In this example, it is realized by a fan filter unit 208 placed on the floor. However, it is possible to place a cleaning process unit outside the room or closed space 201. As described above, the room or closed space 201 is constituted by a wall or a partition (which separates the inside and the outside of the closed space and defines the closed space), and at least a part of it can be made of a membrane not passing through dust particles but passing through gas molecules. When the room or closed space 201 is constituted by a wall, the wall is preferably a wall with an internal space capable of introducing outside air for a room, which has airways communicating the outside and the internal space on the edge of the wall. And at least one of major surfaces forming the internal space is made of the membrane not passing through dust particles but passing through gas molecules. Preferably, the wall is in contact with the inside of the room or closed space via the membrane. However, it is not illustrated here to avoid complication and simplify. To obtain the same gas exchanging ability, a gas exchange device shown in FIG. 35 to FIG. 38, which will be described later, may be used. A pillow 204 is put on the bed 202. For example, a quilt 205 is put on the subject 203. A dust counter 206 is placed in a position different from the position in which the bed 202 is placed in the room or closed space 201. With the dust counter 206, the number density of dust particles inside the room or closed space 201 can be measured. The number density of dust particles n(t) as a function of time t, which is measured by the dust counter 206, can be transmitted to a computer 207 that is placed outside the room or closed space 201 by communication by wire or radio communications. For example, the dust counter 206 and the computer 207 are connected by LAN. With an arithmetic unit of the computer 207, based on n(t) that is measured, an analysis of the characteristic of the change over time, for example, an autocorrelation function analysis or an analysis based on fast Fourier transform can be performed. In this case, analysis and data management may be performed by putting together information by computers placed on bases of Hypnokinetogram analysis, which will be described later, and corresponding service by radio communications using, for example, cellular phones. The bases of Hypnokinetogram analysis and corresponding service may locate within the same building such as a nurse center in a hospital or a nursing home, or locate in certain remote places such as bases of the centralized management of existing security service. The result of the analysis of the characteristic of the change over time can be displayed on a display connected to the computer 207. If necessary, the result can be printed out by a printer connected to the computer 207 and stored in memories of the computer 207 or an external storage device connected to the computer 207. Though not illustrated, a fan filter unit may be placed on the ceiling of the room or closed space 201 and the inside of the room or closed space 201 is cleaned by operating the fan filter unit. Preferably, cleanliness inside the room or close space 201 is determined such that the number density of dust particles corresponding to the attainable cleanliness of the room or closed space 201 when the subject is at rest is smaller than the number density of dust particles emitted inside the room or closed space 201 when, for example, the subject causes body movement, for example, when the subject tosses about. More specifically, for example, cleanliness inside the room or closed space 201 is kept at a cleanliness of US 209D Class100 or better. By keeping cleanliness inside the room or closed space 201 high, background noise due to residual dust particles can be suppressed drastically and the change of the number density of dust particles, which is caused by the change of posture by tossing about of the subject etc., can be definitely extracted.

[A Method of Using the Sleeping State Detection System]

A method of using the sleeping state detection system will now be described.

The inside of the room or closed space 201 is kept at a prescribed cleanliness by operation of the fan filter unit 208 or the fan filter unit placed on the ceiling of the room or closed space 201. The dust counter 206 is always operated. In this state, the subject lies on the bed 202 in a supine position or a recumbent position, puts the head on the pillow 204 and puts the quilt 205. After turning off the light of the room or closed space 201, the subject sleeps. During sleep, the number density of dust particles n(t) inside the room or closed space 201 is measured by the dust counter 206. When the subject changes its posture by tossing about etc. or removes the quilt 205, dust is emitted. As a result, the number density of dust particles n(t) changes. That is, the number density of dust particles n(t) reflects the behavior, in other words, body movement of the subject during sleep and the body movement reflects the health state of the subject. Therefore, the health state of the subject can be ascertained by performing the analysis of the characteristic of the change over time in the number density of dust particles n(t).

Figure 2B:
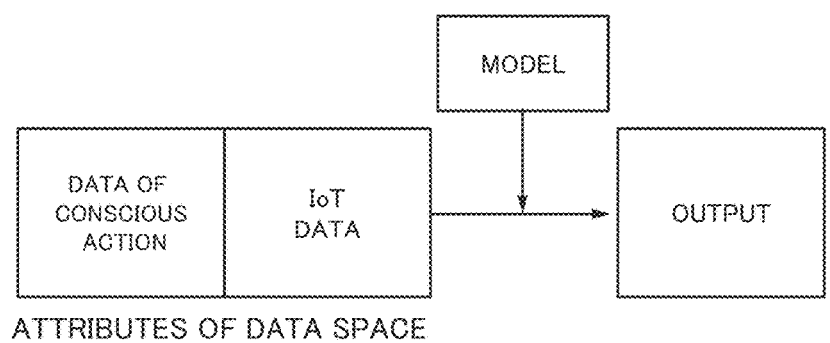
FIG. 2B A block diagram showing a method of analyzing big data using data space with a conventional attribute taken in the conscious state.

If necessary, contact measurement is carried out for the subject during sleep and its result is combined with the result and data of the analysis of the characteristic of the change over time in the number density of dust particles n(t). And multidimensional analysis such as correlation distribution and correlation analysis is carried out, so that the health state of the subject is ascertained. The contact measurement is at least one of measurement of the distribution of the pressure applied to the bed 202 by the weight of the subject, measurement of body temperature by a clinical thermometer or black body radiation spectrum analysis, measurement of a pulse rate with the pulsimeter, measurement of oxygen saturation with the pulse oximeter, etc. With this, it becomes possible to calculate the direct product of a set of measurement data by noncontact measurement and a set of measurement data by contact measurement. And based on the information related to the health state of the subject, higher level analysis, which is impossible so far, becomes possible. This makes possible more accurate understanding of the health state and prediction of the future change in the health state. Therefore, it is possible to take measures based on them. Because it is possible to take measures before a disease state develops, it is expected that suppression of medical expenses, application to preventive medicine, etc. become possible. Especially, as shown in FIG. 2A, data of the noncontact measurement in the involuntary state is combined with a data space of conventional big data analysis shown in FIG. 2B to create a new data space, which is an object of big data analysis. By using the new data space, it becomes possible to analyze from new aspects. That is, the concept of analysis and the creation of a model defining a framework are important for big data analysis. By combining data taken in the involuntary state of persons with the model, extension to modeling including potential decision-making mechanism can be realized. And by combining the modeling with existing POS (Point of Sale) or IoT information, it is expected that new modeling concerning new customer's interest, purchasing activity, etc. can be realized.

The room or closed space 201 is not particularly limited as far as it can be kept a highly clean environment. For example, the room or closed space 201 is a room of a general house or a room of an apartment house.

As described above, according to the sleeping state detection system according to the first embodiment, the sleeping state of the subject can be easily detected by measuring the density of dust particles in a state where the inside of the room or closed space 201 is kept at a high cleanliness, while the subject sleeps. Moreover, because the measurement of the density of dust particles by the dust counter 206 can be carried out without contact and noninvasively with the subject, it is possible to avoid causing the subject unnecessary stress. Because the sleeping state of the subject can easily be detected in this way, the health state of the subject can be ascertained based on the detection results. More specifically, for example, when the frequency of tossing about is very high, the number density of dust particles and the autocorrelation increase or decrease frequently and in this case the health state of the subject tends to be bad, whereas when the change in the number density of dust particles and the autocorrelation is moderate, the health state of the subject tends to be well. When the number density of dust particles and the autocorrelation increase and decrease frequently, there is a possibility that normal respiration of the subject during sleep is impeded for some reason. In this case, various respiration disorders, sleep apnea syndrome, etc. are considered.

2. The Second Embodiment

A sleeping state detection system according to the second embodiment is different from the first embodiment in that a room of a novel system of highly clean rooms is used as the room or closed space 201. Other matters are the same as the first embodiment.

First, a new wall that is used in the system of highly clean rooms is described.

Figure 3A:
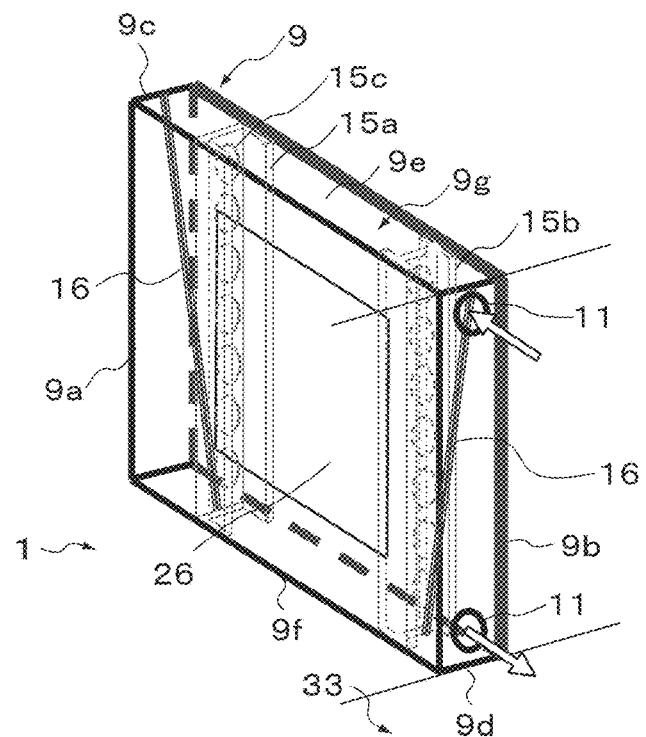
FIG. 3A A perspective view showing an example of a wall of a system of highly clean rooms that is used in a sleeping state detection system according to a second embodiment.
Figure 3B:
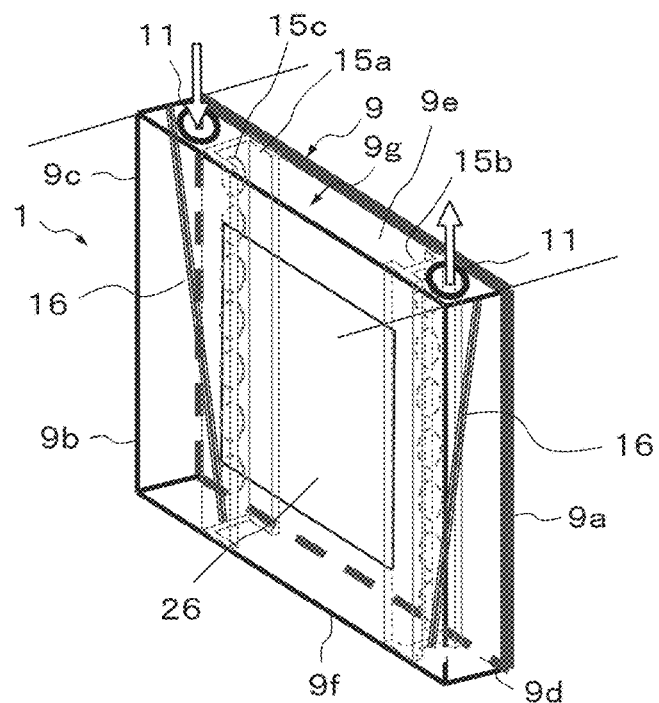
FIG. 3B A perspective view showing another example of a wall of a system of highly clean rooms that is used in the sleeping state detection system according to the second embodiment.

FIG. 3A and FIG. 3B show the wall (partition wall). As shown in FIG. 3A, in the wall 9, an inner wall 9a and an outer wall 9b are facing each other a constant distance apart, and lateral walls 9c to 9f are provided so that four openings formed at edge parts of the walls by facing the two walls are closed. Furthermore, a rectangular parallelepiped is formed by joining the walls 9a to 9f closely and an inner space (hollow part) 9g is formed inside it. The inner wall 9a is provided in contact with a living space of a room 1 that is a closed space. The wall 9 is composed of high strength materials, for example, so that the wall 9 encloses the internal space (hollow part) 9g that can introduce outside air while the wall 9 as a whole has the robust structure. An airway 11 is provided in both end parts of the lateral wall 9d constituting the wall 9. In this case, the airway 11 provided at the upper end part of the lateral wall 9d is an introduction opening (inlet) of outside air and the airway 11 provided at the lower end part is an exhaust opening (outlet). At least a part of the inner wall 9a is constituted of a gas exchange membrane 26. Provided inside the internal space 9g are a C-shape steel 15a facing the lateral wall 9c each other a constant distance apart and an H-shape steel 15b facing the lateral wall 9d each other a constant distance apart so that they are sandwiched between the inner wall 9a and the outer wall 9b. The C-shape steel 15a and the H-shape steel 15b are provided parallel to the lateral wall 9c and the lateral wall 9d. The C-shape steel 15a and the H-shape steel 15b are preferably provided so as to be in contact with the edge part of the gas exchange membrane 26, for example, so that the strength enough to support the room 1 can be obtained. A diagonal brace 16 is provided between the C-shape steel 15a and the lateral wall 9c so as to connect the upper end part of the lateral wall 9c and the lower end part of the C-shape steel 15a. A diagonal brace 16 is also provided between the H-shape steel 15b and the lateral wall 9b so as to connect the upper end part of the lateral wall 9b and the lower end part of the H-shape steel 15b. With this, the strength enough to support the room 1 can be obtained. A hole 15c is provided in the plane of a member in the direction perpendicular to the gas exchange membrane 26 of members composing column materials of the C-shape steel 15a and the H-shape steel 15b and gases flow freely through the hole 15c. By constructing the wall 9 as described above, air is exchanged between the internal space 9g that is the internal space of the wall 9 and open spaces of a house such as a hallway 33 etc. adjacent to the lateral wall 9d through the airway 11. This air exchange is performed preferably by introducing forcibly outside air (fresh air) from the airway 11 provided at the upper end part of the lateral wall 9d and exhausting it from the airway 11 provided at the lower end part of the lateral wall 9d by mechanical ventilation, for example. The gas exchange membrane 26 is provided on the inner wall 9a being in contact with the living space of the room 1 and air inside the room 1 and gases inside the internal space 9g are separated so that an air current is not exchanged as a flow. Mass flow by the air current is not directly exchanged between the living space of the room 1 and the internal space 9g. When there occurs a difference of the concentration of gas molecules constituting air (oxygen, nitrogen, carbon dioxide, etc.) and trace chemical substances such as ammonia etc. emitted by life and activity of persons between both sides of the gas exchange membrane 26, concentration diffusion occurs, so that the molecules are exchanged through the gas exchange membrane 26 and air inside the room 1 being in contact with the wall 9 can be kept to be an environment suitable for life, activity, etc. of persons. The gas exchange membrane 26 may be replaced by a two-dimensional structure obtained by weaving a gas exchange membrane. As members composing the outer wall 9b of the wall 9 supporting the structure of the room 1, for example, high strength materials that are plate materials having enough thickness and strength are preferably used and more preferably, materials added them further with insulating and soundproofing functions are used. By constituting in this way, the wall 9 as a while can obtain the function as the structure having the high insulating and soundproofing performance. On the other hand, two airways 11 are provided in the lateral wall 9e that is the upper lateral wall of the wall 9 shown in FIG. 3B. Other than this, the wall 9 shown in FIG. 3B has the same construction as the wall 9 shown in FIG. 3A. By constructing the wall 9 as described above, air can be exchanged between the internal space 9g and open spaces of the house such as a space between the roof and the ceiling etc. being in contact with the wall 9e.

Here, considered is the area of the gas exchange membrane 26 provided in the inner wall 9a. The area of the gas exchange membrane 26 (or the two-dimensional structure) is denoted as A. When the volume of the living space of the room 1 that is a closed space is denoted as V, the oxygen consumption rate inside the living space of the room 1 is denoted as B, the volume of oxygen inside the living space of the room 1 when it is in equilibrium with the outer space and oxygen is not consumed inside it is denoted as $V_{O_2}$, the diffusion constant of oxygen in the gas exchange membrane 26 (or the two-dimensional structure) is denoted as D and the target oxygen concentration inside the living space is denoted as $\eta$ ($\eta > 0.18$), the area A of the gas exchange membrane 26 (or the two-dimensional structure) is set so as to satisfy at least $$A \geq \frac{BL}{D(\eta_0 - \eta)} \quad (16)$$

When the gas exchange membrane 26 is replaced with the two-dimensional structure, for example, if the two-dimensional structure has the folded structure such as zigzag structure (the structure having plural curved surfaces and/or planes), the two-dimensional area after the structure is enlarged and developed is used as the area A. With this, the oxygen concentration of the room 1 being in contact with the wall 9 can be kept to be $\eta$ or more that is the target value.

As described above, the wall 9 is constructed by providing the outer wall 9b and the inner wall 9a facing each other a constant distance apart, providing the lateral walls 9c to 9f so as to close their openings and constituting at least a part of the inner wall 9a by the gas exchange membrane 26. By composing these walls with high strength materials etc., the wall 9 can have the structure enclosing the internal space (hollow part) 9g that can introduce air while it has the robust structure as a whole. Furthermore, by providing the inner wall 9a of the wall 9 so as to come in contact with the room 1 forming the living space that is a closed space, the wall 9 as a whole can exchange gas molecules without exchanging directly mass flow by the air current while the wall 9 has the function as the structure having enough strength, the insulating and soundproofing performance. More specifically, when there occurs a difference of the concentration of gas molecules constituting air (oxygen, nitrogen, carbon dioxide, etc.) and trace chemical substances such as ammonia etc. emitted by life and activity of persons between both sides of the gas exchange membrane 26, concentration diffusion occurs, so that the molecules are exchanged through the gas exchange membrane 26 and air inside the room 1 being in contact with the wall 9 can be kept to be an environment suitable for life, activity, etc. of persons.

Figure 3C:
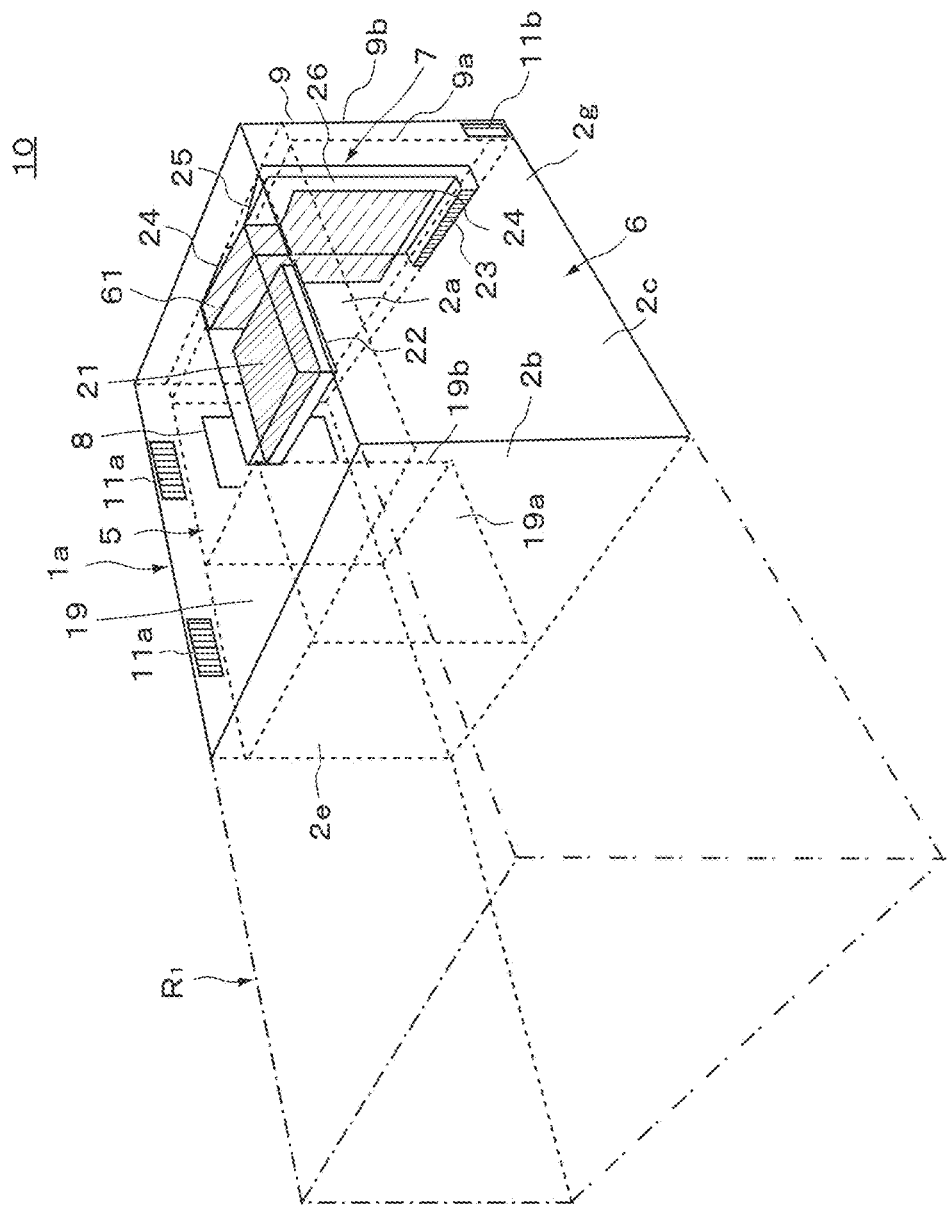
FIG. 3C A perspective view showing a system of highly clean rooms that is used in the sleeping state detection system according to the second embodiment.

FIG. 3C shows the system of highly clean rooms 10 used in the sleeping state detection system according to the second embodiment.

As shown in FIG. 3C, the system of highly clean rooms 10 is constituted by different two independent rooms adjacent to each other. FIG. 3C shows the constitution of the inside of the room perspectively. With respect to the adjacent rooms, a room 1a is provided in the right side of the drawing and a room $R_1$ is provided in the left side of the drawing. In the drawing, the room $R_1$ shown by a dot and dash line is a virtual room and its structure is not limited as far as it has the structure independent from the room 1a. In FIG. 3C, a broken line shows walls such as partition walls, ceiling walls, etc. and the constitution of the inside of the room 1a other than this is shown by a solid line.

The room 1a has a rectangular parallelepiped shape, is the outer most structure in the system of highly clean rooms 10 and forms a closed space. The closed space has the living space 6 and the space 5 between the roof and the ceiling as subspaces constituting it. The space 5 between the roof and the ceiling is an internal space formed by the double ceiling. The double ceiling is constituted by the top surface of the room 1a and the ceiling wall 2a provided so as to face the top surface a constant distance apart. That is, the living space 6 and the space 5 between the roof and the ceiling are separated by the ceiling wall 2a. The wall 9 of the lateral walls constituting the living space 6 on the right side in FIG. 3C has the same constitution as the wall 9 shown in the first embodiment and encloses the internal space 7 having the same constitution as the internal space 9g of the wall 9 shown in the first embodiment. More specifically, the wall 9 enclosing the internal space 7 by the double wall constituted by the outer wall 9b and the internal wall 9a provided parallel to each other a constant interval apart. The lateral walls 9c to 9f constituting the walls shown in FIG. 3A are constituted by the lateral wall 2e, the lateral wall 2c, the ceiling wall 2a and the floor wall 2g constituting the room 1a. A gas flow path 24 is provided inside the internal space 7 and an opening 23 is provided in at least a part of the inner wall 9a. The opening 23 corresponds to an absorption opening of a fan filter unit 21 provided on the plane of the ceiling wall 2a on the side of the space 5 between the roof and the ceiling. The plural openings 23 may be provided. The thickness of the internal space 7, here the distance between the inner wall 9a and the outer wall 9b is preferably 5 cm or more and 40 cm or less, and more preferably 10 cm or more and 20 cm or less. The gas exchange membrane 26 is stretched in the inner wall 9a of the wall 9 separating the living space 6 and the internal space 7. The gas exchange membrane 26 is constituted so that dust particles do not pass through but gas molecules pass through. The gas exchange membrane 26 constitutes a part of the inner wall 9a that is the partition wall between the living space 6 and the internal space 7. When the living space 6 is of Japanese style or like Japanese-Style room, shoji paper is preferably used as the gas exchange membrane 26. The wall structure having the ability that dust particles do not pass through and gas molecules pass through is obtained by providing an opening communicating the living space 6 and the internal space 7 in the inner wall 9a and thereafter the gas exchange membrane 26 is stretched so as to close the opening completely. The gas exchange membrane 26 may be replaced by the two-dimensional structure obtained by weaving the gas exchange membrane. The wall 9 is preferably constituted so that directions of air flowing in the living space 6 and the internal space 7 separated by the inner wall 9a of the wall 9 coincide and furthermore velocities of their flow coincide. As such constitution, a fan is preferably provided in the living space 6, for example. By constituting in this way, gas exchange by the gas exchange membrane 26 can be performed smoothly. The living space 6 has a utility space 19 that is a closed space surrounded by the lateral walls 2b and 2e constituting the inner corner on the left side of the room 1a, the lateral walls 19a and 19b facing with these lateral walls and the ceiling wall 2a. The utility space 19 is utilized as a lavatory, a bathroom, a sink, etc.

An opening corresponding to a blow opening of the fan filter unit 21 is provided in the ceiling wall 2a at the part that the fan filter unit 21 is provided and the blow opening 22 is formed by connecting the opening and the blow opening of the fan filter unit 21 airtightly. The blow opening 22 and the blow opening of the fan filter unit 21 are formed as one body airtightly. Clean gases are supplied to the living space 6 by emitting gas flow from the blow opening of the fan filter unit 21. The fan filter unit 21 may be also installed inside the internal space 7 of the wall 9.

In the internal space 7 formed inside the wall 9, a gas flow path 24 communicating the opening 23 and the gas inlet of the fan filter unit 21 airtightly is provided at the position withdrawn from the plane of the gas exchange membrane 26 by a half of the thickness of the wall 9, for example, a length of 5 cm or more and 10 cm or less. With this, the volume allowing enough gases to exist can be obtained on both sides of the gas exchange membrane 26. The gas flow path 24 has a duct structure having a thickness of 5 cm or more and 15 cm or less and a width of about 90 cm, for example. The opening 23 is an absorption opening for introducing air inside the living space 6 inside the gas flow path 24. All of gases entering from the opening 23 are fed back to the absorption opening of the fan filter unit 21 through the gas flow path 24. Thus, the 100% circulation feedback system is completed. Because the internal space 7 of the wall 9 has two functions of the gas exchange ability and storing of the gas flow path constituting the 100% circulation feedback system, the internal space of the wall 9 can be effectively utilized. The fan filter unit 21 generally may be provided anywhere in the 100% circulation path annexed to the living space 6. The fan filter unit 21 may be provided on the ceiling space 6 as described above or stored, for example, inside the wall 9 by placing it on the floor. In this way, as apparent from the situation shown in FIG. 3C, extremely clean room system can be constituted without narrowing compared with rooms of the conventional houses.

The space 5 between the roof and the ceiling and the internal space 7 are configured to communicate through an opening provided in the ceiling wall 2a constituting the internal space 7. An airway 11a is provided in the lateral wall 2e being in contact with the space 5 between the roof and the ceiling. The lateral wall 2e being in contact with the living space 6 of the room 1a has a doorway 8 through which persons can move between the living space 6 and the outside space. For example, persons can move freely between a hallway (not shown) and the living space 6 through the doorway 8. An airway 11b is provided in the lateral wall 2c being in contact with the internal space 7. The airways 11a and 11b play a role of an inlet for introducing outside air and an outlet. For example, fresh air flowing from the airway 11a is introduced into the internal space 7 of the wall 9 of the room 1a through the space 5 between the roof and the ceiling. Via the gas exchange membrane 26, there occur concentration diffusion of carbon dioxide generated in the living space 6 etc. into the internal space 7 and concentration diffusion of oxygen from the internal space 7 of the wall 9 into the internal space 6 in which oxygen is consumed, so that gas exchange is performed. Air after gas exchange is exhausted from the airway 11b. Gases and chemical substances generated in the room are also exhausted outside through the internal space 7 of the wall 9. Roles of the airway 11a and the airway 11b as the inlet and the outlet can be exchanged by ventilation mechanism of the whole building. That is, it is possible to introduce fresh air from the outside through the airway 11b and exhaust dirty air outside through the airway 11a. Furthermore, in cases where plural airways 11a are provided, the combination of the inlet and the outlet can be selected as necessarily. This is the same also for the airway 11b. It is possible to configure so that no opening is provided in the ceiling wall 2a and the space 5 between the roof and the ceiling and the internal space 7 do not communicate. As a result, the airway 11a and the airway 11b can be completely independent.

Regardless of communication between the roof and the ceiling and the internal space 7, gas molecules are exchanged via the gas exchange membrane 26 between the internal space 7 inside the wall 9 and the living space 6. That is, diffusion of oxygen, carbon dioxide, or chemical substance molecules causing life smell occurs through the gas exchange membrane 26 by concentration gradient depending on the concentration difference on both sides of the gas exchange membrane 26, so that air inside the living space 6 can be kept to be suitable for life and activity. When flat shoji paper like two-dimensional membrane (shoji paper) is used as the gas exchange membrane 26, its area is preferably selected to be 135 cm×135 cm, for example. Air is blown downward from the blow opening 22 of the fan filter unit 21 and air is supplied to the living space 6. In this case, air supplied to the living space 6 forces dust in air downward inside the living space 6, and at the same time, air flows into the gas flow path 24 communicating the opening 23 and the absorption opening of the fan filter unit 21 airtightly from the opening 23 provided at the lower part of the inner wall 9a of the wall 9 forming the internal space 7, so that all of air is fed back to the fan filter unit 21 through the gas flow path 24. In this way, it is configured that all of gases flowing inside the living space 6 from the fan filter unit 21 is fed back to the fan filter unit 21, so that the 100% circulation flow path is completed. As described above, by constructing at least one of the lateral walls of the room 1a by the wall 9 shown in the second embodiment, it is possible to make the internal space 7 enclosed in the wall 9 have the both functions of gas exchange and storing of the gas flow path constituting the 100% circulation feedback system. With this, the space inside the room 1a can be effectively utilized, and a super clean environment can be realized very naturally as a room with design like fitting type shoji paper on the lateral wall of the room seen from the inside without narrowing the room compared with the room of the conventional house. By placing lighting devices at the rear of the shoji paper like gas exchange membrane 26 provided on the lateral wall, it is also possible for the wall to play a role of indirect lighting where the wall itself shines. In this case, the wall 9 functions as a three-way highly functional wall.

When it is desired not only to remove dust but also to decompose smell etc., it is better to provide a photocatalyst 61 inside the gas flow path 24. The photocatalyst 61 may be of simple photocatalyst, or the combination of photocatalyst and dust filter. The photocatalyst 61 is provided inside the gas flow path 24, for example. In the embodiment, the photocatalyst 61 is provided in the upper stream with respect to the dust filter of the fan filter unit 21 in a series connection with the fan filter, however its installation mode is not limited to this. Because the photocatalyst 61 is operated in almost dust fee condition in the system of highly clean rooms, the photocatalyst 61 is free from the problem of choking up by dust and it is possible to operate the photocatalyst 61, utilizing only its primary photocatalytic function, so that the photocatalytic function is kept for a very long time. The photocatalytic device is a system having very good compatibility with the 100% circulation system of the present invention as the same as generally used functional devices such as a plasma cluster (registered trademark) and a nano-e (registered trademark).

According to the second embodiment, the following advantage can be obtained in addition to the same advantages as the first embodiment. That is, because at least one of the lateral walls of the room 1a is constituted by the wall 9, one internal space has both functions of gas exchange and storing of the gas flow path constituting the 100% circulation feedback system. Therefore, the space inside the room 1a can be effectively utilized and the key part of the system of highly clean rooms can be embedded without narrowing the room compared with the conventional house. Also, because it is necessary to provide only one 100% feedback path, an advantage capable of building the system of highly clean rooms simply and easily with low cost can be obtained. The system of highly clean rooms can be a suitable system when the frequency of going in and out the room 1a is small and the stay time inside the living space 6 is long relatively.

More precisely, according to the sleeping state detection system using the system of highly clean rooms, the following various advantages can be obtained. The population of the aged and the ratio of persons living alone are steadily increasing in Japan (see nonpatent literature 5). According to an estimate of 2035 by the Ministry of Health, Labour and Welfare, families of the aged will exceed 40% and the number of persons living alone will be 18,450,000. In addition, an aging rate in Japan is expected to further increase and therefore it is an urgent issue to take measures. In investigation of an opinion poll concerning an aging society, the ratio occupied by persons who answered that they live alone is high. Persons are worried about living alone. There are many persons who "desire to continue to live in the present place where they live so long" and "desire to move into a common rental house for the aged that can take life support", even though they become weak. However, it is not easy to correspond to it medically, financially and by administration. An environment of rooms of nursing homes for the aged (nursing welfare facility for the aged), a hospital, etc. corresponding to the aging society in the future is not satisfactory because there are problems of cleanliness, odor, etc. Sometimes the problem of infection happens. There exists no clean technology capable of dealing with a general sickroom of a nursing home for the aged or a room of a general house. With respect to a ward of the general hospital, there exists also no clean technology capable of dealing with the ward except a part of negative pressure rooms for quarantine. According to conventional clean room technology, the inside of the clean room is kept to be positive pressure for manufacture of semiconductor devices and the inside of the room is kept to be negative pressure to prevent microbes and viruses escaping out for medical use. However, it is essentially impossible to solve the problem of PM2.5 or infection with the conventional technology because the actual living environment is narrowed or it costs a lot. Many of the aged tend to live as ever in a room with "tatami" and "futon" or such as a Japanese-style room, which is relatively not easy to prepare a clean environment and therefore it is very important to apply clean technology capable of dealing with the room. According to the sleeping state detection system using the novel system of highly clean rooms, it is possible to flower potential ability of a highly clean environment and prepare for an aging society in the future while complying with the demands of the aged or persons living alone. In addition, it is possible to establish elemental technology for (1) suppression of medical expenses of the aged, (2) development of new industry, (3) the realization of easing the burden for the administration for the aged. The system of highly clean rooms can be easily realized by reforming rooms of an ordinary general house. Therefore, the sleeping state detection system can be easily realized in general houses. That is, it was demonstrated that it is possible to attain cleanliness higher than super clean rooms for, for example, manufacture of LSIs in a room of a general house. For example, remote computer control of measurement of the number of particles by the dust counter 206 via LAN cables was realized and it is possible to detect the sleeping state based on the analysis of the characteristic of the change over time in the density of dust particles in a clean, microbe-free environment. Furthermore, it is possible not only to solve the problem of PM2.5 and the problem the of pollinosis these days but also to ascertain the health state by measuring the spectrum reflecting tossing out during sleep by the system of highly clean rooms with the 100% circulation feedback system. As described above, according to the sleeping state detection system using the system of highly clean rooms, it is possible to realize a highly clean environment at a low price and stably in hospitals, nursing homes for the aged and general houses and further realize simple health care corresponding to an extraordinary aging society by detection of the sleeping state. That is, the system of highly clean rooms in which Shoji paper etc. are used as the gas exchange membrane is a system that can realize a highly clean environment in Japanese style and is suitable for persons to sleep inside. More specifically, with the system of highly clean rooms, it is possible to realize a clean space of US 209D Class100 level (cleanliness corresponding to a dust-free room or an operating room of a hospital) in a room of a general house. And when persons sleep in the room, it is possible to decrease intake of dust into lungs to about one-thousandth compared with a case where persons sleep in a room as it is (sleep for about seven hours in a space in which the total number of dust particles having the particle size of 0.5 μm or above per cubic feet amounts to about a hundred thousand) and refresh well the respiratory system every night. Because the background level of dust is decreased, it becomes possible for the first time to take information of tossing out (its magnitude and frequency), that is never taken before, with a noninvasive, noncontact method and easily in a house (See spike-like signals in FIG. 47~FIG. 55 described later). This information is information of involuntary body movement during sleep (information taken in the real usual life and the sleeping state because no prove is attached to the body). Therefore, it is possible to create new useful measurement technology "Hypnokinetogram" and data analyzing system. By using an enlarged data space including Hypnokinetogram data, which are time series data of body movement during sleep (involuntary state), as a subspace in the field of medical treatment and nursing, it is possible to keep health and return to the healthy condition from the condition in which a person is likely to become ill. Furthermore, by combining the data space with new attributes with data space that is an object of existing big data analysis, it is possible to combine an enormous data space of information of activity of persons in the conscious state (the data space in the conscious state [↑] of a person [↑] is denoted here as (↑,↑)) with a data space by IoT (the data space in the involuntary state [↓] of inorganic matter and nonliving things [↓] is denoted here as (↓,↓), such that the Hyptokinetogram information space (the involuntary state [↓] of the person [↑] is denoted here (↑,↓)) is expressed as (↑,↑) (↑,↓) (↓,↓) and therefore it is possible to deepen and enlarge data in big data analysis. The new data space becomes the base for changing rapidly the state of medical treatment to a better stage even in the current trend such as mobile health that may change the state of a clinical site.

From the above, it becomes possible to monitor the safely of sleeping persons from a remote place while guarding the privacy of the persons because no image information such as video image is used. This may become the big pillar of business of nursing care with services. Furthermore, it is possible to accumulate information of tossing out of sleeping persons (take as big data of information of body movement) from higher order information (the change over time in the number of dust particles) obtained with a bit sequence. And based on this, it is possible to extract depth of sleep, finally information of health etc. in a very natural condition in which no probe is attached to the body (it is possible to take highly objective data by obtaining a vital signal in the involuntary state). Applications are not limited to the correlation in the individual. For example, when members of a family live away, if they share mutual data, they can virtually "live together" such that "they live together in one house". Furthermore, by enlarging this to a level of a self-governing body, it is possible to accumulate data of persons living alone, especially the data from the stage where they are healthy and do not need nursing before they become ill. Therefore, it is expected to contribute to keep QOL well. Finally, it is expected that it is possible to suppress medical expenses and ease the burden of administration for the aged. Though opinions concerning short-term exposure to PM2.5 are limited in study in Japan and the foreign countries, its relation to the change in functions of a heart and a circulatory system, symptoms of a respiratory system, more widely, effect on health is studied. It is possible to introduce a clean environment that can reduce the risks drastically into not only hospitals and schools but also to general houses and protect high sensitive persons (persons suffering from diseases of a respiratory system or a circulatory system, infants, the aged, etc.). That is, it is possible to realize a "tent" room and a house system that can ascertain the health state of persons and give various advices just like a full-time home doctor. Only by sleeping in a room of the system of highly clean rooms, it is possible to reduce the burden on a respiratory system to about zero for about seven hours. Furthermore, from information of the magnitude of tossing out and frequency (appeared by making the background noise to zero), it is possible not only to confirm the safety of sleeping persons (users) but also to examine whether there are deviations from the normal state, depth of sleep and an early symptom of a disease. If abnormalities are found, the house is connected to a hospital, so that risks taking suddenly ill of persons living in the house are reduced. More specifically, it becomes possible to realize new ground of houses as a living space itself (a living environment that is backward compatible for nursing and medical treatment), which is targeted but not realized before, with a combination of the system of highly clean rooms (environment) and remote monitoring (information and communication). It is expected to decrease the number of PM2.5 particles, which are one of air pollution substances, easy to penetrate deep into lungs and may have a bad effect on the respiratory system and the circulatory system, to about zero (see FIG. 10, FIG. 11 and FIG. 59A). Furthermore, it is expected to realize health care, care before contracting an ill, accumulation of data of individuals and families, virtual integration of persons living alone by sharing of information of health among nuclear families with big data of information of tossing about, which is made possible for the first time with the sleeping state detection system, and the autocorrelation function analysis of the change over time in the number of just particles during sleep. This will lay the foundations of a new society of Japan. According to the system of highly clean rooms, it is possible to reduce drastically odor, which is the problem of nursing homes for the aged etc., by gas exchange. By using the tent-like highly clean system shown in FIG. 46A and FIG. 46B described later instead of the system of highly clean rooms, it is possible to realize well-being of high sensitive persons (persons suffering from diseases of a respiratory system or a circulatory system, infants, the aged, etc.) in not only hospitals and nursing homes for the aged but also general houses. In this case, high cleanliness is realized by covering bedding like a traditional Japanese mosquito net during sleep. Especially, it is possible to realize a cleanliness of US 209D Class100 while persons sleep inside (resting time). As described before, according to the investigation of an opinion poll concerning the aging society, with respect to inquiry about the way persons live when they worry about living alone or they become weak, the desire of people "to continue to live in the present place where they live so long" and "to move into a common rental house for the aged that can take life support" is very strong. A highly clean environment realized by the system of highly clean rooms and the tent-like highly clean system and the autocorrelation analysis and the FFT of tossing about during sleep and data mining and software for big data meet the needs. When the autocorrelation function analysis is used as the analysis of the characteristic of the change over time, it becomes fully possible to realize a remote care at a low price based on the sleeping state. With the clean environment, it is possible to protect high sensitive persons (persons suffering from diseases of a respiratory system or a circulatory system, infants, the aged, etc.) in not only hospitals and nursing homes for the aged but also general houses. Establishment of countermeasures against PM2.5 leads to prevention of passive smoking due to side stream smoke on smoking, measures against pollinosis, and measures against airborne infection. Therefore, it becomes possible to keep and improve health of people in Japan in which the ratio of the aged will increase in the future. As a result, suppression of medical expenses for the aged and creation of industry and vitality become compatible. It becomes possible to support health and safety of persons living alone, the number of which will be about twenty million, by the remote monitoring and aid people with well-being and maintenance of health.

For example, lungs are exposed to a mass of allergic reaction inducing substances (antigen) such as airborne dust particles, pollen, eumycetes and chemical substances and easy to cause an allergic reaction. Persons are often exposed to stimulative dust particles and substances in air during working and the possibility of causing the allergic reaction of respiratory organs may be high. This situation can be improved by living in the clean space of the invention for about 7~8 hours of a day almost without a burden on respiratory organs. It is common that clusters called iBALT produced by crowding of immune cells are observed in patients suffering from chronic obstructive pulmonary disease. It is considered that iBALT promotes sharp immune response against intake of allergen or particles such as soot and smoke of cigarettes, continue chronic inflammation of lungs and cause damage of tissues. Formation of a clean closed space with a curtain-like structure made of gas exchange membranes by using curtain rails etc. can be introduced with a high cost versus performance and without almost changing the situation that a curtain is used as a screen to hide the inside from surroundings in a sickroom (a room for many persons). This may be good news for patients suffering from a chronic obstructive pulmonary disease. Hypersensitivity pneumonitis (extrinsic allergic alveolitis) is a kind of inflammations caused inside or around small air sacks in lungs (alveoluses) or the thinnest respiratory tracts (bronchioles) and caused by allergic reactions due to intake of dust particles of organic substances or chemical substances, though rarely. This disease is usually cured if the patient is not again exposed to these substances. Therefore, it is expected that the patient will recover very fast by living in an environment of US 209D Class100-1000 that is cleaner than the usual room one thousand fold by putting bedding such as futon etc. in the clean closed space of the tent-like structure of the invention rather than waiting recovery in dust particles of US 209D Class hundreds of thousands in general houses and office environment. Furthermore, allergic bronchopulmonary aspergillosis is a kind of allergic reactions of lungs against a kind of eumycetes (many of them are aspergillus fumigatuses) and may occur in patients suffering from asthma and cystic lung fibrosis. Aspergillus exists everywhere in a living environment. Therefore, it is considered to be difficult to avoid contact with the eumycetes. However, by putting bedding such as futon etc. in the tent-like clean closed space of the invention or a closed space formed by the gas exchange membrane that is movable by curtain rails and sleeping in the clean space, it is possible to limit contact with the eumycetes below one-hundredth~one-thousandth for 7~8 hours on the average of the sleeping time in one day. Therefore, it is expected to reduce contact with the eumycetes to negligible levels for the time.

3. The Third Embodiment

Figure 4:
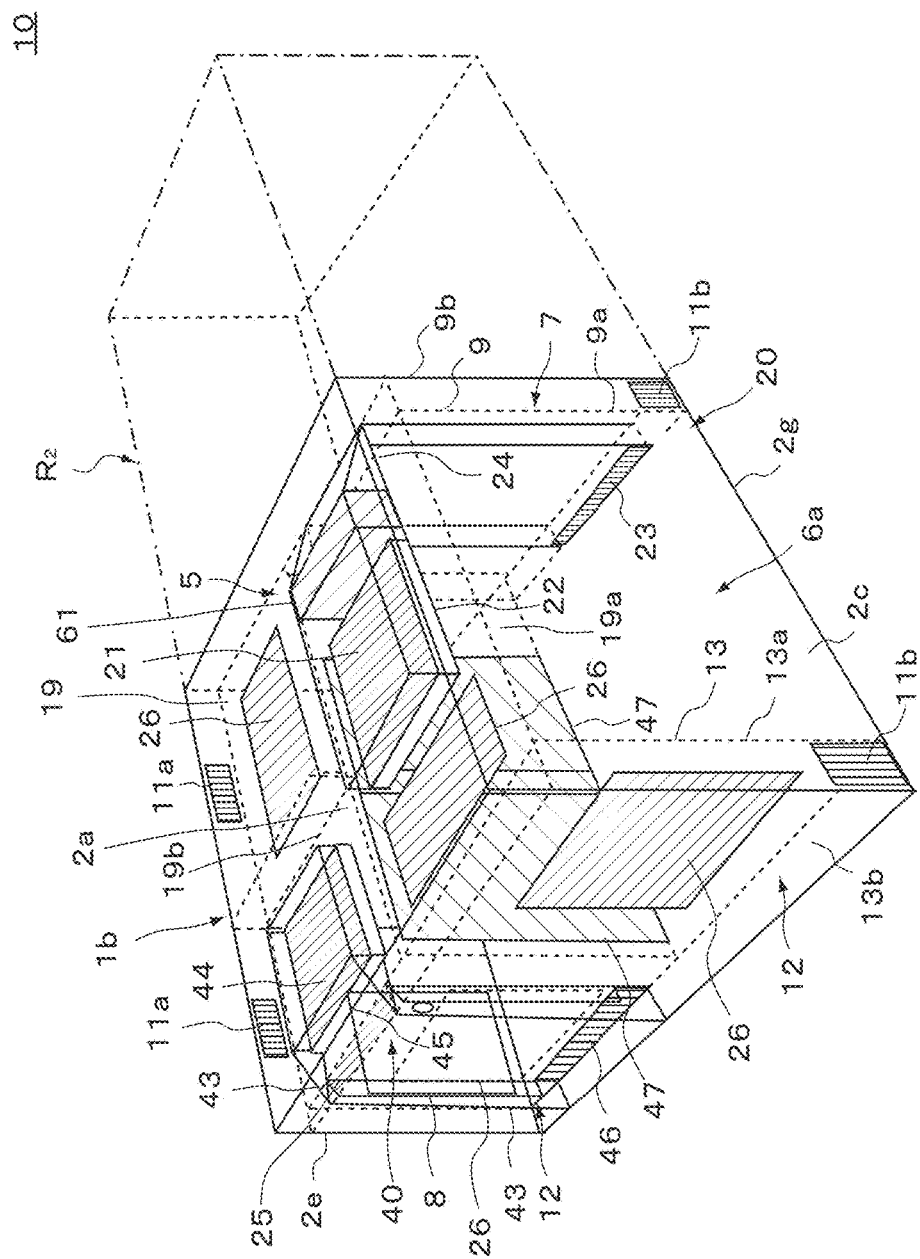
FIG. 4 A perspective view showing a system of highly clean rooms that is used in a sleeping state detection system according to a third embodiment.

FIG. 4 shows a system of highly clean rooms 10 used in a sleeping state detection system according to the third embodiment. The sleeping state detection system is different from the first embodiment in that a room of a novel system of highly clean rooms 10 is used as the room or closed space 201. Other matters are the same as the first embodiment.

Figure 10:
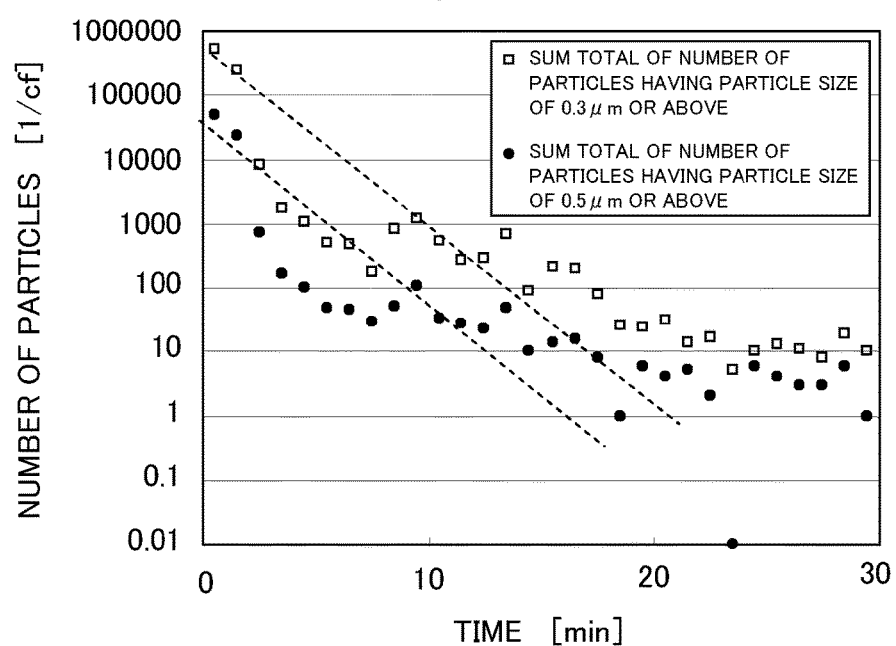
FIG. 10 A schematic view showing the change in the number of dust particles inside the main room in a short time when the fan filter unit of the system of highly clean rooms according to the example is operated.

As shown in FIG. 4, in the system of highly clean rooms 10, the room 1b of the adjacent rooms is provided in the left side in the drawing and the room $R_2$ of the adjacent rooms is provided in the right side in the drawing. In FIG. 10, the room $R_2$ shown by the dot and dash line is a virtual room and its structure is not limited as far as it has a structure independent from the room 1b. In FIG. 10, the broken line shows walls provided inside the room 1b such as a partition wall, a ceiling wall, etc. and other structures inside the room 1b are shown by the solid line.

With respect to the system of highly clean rooms, a need for obtaining the higher performance than the system of highly clean rooms shown in the second embodiment may be raised. For example, such a system of highly clean rooms is applied to treatment of an immunodeficiency disease in the hospital, more perfect prevention of infectious diseases in the nursing home for the aged, recuperation at home in general homes, etc. In this case, it is necessary to devise not to deteriorate cleanliness of the space at the moment going in and out between the living space 6 served as a sick room or a nursing room and the outdoors or hallways. For this, a further additional structure is introduced while utilizing the structure of the room 1a of the second embodiment.

That is, in the room 1b, the lateral wall facing the wall 9 that is the lateral wall constituting the room 1a shown in the second embodiment is replaced with a wall 13 enclosing the internal space 12 constructed similar to the wall 9. In other words, among the lateral walls constituting the room 1b, both walls facing each other on the side without the doorway 8 are constituted by the wall 9 and the wall 13 each enclosing the internal space. Here, the internal space 7 enclosed in the wall 9 and the internal space 12 enclosed in the wall 13 are independent each other. The structure of the wall 13 and the internal space 12 may be similar to the structure of the wall 9 and the internal space 7. The wall on the left side in the drawing of the room 1b is constituted by the wall 13 having the same structure as the wall 9 shown in the second embodiment and the wall 13 is constituted by the outer wall 13b and the inner wall 13a. The wall 13 has the internal space 12, i.e., the second internal space, and the internal space 12 is a space adjacent to the living space 6 via the gas exchange membrane 26. The thickness of the internal space 12 is specifically 5 cm or more and 40 cm or less, and preferably 10 cm or more and 20 cm or less, for example. As described later, because the internal space 12 does not need to store the gas flow path 24 in it, the internal space 12 may be of the thin structure having the thickness of 15 cm and less.

The gas flow path 24 provided inside the internal space 7 may be provided on the inner wall 9a. This is because a part of the internal wall 9a is not constituted by the gas exchange membrane 26. The walls 9 and 13 themselves may be used as the gas flow path. In cases where the wall itself is used as the feedback path, the airway 11b provided in the wall 9 is shut. The thickness of the gas flow path 24 is preferably 5 cm or more and 10 cm or less as described above. It is possible to increase the thickness of the gas flow path 24 to the thickness of the internal space 7 to increase the cross sectional flow rate and increase the conductance of the flow. A part of the inner wall 13a of the wall 13 is constituted by the gas exchange membrane 26.

The space 5 between the roof and the ceiling and the internal spaces 7 and 12 constituted by double walls may or may not communicate through the space 5 between the roof and the ceiling each other. Any one of the internal space 7 and the internal space 12 may communicate with the space 5 between the roof and the ceiling. Introduction of outside air into the internal spaces 7 and 12 can be performed as the same as the second embodiment and the combination of the inlet and the outlet of the airways 11a and 11b are selected for uses as necessary. For example, although two airways 11a provided in the lateral wall 2e being in contact with the space 5 between the roof and the ceiling are used as a pair of the inlet and the outlet in the room 1b, it is possible to use both of the airways 11a as inlets and the airway 11b in the lower part of the lateral wall is used as the outlet.

An anteroom 40 that is a subspace of the living space 6 is formed by providing a partition so as to face the doorway 8. More specifically, the anteroom 40 is constituted by providing a sliding door 47 so that an opening of the space surrounded by the lateral wall 2e of the room 1b having the doorway 8, the inner wall 13a of the wall 13, the partition 19b of the utility space 19 and the ceiling wall 2a is closed. The sliding door 47 functions as the partition. The sliding door 47 may be constituted in a part of the partition wall provided so as to close the opening. The space of the living space 6 other than the anteroom 40 constitutes a main room 20. That is, the sliding door 47 has the partition function partitioning the anteroom 40 and the main room 20. The sliding door 47 is provided so that when it is opened, it opens along the lateral wall 19a constituting the utility space 19 to prevent generation of unnecessary dead space upon opening and shutting of the sliding door 47. When the sliding door 47 opens, the anteroom 40 and the main room 20 communicate. When the sliding door 47 shuts, the anteroom 40 and the main room 20 are completely isolated. At least a part of the major surface of the sliding door 47 is preferably constituted by the gas exchange membrane 26. As the gas exchange membrane 26, for example, shoji paper, shoji paper like filter cloth or nonwoven fabric filter materials is selected, so that the sliding door 47 is invested with the gas exchange ability while producing Japanese old Shoin construction flavor. In cases where the gas exchange membrane 26 is provided in the sliding door 47, concretely, for example, the sliding door 47 is provided with an opening communicating both sides of it, and the gas exchange membrane 26 is stretched so as to cover the whole of the opening. With this, gas exchange can be performed between the inside and the outside of the anteroom 40 without movement of the air current between the inside and the outside of the anteroom 40.

The wall on the left side in the drawing forming the anteroom 40 is constituted by the wall 13. The gas exchange membrane 26 is stretched on the inner wall 13a separating the anteroom 40 and the internal space 12 of the wall 13 and the gas exchange membrane 26 constitutes a part of the inner wall 13a. A gas flow path 43 is stored in the internal space 12 parallel to the gas exchange membrane 26 withdrawn from the membrane by a distance of about half of the distance between the inner wall 13a and the outer wall 13b, i.e., the distance of 5 cm or more and 20 cm or less. The gas flow path 43 communicates airtightly an opening 46 provided at the lowest part of the inner wall 13a and a gas inlet of a fan filter unit 44 provided on the ceiling wall 2a inside the space 5 between the roof and the ceiling. The fan filter unit 44 is connected to a blow opening 45 so that air is supplied inside the anteroom 40. The gas outlet 45 is constituted as the same as the blow opening 22. The gas flow path 43 is constituted as the same as the gas flow path 24. The gas flow path 43 is constituted, for example, by using a duct having a rectangular cross section or by connecting plural bellows pipes in parallel. The gas flow path 43 is connected to the opening 46 airtightly. Air inside the anteroom 40 is introduced inside the gas flow path 43 through the opening 46, and all of air is returned again inside the anteroom 40 from the blow opening 45.

Furthermore, as a more convenient type, it is possible to omit the gas exchange membrane 26 provided in the inner wall 13 inside the anteroom 40 and to substitute it by the function of the gas exchange membrane 26 (shoji paper) constituting the sliding door 47. The gas flow path 43 has only to be constituted inside the internal space 12 isolated from it. The gas flow path 43 can be realized, for example, by simply connecting the bellows pipes. In the embodiment, although at least a part of the ceiling wall 2a constituting the main room 20 and at least apart of the ceiling wall 2a constituting the utility space 19 are constituted by the gas exchange membrane 26 to invest the gas exchange ability as much as possible, whether the gas exchange membrane 26 is placed or not, its area, etc. are properly designed and selected according to the consumption of oxygen inside the room.

The operation of the system of highly clean rooms 10 is now described. A person entering through the doorway 8 from the outside space such as the hallway etc. once waits in the anteroom 40 for dozens of seconds to several minutes, for example, thereafter the person enters the main room 20 by opening the sliding door 47. With this, the person can enter the main room 20 without deteriorating cleanliness of the living space at all. On the other hand, when the person leaves the main room 20, he enters the anteroom 40 from the main room 20, shuts the sliding door 47, and thereafter goes out from the doorway 8. With this, he can go out to the hallway or the outdoor without deteriorating cleanliness of the main room 20 at all. Other than the above description are the same as the first and second embodiments.

<Example of the System of Highly Clean Rooms>

The system of highly clean rooms can be applied not only to a newly built construction such as a house, a building, etc. but also to reconstruction etc. of the existing construction. In the example, the system of highly clean rooms 10 has been constructed by building in a room of a general house with the mechanism of the system of highly clean rooms.

Figure 5:
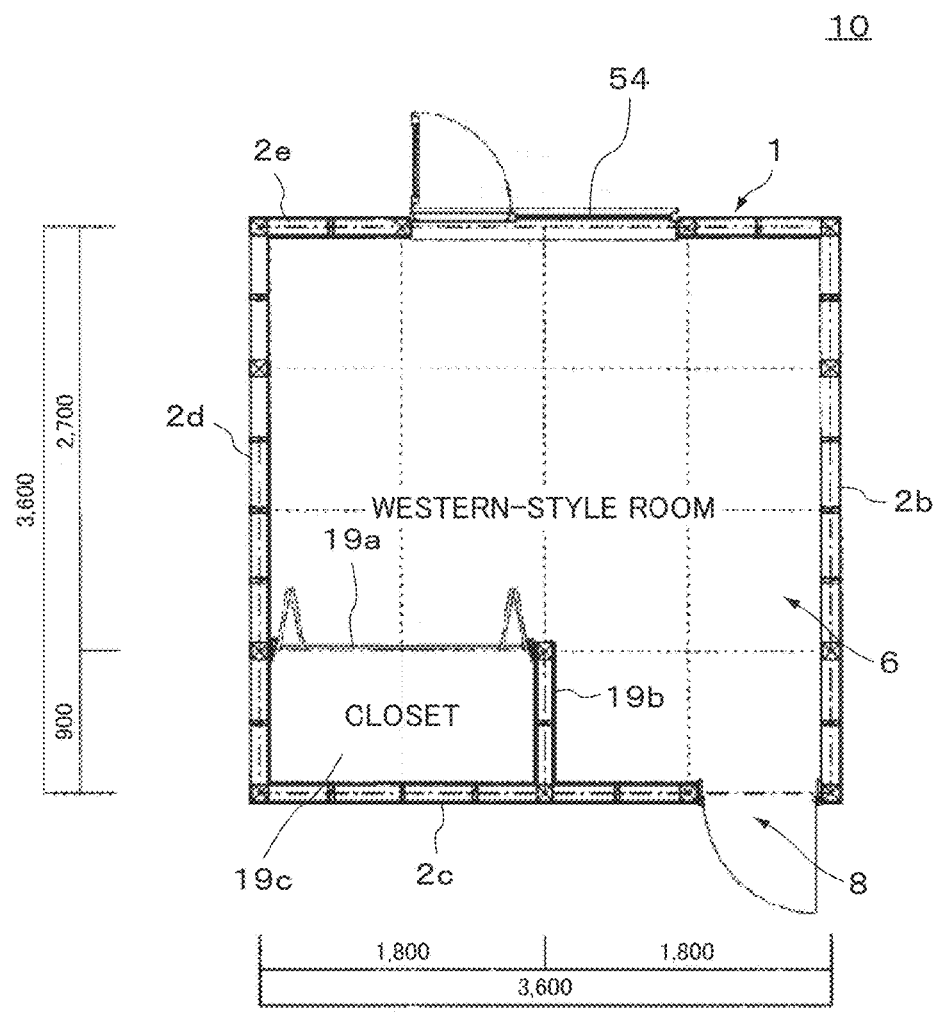
FIG. 5 A top view showing a room before installing a system of highly clean rooms according to the example.

FIG. 5 is a top view showing the room before the mechanism of the system of highly clean rooms is built in.

As shown in FIG. 5, the room 1 has a parallelepiped shape 3600 mm square and about 2300 mm in height. The doorway 8 is provided in the part adjacent to the one corner part of the lateral wall facing the hallway (not shown) of the room 1. On the other corner part of the lateral wall, formed is a parallelepiped storage part 19c 1800 mm in width, 900 mm in depth and 2300 mm in height. If this space is regarded as a part corresponding to the utility space 19 in the third embodiment described above, the example can realize the performance as the same as the third embodiment that is a mode applying the system of highly clean environment to a newly built house etc. in a mode applying the system of highly clean environment by reconstructing a room of a general house etc. existing quite common. That is, the room 1 can be regarded to have the storing part 19 as the utility space 19 in a part of the room 1 having the doorway 8 and can be regarded as a space equal to the room 1a shown in the second embodiment, for example. And by reconstructing the room, the constitution of the system of highly clean rooms 10 can be added, and the performance equal to the system of highly clean rooms described in the third embodiment can be realized for the room of a general house etc. existing quite common. Here, the internal constitution of the room 1 is described. On the side facing the side provided with the doorway 8 of the room 1, a window part 54 1690 mm in width and 1170 mm in height is provided. The living space 6 that is a space other than the storing part 19c inside the room 1 is constituted by connecting two rectangular parallelepiped spaces with different sizes. One of the two rectangular parallelepiped spaces is a rectangular parallelepiped space surrounded by the lateral wall 19b of the storing part 19c, parts of the lateral wall 2b facing the lateral wall 19b each other and a part of the lateral wall 2c sandwiched between the lateral wall 19b and the lateral wall 2b and this space is a space next to the living space 6 from the doorway 8. Concrete size of the rectangular parallelepiped space is depth×width×height=900 mm×1800 mm×2300 mm. The parallelepiped space constitutes the anteroom 40 and the internal space 57 after reconstruction described below. The other one of the two rectangular parallelepiped spaces is a rectangular parallelepiped space surrounded by the lateral wall 2e, the lateral wall 19a of the storing part 19c, a part of the lateral wall 2d sandwiched between the lateral wall 2e and the lateral wall 19a and a part of the lateral wall 2b facing the part of the lateral wall 2d and this space is a space on the window side of the room 1. Concrete size of the rectangular parallelepiped space is depth×width×height=2700 mm×3600 mm×2300 mm. The rectangular parallelepiped space constitutes the main room 20 and the internal space 12 after reconstruction described below.

Figure 6:
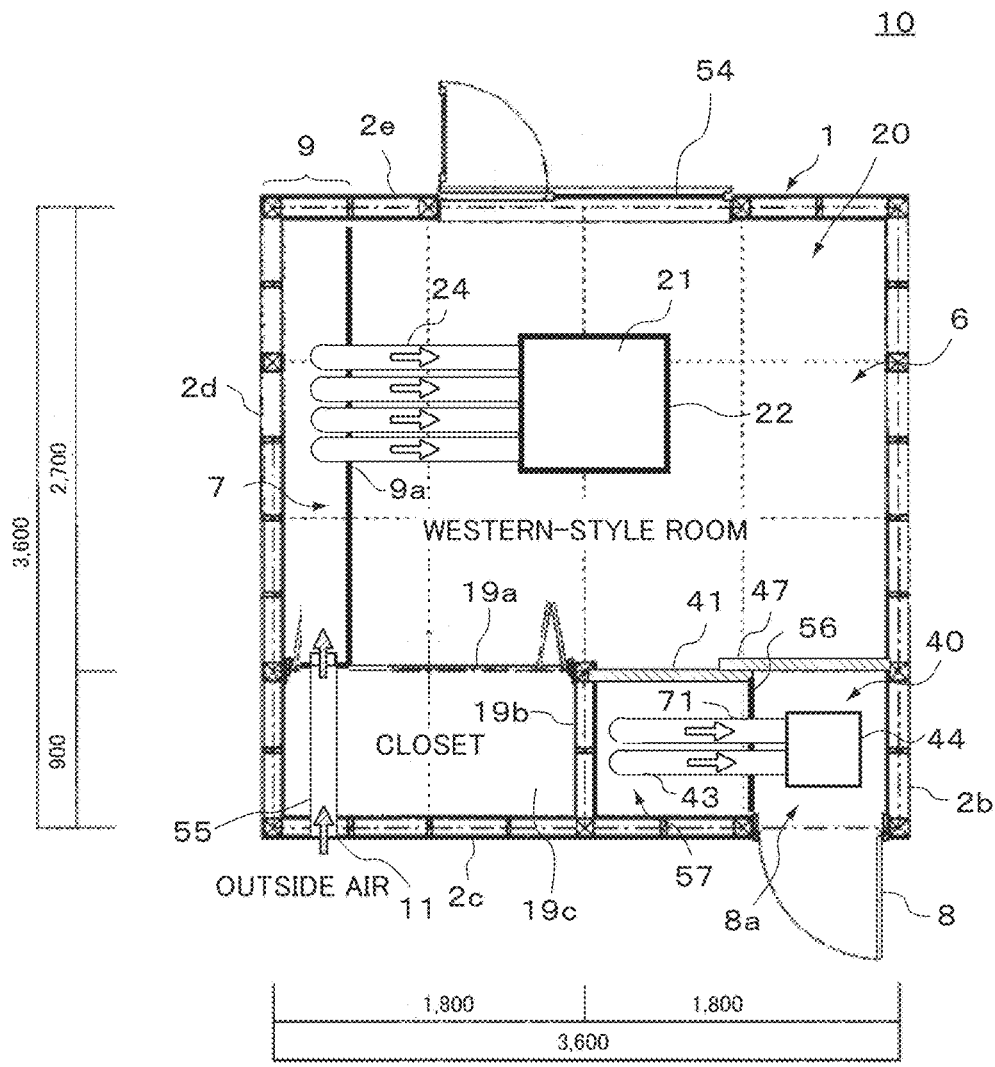
FIG. 6 A top view showing the room after installing the system of highly clean rooms according to the example.
Figure 7:
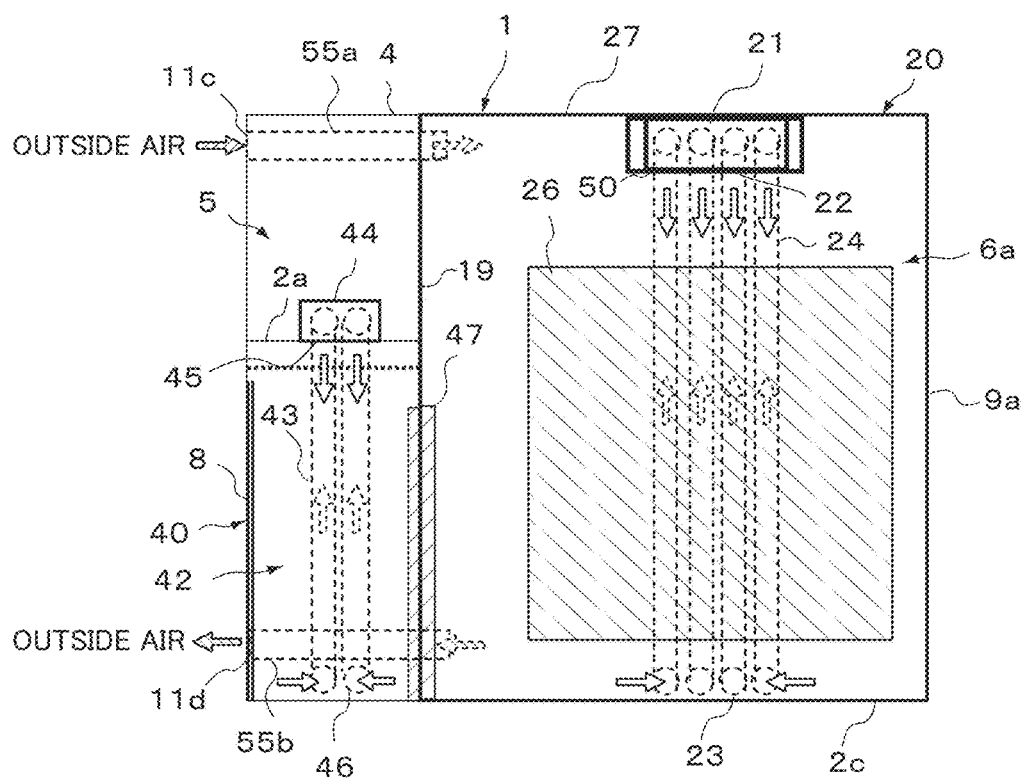
FIG. 7 A longitudinal sectional view showing the room after installing the system of highly clean rooms according to the example.
Figure 8:
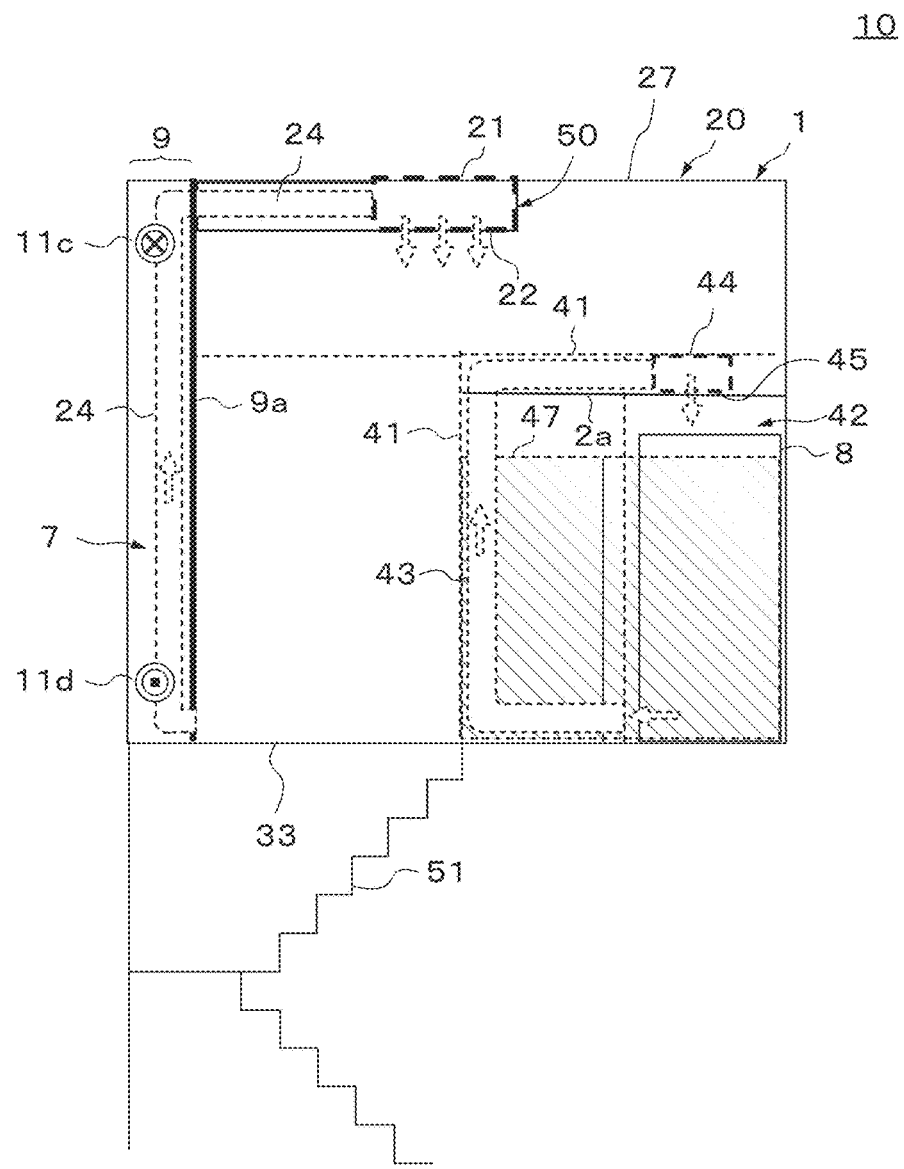
FIG. 8 A perspective view showing the room after installing the system of highly clean rooms according to the example seen from a hallway.

FIG. 6 is a top view showing the room 1 after the mechanism of the system of highly clean rooms was built in. FIG. 7 is a cross sectional view (perspective view) seen from the side of the lateral wall 2b. FIG. 8 is a cross sectional view (perspective view) seen from the side of the lateral wall 2c.

As shown in FIG. 6 to FIG. 8, the living space 6 is formed inside the room 1. After reconstruction, by partitioning the two parallelepiped spaces with the partition 41 and the sliding door 47, the living space 6 is divided into a space having the main room 20 and the internal space 7 and a space having the anteroom 40 and the internal space 57. Furthermore, by providing a panel parallel to the ceiling wall 27 of the room 1 and surrounding the space formed by the ceiling wall 27 and the panel airtightly, an fan filter unit storing part 50 with the fan filter unit 21 and the gas flow path 24 stored in it is formed. And by providing the wall 9a parallel to the lateral wall (conventional wall) 2d apart from it about 15 cm, the wall 9 that is a hollow wall unifying the lateral wall (conventional wall) 2d and the internal wall 9a is formed. The wall 9 has preferably the constitution of the wall shown in the first embodiment. Because the thickness of the lateral wall 2d is about 10 cm and the thickness of the inner wall 9a is about 0.6 cm, the total thickness of the wall 9 that is a double wall having an internal space is about 26 cm. With this constitution, the thickness of the internal space 7, a hollow space that the new wall 9 has, is 15 cm. A space surrounded by the lateral wall 2b, the lateral wall (conventional wall) 2c having the doorway 8, the lateral wall (conventional wall) 19b of the room 1 facing the lateral wall (conventional wall) 2b, the partition 41 and the sliding door 47 is divided into the anteroom 40 and the internal space 57 by partitioning with the partition 56. The partition 56 is provided so as to face the lateral wall (conventional wall) 19b in the manner such that the partition 56 closes the space between the edge of the lateral wall 2c on the side of the doorway 8 and the partition 41. The anteroom 40 is a space that a person enters first when the person enters the room 1 from the outside space. On the other hand, the internal space 57 becomes a space storing the 100% circulation feedback flow path in the anteroom 40.

The sliding door 47 is provided so as to slide on the face of the partition 41. When the sliding door 47 is shut, the space forming the main room 20 and the space forming the anteroom 40 are completely isolated. When the sliding door 47 is opened, it slides to move to the position on the major surface of the partition 41 of the main room 20. The sliding door 47 is constituted so as to keep airtightness of the anteroom 40 when the sliding door 47 is in the shut state. The partition 41 and the sliding door 47 are preferably provided on the same plane as the lateral wall 19a so as to make smooth the main room 20 as much as possible because dead space is reduced and the living performance is improved. When both of the doorway 8 and the sliding door 47 are shut, the anteroom 40 becomes the closed state without movement of dust particles. A person can enter the room 1 from the outside by opening the doorway 8. The fan filter unit 44 is provided in the ceiling wall 2a in the space 5 between the roof and the ceiling. In the anteroom 40, the opening 46 corresponding to the absorption opening of the fan filter unit 44 is provided at the lowest part of the wall 56. All of gases flowing inside the anteroom 40 from the blow opening of the fan filter unit 44 pass through the opening 46, further pass through the gas flow path 43 communicating the absorption opening of the fan filter unit 44 and the opening 46 airtightly and fed back to the fan filter unit 44, so that the 100% circulation feedback system is constituted.

The inner wall 9a is provided parallel to the lateral wall 2d of the room 1 a constant distance apart as described above, and the wall 9 encloses the space 7 being in contact with the main room 20 via the gas exchange membrane 26. The wall 9 has the inlet and the outlet for an air current on its edge, and the internal space 7 and the hallway that is the outside space are connected by pipes 55a and 55b. In this way, because gases can be exchanged between the outside space and the internal space 7, the internal space 7 functions as the space for introducing outside air. The pipe 55a is an inlet pipe having the absorption opening 11c and the pipe 55b is an outlet pipe having the exhaust opening 11d. Its diameter is 10 cm. It is desirable to provide, for example, a mechanical ventilation device to the absorption opening 11c and/or the exhaust opening 11d. Concretely, the mechanical ventilation device has preferably the flow rate generation ability that air inside the main room 20 circulates one turn or more in two hours, for example. One turn per two hours means that all air inside the main room 20 is ventilated in two hours. At least a part of the inner wall 9a is constituted by shoji paper that is the gas exchange membrane 26. With this, the main room 20 becomes the closed space surrounded by general wall materials or the lateral wall including the gas exchange membrane 26 as a part of it, and gas molecules can be exchanged between the main room 20 and the internal space 7 communicating with the outside without movement of air as the air current between the internal space 7 and the outside space. With this, when there exists the concentration difference in gas constituent constituting air between the main room 20 and the internal space 7 communicating with the outside, there occurs concentration diffusion of gas molecules constituting air or various molecules contained in air inside the room generated during life and activity inside the room and gas constituent constituting air inside the main room 20 moves so that its concentration reaches in equilibrium with that of the outside. That is, if the oxygen concentration inside the main room 20 falls, oxygen is supplied to the main room 20 via the gas exchange membrane 26 from the internal space 7 and if the carbon oxide concentration rises in the main room 20, carbon dioxide is exhausted through the gas exchange membrane 26 from the internal space 7. Furthermore, when various smell and chemical substances are generated in the main room 20, their originating molecules are exhausted to the outer space according to the above mechanism.

The 100% circulation feedback system constituted by the fan filter unit 21 and the airtight gas flow path 24 is connected with the main room 20. The opening 23 that is the absorption opening constituting the 100% circulation feedback system is provided in the inner wall 9a separating the main room 20 and the internal space 7. Gases absorbed from the opening 23 enters the absorption opening of the fan filter unit 21 through the gas flow path 24 communicating the opening 23 and the fan filter unit 21 airtightly, then gases are filtered in the fan filter unit 21, further gases are pushed (exhausted) to the main room 20 via the blow opening 22, and this air is returned again to the opening 23 while taking in dust inside the room, so that the 100% circulation feedback system is formed. In the embodiment, the gas flow path 24 is a bellows pipe having a diameter of about 10 cm. Although only a concept is presented and sizes and distances are not shown in the strict scale in the example shown in FIG. 6 to FIG. 8, the gas flow path 24 retreats from the gas exchange membrane 26 about 5 cm and is almost in contact with the wall 2d. Furthermore, by constituting at least a part of the inner wall 9a separating the main room 20 and the internal space 7 with shoji paper that is an example of the gas exchange membrane 26, gas exchange can be performed between the internal space 7 and the main room 20 by the inner wall 9a.

Figure 22:
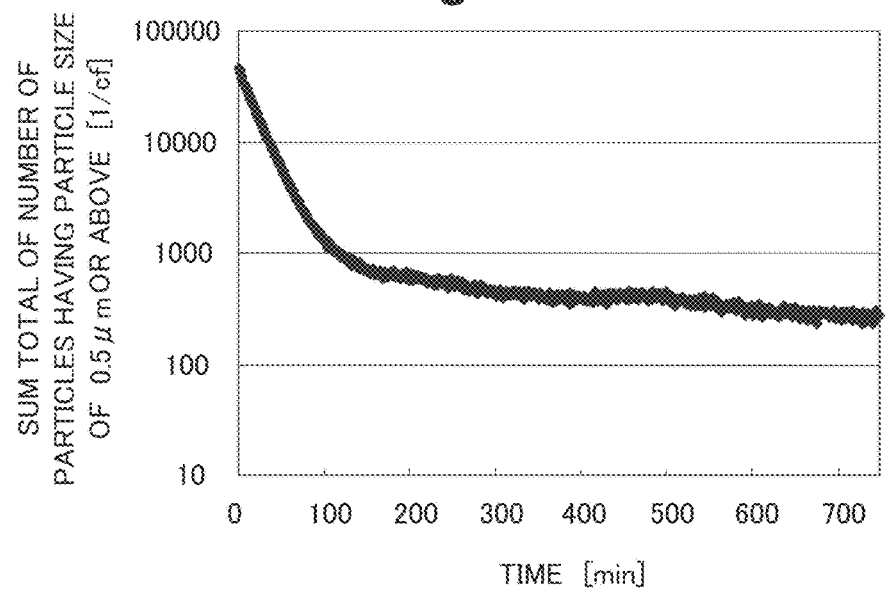
FIG. 22 A schematic view showing the total number per cubic feet of dust particles having the particle size of 0.5 [μm] among dust particles inside the main room shown in FIG. 21.
Figure 26:
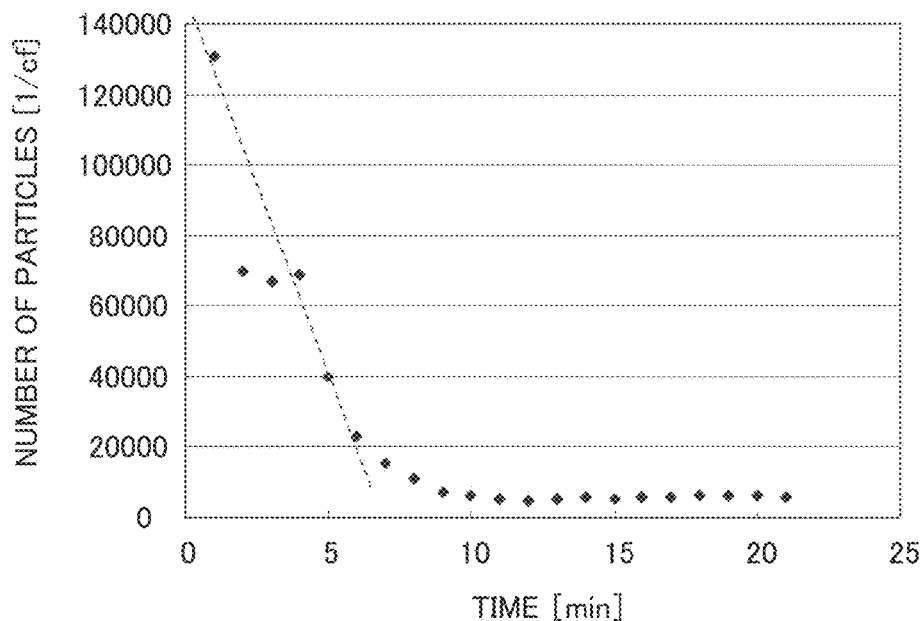
FIG. 26 A schematic view showing the change in a short time of the number of dust particles when the fan filter unit 44 provided in the anteroom is operated in the anteroom.

When a person moves between the outside space and the anteroom 40 through the doorway 8, cleaning of air inside the anteroom 40 is performed under the state that both of the doorway 8 and the sliding door 47 are shut. More specifically, after the anteroom 40 is set to be the closed space, the 100% circulation feedback system using the fan filter unit 44 described above is operated. As shown in FIG. 22 and FIG. 26 described later, after forty seconds to several minutes have passed from the start of operation of the fan filter unit 44, cleanliness of the anteroom 40 is remarkably improved. Thereafter, by opening the sliding door 47, a person can enter the main room 20 from the anteroom 40. By constituting at least a part of the sliding door 47 with a membrane having the gas exchange ability such as shoji paper etc., even though there is no movement of air as the air current between the main room 20 and the anteroom 40, exchange of gas constituent described above can be performed.

Figure 9:
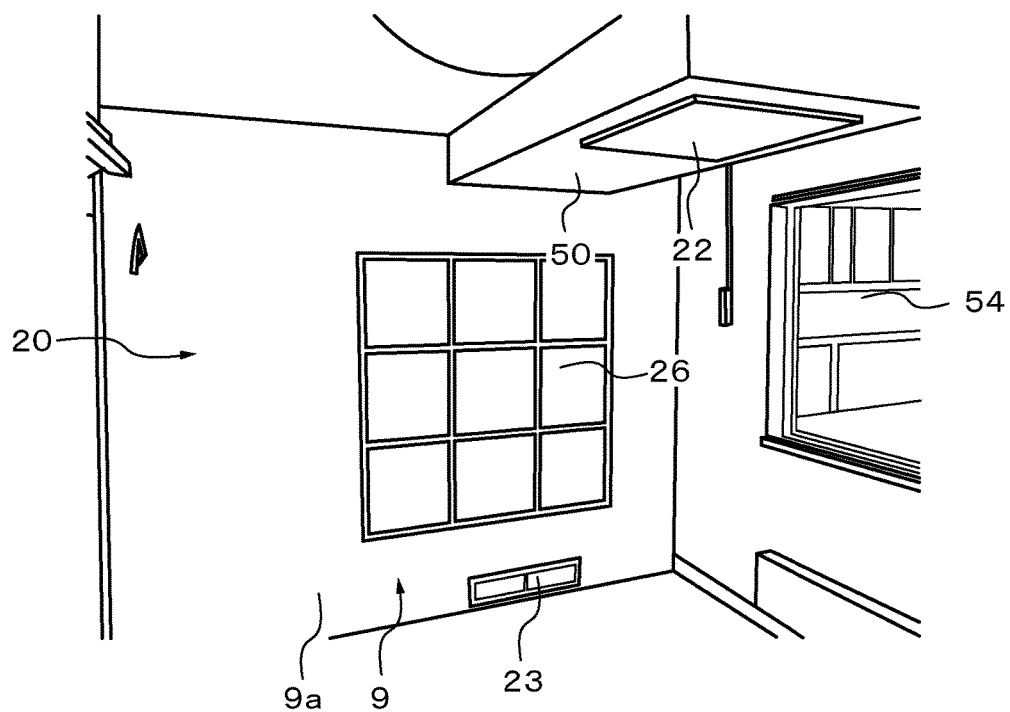
FIG. 9 A substitute picture for a drawing showing a main room, which is a living space, of the room after installing the system of highly clean rooms according to the example.

FIG. 9 is a photograph taken by a digital still camera, showing the complete shape of the system of highly clean rooms 10 according to the example.

As shown in FIG. 9, the wall 9 that is the back wall is the wall 9 shown in the example and the photograph shows inside the main room 20 of the room 1 built in the wall 9 as one lateral wall. The fan filter unit 21 and the gas flow path 24 stored in the storing part 50 are provided in the ceiling part of the room 1 having the window part 54 and clean air is sent downward from the blow opening 22. The wall 9 has the inner wall 9a separating the main room 20 and the internal space 7 and the fan filter unit storing part 50 extends to the wall 9a and is in contact with it. A part of the inner wall 9a is constituted by the gas exchange membrane 26 having the area of 135 cm×135 cm and is constituted by shoji paper that is the gas exchange membrane 26. The opening 23 that is the absorption opening is provided at the lower edge of the wall 9a. A net is provided on the opening 23 to prevent invasion of large dust into the gas flow path 24.

Determination (order estimation) of the area of shoji paper is based on the consideration described below. A shoji paper used as the gas exchange membrane 26 is a commercially available multipurpose one for consumer (plain shoji paper made by ASAHIPEN CORPORATION) and values of its physical properties such as permeability etc. are not presented. Therefore, assuming that the shoji paper to be used has modestly estimated value of permeability [~1 l/(dm²/min)]:200 Pa) among typical values of permeability of filter cloth shown in nonpatent literature 9, the shape, the size, etc. of the shoji paper are designed and the area is determined. This is because a person actually enters the main room 20 and experiments are carried out as described later, it is preferable to modestly estimate permeability and set the area A rather largely from the safety aspect. Because the second term of the equation (12) described above denotes the volume F (its unit is [m³/min], for example) occupied by oxygen molecules diffused through the gas exchange membrane per unit time, it is considered as a function of the pressure (partial pressure) difference based on the function of the concentration difference. Based on that permeability is the volume occupied by gas molecules diffused in the pressure difference per unit time and unit area, D/L of the gas exchange membrane appeared in the equation (12) shown above can be calculated from permeability. Setting the target oxygen concentration η=20.8% from the safety aspect, a condition that the area A of the gas exchange membrane 26 should satisfy is as follows.

$$A \geq \frac{B}{\frac{D}{L}\left(\frac{V_{O_2}}{V} - \eta\right)} \sim \frac{5 l/min}{\frac{1 l/(0.1 \text{ m}^2 \text{ min})}{\frac{200 \text{ Pa}}{1013 \text{ hPa}}}(20.9\% - 20.8\%)} \sim 1 \text{ m}^2 \quad (17)$$

As shown in the middle equation deriving the equation (17), D/L corresponds to the precoefficient of denominator in the equation (17) and in this time, it is calculated as about 5[m/min] based on the value of permeability.

Furthermore, by constituting the gas exchange membrane 26 as a shoji window constructed like lattice by a wooden frame, although it is possible to improve remarkably cleanliness inside the main room 20, the main room 20 can produce a Japanese style atmosphere. Connected with the opening 23 provided at the lowest part of the inner wall 9a is the gas flow path 24 communicating airtightly the opening 23 and the gas inlet of the fan filter unit 21. The gas flow path 24 runs inside the internal space 7. In this way, the system of highly clean rooms 10 can accomplish very high cleanliness while producing a Japanese-style appearance without feeling discomfort compared with the conventional room space.

The above structure connecting the main room 20 and the anteroom 40 is not limited to the above example, but it can be applied to, for example, a Japanese traditional Japanese-style room and rooms of a Japanese-style hotel. Rooms of the Japanese traditional Japanese-style hotel have the so-called alcove (space for taking off shoes and Japanese wooden clogs) that is separated from the back room (the main room 20) by shoji etc. just behind the entrance. The above structure of the anteroom 40 can be introduced to the space. Taking off shoes is just Japanese old wisdom that dust is not brought into the back main room 20, and by adding the cleaning technology of this invention to it, the Japanese-style room shows the highest cleanliness in the world both in name and in reality in the greatest mode in the world without losing the traditional manner at all and the Japanese-style room can be put to practical use. In the Japanese traditional house etc., the outside is used as an air introduction source to the internal space 7 that is an air introduction space, a concrete floor space is used as the anteroom 40 and the back room is used as the main room 20. In the modern room in Japan (rooms in the apartment house etc.) etc., the outside is used as an air introduction source to the internal space 7 that is an introduction space, a front door space (for taking off shoes and Japanese wooden clogs) is used as the anteroom 40 and the back room is used as the main room 20. Furthermore, in the Western detached house, etc., the hallway and the outside are used as an air introduction source to the internal space 7 that is an air introduction space, a front door space (for taking off shoes and Japanese wooden clogs) is newly provided like Japanese-style as the main room 40 and the remaining space of the room is used as the main room 20, so that preventive measures against pollinosis etc. can be taken.

The operation of the system of highly clean rooms according to the example is now described. First, a change of cleanliness of air inside the main room 20 when the fan filter unit 21 provided in the main room 20 is solely operated.

Figure 11:
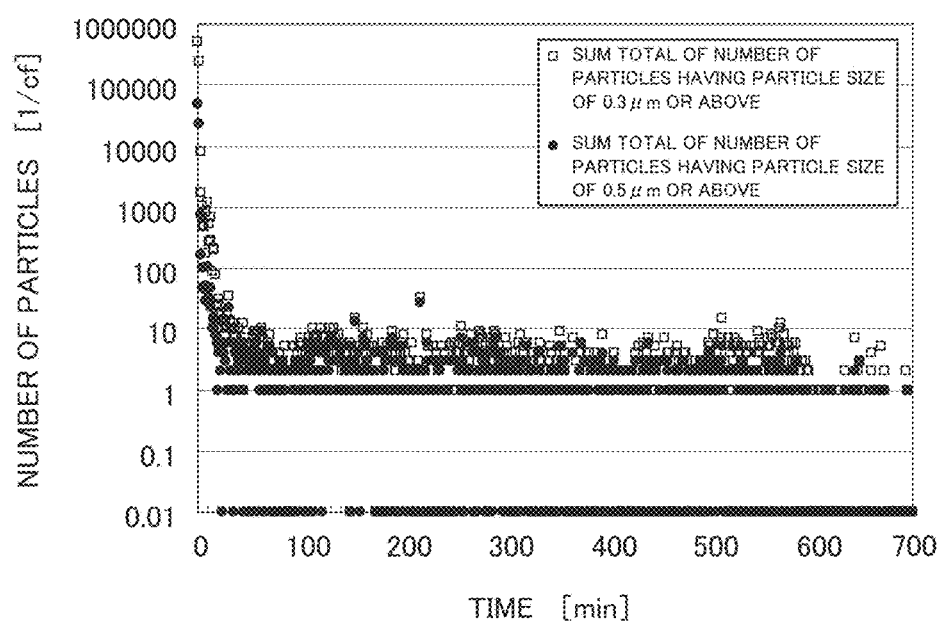
FIG. 11 A schematic view showing the change in the number of dust particles inside the main room in a long time when the fan filter unit of the system of highly clean rooms according to the example is operated.

FIG. 10 is a schematic diagram showing a time change of the number of dust particles in a short time scale when the fan filter unit 21 constituting the 100% circulation feedback system provided in the main room 20 is operated, and FIG. 11 is a schematic diagram showing time change in a long time scale.

As shown in FIG. 10 and FIG. 11, at the start of operation of the fan filter unit 21, the sum of the number of dust having the particle diameter equal to or larger than 0.5 μm exceeds a hundred thousand/cubic feet (US 209D class 100000) and the sum of the number of dust having the particle diameter equal to or larger than 0.3 μm exceeds a million per cubic feet. In the environment there is very large number of dust particles and the environment is not definitely clean. After the start of operation of the fan filter unit 21, the number of dust particles in the main room 20 reduces to about ten thousand in an about five minutes from the start of operation and after about ten minutes have passed, good cleanliness having the number of dust particles equal to or less than 100 per cubic feet, i.e., equal to or higher than US209D class 100 is obtained. Furthermore, particularly, as shown in FIG. 11, after about ten hours have passed from the start of operation, not only the sum of the number of dust having the particle diameter equal to or larger than 0.5 μm but also the sum of the number of dust having the particle diameter equal to or larger than 0.3 μm show zero count. Here, the vertical axis of the schematic diagram shown in FIG. 11 is of logarithmic plot, the measured value zero cannot be plotted (because the measured value jumps infinitely downward). Therefore, the zero count obtained by measurement was conveniently plotted at 0.01. As apparent from FIG. 17, at a time range after six hundreds minutes (ten hours) have passed from the start of operation, not only the sum of the number of particles having the particle diameter equal to or larger than 0.5 μm but also the sum of the number of particles having the particle diameter equal to or larger than 0.3 μm frequently show zero count and this shows very good cleanliness is obtained. Here, the particle diameter means the average diameter of the primary particles (this is the same hereunder). This result is much higher than cleanliness of US209D class 1 of the super clean room used in a high quality semiconductor factory etc. and cleanliness is accomplished for the first time in the world in a room having appearance like a quite common general home shown in the example. This is extremely meaningful because the visual affinity in a daily life environment and the super clean environment are compatible.

Figure 12:
FIG. 12 A substitute picture for a drawing showing a situation carrying out an experiment of consuming oxygen in the main room of the system of highly clean rooms according to the example.

Described now is a case where persons stay in the main room 20, for example, and oxygen is consumed. FIG. 12 is a substitute picture for a drawing showing the scene carrying out the experiment consuming oxygen in the main room 20. As shown in FIG. 12, butane gas is burned by a cassette range in the main room 20, further two persons stay in the main room 20 and the oxygen concentration inside the main room 20 is measured while consuming oxygen in the room.

Figure 13A:
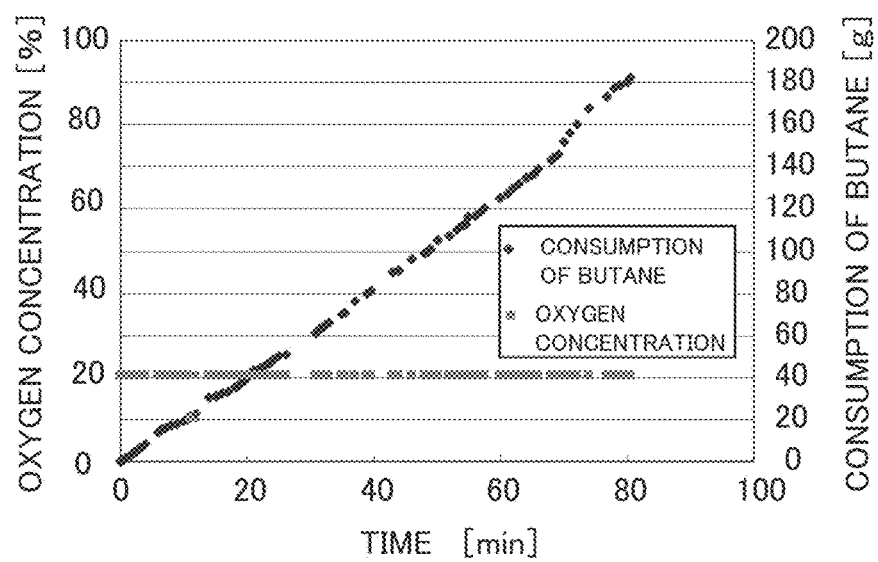
FIG. 13A A schematic view showing the quantity of combustion of butane gas and the concentration of oxygen in the main room when an experiment of consuming oxygen is carried out in the main room of the system of highly clean rooms according to the example.
Figure 13B:
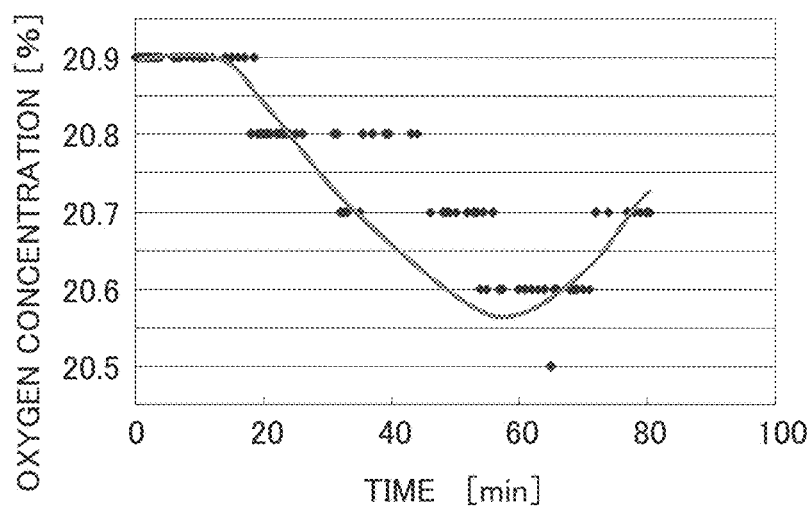
FIG. 13B A schematic view showing the concentration of oxygen in the main room when an experiment of consuming oxygen is carried out in the main room of the system of highly clean rooms according to the example.

FIG. 13A is a schematic diagram showing the butane ($C_4H_{10}$) gas combustion quantity from the start of the experiment to eighty minutes and the oxygen concentration inside the main room 20. FIG. 13B is a schematic diagram showing the change of the oxygen concentration in the graph of FIG. 13A enlarged in a range near 20%.

$$C_4H_{10}+6.5O_2 \rightarrow 4CO_2+5H_2O \tag{1}$$

From the chemical equation (1), taking into consideration that one mole of butane is 58 g and one mole of oxygen is 32 g, it is understood that the consumption quantity of oxygen when butane gas is burned 2 g per minute is about 5 [l/min.]. This corresponds to the consumption quantity of oxygen by about twenty persons. This number of persons is too many numbers to enter the living space having an area of about a six-tatami of the room 1 and the consumption quantity is enough to watch the oxygen supply ability. The gas range used in the measurement is placed in a position near the middle of the room but offset from the position just below the fan filter unit. The oxygen concentration meter used in the measurement is placed at a position of the wall facing the gas exchange membrane, i.e., the most distant position from the gas exchange membrane.

As shown in FIG. 13A and FIG. 13B, the oxygen concentration inside the main room 20 reduces by about 0.3% from twenty minutes to sixty minutes and reaches 20.6% temporarily, thereafter switches to increase. This shows a good agreement with the value 20.8% that is the target oxygen concentration in the equation (16) described above. Reducing of the oxygen concentration temporarily to a little less than 20.6% is supposed undershooting and is explained as follows. Here, it is assumed that in analysis by the equations (9) to (15), there is no location dependence of the concentration for simplicity, taking into consideration the position of the gas range and the position of the oxygen concentration meter. That is, it is natural that there is a spatial distribution of the oxygen concentration in view of the construction of the main room 20. Here, by the effect of ventilation power of the fan filter unit provided on the ceiling, the equations (9) to (15) were solved based on the approximation that "air in the room is stirred with the enough speed and there is no unequality of the oxygen concentration depending on the position". Therefore, the undershooting is supposed, and the arrival point attained after switching to increase is considered to be 20.8%, which shows that the calculation and the experimental result match well. In this way, with respect to the oxygen concentration inside the main room 20, if the concentration difference occurs between the living space and the internal space 7 of the wall 9 communicating with the outside, concentration diffusion of oxygen occurs to cancel the concentration difference. With this, even though much oxygen is consumed inside the main room 20, it is shown that the oxygen concentration almost near 20.9% based on the equation (15) shown above can be realized. In the main room 20 adjacent to the wall 9 having shoji paper, which is material of the gas exchange membrane 26 having a square shape of 135 cm×135 cm, 22 persons can stay for a long time without a deficiency of oxygen. This shows that shoji paper, which is the gas exchange membrane 26 separating the main room 20 and the internal space 7 of the wall 9, functions well as a membrane balancing various kinds of molecules between outside air introduced into the internal space 7 and gases inside the main room 20.

Based on the experimental result that the oxygen concentration inside the main room 20 begins to reduce and stops to reduce after about forty minutes, D/L can be calculated. That is, the equation (12), which is the differential equation depicting the change of the oxygen concentration of this system has the same form as the differential equation of the equation (3) and its exact solution has the same form as the equation (4) (especially, their time dependence are the same and shows an exponential function like change with respect to t. More specifically, it is enough only to substitute $\gamma F/V$ of the equation (4) for AD/VD of the equation (12) and behavior of the system with respect to time can be understood). As described before, an exponential function like behavior becomes steady after the time of about 10 times the inverse of the coefficient of t in the shoulder of the exponential function. From this, based on the result of FIG. 13B, it can be estimated that $\{1/(AD/VL)\} \times 10 \sim 40$ min. Because A=1.35 m×1.35 m=1.8 m², the area is about six-tatami from FIG. 6 and the height of the ceiling is about 2.5 m, the volume V of the main room 20=24 m³, D/L~(24 m³/1.8 m²)·10·(1/40 min)~3.3 m/min and almost coincide with D/L~5 m/min obtained in connection with the determination of the area of the shoji paper described above. That is, according to the system adopting the wall 9 of the invention having the membrane that does not pass through dust particles but allows concentration diffusion of molecules and the internal space being in contact with this membrane and the 100% circulation feedback system, D/L that is an important parameter of the membrane can be obtained by carrying out oxygen consumption experiment (gas combustion experiment) inside. After the value is once obtained, based on the fact that the equation (12) is satisfied in good approximation and the parameter characterizing the system is VL/AD, VL/AD is rewritten as $\{(V/A)/(D/L)\}$. As a result, it is understood that newly presented is a method for designing the room adjacent to the gas exchange membrane (setting of V and A etc.) according to the scaling rule based on the parameter D/L depending only on the property of the gas exchange membrane 26 with very good prospects. That is, obtained here is a ratio of V/A, i.e., depth of the room or "effective aspect ratio" concerning gas exchange to the abstract aspect ratio D/L in "functional space" with respect to gas exchange (according to dimensional analysis, with respect to (V/A)/(D/L), the numerator having the dimension of m³/m² is divided by the denominator having the dimension of m²/(m/s)). According to space dimension, by dividing a ratio of 3D (dimension) to 2D by 2D/1D in functional space, space dimension is canceled, so that the remained dimension (1/hour) of the denominator finally gives a quantity having the dimension of time as a whole and this becomes the time constant of gas exchange of the system. By scaling of (V/A)/(D/L) as described above, it is understood that it is effective to equalize air flow sent out from the fan filter unit in the whole surface of the ceiling in view of measures against dust as means for improving the function of the example shown in FIG. 12 (For example, a mesh with fine holes is provided under the fan filter unit and a mesh with large holes is provided at the place apart from the position). Furthermore, it is understood that as an additional improvement in view of gas exchange based on the ratio (V/A)/(D/L), it is better to lay the fan filter unit to the wall facing the wall 9, not to the wall 9 and make "size of the holes of the mesh" larger in the side far from the wall 9 and smaller in the side near to the wall 9. As described above, according to the scaling rule, a new method for designing the room in view of high cleanliness and gas exchange with very good prospects is obtained.

As described above, by using the equation (15), the area of the gas exchange membrane 26 can be calculated regardless of the consumption quantity of oxygen inside the main room 20. With respect to other gas exchange membranes having the same fine structure and the same diffusion constant, even though the gas exchange membrane different in its thickness is used, it is also possible to calculate the appropriate area by the equation (15). Furthermore, even though the performance such as permeability etc. of the gas exchange membrane is not known, by carrying out the experiment described above once based on the area and thickness of the gas exchange membrane, it is possible to know the performance of the gas exchange membrane, calculate its area depending on operations carried out according to various modes, and thereafter design the main room 20 freely. Here, the equation (12) is an equation in the case where rotation of air flow inside the room is enough and it is not necessary to consider space dependence. Therefore, with respect to the room without such a mechanism, or with respect to the case where such a mechanism is provided, but it is stopped, it is necessary to take space dependence into consideration. However, even in such a case, once the experimental value of the oxygen concentration in the room in certain conditions of the area A and the oxygen consumption rate can be obtained by measurement by experiments, thereafter it is possible to obtain the necessary area A of the gas exchange membrane 26 according to L dependence, B dependence and D dependence even under different oxygen consumption situations. This is important. It should be noted that the area A calculated in this way can give the appropriate ability of supplying oxygen to the main room 20 even in the case where the wall 2d shown in FIG. 12 is infinitely apart from the gas exchange membrane 26, i.e., the width of the cavity of the double wall 9 is very large, in other words, the gas exchange membrane 26 is substantially in contact with the outside (for example, outdoors and space in the hallway) directly. That is, a case where the gas exchange membrane 26 solely exists at the interface between the main room 20 and the outer space as a case where the thickness of the double wall 9 is substantially infinite is included in the example of the present invention.

Figure 14A:
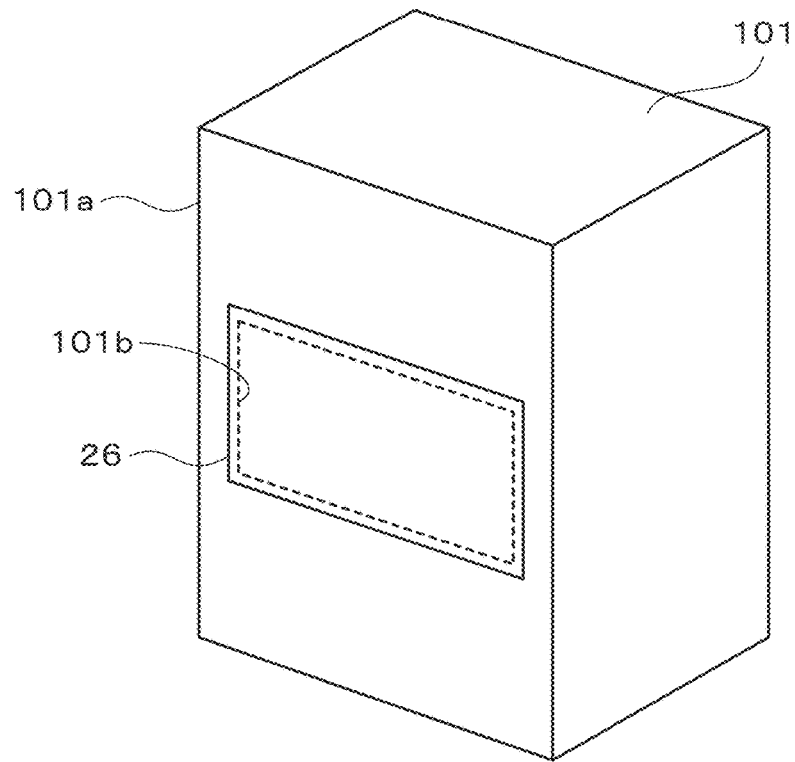
FIG. 14A A perspective view showing a measurement device of the ability of oxygen penetration used to measure the ability of oxygen penetration of various gas exchange membranes.
Figure 14B:
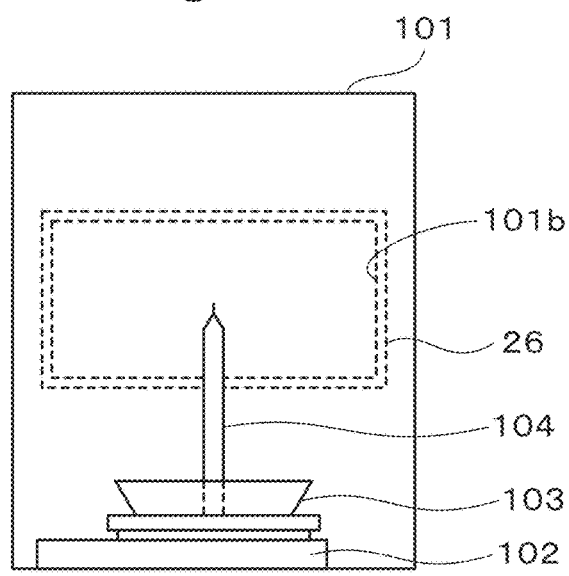
FIG. 14B A rear view showing the measurement device of the ability of oxygen penetration used to measure the ability of oxygen penetration of various gas exchange membranes.
Figure 15:
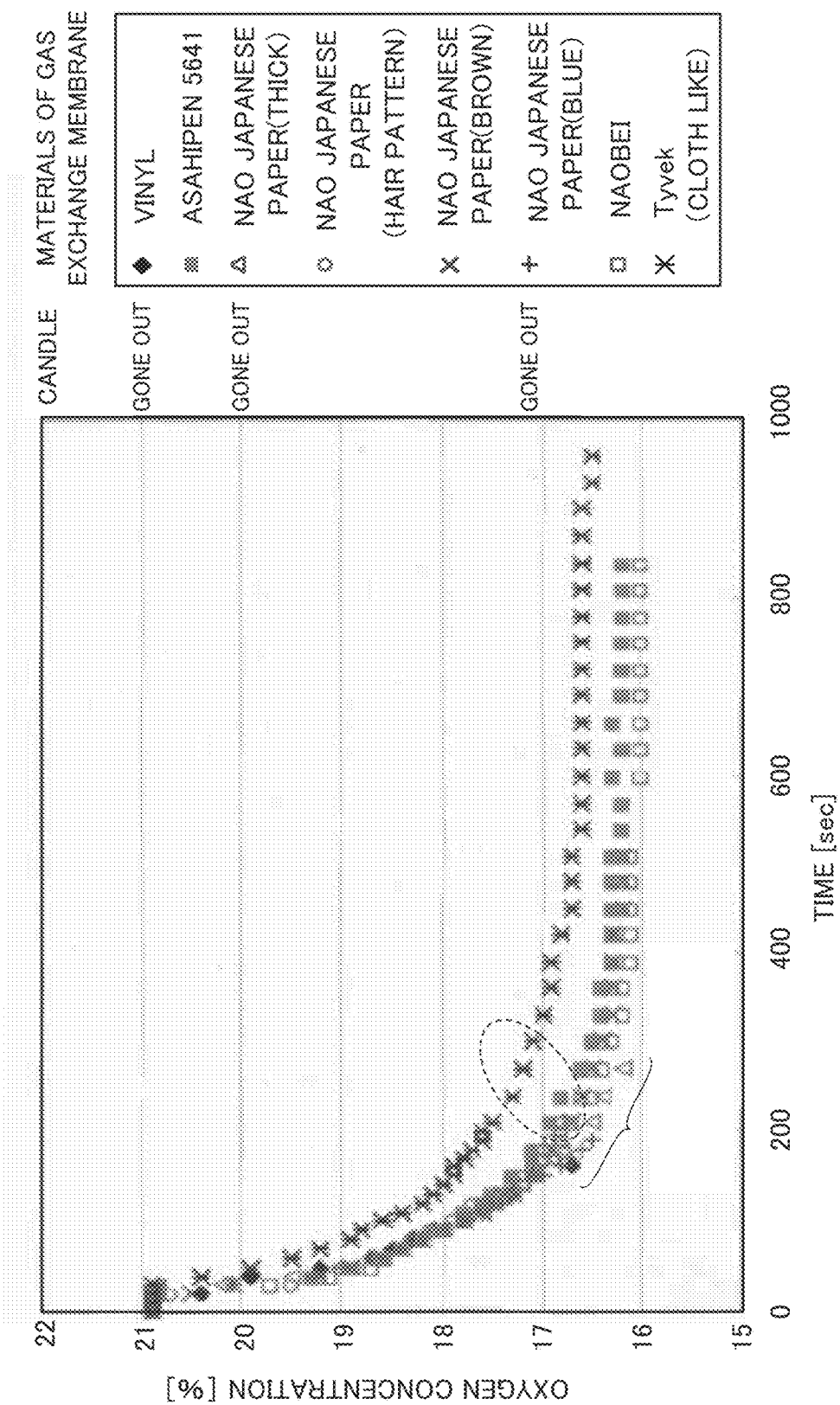
FIG. 15 A schematic view showing the result of measuring the concentration of oxygen in a chamber as a function of time using the measurement device of the ability of oxygen penetration shown in FIG. 14A and FIG. 14B.
Figure 16:
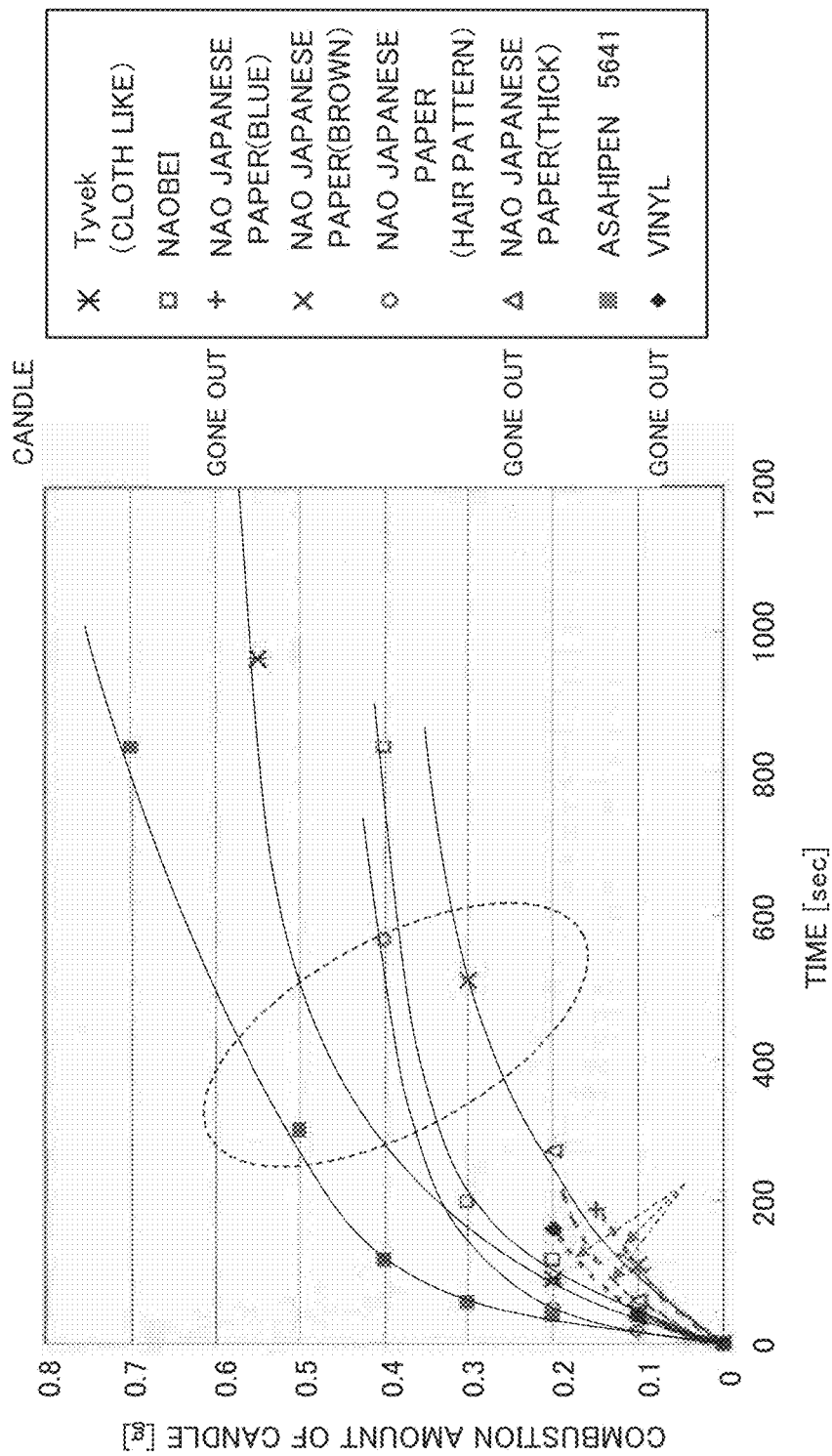
FIG. 16 A schematic view showing the result of measuring the quantity of combustion of a candle in a chamber as a function of time using the measurement device of the ability of oxygen penetration shown in FIG. 14A and FIG. 14B.

The value of D/L for the gas exchange membrane 26 to be used can be calculated as follows. For this, oxygen permeability was measured changing kinds of the gas exchange membrane 26. In order to measure the permeability, a measurement device of the ability of oxygen penetration shown in FIG. 14A and FIG. 14B was made. As shown in FIG. 14A and FIG. 14B, a parallelepiped like chamber 101 was made using transparent acrylic plates. The size of the chamber 101 is the width of about 20 cm, the depth of about 15 cm and the height of about 30 cm. A rectangular opening 101b was formed at the center of a front wall 101a of the chamber 101 and the gas exchange membrane 26 for measuring oxygen permeability was put up from the outside so as to cover the opening 101b. Tape etc. were attached so as to seal between the peripheral part of the gas exchange membrane 26 and the wall 101a. A commercially available digital platform scale 102 capable of measuring by a unit of 0.1 g was placed on the base of the chamber 101 and a plastic cage 103 was mounted on it. A candle 104 was stood on the base of the cage 103. The candle 104 was lighted and the oxygen concentration inside the chamber 101 and the combustion quantity of the candle 104 (this means the weight of the candle 104 burned and corresponds to the oxygen consumption quantity) was measured as functions of time. As the gas exchange membrane 26, various shoji papers (ASAHIPEN5641 (made by ASAHIPEN CORPORATION), Nao Japanese paper (thick type), Nao Japanese paper (hair pattern), Nao Japanese paper (brown), Nao Japanese paper (blue), and Naobei (registered trademark) that is shoji paper made by ONAO CO., LTD) and cloth like Tyvek (registered trademark) made by Du Pont Kabushiki Kaisha) were used. FIG. 15 shows a time change of the oxygen concentration inside the chamber 101 and FIG. 16 shows the change of the combustion quantity of the candle 104 with respect to time. With respect to the gas exchange membrane 26 included in a part shown by {in FIG. 15, the decrease of the oxygen concentration was rapid and finally the candle 104 went out. That is, in the case of a vinyl film (marked by ♦) (its gas exchange ability is deemed to be almost zero) used as a reference, the candle 104 went out in a little less than three minutes most fast, and in the case of the Nao Japanese paper (blue) made by wax paper (marked by +) and the Nao Japanese paper (thick type) (marked by Δ), the candle 104 went out in about three and a half minutes and four and a half minutes, respectively. In the case of the gas exchange membranes included in a part enclosed by the broken line in FIG. 15 (ASAHIPEN5641; marked by ■, cloth like Tyvek; marked by *, Nao Japanese paper (hair pattern); marked by ○, Nao Japanese paper (brown); marked by x, Naobei; marked by □), the candle 104 essentially did not go out finally, though its flame became small. With respect to the gas exchange membranes shown by broken line arrows in FIG. 16, the oxygen concentration rapidly decreased, finally the candle 104 went out and the combustion quantity was small. On the other hand, in the case of the gas exchange membranes included in a part enclosed by the broken line in FIG. 16 (ASAHIPEN5641; marked by ■, cloth like Tyvek; marked by *, Nao Japanese paper (hair pattern); marked by ○, Nao Japanese paper (brown); marked by x), the candle 104 did not go out finally, though its flame became small. From FIG. 16, it is understood that the ASAHIPEN5641 (marked by ■) has high oxygen permeability because the oxygen concentration is high relative to other shoji papers as shown in FIG. 15, though the combustion quantity is large. The cloth like Tyvek also has a good quality. With respect to paraffin ($C_nH_{2n+2}$, n=24~33), the main constituent of the candle, the same chemical equation as the chemical equation (1) is obtained. And by calculating the combustion rate B from FIG. 15 and $V_{O_2}$-η (here, the difference of the oxygen concentration at two different times) from FIG. 16, D/L can be calculated. It can be confirmed by this actual measurement that D/L has values of about 0.01 m/min~0.6 m/min depending on materials of the gas exchange membrane 26. The result almost matched with the result of analysis described in connection with the determination of the area of the shoji paper, which is independent from this experiment.

As described above, it is possible to obtain an extremely clean space in the room, in which cleanliness of air is well over US209D class 100 and near to the class 1. At the same time, the room constitutes the Japanese-style space having shoji doors or shoji windows and the room can be kept to be a room accommodating to the conventional Japanese-style construction. Furthermore, when operations or activities consuming a great deal of oxygen are carried out, an air environment inside the room can be kept to be favorable for existence of persons. At the same time, as described above, by making the gas exchange membrane 26 by Japanese old shoji papers, it is possible to present again a traditional "Shoin construction" proper appearance while having a modern high clean environment quality, which is suitable for restaurants or bars. Furthermore, it is expected that bad influence of passive smoking can be reduced in the space. It is highly expected to develop such spaces to houses, restaurants, hospitals and nursing institutions in the world and greatly contribute to peace of the future of human beings on the earth.

Figure 17:
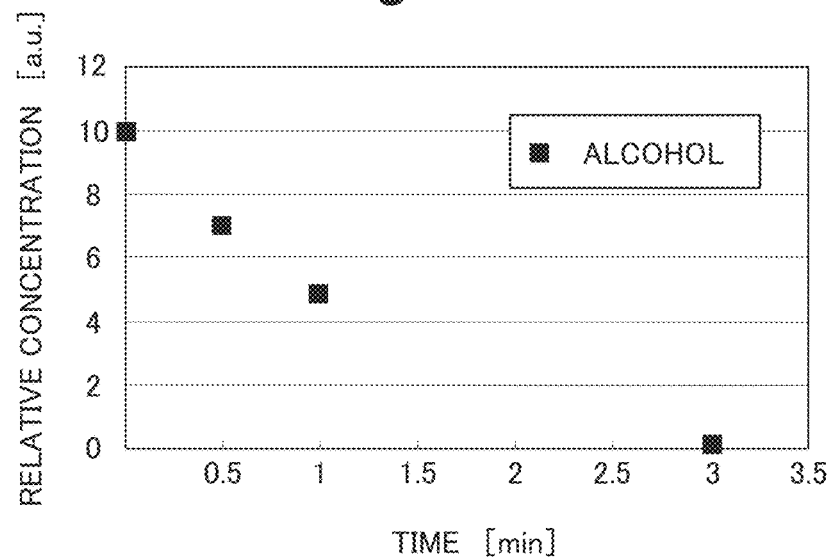
FIG. 17 A schematic view showing the change in the concentration of alcohol contained in air inside the main room when a photocatalytic filter is further provided inside a 100% circulation feedback system of the system of highly clean rooms according to the example and the system of highly clean rooms according to the example is operated.

In the system of highly clean rooms 10 according to the example, a photocatalytic filter (photocatalyst deodorizing unit for central air conditioning MKU40; made by NIPPON TOOKAN PACKAGE CORPORATION) was further placed inside the gas flow path 24 on the upper stream side of the fan filter unit 21 in a series connection with it. FIG. 17 is a schematic diagram showing a change of the concentration of alcohol contained in air inside the main room 20 in the case where the fan filter unit 21 was operated at a ventilation quantity of 11 [$m^3$/min.] after a fixed quantity of alcohol was vaporized. As shown in FIG. 17, after one minute from the start of operation of the fan filter unit 21, a stink of alcohol contained in air inside the main room 20, sensed by persons decreased to a half of the quantity before the start of operation and becomes almost zero after three minutes.

Figure 18:
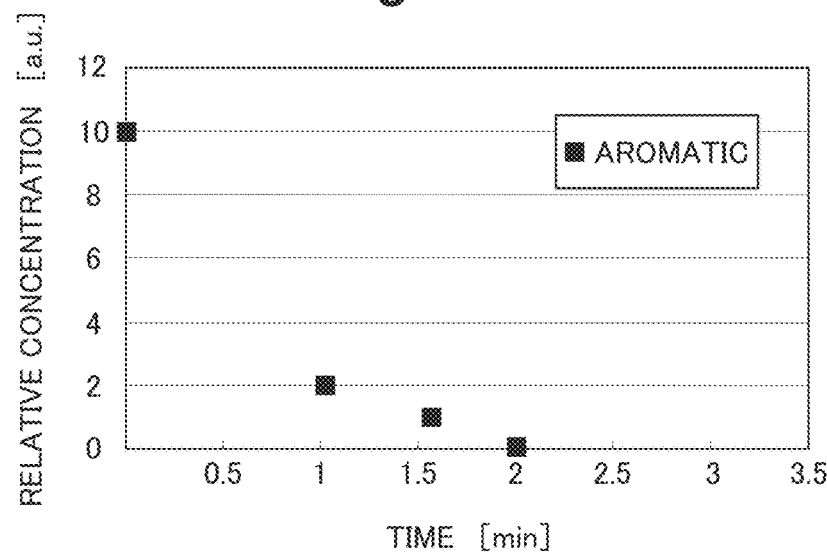
FIG. 18 A schematic view showing the change in the concentration of aromatic contained in air inside the main room when a photocatalytic filter is further provided inside the 100% circulation feedback system of the system of highly clean rooms according to the example and the system of highly clean rooms according to the example is operated.

FIG. 18 is a schematic diagram showing the degree of stink by aromatic contained in air inside the main room 20 in the case where the fan filter unit 21 was operated after a fixed quantity of aromatic was vaporized in the main room 20 in the same configuration as the above. As shown in FIG. 18, after one minute from the start of operation of the fan filter unit 21, a stink by aromatic (propylene glycol etc.) contained in air inside the main room 20, sensed by persons decreased to one fifths of the quantity before the start of operation and becomes almost zero after two minutes. In this way, it is possible to decrease the concentration of substances causing a stink in the main room 20 in a very short time.

The results shown in FIG. 17 and FIG. 18 show the outcome of the multiplier effect of the effect obtained by the above equation (3) in which sσ is read as the generation quantity of chemical substances, n is read as the concentration of chemical substances and γ is read as the decomposition efficiency per passage through the photocatalyst, and exponential decrease of the concentration shown by its solution (see the equation (4)) in the situation that the photocatalyst is provided and there is no movement of air inside and outside, and the effect of approaching to the equilibrium state with the outside through the gas exchange membrane 26. This is evidence of the very effective action of the present invention.

As described above, by using the 100% circulation feedback system provided inside with the photocatalyst, it is possible to decrease the concentration of chemical substances generated in the closed space and staying inside very quickly. This is originated from the multiplier effect obtained by the photocatalyst and the 100% circulation feedback system that can decrease exponentially the chemical substances in the closed space by contacting them with the photocatalyst repeatedly and the gas exchange function of the gas exchange membrane 26. That is, if the photo catalyst is incorporated into a conventional clean unit without the closed circulation feedback system, the photocatalytic effect is small in the open system. On the other hand, in the system of highly clean rooms 10 according to the example, the function of the photocatalyst can be specialized to the primary role of decomposing chemical substances etc. with the decrease of dust by the closed circulation system. With these, the system of highly clean rooms 10 according to the example can realize the long lifetime and the high function for both of the dust filter and photocatalyst.

From the above, by applying the system of highly clean rooms 10 to closed space in care homes, nursing homes, sickrooms, etc., it is possible to decompose stinks generated in the room instantly and improve the living environment drastically. Furthermore, even though chemical substances enter from the outside and chemical substances are generated inside, for example, by operating the 100% circulation feedback system after closing the space, it is possible to decrease the concentration of chemical substances inside the closed space to almost zero in several minutes. Particularly, according to the example, it is possible to realize the environment free of germs, dust, harmful gases/stinks inside the room 1, especially the main room 20. Therefore, by placing plants with effects favorable for persons such as, for example, small trees, foliage plants, herbs, etc. inside the main room 20, one can experience, for example, the highest class "forest bathing" in the middle of the city regardless of places. Furthermore, by positively introducing scents of aromatic matching with needs of respective users such as lavender etc., the quality of the environment, especially air, which is the greatest luxury for people of today in the future, can be improved to the maximum. As a result, it is possible to enhance the positive effect concerning bodies of people such as relaxation etc. to the maximum. Furthermore, by constructing a part of the inner wall of the closed space with the gas exchange membrane 26, it is possible for patients with irritation for chemical substances causing an allergic symptom for the particular chemical substance and asthmatics to stay in the space for a long time without making seriously asthma and allergic symptoms. In addition, by carrying out "operation without load" of respiratory organs in the environment free of dust and germs for about eight hours of bedtime per day, it is expected to obtain the same effect as the effect on the respiratory organs obtained by a short time fast. Furthermore, for example, by setting the inside of the living and curing space to a clean space of class 1 to 10, for example, it is possible to administer medicine through respiratory organs, especially lungs in the "low background noise" environment free of dust and chemical substances and cure in the situation that the "S/N ratio" is drastically improved. That is, it is possible to carry out medical processes such as administration etc. without effect of dust exceeding one hundred million of the existing environment. Applications of the system of highly clean rooms 10 to hospitals and home medical care are very promising in Japan with an increasing population of aged persons and respective countries in the world to be predicted to show the same tendency in future.

When the 100% circulation feedback system provided with a photocatalytic filter connected in a series connection in the flow direction with the dust filter provided inside the fan filter unit 21 is connected with the closed space and operated, it is possible to improve drastically the decomposing effect of chemical substances in the closed space. On the other hand, because the 100% circulation feedback system is provided with the dust filter and the photocatalytic filter in the flow direction in a series connection, the pressure loss for the flow becomes large and the quantity of air that can be supplied inside the closed space reduces. To cope with this problem, it is considered to use a high power fan with the large maximum static pressure as the fan of the fan filter unit 21 or decrease the pressure loss of the filter for removing dusts. If possible, it is better not to adopt the former method for the energy saving purpose because costs increase and also the power consumption increases. The latter method reduces the pressure loss by the filter by decreasing the dust collection efficiency of the filter, so that the dust collection performance falls in a conventional air cleaning system depending largely on the dust collection efficiency of the filter. That is, the conventional clean system cannot adopt the latter method. On the other hand, the system of highly clean rooms 10 satisfying the equation (4) can adopt the latter method and demonstrate the high performance.

Figure 19:
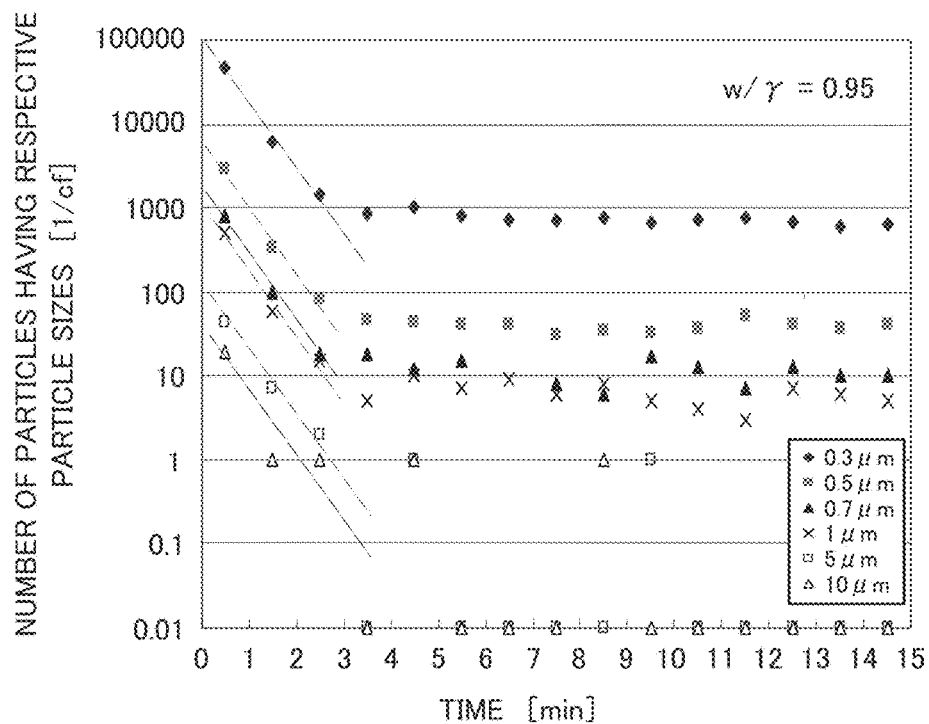
FIG. 19 A schematic view showing the number of dust particles inside the main room for time in the system of highly clean rooms according to the example when the dust filter is operated as a medium performance filter having the dust collection efficiency of 0.95.
Figure 20:
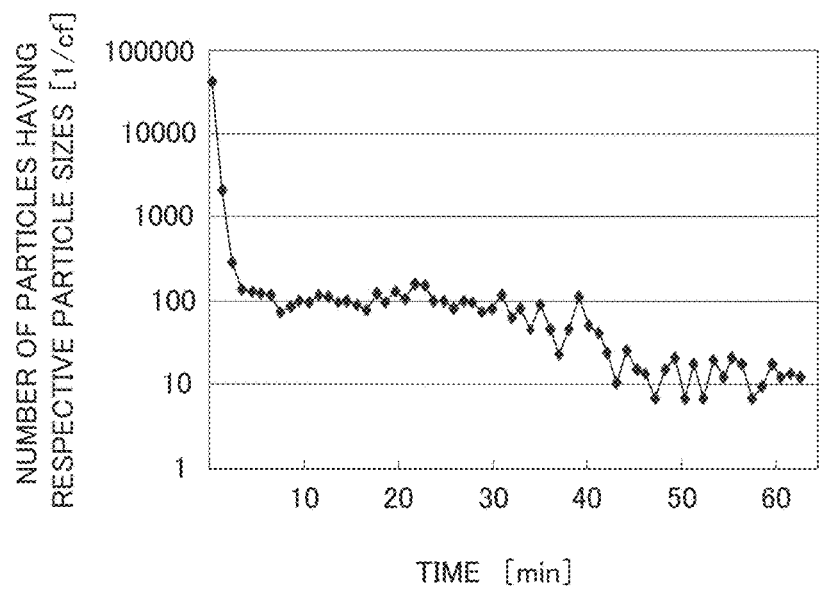
FIG. 20 A schematic view showing the total number per cubic feet of dust particles having the particle size of 0.5 μm or above among dust particles inside the main room measured and shown in FIG. 19.

FIG. 19 is a schematic diagram showing the number of dust for respective particle diameters in the main room 20 when the dust filter provided inside the fan filter unit 21 is operated as the medium performance filter with the dust collection efficiency $\gamma$ of 0.95. FIG. 20 is a schematic diagram showing the total number of dust having the particle diameter of 0.5 [μm] or more per cubic feet of dust inside the main room 20 measured in this experiment, and this directly corresponds to cleanliness of the main room 20 evaluated with US FED-STD-209 D standard.

As shown in FIG. 19, with respect to the number of dust inside the main room 20 after four minutes from the start of operation of the fan filter unit 21, the number of dust having the particle diameter of 0.3 [μm] is kept to be below one thousand, whereas the number of dust having the particle diameter of 0.5 [μm] falls well below one hundred and the number of dust having the particle diameter larger than 0.5 [μm] is smaller than ten. With respect to the total number per cubic feet of dust having the particle diameter of 0.5 [μm] or more, as shown in FIG. 26, the total number of dust having the particle diameter of 0.5 [μm] or more per cubic feet begins to decrease below 100 after ten minutes from the start of operation, the total number of dust per cubic feet reaches to about ten after forty minutes from the start of operation, and thereafter the value is kept, so that a space having cleanliness of US209D class 1 can be obtained.

As described above, even though the dust collection efficiency $\gamma$ is 0.95, the high quality clean environment having cleanliness of US209D class 1 can be obtained. From this, according to the system of highly clean rooms 10, it is possible to lower the level of demand for the dust collection efficiency of the filter "to be near 1" remarkably, and the resultant margin can be used to add value such as photocatalytic function etc. With this, choking of the dust filter becomes hard to occur and its lifetime is drastically extended. In this case, plural 100% circulation feedback systems may be connected with the main room 20. By constituting one of the plural 100% circulation feedback systems as the 100% circulation feedback system having the fan filter unit 21 provided with a filter having the low dust collection efficiency with a photocatalyst, specialized for decomposing chemical substances, and the other as the 100% circulation feedback system having the fan filter unit 21 with a filter specialized for collecting dust, it is possible to make the most of both advantages. Here, the main 100% circulation feedback system is provided with the gas flow path 24 communicating the inlet and the gas flowing opening to the fan filter unit 21 airtightly as described above, and the blow opening 22 and the opening 23 that is an inlet provided on the lower part of the partition are separate. Therefore, if the "subordinate" circulation feedback system going along with the "main" 100% circulation feedback system is strong enough to move air inside the room without "short circuiting" on the whole, it does not always need a strict gas flow path such as the main loop in the 100% circulation feedback system. It is also recommended that an air cleaning device having the same expelled quantity and inhaled quantity is placed in the part inside the room in which air moves by the main circulation system. With this, it is possible to realize high cleanliness that cannot be realized by operating the device in a semi open space.

Figure 21:
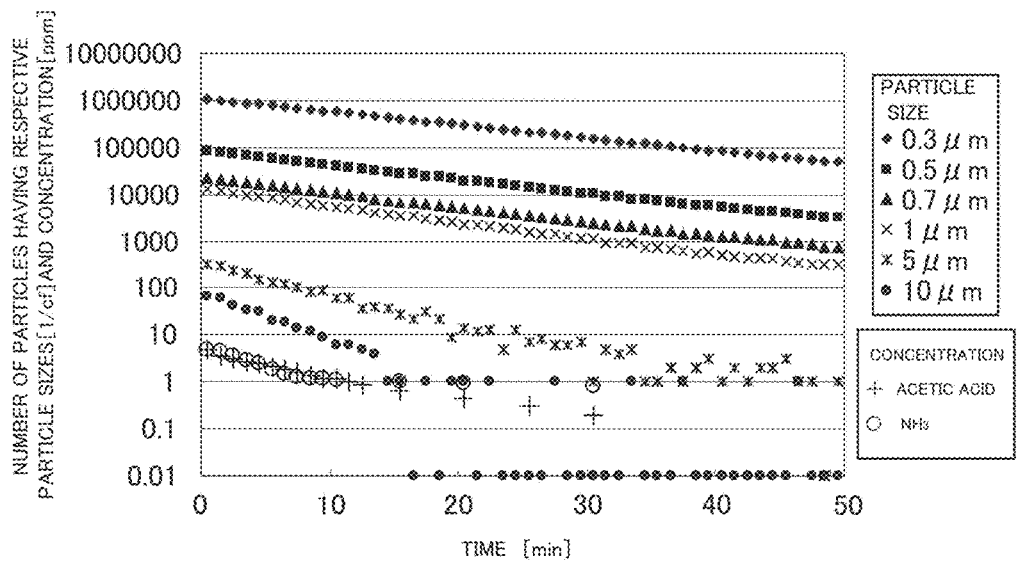
FIG. 21 A schematic view showing the number of dust particles inside the main room for respective particle sizes when a commercially available photocatalytic air cleaning device is placed and operated inside the living space in the system of highly clean rooms according to the example.

FIG. 21 is a schematic diagram showing the number of dust inside the main room 20 for respective particle diameters after the commercially available air cleaning device utilizing photocatalyst and metal radicals (made by FUJIFILM CORPORATION KDP1000) used as the fan filter unit 21 constituting the 100% circulation feedback system provided inside the main room 20 was operated for dozens of minutes. FIG. 22 is a schematic diagram showing the total number of dust having the particle diameter of 0.5[μm] or more per cubic feet of dust measured inside the main room 20. The KPP1000 was operated at the flow rate of 0.55[m³/min.].

Figure 23:
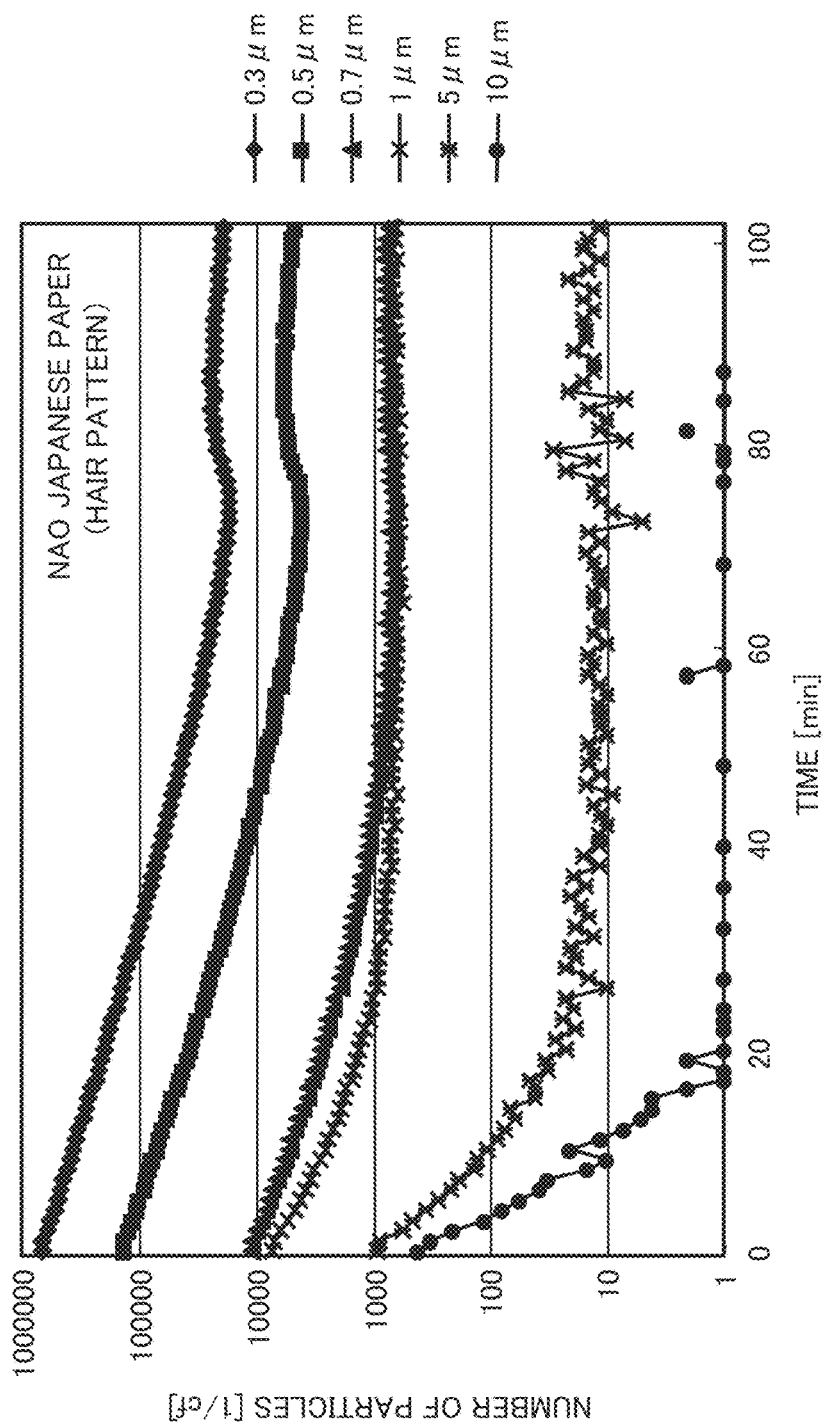
FIG. 23 A schematic view showing the change over time in the number of dust particles when Nao Japanese paper is used as the gas exchange membrane.
Figure 24:
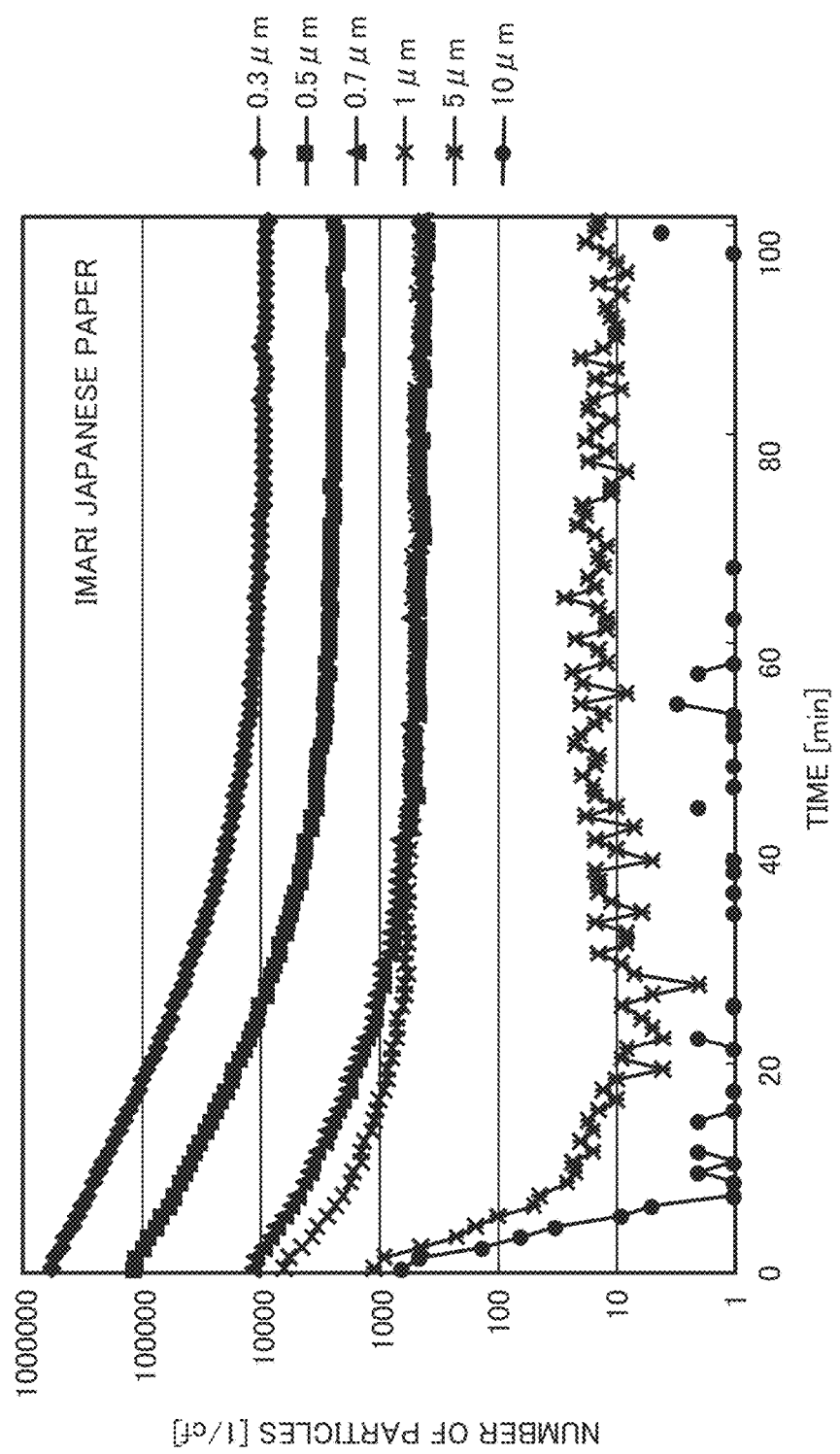
FIG. 24 A schematic view showing the change over time in the number of dust particles when Imari Japanese paper is used as the gas exchange membrane.
Figure 25:
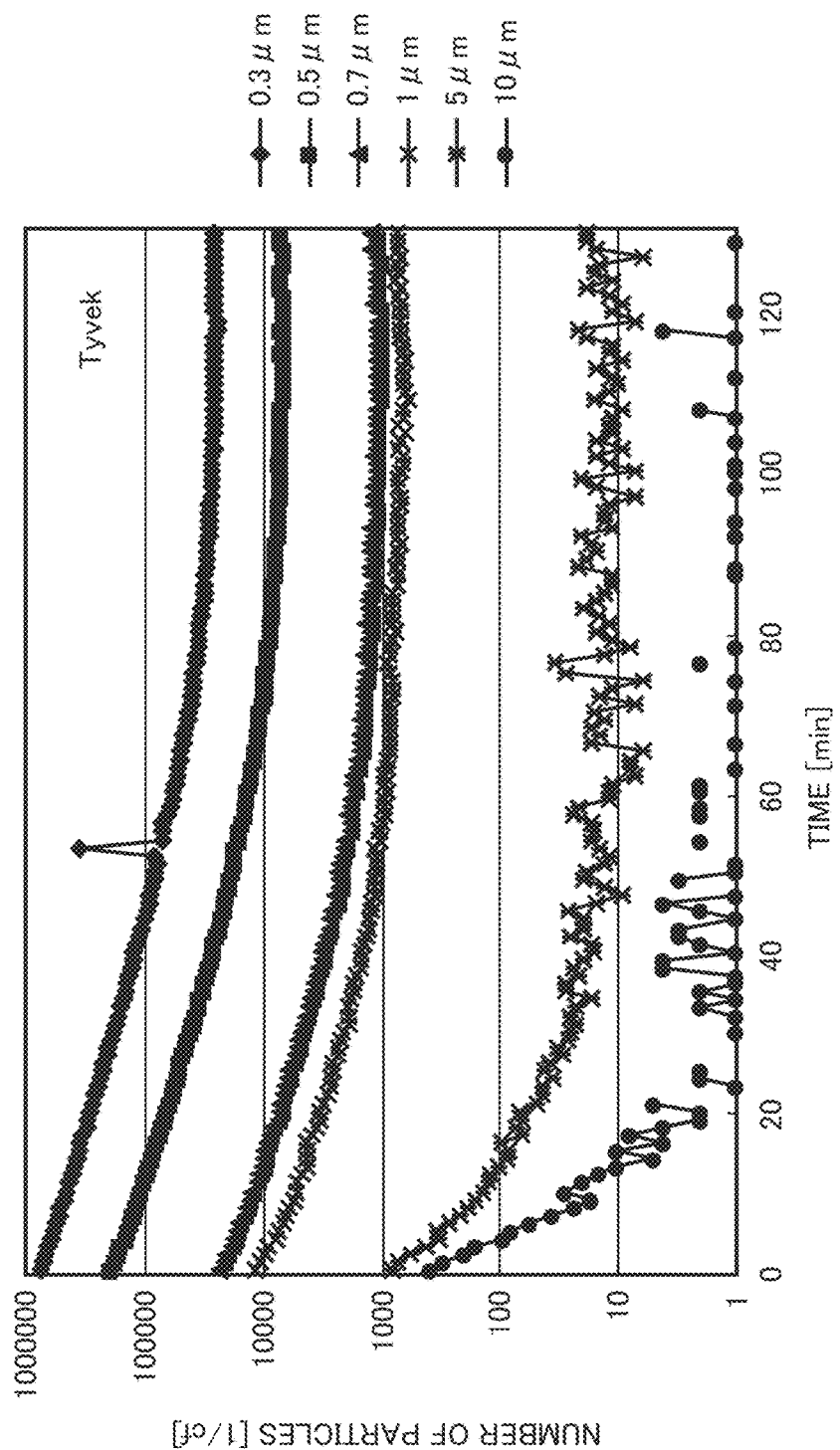
FIG. 25 A schematic view showing the change over time in the number of dust particles when Tyvek (cloth like) is used as the gas exchange membrane.

As shown in FIG. 21, the reduction rate of the number of particles also depends on $\gamma$ shown in the equation (1). This is apparent from the equation (4). In the drawing, the number of particles rapidly reduces with respect to particles having the large particle diameter of 10 [μm] and $\gamma \sim 1$ is satisfied in a good approximation. It is understood that as the particle diameter decreases as 5 [μm], 1 [μm], 0.7 [μm], 0.5 [μm] and 0.3 [μm], the reduction rate of the number of particles becomes smaller. That is, with respect to KPD1000, the collection efficiency $\gamma$ changes depending on the particle diameter. By comparing the reduction rate of the number of particles obtained by data shown in FIG. 22 and the coefficient multiplied by time t in the exponential part of the equation (4), it is possible to calculate $\gamma$ with known V and F. With this calculation, it is possible to obtain $\gamma$ as $\gamma=0.75$ for the particle size of 5 [μm], $\gamma=0.37$ for the particle sizes of 1 [μm] and 0.7 [μm], $\gamma=0.33$ for the partied size of 0.5 [μm] and $\gamma=0.29$ for the particle size of 0.3 [μm]. As described above, it is understood that $\gamma$ for particles having the particle diameter smaller than 1 [μm] is a fraction of $\gamma$ for the particles having the particle diameter of 10 [μm]. Here, KPD1000 is a filter aiming mainly removal of virus and odor, provided with ostrich egg filter and its dust collection efficiency $\gamma$ falls fairly below 1 for the small particle diameter. This shows that it is possible to realize relatively good cleanliness of US209D class 200 with a filter having only such a small $\gamma$. By incorporating a low cost and accordingly low performance filter and a photocatalyst system into the 100% circulation feedback system in the example, a unique characteristic capable of obtaining the performance equal to the high performance filter is fully demonstrated. Furthermore, by using the 100% circulation feedback system that is a constituent of this invention, as shown in FIG. 23 to FIG. 25, it is possible to obtain the collection efficiency for respective particle diameters in the case where Nao Japanese paper (hair pattern), Imari Japanese paper or cloth like Tyvek (registered trademark) is used as a filter of the fan filter unit. This makes it possible to control a microbial environment and realize a new medical and nursing environment.

The calculation method described above can be applied to shoji papers, order estimation of the necessary area of which was carried out in determination of the area of shoji papers, described above. That is, a filter was prepared by folding shoji papers and a fan filter unit incorporated the filter was operated in the 100% circulation feedback mode inside the closed space of the constant volume. And by measuring a change of the number of particles for respective particle diameters, it turned out that the same performance as the one shown in FIG. 21 could be obtained, even though the shoji paper filter was used. For example, in the case where the shoji paper "Naobei" made by ONAO CO. LTD. was used as the shoji paper filter, $\gamma$ was 0.12, 0.14, 0.18, 0.28, 0.56 and ~1 for the particle diameter of 0.3 [μm], 0.5 [μm], 0.7 [μm], 1.0 [μm], 5.0 [μm] and 10 [μm], respectively. In the case where the shoji paper "plain No. 5641" made by ASAHIPEN CORPORATION was used as the shoji paper filter, $\gamma$ was 0.18, 0.21, 0.24, 0.42, 0.71 and ~1 for the particle diameter of 0.3 [μm], 0.5 [μm], 0.7 [μm], 1.0 [μm], 5.0 [μm] and 10 [μm], respectively. Conventionally, with respect to a low or medium performance filter, the dust collecting efficiency could not be observed in the case where the number of particles decayed and only a weighing method and a colorimetric method were used (Therefore, accurate measurement was impossible). In contrast to this, the method of measuring in combination to the 100% circulation feedback system can provide a new measuring method because the particle diameter can be discriminated while the simultaneous measurement is possible. On the other hand, scaling of a room by (V/A)/(D/L) is a new method that was devised from another point of view, and this method has a great advantage. In future, these two advantages will be combined to result a multiplier effect. Therefore, the system shown in the example will play a great role and have a great significance in developing technology and analyzing a clean environment.

Cleanliness of US209D class 200 described above is a miraculous value as the value obtained by using a filter having the collection efficiency $\gamma$ much smaller than 1 for 0.5 μm size particles. For example, when the air cleaning device (KPD1000: made by FUJIFILM CORPORATION) is used as in a conventional clean room, the amount of dust reduces only to about half of the number density of dust No of the atmosphere (hundreds of thousands/cubic feet) at most. On the other hand, as apparent from the graph shown in FIG. 22, when the air cleaning device is used in the system configuration of the above example, it is possible to reduce the number density of dust to a value smaller than $N_0$ by about three orders of magnitude. This is the direct consequence of the equation (5) shown in the above. As shown in FIG. 21, the concentrations of acetic acid and $NH_3$ measured at the same time reduce below 1 ppm after ten minutes from the start of operation. In this way, by operating the air cleaning device and the 100% circulation feedback system at the same time, it is possible to improve the performance of the air cleaning device remarkably.

As described above, in the system of highly clean rooms 10 that is a cleaning system of closed circulation construction, the collection efficiency of dust does not depend on the dust collecting efficiency of a filter largely. Therefore, even if the dust collection efficiency of the filter decreases, no serious decrease of the dust collection efficiency observed in the open type air cleaning system is not observed. According to the system of highly clean rooms 10, the margin obtained as a result that the dust collection efficiency is not necessary to be near 1 can be used for sterilization. It is possible to obtain a highly clean environment only by placing a fan filter unit provided with a ventilation opening and an absorption opening such as a commercially available air cleaning device in the closed space to which the 100% circulation feedback system is connected and also lengthen the lifetime of the filter provided in the fan filter unit. It is very effective to provide a commercially available air cleaning device using photocatalyst and metal radicals such as KPD1000 independently inside the main room 20 provided with the 100% circulation feedback system. By providing the above air cleaning device specialized for control of viruses and removal of odor rather than control of dust in a low dust environment, it is possible to reduce deterioration of the performance due to choking of the filter by dust to almost zero and concentrate on the original role of inactivation of viruses, removal of odor, etc. Furthermore, because choking of the filter scarcely occurs, it is possible to obtain the long time reliability. As described above, the system using a commercially available air cleaning device and air conditioning device in addition to the system of the example provided with the 100% circulation feedback system can enhance the performance of cleaning in the mode of not sum but product and keep the initial performance of the system used at the same time semipermanently.

Cleanliness of air inside the anteroom 40 when the fan filter unit 44 (Purespacel, expelled flow rate=[1 m$^3$/min]: ASONE Corporation) provided inside the anteroom 40 is operated alone is now described.

FIG. 26 is a schematic diagram showing the change of the number of dust in a short time when the fan filter unit 44 constituting the 100% circulation feedback system connected to the anteroom 40 was operated. As shown in FIG. 26, the total number of dust having the particle diameter of 0.5[μm] or more per cubic feet inside the anteroom 40 was hundreds of thousands before the start of operation of the fan filter unit 44, but after the operation of the fan filter unit 44, it reduced to forty thousand per cubic feet, one third of the initial value in five minutes and to ten thousands per cubic feet after about ten minutes. Thereafter, cleanliness could be kept for a long time. In this way, it is possible to effectively reduce the quantity of dust inside the anteroom 40 in about five minutes from the start of operation of the fan filter unit 44.

Figure 27:
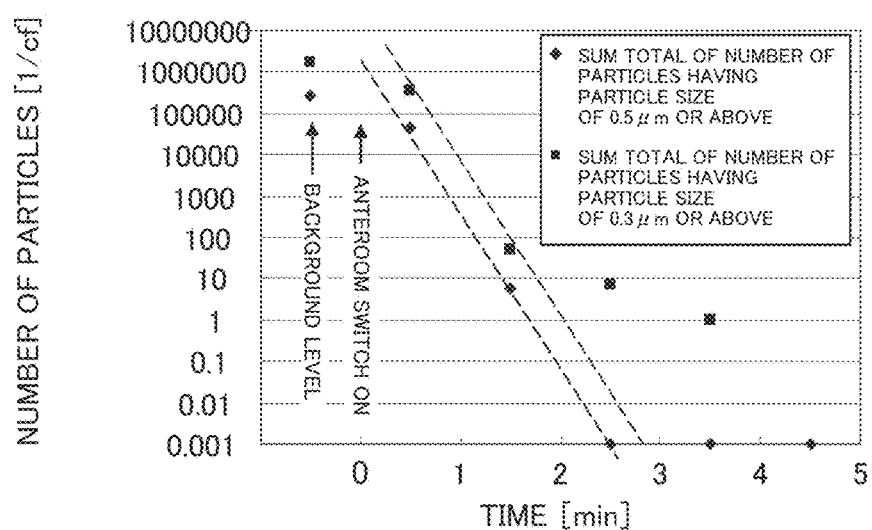
FIG. 27 A schematic view showing the change in a short time of the number of dust particles inside the anteroom when the fan filter unit 44 provided in the anteroom is replaced with the one having the larger exhaust flow rate and operated.

FIG. 27 is a schematic diagram showing the result obtained when the fan filter unit 44 provided inside the anteroom 40 was changed to Purespace 10 (maximum expelled flow rate=11[m$^3$/min]) made by ASONE Corporation, which is a large capacity fan filter unit and operated in the expelled flow rate=11[m$^3$/min]. As shown in FIG. 27, the total number of dust particles having the particle diameter of 0.5 [μm] or more of the number of dust particles inside the anteroom 40 was about a million per cubic feet before the start of operation of the Purespace 10, but it reduced to almost zero in two and half minutes from the start of the Purespace 10. Furthermore, the total number of dust particles having the particle diameter of 0.3 [μm] or more was about ten millions per cubic feet before the start of operation of the Purespace 10, but it reduced to less than ten in about two minutes from the start of operation of the Purespace 10. In this way, by designing properly the fan filter unit 44 used according to the volume of the anteroom 40, it is possible to make space inside the anteroom 40 a super high clean environment in a very short time. As described above, it is demonstrated that the anteroom 40 of the system of highly clean rooms 10 according to the example has the very high performance as an anteroom. This shows that for example, when one sits down on "fumikomi" (space for taking off shoes) of a Japanese-style hotel and unties shoestrings of leather shoes slowly, it is possible to improve cleanliness of the space for taking off shoes (anteroom) to about US209D class 0.1 in a very short time (about one to two minutes) during such actions.

A case where a person enters the main room 20 of the system of highly clean rooms 10 through the anteroom 40 is now described. Before a person enters the main room 20, the doorway 8 and the sliding door 47 are completely shut and the outside, the anteroom 40 and the main room 20 are completely separated. Furthermore, the inside of the main room 20 is kept to be clean beforehand by the 100% circulation feedback system.

When a person enters the anteroom 40 from the doorway 8, shuts the doorway 8 and then operates the 100% circulation feedback system of the anteroom 40, dust inside the anteroom 40 is quickly collected by the filter as described above and cleanliness of the anteroom 40 is rapidly improved. In this time, oxygen in the anteroom 40 is consumed by breathing of the person. However, because the shoji paper is put up on the sliding door 47 as the gas exchange membrane 26 and oxygen is supplied by the gas exchange function, the person can stay inside the anteroom 40 without any trouble.

As described above, by waiting for about two minutes in the anteroom 40 in the stare that the doorway 8 and the sliding door 47 are shut, thereafter opening the sliding door 47 and entering the main room 20, it is possible for persons etc. to move in the main room 20 from the outside without deteriorating cleanliness of the main room 20.

Figure 28:
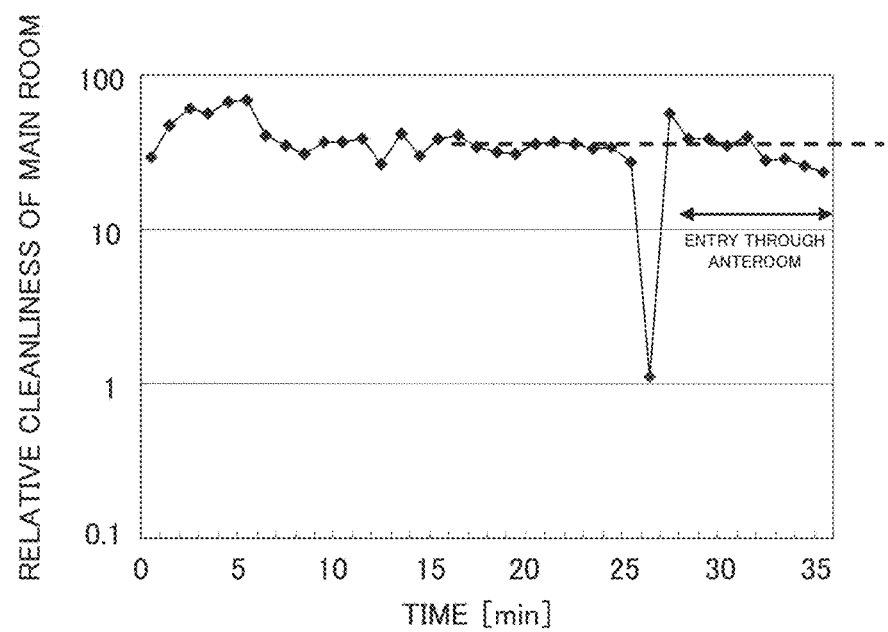
FIG. 28 A schematic view showing the change in relative cleanliness of the main room when a person enters the main room from the anteroom.

FIG. 28 is a schematic diagram showing the change of the relative cleanliness of the main room 20 when a person entered the main room 20 from the anteroom 40 through the sliding door 47. As shown in FIG. 28, it was demonstrated that there was no change of cleanliness of the main room 20 before and after the person entered the main room 20 from the outside space through the doorway 8, the anteroom 40 and the sliding door 47. Because the doorway provided between the anteroom 40 and the main room 20 is constituted of the sliding door 47, there is no volume change when the sliding door 47 is opened or shut, and therefore there is no pressure change and air pushing effect (piston effect). As a result, when a person moves in the main room 20, there is no movement of air as an air current for the main room 20. Therefore, there is no inflow of outside fresh air with plenty of dust and this shows that cleanliness of the main room 20 can be always kept well. As described above, by constituting the system of highly clean rooms 10 by the anteroom 40 and the main room 20 and using the sliding door 47 as a doorway separating the anteroom 40 and the main room 20, it is possible to move between the main room 20 and the outside while keeping cleanliness inside the main room 20. Although it is possible to keep the doorway 8 to be a door in order to hold remodeling to a minimum, it is more preferable to use a sliding door as the doorway 8 in order to avoid the pressure generation and the air pushing effect (piston effect), avoid a collision of persons passing through a hallway and a wheelchair in hospitals, special nursing homes, etc. and make the doorway 8 in a new house. Other than those of the above is the same as the first or second embodiment.

According to the third embodiment, the same advantages as the first and second embodiments can be obtained. In addition, the living space 6 is divided into the anteroom 40 and the main room 20 by the sliding door 47 and the doorway 8 for moving of persons etc. from the outside is provided on the side of the anteroom 40. Therefore, persons etc. that enter through the doorway 8 from the outside space once wait in the anteroom 40 for dozens of seconds to two minutes, and thereafter open the sliding door 47 and enter the main room 20, so that the persons can reach the main room 20 from the outside space without deteriorating cleanliness inside the main room 20. Furthermore, by putting up the gas exchange membrane 26 such as shoji papers etc. on the sliding door 47, it is possible to add the gas exchange function, creating appearance of Japanese old shoji. As described above, by constituting the gas exchange membrane 26 forming a part of the wall 9 constructing the room 1 by shoji like filter paper or shoji paper and using a sliding door as a doorway and a partition between the main room and the anteroom (fumikomi), it is possible to construct the living space 6 in Japanese style and refine style cultivated by history for over a thousand and several hundred years of Japan through the modern technology and the equations (1) to (17), theoretical analytic equations. As a result, it is possible to revive in our time the best air environment, i.e., further clean air environment, which existed generally in ancient Japan, as the one capable of savoring in daily life, beyond the concept of long-term excellent houses and energy management. Furthermore, it is possible to realize again the Japanese old life style such as shoji, fusuma, sliding door, etc. as natural and necessary preparation and procedure, not forced, through the present invention. As a result, it is possible to present a sliding door style Japanese-style room with walls having a shoji paper gas exchange membrane and an internal space and the 100% circulation feedback system all over the world as the most advanced 21th century excellent living space. Furthermore, because dusts generated inevitably in general living space can be actively removed by dust filters etc., it is possible to make the inside of the room remarkably highly clean compared with the conventional clean room etc. that only push out dust generated in the room to the outside and keep the high cleanliness, though dust is generated inside.

4. The Fourth Embodiment

Figure 29:
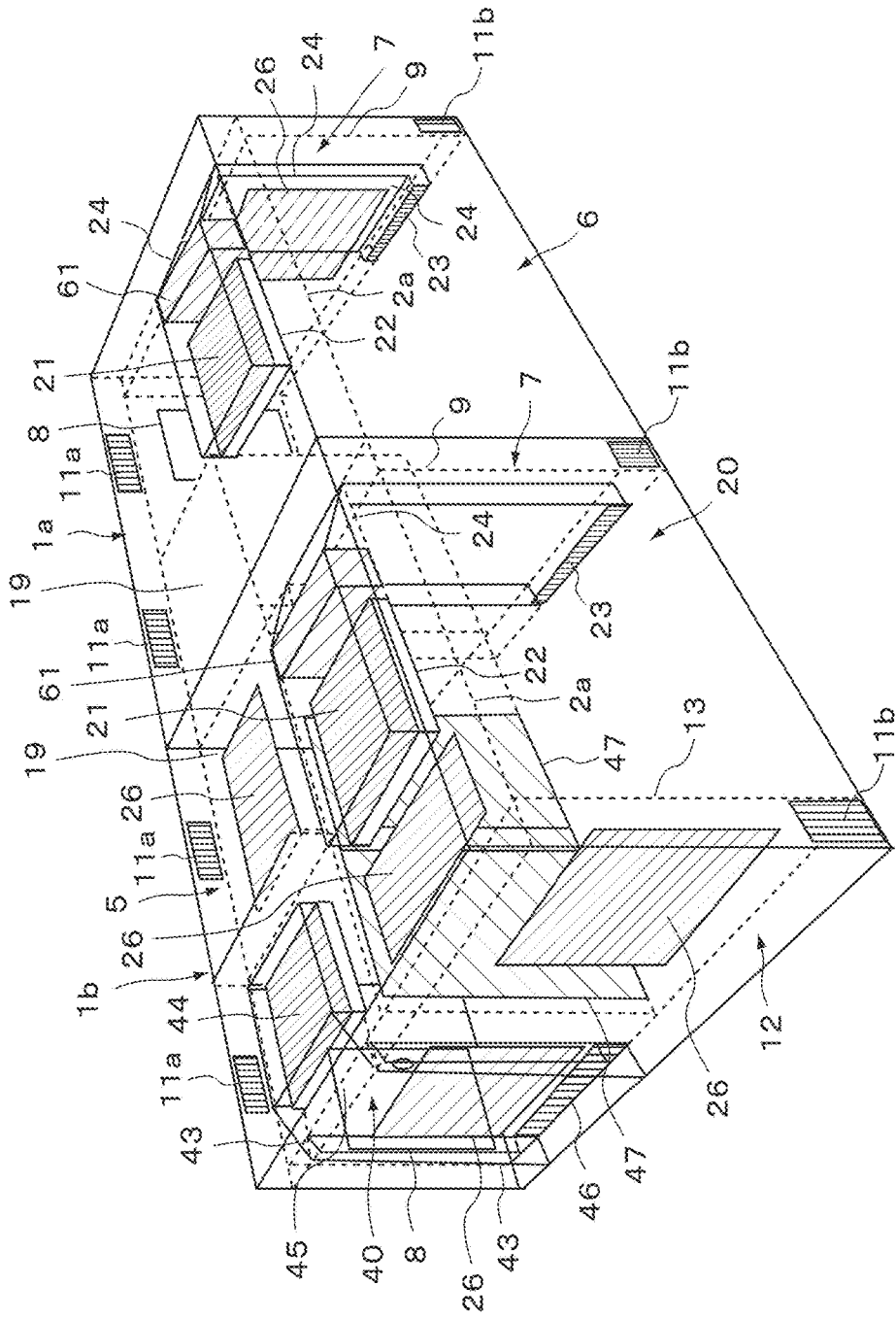
FIG. 29 A perspective view showing a system of highly clean rooms that is used in a sleeping state detection system according to a fourth embodiment.

FIG. 29 shows the system of highly clean rooms 10 used in a sleeping state detection system according to the fourth embodiment. In the drawing, broken lines show walls such as partition, ceiling wall, etc. provided inside the room 1*a* and 1*b* and other constructions inside the room 1*a* and 1*b* are shown by solid lines.

As shown in FIG. 29, the system of highly clean rooms 10 is constructed by two independent rooms that are different and adjacent to each other. In the drawing, on the right side of the rooms being adjacent to each other the room 1*a* in the second embodiment is provided and on the left side of the rooms the room 1*b* in the third embodiment is provided. The utility space 19 of each room is placed in the position of line symmetry with respect to the wall 9 separating the room 1*a* and the room 1*b*. Because the utility space 19 is placed in this way, this configuration can be used in not only a hospital and a nursing home but also a hotel and an apartment house. Therefore, the system of highly clean rooms 10 can be easily applied to existing structures. This configuration works very well in all structures in which entry and exit are carried out in two steps. This configuration can be applied to existing structures such as, for example, the body care industry like a public bath house, a pool, a porcelain tile bath, a bedrock bath, a nail salon, etc., nursing homes, special nursing homes, hospitals, kindergartens, schools, etc.

As described above, by incorporating the above system into an apartment house, a care home, a hospital, etc. having many rooms as necessary, it is possible not only to obtain a low dust space easily but also to obtain a super high clean space that can decompose chemical substances, odor, etc. in an instant. It is also possible to connect the internal space 7 of the wall 9 of the room 1 to form a common space. This configuration will be described in detail in the eleventh embodiment described later. It is also possible to clean plural rooms together by a central system in which the plural rooms 1 are connected and one or a few fan filter units 21 are placed in the part communicating with air of the plural living space or the main room. That is, plural gas flow paths 24 provided in each room 1 are connected airtightly and clean air is supplied to the plural rooms 1 by one or a few fan filter units 21. This connection can be done by, for example, duct, etc. For example, the internal space 7 of the wall 9 of each room 1 is connected in turn and the fan filter unit 21 is connected, and thereafter respective ventilators provided in the room 1 are connected so that the living space 6 or the main room 20 of each room 1 is ventilated. This configuration will be described in detail in the twenty first embodiment described later. Other than those is the same as any one of the first to third embodiments.

According to the fourth embodiment, the same advantages as the first to third embodiments can be obtained. In addition, it is possible to obtain the system of highly clean rooms 10 that can be easily applied to existing structures.

5. The Fifth Embodiment

Figure 30:
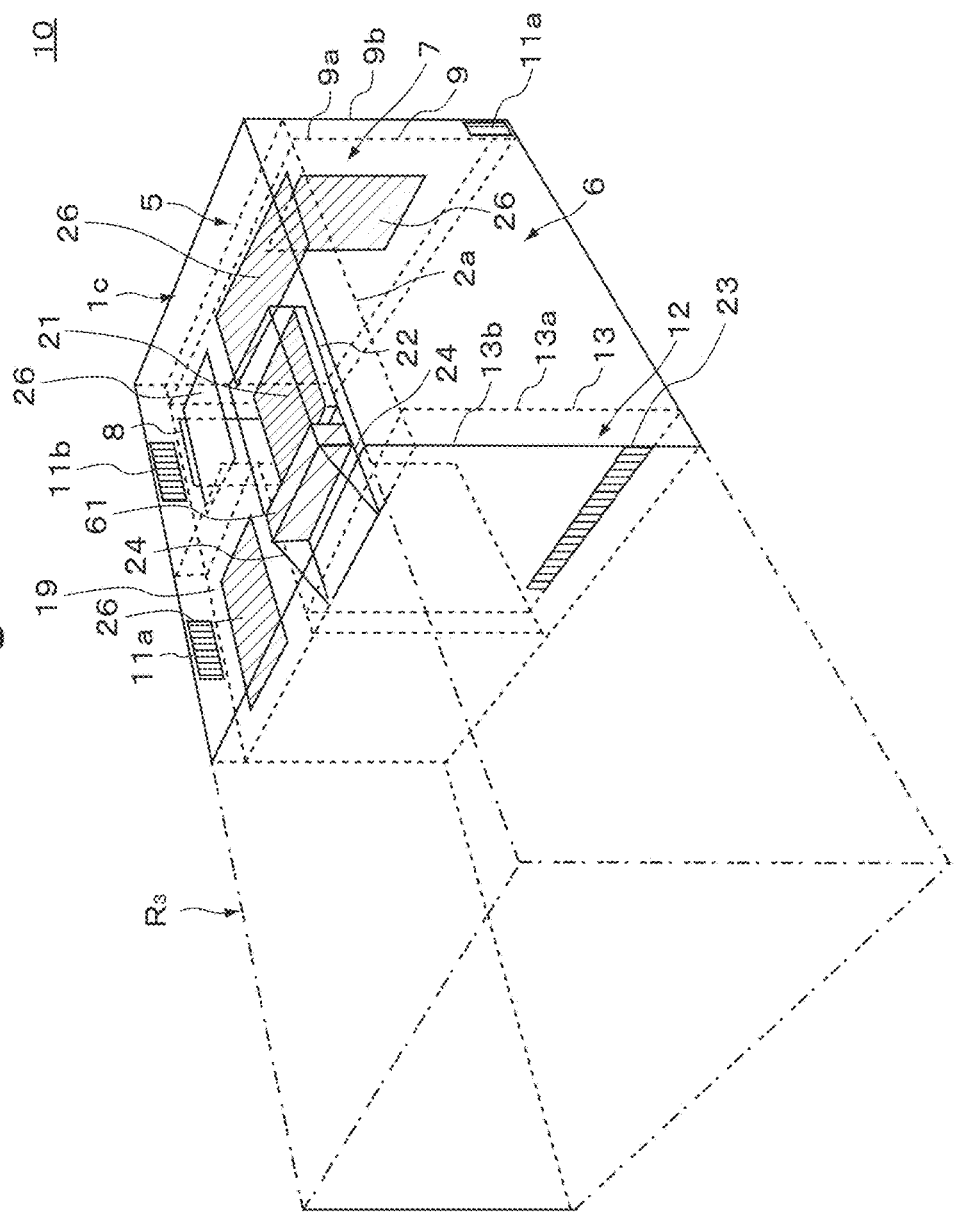
FIG. 30 A perspective view showing a system of highly clean rooms that is used in a sleeping state detection system according to a fifth embodiment.

FIG. 30 shows the system of highly clean rooms 10 used in a sleeping state detection system according to the fifth embodiment.

As shown in FIG. 30, the system of highly clean rooms 10 is constructed by two independent rooms that are different and adjacent to each other. In the drawing, on the right side of the rooms being adjacent to each other the room 1*c* is provided and on the left side of the rooms the room $R_3$ is provided. In the drawing, the room $R_3$ shown by dot and dash lines is a virtual room and its construction is not limited as far as it has a construction independent from the room 1*c*. In the drawing, parts shown by dotted lines show walls such as a partition, a ceiling wall, etc. provided inside the room 1*c* and other constructions inside the room 1*c* are shown by solid lines.

In the room 1*c*, the wall 9 on the right side in the drawing of the room 1*a* shown in the second embodiment is constructed as a wall specialized in only gas exchange. More specifically, an opening communicating the internal space 7, which is the first internal space, and the living space 6 is provided in a part of the inner wall 9*a* of the wall 9 and the gas exchange membrane 26 is provided so as to cover the opening completely, so that one internal space is constructed so as to specialize in only gas exchange. The internal space 12 formed by the wall 13 that is the lateral wall provided facing the wall 9, which is the second internal space, is completely separated from the space 5 between the roof and the ceiling and the outside. By providing the opening 23 in the inner wall 13*a* of the wall 13 and connecting the internal space 12 and the inlet of the fan filter unit 44 airtightly by the gas flow path 24, the whole internal space 12 is constructed as a part of the gas flow path 24 and one internal space is constructed so as to specialize in for only 100% circulation feedback. For example, the width of the opening 23 may be arbitrary within the range from one side to the other side of the wall 9. By increasing the width of the opening, it is possible to absorb the whole air inside the living space 6 uniformly. By constructing like this, the construction can be simplified. Furthermore, by constructing the whole wall as a circulation path, it is possible to absorb air flow from the lower part of the lateral wall uniformly and feedback, so that uniform cleaning of the whole living space 6 is possible. As described above, by not providing one internal space with both functions of gas exchange and 100% circulation feedback but separating the functions, it is possible to increase drastically the cross sectional flow rate of the circulation path, increase conductance of flow, improve gas exchange efficiency, etc. Other than those is the same as any one of the first to fourth embodiments.

According to the fifth embodiment, the same advantages as the first to fourth embodiments can be obtained. In addition, by not providing one internal space with both functions of gas exchange and 100% circulation feedback but separating the functions, it is possible to increase drastically the cross sectional flow rate of the circulation path, increase conductance of flow, improve gas exchange efficiency, etc.

6. The Sixth Embodiment

Figure 31:
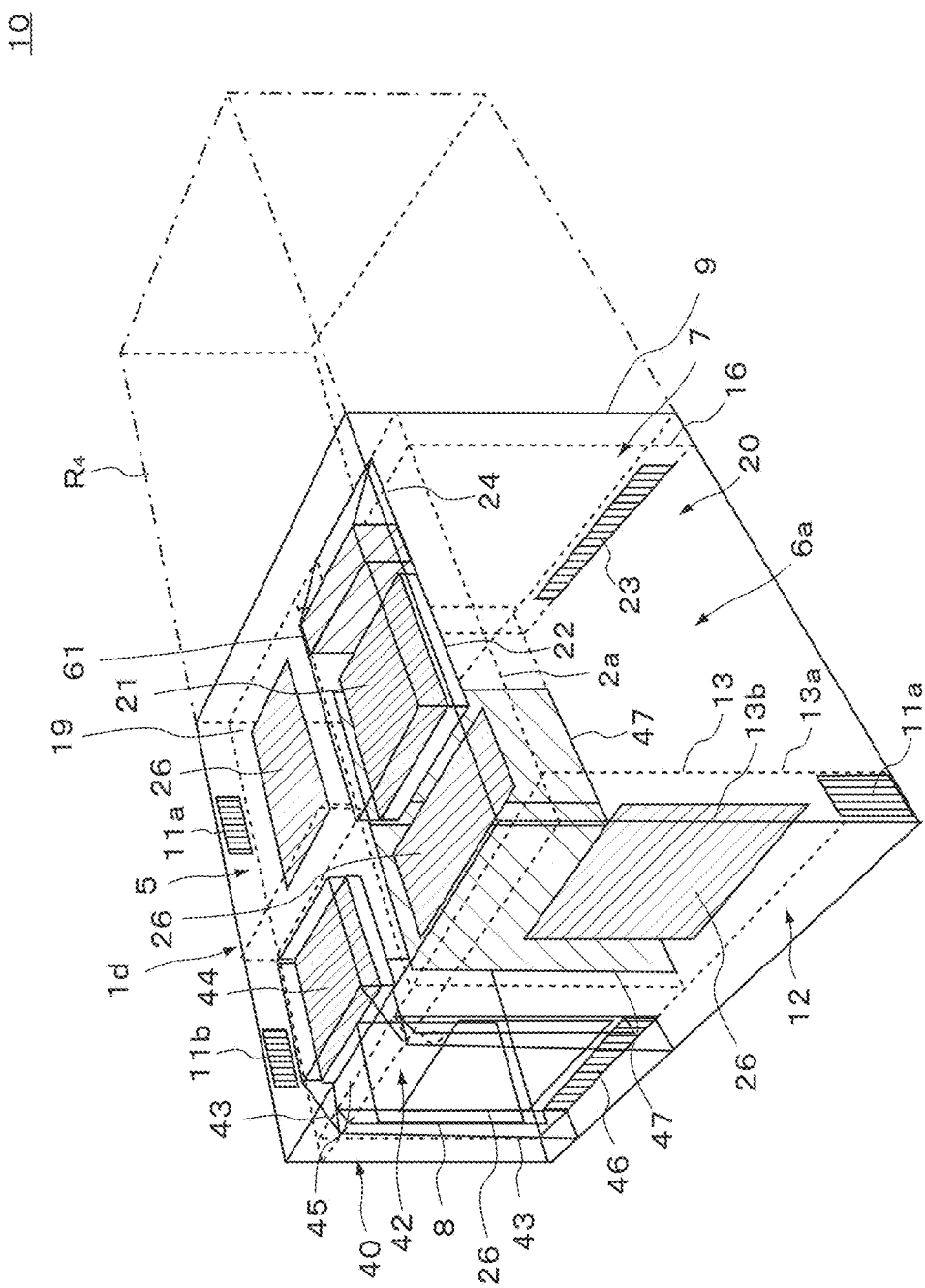
FIG. 31 A perspective view showing a system of highly clean rooms that is used in a sleeping state detection system according to a sixth embodiment.

FIG. 31 shows the system of highly clean rooms 10 used in a sleeping state detection system according to the sixth embodiment.

As shown in FIG. 31, the system of highly clean rooms 10 is constructed by two independent rooms that are different and adjacent to each other. In the drawing, on the left side of the rooms being adjacent to each other the room 1d is provided and on the right side of the rooms the room $R_4$ is provided. In the drawing, the room $R_4$ shown by dot and dash lines, which are virtual lines, is a virtual room and its construction is not limited as far as in has a construction independent from the room 1d. In the drawing, parts shown by dotted lines show walls such as a partition, a ceiling wall, etc. provided inside the room 1d and other constructions inside the room 1d are shown by solid lines.

In the room 1d, the wall 9, which is the lateral wall, on the right side in the drawing of the room 1b shown in the third embodiment and the internal space 7, which is the first internal space, formed by the wall 9 have the same construction as the wall 13 provided in the room 1c shown in the fifth embodiment and the internal space 12, which is the second space, formed by the wall 13. With this, the whole internal space 7 is constructed a part of the gas flow path 24 and one internal space is constructed so as to specialize in for only 100% circulation feedback. By constructing like this, the construction can be simplified and the whole wall can be constructed as a circulation path. Furthermore, it is possible to absorb air flow from the lower part of the lateral wall uniform and feedback, so that uniform cleaning of the whole living space 6 is possible. Other than those is the same as any one of the first to fifth embodiments.

According to the sixth embodiment, the same advantages as the first to fifth embodiments can be obtained.

7. The Seventh Embodiment

Figure 32:
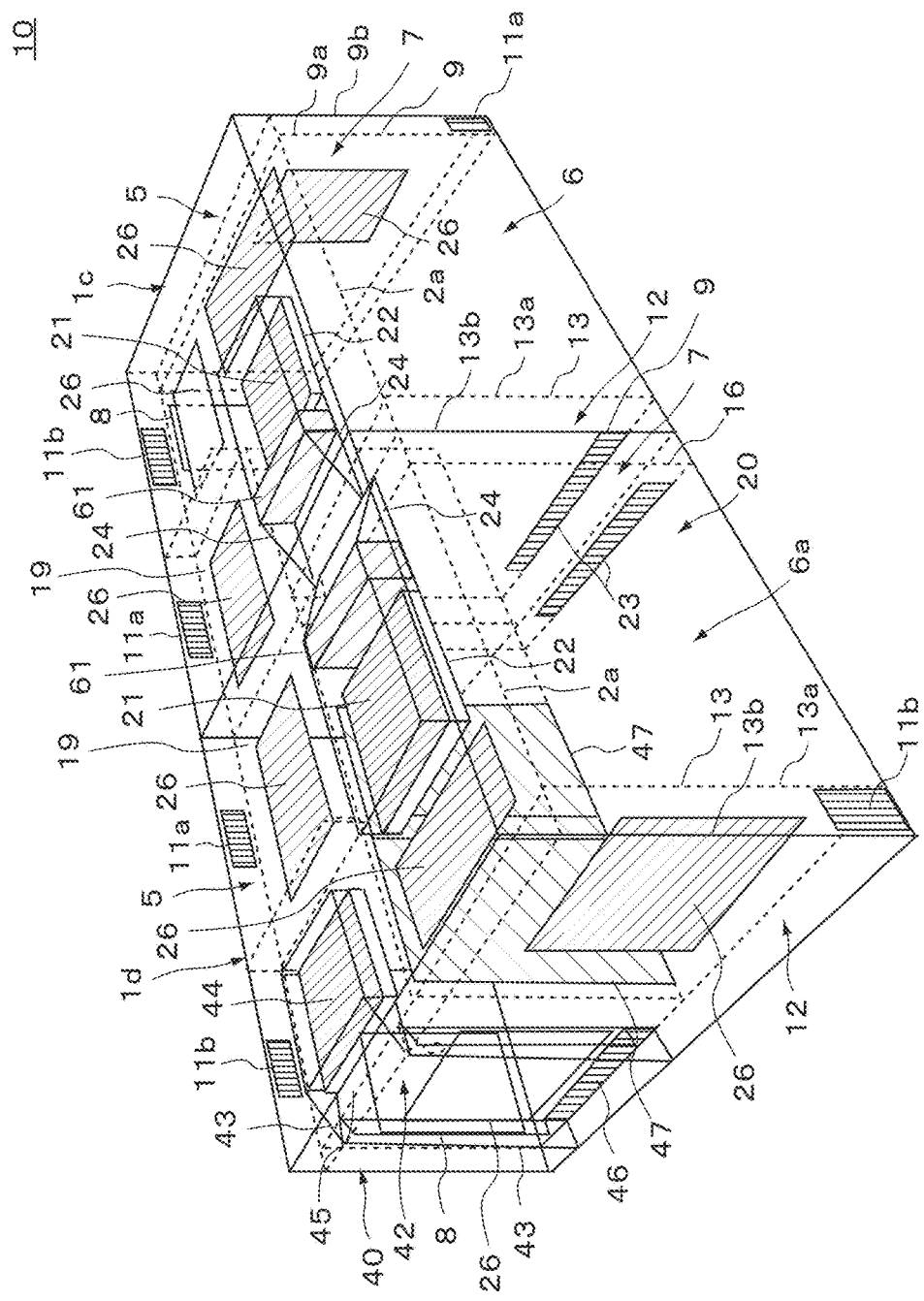
FIG. 32 A perspective view showing a system of highly clean rooms that is used in a sleeping state detection system according to a seventh embodiment.

FIG. 32 shows the system of highly clean rooms 10 used in a sleeping state detection system according to the seventh embodiment. In the drawing, parts shown by dotted lines show walls such as a partition, a ceiling wall, etc. provided inside the rooms 1c and 1d and other constructions inside the rooms 1c and 1d are shown by solid lines.

As shown in FIG. 32, the system of highly clean rooms 10 is constructed by two independent rooms that are different and adjacent to each other. In the drawing, on the right side of the rooms being adjacent to each other the room 1c shown in the fifth embodiment is provided and on the left side of the rooms the room 1d shown in the sixth embodiment is provided so that the gas flow path 24 is placed in line symmetry with respect to the wall separating both rooms.

Figure 33:
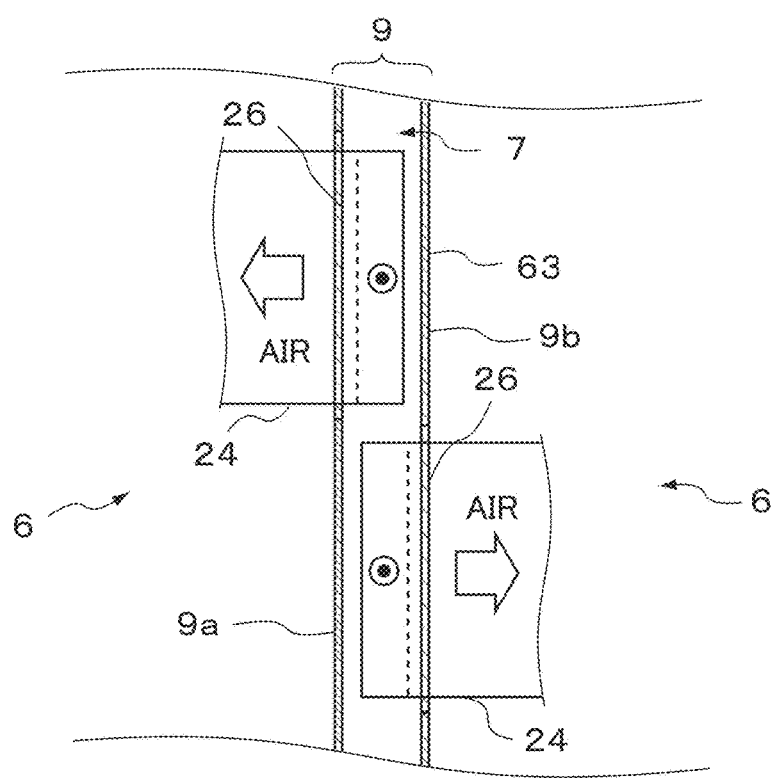
FIG. 33 A cross sectional view showing a circulation path of two-duct wall buried type that is a modification of the system of highly clean rooms that is used in the sleeping state detection system according to the seventh embodiment.

FIG. 33 is a schematic drawing showing a circulation path of two-duct wall buried type, which is a modification of the embodiment.

As shown in FIG. 33, the internal space 7 of the room 1d has a common space with the internal space 12 of the room 1c and the two gas flow paths 24 provided in the room 1c and the room 1d, respectively are stored inside the internal space 12. In this case, the wall 9 has the function of partition wall and the wall 9 is constructed by the two inner walls 9a facing each other. A symbol of double circles having a central black circle shows that an air current goes upward direction from the surface of the paper. As described above, the gas flow path 24 is stored in the internal space 7, one fitting inside another, for example, so that the 100% circulation feedback system is constructed. A part of the wall material 63 to which the gas flow path 24 is provided is constructed by the gas exchange membrane 26, so that gas exchange is possible between the living space 6 of the room 1c and the living space 6 of the room 1d, which are space separated by the gas exchange membrane 26. When gases are made to flow in the internal space 7, it is possible to make highly clean the living space 6 of both of the room 1c and the room 1d all at once. This is possible without narrowing both rooms. That is, this structure is the ultimate structure capable of suppressing narrowing of the room to a limit. It is possible to make additional volume consumed to zero in the structure of the existing room and keep the living space 6 of the room 1 in extremely high cleanliness without reducing the floor area and the volume ratio of the clean living environment space (room) to the whole structure and causing emission of dust to the outside space from the clean living room. It is possible to replace the living space 6 with the main room 20, the anteroom 40, etc. in the embodiment.

For example, it is possible to connect an outside air introduction space of the internal space 7 of the wall 9 of the room adjacent to each other and make them a common space. It is possible to clean the plural rooms 1 together by the central system in which one or a few fan filter units 21 are placed at both edges or midway of the gas flow path 24 connecting the plural rooms 1 and connecting parts communicating air with the plural living space 6, that is, one plane being in contact with the living space 6 and the opening 23, which is another plane satisfying the above condition. This configuration works very well in all structures in which entry and exit are carried out in two steps, such as the structure constituted by the anteroom 40 and the main room 20. This configuration can be applied to the body care industry such as a public bath house, a pool, a bedrock bath, a nail salon, a massage room, etc., nursing homes, special nursing homes, hospitals, kindergartens, schools, etc. Other than those is the same as any one of the fourth to sixth embodiments.

According to the seventh embodiment, the same advantages of fourth to sixth embodiments can be obtained. In addition, by constructing the gas flow path 24 provided back to back in the rooms 1 adjacent to each other by the circulation path of two-duct wall buried type, it is possible to make additional volume consumed to zero in the structure of the existing room and keep the internal space of the room in extremely high cleanliness without reducing the floor area and the volume ratio of the clean living environment space (room) to the whole structure and causing emission of dust to the outside space from the clean living room.

8. The Eighth Embodiment

Figure 34:
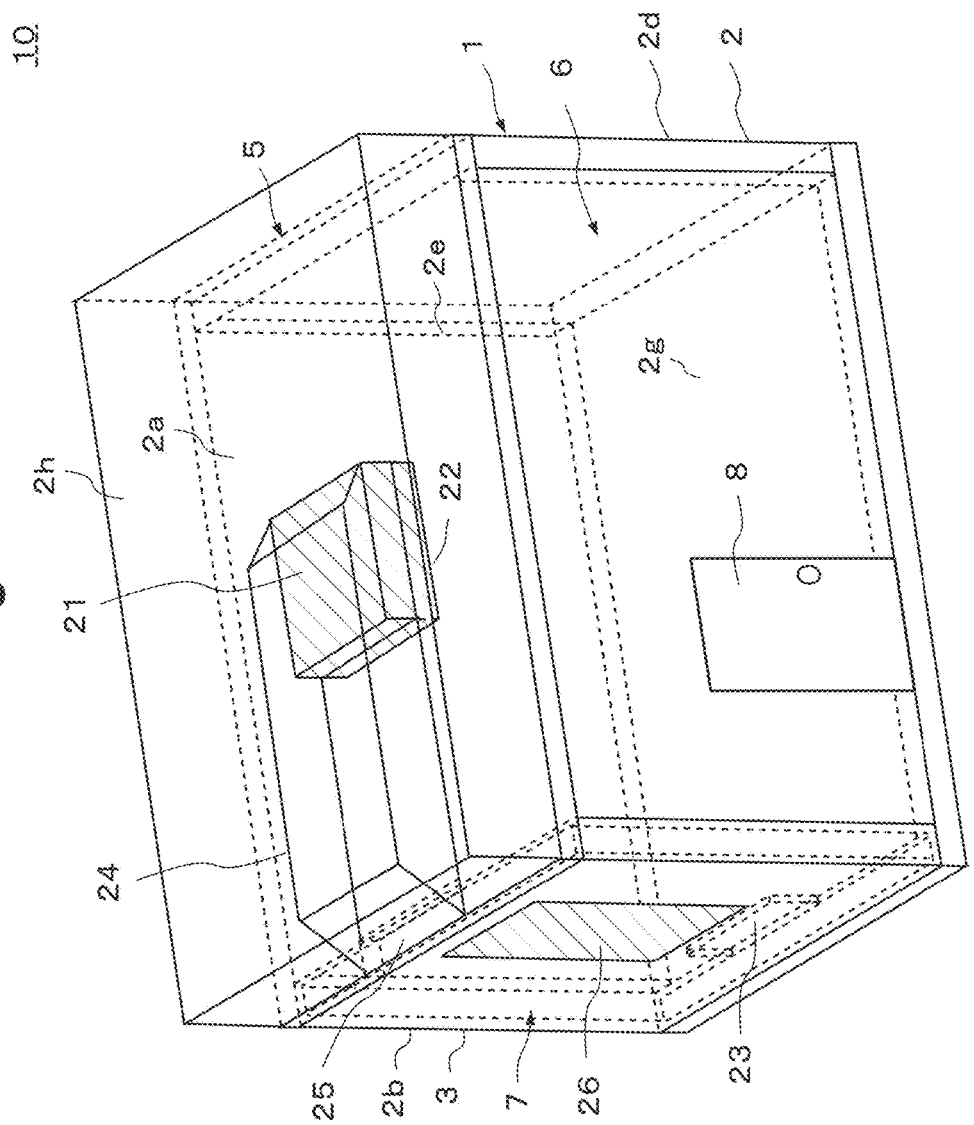
FIG. 34 A perspective view showing a system of highly clean rooms that is used in a sleeping state detection system according to an eighth embodiment.

FIG. 34 is a perspective view showing the system of highly clean rooms 10 used in a sleeping state detection system according to the eighth embodiment. In the drawing, hatched parts are shown to make clear the structure of the system of highly clean rooms 10 and they do not show the cross section. In the drawing, parts shown by dotted lines show walls such as a partition, a ceiling wall, etc. provided inside the room 1 and other structures inside the room 1 are shown by solid lines.

As shown in FIG. 34, the system of highly clean rooms 10 is constructed by incorporating a 100% circulation feedback system in the closed rectangular parallelepiped room 1. The hollow wall 3 is formed integrally with the wall 9 having the inner wall 9a and the outer wall 9b in the above embodiments and the internal space 7 formed by the hollow wall 3 is completely hollow. The room 1 is constructed by closing and surrounding by the wall 2. More specifically, the room 1 is constructed by closing and surrounding by the ceiling wall 2a, the floor wall 2g and the plural lateral walls 2b to e. At least one of the lateral walls 2 constructing the room 1 is constructed by the hollow walls 3. The hollow wall 3 has a cylinder shape having the rectangular hollow cross section. The hollow wall 3 and the lateral wall 2b are provided so as to be sandwiched between the ceiling wall 2a and the floor wall 2g. That is, the lateral wall 2d facing the lateral wall 2b is provided in contact with the major surface of the ceiling wall 2a and the major surface of the floor wall 2g, respectively. The hollow wall 3 is provided so that its bottom surface and top surface become the openings of the cylinder. By closing those two openings by the major surface of the ceiling wall 2a and the major surface of the floor surface 2g, respectively, a closed space is formed. The room 1 forms the living space 6, which is the closed space closed by being enclosed by the plural walls in this way. The internal space 7 is constructed by a space formed by the hollow wall 3, the ceiling wall 2a and the floor wall 2g. The doorway 8 through which persons can enter from the outside and exit is provided in the room 1. The top surface of the room 1 is constructed by the top wall 2h and a space sandwiched by the ceiling wall 2a and the top wall 2h of the room 1 forms the space 5 between the roof and the ceiling.

The fan filter unit 21 shown by hatching in the drawing is provided on the ceiling wall 2a inside the space 5 between the roof and the ceiling. An opening corresponding to the blow opening of the fan filter unit 21 is provided and the opening and the blow opening of the fan filter unit 21 are connected airtightly, so that the blow opening 22 for exhausting air inside the living space 6 is formed. It is also possible to use the blow opening of the fan filter unit 21 as the blow opening 22 by placing the fan filter unit 21 on the side of the living space 6 of the ceiling wall 2a. An opening 23 for collecting air inside the living space 6 is provided on the surface of the hollow wall 3 on the side of the living space 6. The opening 23 is preferably provided on the lowest part of the surface of the hollow wall 3. The inlet of the gas flow path 24 provided inside the space 5 between the roof and the ceiling is connected airtightly with the top part of the hollow wall 3 and the outlet of the gas flow path 24 is connected airtightly with the absorption opening of the fan filter unit 21. Furthermore, by providing an opening 25 on the ceiling wall 2a closing the opening of the hollow wall 3, the internal space 7 and the gas flow path 24 are inserted airtightly and the opening 23 and the absorption opening of the fan filter unit 21 are airtightly connected. In this case, by constructing the internal space 7 as a part of the gas flow path 24, the 100% circulation feedback system is formed for the living space 6. The fan filter unit 21 and the gas flow path 24 connected to it may be provided on the ceiling wall 2a on the side of the living space 6. In this case, an opening is provided on the surface of the hollow wall 3 on the side of the living space 6 and the gas flow path 24 is connected airtightly with the opening. As a result, the internal space 7 and the gas flow path 24 are inserted. In the case where the fan filter unit 21 is provided inside the living space 6, it is provided in a fan filter unit storing unit constructed to be closed, for example.

The living space 6 is a closed space in which persons etc. stay, etc. The doorway 8 provided on the lateral wall constituting the room 1 is provided so that persons etc. can move in the living space 6 from the outside. When the doorway 8 is shut, the living space 6 is completely closed from the outside. Airtightness of the doorway 8 for entering the living space 6 is improved. As a result, the living space 6 has an airtight structure without an outflow and an inflow (air communication between the inside and the outside of the living space 6) other than direct outflow and inflow of air through the doorway 8. It is preferable to make the doorway 8 as the sliding door 47. With this, it is possible to minimize pressure variation between the outside and the living space 6 due to opening and shutting of the doorway 8. As described above, because the living space 6 is completely closed from the outside space when the doorway 8 is shut, a mechanism for supplying oxygen to the living space 6 is necessary. Therefore, at least a part of the surface being in contact with the outside space of the hollow wall 3 is constituted by the gas exchange membrane 26 shown by hatching in the drawing. With this, exchange of gas molecules is performed between the internal space 7 and a space constituting the hallway 33. For example, exchange of oxygen, carbon dioxide, etc. is performed between the living space 6 and the outside space.

The gas flow path 24 and the internal space 7 are connected airtightly and the opening 23 is provided on the surface of the hollow wall 3 on the side of the living space 6, so that all gases exhausted from the blow opening 22 pass through the fan filter unit 21 via the opening 23, the internal space 7 and the gas flow path 24 and air is exhausted again to the living space 6. With this, the 100% circulation feedback system is formed as described above. In this way, by forming the 100% circulation feedback system for the living space 6 and operating the fan filter unit 21 constituting the 100% circulation feedback system, cleanliness of air inside the living space 6 is drastically improved. As described above, by constructing the room 1 so that a part of the gas flow path 24 is constructed by the internal space 7 formed by the hollow wall 3 etc., the system of highly clean rooms 10 can be constructed without narrowing compared with the room 1.

Photocatalyst is provided inside the flow path of the gas flow path as necessary. The flow path of the gas flow path includes the inside of the internal space 7 and the flow path of the gas flow path 24. A location of providing a photocatalytic filter is not essentially limited, but the location is preferably a location capable of receiving light. For example, it is preferable to construct the surface of the wall constituting the gas flow path 24 by a transparent body made by transparent materials. As materials of the transparent body, transparent inorganic materials such as glass etc., transparent resin materials, etc. are exemplified. The transparent body provided in the room 1 is a bow window etc., for example. It is possible to supply light to the photocatalytic filter by using a waveguide such as lens, prism, optical fiber, etc., for example. It is also preferable to use tungsten oxide-based materials capable of utilizing visible light, for example.

The shape of the gas flow path 24 is not essentially limited as far as it has a construction completely closed from the outside capable of exhausting all gases introduced from the internal space 7 from the blow opening 22, but it has preferably a shape with small loss of flow. Concretely, the shape of the gas flow path 24 is preferably a cylinder shape having the cross sectional shape such as a rectangular shape, a square shape, a circular shape, an elliptic shape, etc. The gas flow path 24 may be constructed by combining the plural gas flow paths 24 having these shapes. The cylinder shape is preferably a shape of a cylinder extending like a straight line, for example. The gas flow path 24 may be constructed by placing the plural gas flow paths in parallel. The gas flow path 24 has preferably the same shape as the cross section of the hollow wall 3, for example.

The location of providing the gas exchange membrane 26 is not essentially limited, but it is preferable that the location of connecting with the internal space 7 is the central region of the opening of the hollow wall 3. Concretely, the gas flow path 24 is provided on the ceiling wall 2a on the side of the space 5 between the roof and the ceiling so as to extend parallel to one side of the surface of the ceiling wall 2a and connected airtightly with the internal space 7, so that the gas flow path 24 having a right-angle bent part is constituted. By constituting like this, the gas flow path 24 is completely separated from the internal space 7. For example, the gas flow path 24 is preferably provided so that the position of the blow opening 22 is parallel to the position of the opening 23.

The location of providing the gas exchange membrane 26 is not essentially limited, but may be the position constituting at least a part of the wall constituting the room 1. The location is preferably a place without the influence by rain, wind, etc. In the case where the gas exchange membrane 26 constitutes at least a part of the surface being in contact with the outside space of the hollow wall 3, it is preferable to provide a mechanism that can equalize the direction and velocity of the flow of gases on both sides of the gas exchange membrane 26. More specifically, gases are flown in the region facing the internal space 7 with respect to the gas exchange membrane 26 so that the direction and velocity of the flow of gases are the same as those of gases flowing in the internal space 7. By constituting the gas exchange membrane 26 constituting a part of the surface of the inner wall of the room 1 like shoji, for example, it is possible to construct the living space 6 as a Japanese-style room. Here, the doorway 8 may be constituted by a shoji door as a sliding door.

When oxygen is supplied to the living space 6 from the outside space such as a hallway etc. through the internal space 7, the gas exchange membrane 26 does not pass through dust inside the internal space 7. Because the internal space 7 and the gas flow path 24 are formed to be closed and further the internal space 7 and the gas flow path 24 are airtightly connected, outside air introduced inside the space 5 between the roof and the ceiling etc. does not go into the gas flow path 24. As a result, even though oxygen is supplied inside the living space 6, dust is not supplied inside the living space 6 and therefore cleanliness is kept.

Shapes of the opening 23 and the blow opening 22 are not essentially limited, but they are preferably a rectangular shape, a square shape, a circular shape, an elliptic shape, etc., for example. The location of providing the opening 23 is not essentially limited as far as it is a part of the hollow wall 3. The opening 23 is preferably provided in the position as near to the floor wall 2g as possible. The location of providing the blow opening 22 is not essentially limited. The blow opening 22 is preferably provided on the position as high as possible. The blow opening 22 is also preferably provided as near to the central part of the ceiling wall 2a as possible. The opening 23 and the blow opening 22 are preferably provided in the positions parallel to each other, as described above.

The distance between the opening 23 of the gas flow path 24 and the blow opening 22 is preferably an enough distance. The distance between the opening 23 and the blow opening 22 is preferably set so that the longest distance x of the distribution of the distance between the opening 23 and the blow opening 22 is selected for the distance X of the living space 6 in the direction defining x such that there is at least one direction in which the ratio x/X is larger than 0.3, preferably the ratio x/X is equal to or larger than 0.35, most preferably the ratio x/X is equal to or larger than 0.4 and equal to or smaller than 1.0.

The volume of the internal space 7 is not essentially limited, but it is preferably as small as possible. In the case where the hollow wall 3 is constructed by walls having the rectangular hollow cross section, the length (thickness) of the short side of the hollow part of the cross section is preferably 5 cm or more and 40 cm or less, typically about 8~20 cm. It is desirable that braces or steels having the C-shape cross section are used for a part adjacent to the hollow part to give the strength as walls. The thickness of the internal space 7 is preferably the minimum thickness necessary to support the structure of the room 1, but not limited to this.

The gas exchange membrane 26 may be provided in any position essentially as far as it constitutes at least a part of walls constituting the system of highly clean rooms 10. For example, the gas exchange membrane 26 is preferably provided on a wall of walls constituting the system of highly clean rooms 10 other than outside walls to be exposed to wind and rain and preferably provided near the airway 11, for example. Furthermore, the gas exchange membrane 26 is preferably provided in the position that flow of outside air introduced from the airway 11 is not obstructed by the gas flow path 24.

The shape of the gas exchange membrane 26 is not essentially limited, but preferably square, rectangular, etc., for example. The size of the gas exchange membrane 26 is not essentially limited, but a sheet of the gas exchange membrane 26 has preferably a size of 135 cm×135 cm. The total area of parts of the gas exchange membrane 26 being in contact with the living space 6 for a person staying in the living space 6 is preferably equal to or larger than 500 $cm^2$/person, more preferably equal to or larger than 700 $cm^2$/person and most preferably equal to or larger than 900 $cm^2$/person.

The gas exchange membrane 26 is not essentially limited as far as it has the function that dust particles are not exchanged but gas molecules are exchanged in both spaces separated by the gas exchange membrane 26. For example, the gas exchange membrane 26 has preferably the oxygen molecule diffusion ability equal to or larger than 0.25 L/min when there is the oxygen concentration difference between spaces separated by the gas exchange membrane 26. Concretely, the gas exchange membrane 26 is preferably cloth, nonwoven fabric, shoji paper, Japanese paper, etc., for example. In the case where the gas exchange membrane 26 is constituted by shoji paper, it can be made as a shoji window that is a shoji-like window combined with timbering lattice. By constituting like this, it is possible to construct the hallway 33 in Japanese style. It is also possible to provide a shoji window in a part of walls constituting the room 1 and decorate the inside of the room 1 in Japanese style.

The doorway 8 is not essentially limited as far as persons can move between the outside space and the living space 6 and further it has the function of blocking both spaces. As the doorway 8, it is possible to use the one selected from doorways exemplified above. The doorway 8 is preferably a sliding door that has a small pressure difference between both spaces when it is opened and shut. For example, the sliding door can be made as a shoji door by combining with shoji paper as the gas exchange membrane 26.

FIG. 35~FIG. 38 are the perspective views showing examples of the gas exchange device 80. As shown in FIG. 35~FIG. 38, by providing the plural gas exchange membranes 26 inside the gas exchange device 80, dirty air inside the room 1 including air of which oxygen decreases, air of which carbon dioxide increases, or odor and chemical substances are subjected to gas exchange and mutual concentration diffusion of molecules with outside air, and its concentration of molecules is returned to a value very close to the concentration of molecules of outside air, which is returned inside the room 1. At this time, because there is no exchange of the net air flow, there is no incorporation of dust from outside air and air is cleaned only for molecular components. That is, outside air introduced from the introduction opening 71 and gases inside the room 1 introduced from the inside air collection opening 72 exchange gas constituents through the multiple gas exchange membranes 26, and the gas constituents of the inside air becomes almost equal to the gas constituents of the outside air, and the resultant air returns inside the room again.

Figure 35:
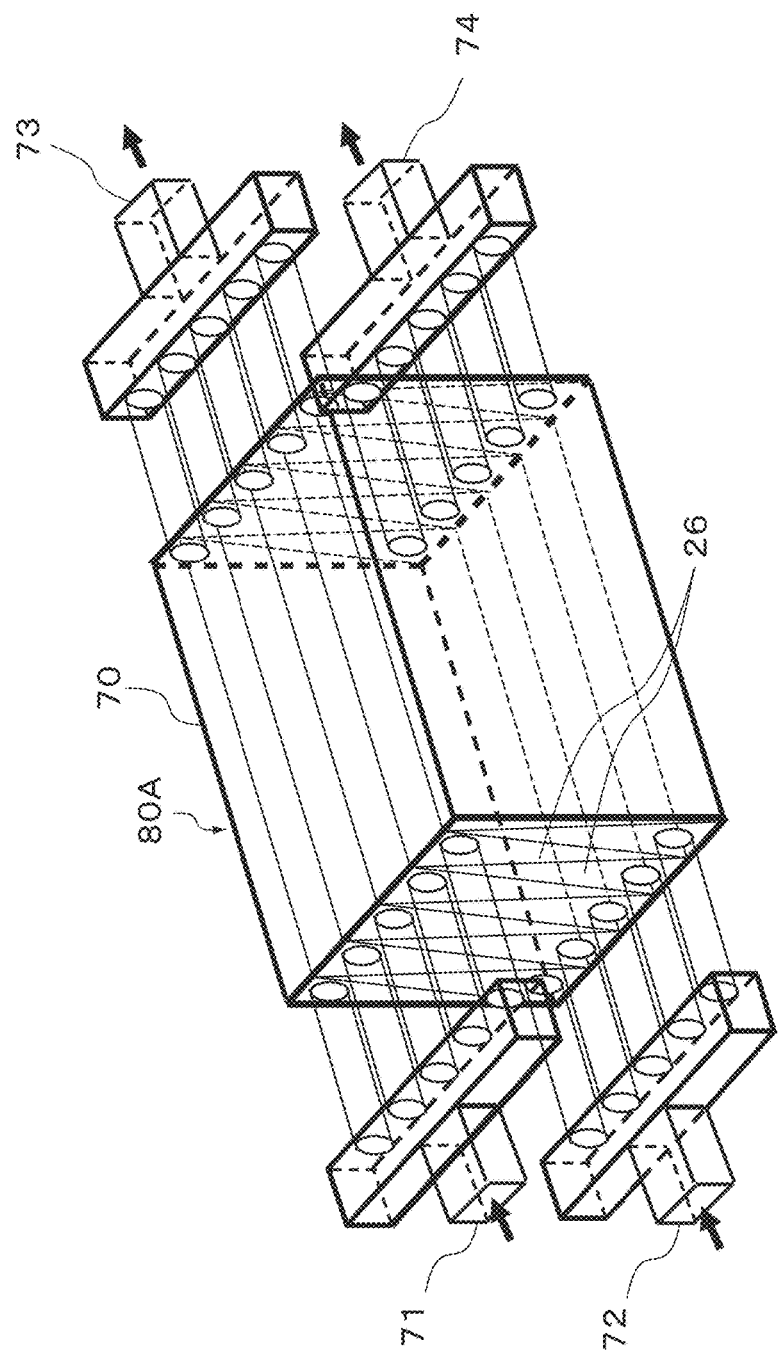
FIG. 35 A perspective view showing an example of the gas exchange device used in the system of highly clean rooms that is used in the sleeping state detection system according to the eighth embodiment.
Figure 36:
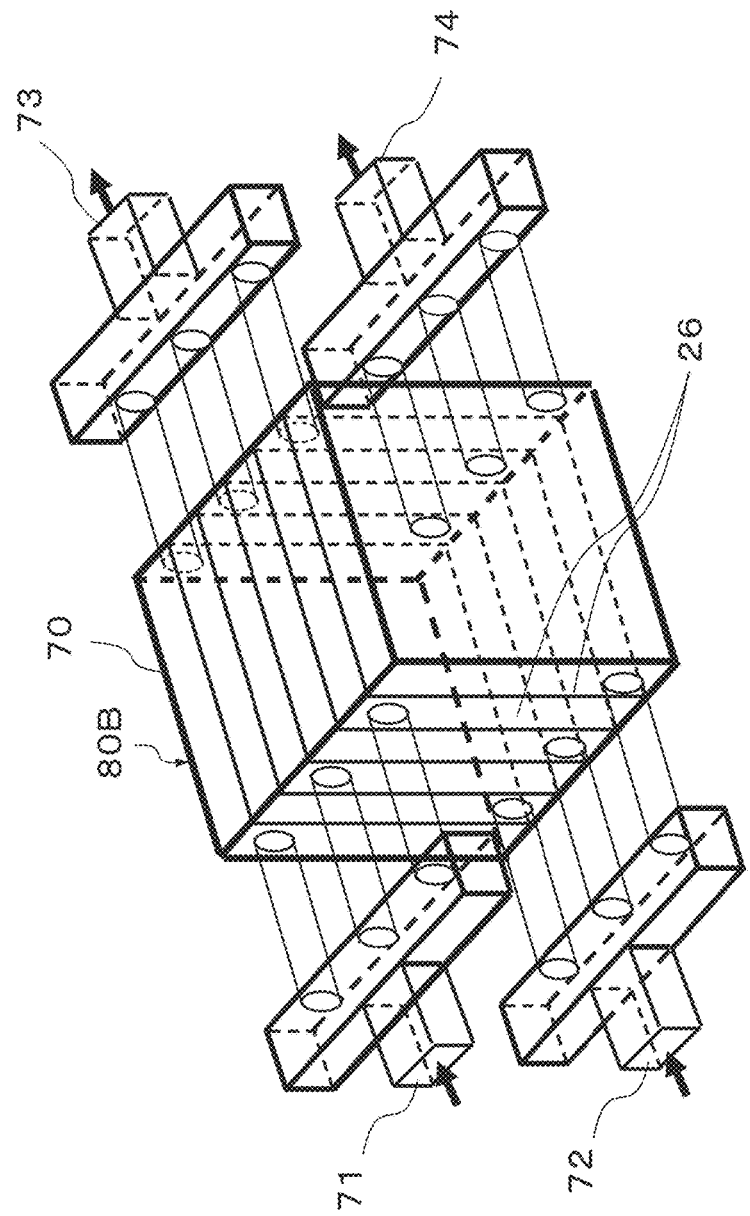
FIG. 36 A perspective view showing another example of the gas exchange device used in the system of highly clean rooms that is used in the sleeping state detection system according to the eighth embodiment.
Figure 37:
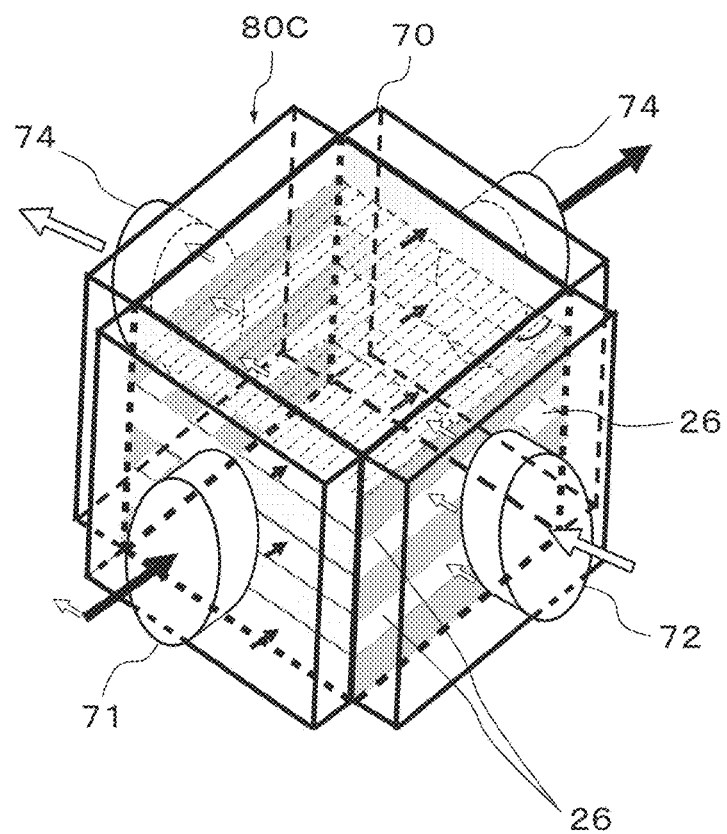
FIG. 37 A perspective view showing still another example of the gas exchange device used in the system of highly clean rooms that is used in the sleeping state detection system according to the eighth embodiment.
Figure 38:
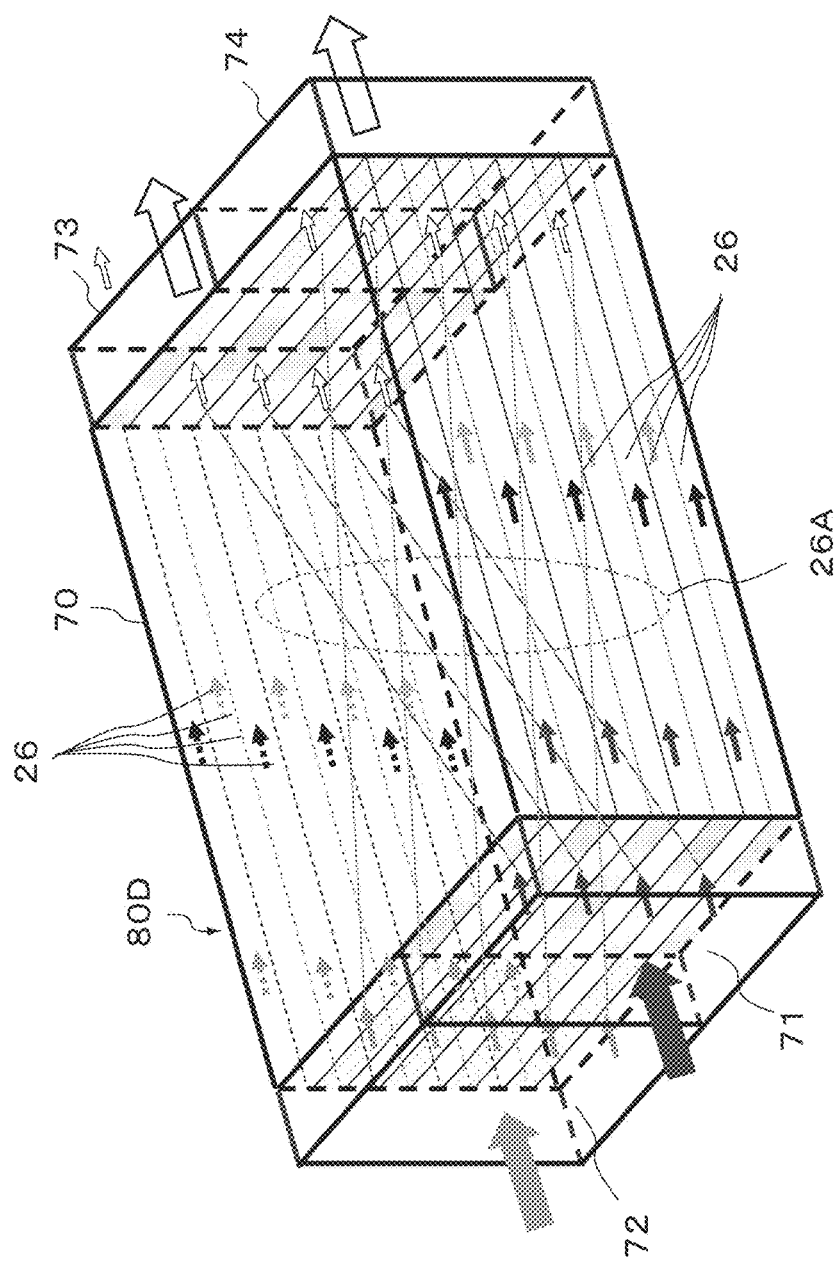
FIG. 38 A perspective view showing a further example of the gas exchange device used in the system of highly clean rooms that is used in the sleeping state detection system according to the eighth embodiment.

The gas exchange devices 80 will be explained respectively. As shown in FIG. 35, the gas exchange device 80A is a type in which the handling of the air current is easy because the outside air and the inside air are introduced and sent in parallel. This type of the gas exchange device 80A has a merit that the gas exchange membrane 26 can be constituted with a single-membrane because the gas exchange membrane 26 is arranged in a box in a zigzag manner and unicursal way. Also, as shown in FIG. 36, the gas exchange device 80B has a constitution which introduces and sends the inside air and the outside air in parallel as the same as the gas exchange device 80A, further, is a type that arranges many gas exchange membranes 26 in parallel, and introduces the outside air and the inside air separately every each slot. Being constituted like this, there is a merit that the distance of the surface of the gas exchange membrane 26 can be made constant and there is less stagnant layer in the air current. Also, as shown in FIG. 37, the gas exchange device 80C is also a type that arranges many gas exchange membranes 26 in parallel, but by making the introduction direction of the outside air and the inside air perpendicular, the introduction openings 71 can be gathered together and the constitution can be simplified. Also, as shown in FIG. 38, the gas exchange device 80D is the one in which the advantages of the constitution of the gas exchange devices 80B and 80C are combined and there is a merit that the introduction and sending of the outside air and the inside air can be done in parallel and the introduction openings of the outside air and the air inside the room 1 can be gathered together. The size of the gas exchange part 70 of the gas exchange device 80D is specifically, for example, about 45 [cm] in height, 90 [cm] in width, and 180 [cm] in length, and the gas exchange membrane 26 is stretched, for example, with the clearance d of about 3 [mm] or more and 60 [mm] or less. By this, it is possible to exchange gases in the very large effective area of 12 [m$^2$] or more and 240 [m$^2$] or more. However, d is not limited to this, and 1~2 [mm] is also very effective for shortening the gas exchange time. Therefore, the gas exchange device 80D has an ability more than dozens of times to hundreds of times of the gas exchange ability of the gas exchange membrane 26 shown in FIG. 11. As described above, because the gas exchange device 80D is provided with two-system ventilation fan for outside air and air returned to the room (inside air), which sends air actively, it is possible to improve the gas exchange ability to about ten times taking further velocities of the two air currents on both sides of the gas exchange plane into consideration.

If the total area of the gas exchange membrane 26 in the gas exchange device 80 satisfies at least the equation (15), enough oxygen density for people to act inside is secured. And the larger the area is, in addition to this, the higher the functions of deodorizing and harmful gas exhaust become. That is, the scaling by (V/A)/(D/L) also can be applied to the "unit cell" having the repeat structure of "gas exchange membrane/inside air/gas exchange membrane/outside air", which the gas exchange part 70 of the gas exchange device 80 has. For example, in the case of the system of highly clean rooms 10 shown in FIG. 9 or FIG. 12, while about V(~24 [m$^3$])/A (~1.8 [m$^2$])~13 [m], the clearance d of the surface of the gas exchange membrane 26 of the gas exchange device 80 shown in FIG. 35~FIG. 38 is typically a few [mm] order, so V(=A×d)/A=d~3 [mm]. Because the ratio of the both is 13 [m]/3 [mm]~4000 [mm], it is known that from the quantity of the "forty minutes" order observed in FIG. 13B, the time constant of the gas exchange of the gas exchange device 80 is, for example, only ¼₀₀₀ of it, that is, the time of about less than one second order. For example, for the living space of volume 30 [m$^3$], the flow rate of the outside air and the inside air flowing into the gas exchange device 80 is about 0.25 [m$^3$/min]~several dozen [m$^3$/min] (the value scales for the volume of the room) depending on the steady situation or emergency situation. Therefore, considering the typical size (0.45×0.9×1.8 [m$^3$]~0.8 [m$^3$]) of the gas exchange device 80, the time while the air current passes through inside the device becomes a few second~about one minute. Because this is more than several times of the time constant of gas exchange of the gas exchange device 80, it is known that the outside air and the inside air fully make gas exchange during flowing inside the gas exchange device 80, and at the outlet both air can reach an almost equilibrium state. As described above, according to the gas exchange of the outside air with the air inside of the room 1, the mutual concentration diffusion of molecules can be made effectively between the two air current flowing on both sides of the central part of each gas exchange plane. It is preferable that for the flow rate of the inside air flowing into the gas exchange device 80, the flow rate of the outside air flowing into the gas exchange device 80 is made to be equal or more than that. Preferably, for the flow rate of the inside air flowing in the gas exchange device 80, the flow rate of the outside air flowing into the gas exchange device 80 is made to be several times to 10 times or more. In this case, it is preferable to make the pressure difference via the gas exchange membrane almost zero according to the Bernoulli's theorem by adopting the arrangement with the large parallel components in the velocity vector of the two air currents of the inside air and outside air flowing on both sides of the gas exchange membrane 4 at the same time. It is the best that the velocity vector of the two air currents is perfectly parallel with each other, but next to this, it is very effective to make cross diagonally on both sides of the plane at the central part of each gas exchange plane. For this, it is important to make the cross-sectional area of the flowing part of the outside air larger than that of the inside air so as to cancel with the above ratio of the flow rate. That is, it is preferable to make the ratio of the outside air flow rate/the inside air flow rate in the gas exchange device 80 equal to the ratio of the gas exchange membrane clearance in the outside air flow path/the gas exchange membrane clearance in the inside air flow path. Also, in the case where air currents on both sides of the gas exchange membrane 26 is in parallel or in subparallel, it is effective to make the cross section of the gas exchange membrane 26 cut by the plane vertical to the flowing direction a zigzag shape (mountain fold, valley fold) and increase effective area and thereby enhance gas exchange ability.

Figure 39A:
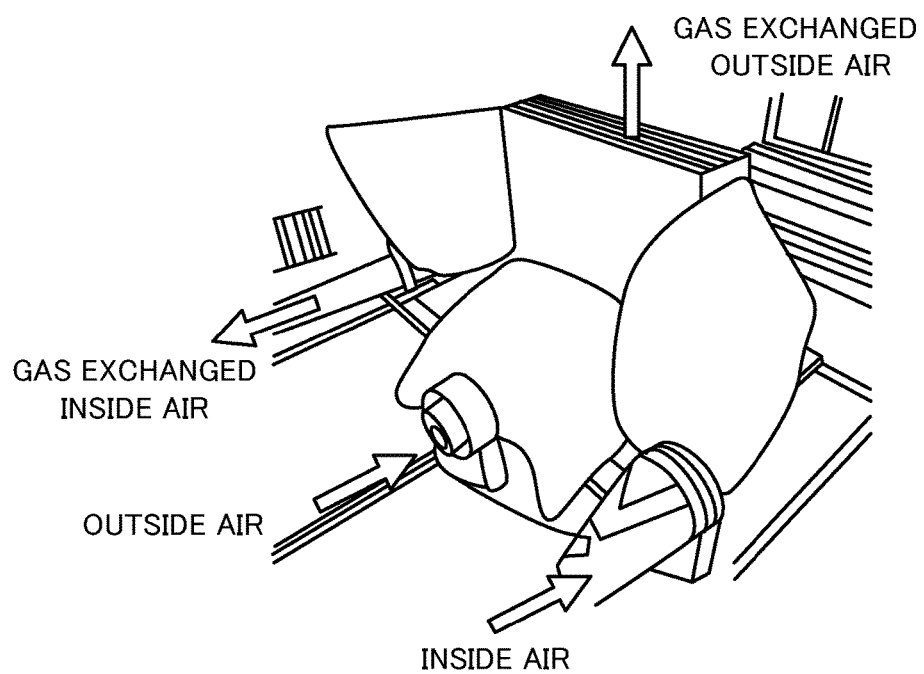
FIG. 39A A substitute picture for a drawing showing the trial product of the gas exchange device.
Figure 39B:
FIG. 39B A substitute picture for a drawing showing the trial product of the gas exchange device.
Figure 40:
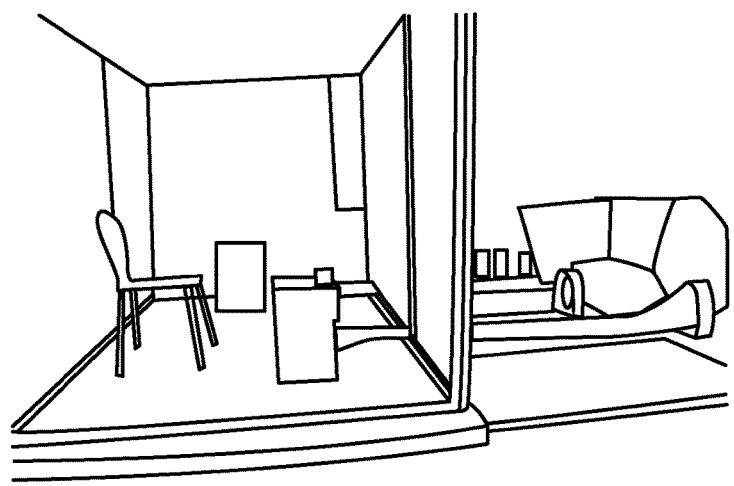
FIG. 40 A substitute picture for a drawing showing an example in which the gas exchange device shown in FIG. 39A
Figure 41:
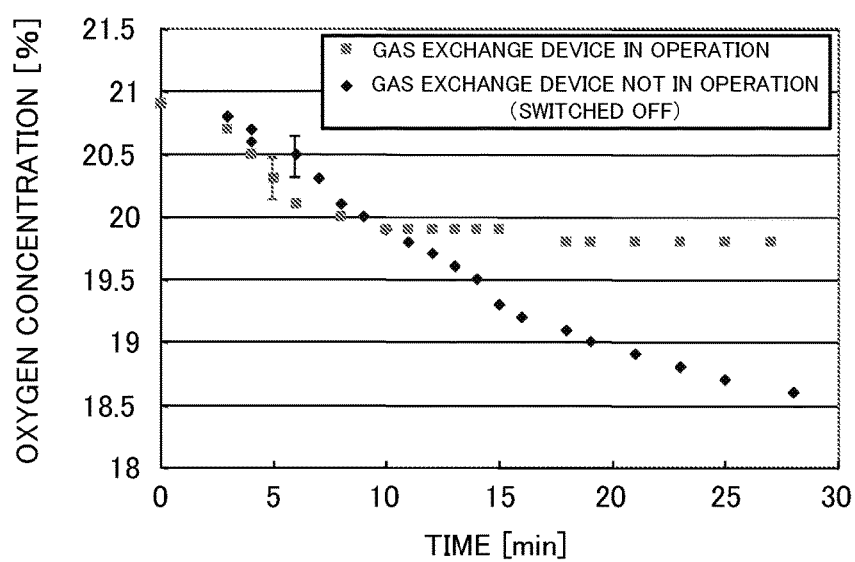
FIG. 41 A schematic view showing the result of an experiment of consuming oxygen carried out inside the completely closed room of the system of highly clean rooms shown in FIG. 40.

FIG. 39A shows the actual device (test device) of the gas exchange device shown in FIG. 37, and FIG. 39B is the top view of the filter part of the gas exchange device shown in FIG. 39A. FIG. 39A shows the arrangement of air flow of the gas exchange device. The length of the gas exchange device is about 90 cm, the width is about 60 cm, and the total thickness of the multi-layer membrane structure is about 20 cm. FIG. 40 shows an example in which the gas exchange device shown in FIG. 39A is incorporated into the room of the system of highly clean rooms 10. In the rectangular parallelepiped room on the left side in FIG. 40, the five planes among the six planes is made by vinyl for and the rest one plane is made by Tyvek, and the space is completely sealed. Then, oxygen is consumed by lighting a fire in a gas range inside the room. Under the circumstances, the oxygen concentration in the closed space with or without the operation of the gas exchange device was measured. Its result is shown in FIG. 41. As shown in FIG. 41, when the gas exchange device was not operated, the oxygen concentration continued to decline under 19%. However, when the gas exchange device was operated, the oxygen concentration of the inside stopped to fall and became constant at less than 20%. It is proved that the gas exchange device has excellent gas exchange ability. Based on the D/L obtained by the method described above, according to the prescription and the equation 17 described above, by setting the size of the gas exchange membrane, the total number of the membrane and the flow rate of air flowing, the target oxygen concentration can be realized. Because the gas exchange device can be considered as the utmost limits in the case where V/A of the room of the present invention is small from the understanding by the above analysis. Therefore, the gas exchange device can be considered as the limit form of the hollow wall provided with the gas exchange membrane of the present invention. Thus, this gas exchange device can alternate the hollow wall provided with the gas exchange membrane of the present invention according to usage.

Also, for example, when the gas exchange device 80D is used as the gas exchange device 80 to be provided in the system of highly clean rooms 10 shown in the embodiment, the gas exchange membrane 26 provided inside the gas exchange part 70 of the gas exchange device 80D lines vertically for the ceiling wall 2a. That is, a normal vector of the plane of the gas exchange membrane 26 lies at right angles to the direction of gravitational force. Therefore, various dust included in the outside air does not fall on to the plane of the gas exchange membrane 26 but remain on the wall constituting the gas exchange part 70, for example, on the front plane in FIG. 49. Therefore, the gas exchange ability of the gas exchange membrane 26 of the gas exchange device 80D is remarkably relieved from the issue of choking.

By constituting the system of highly clean rooms 10 as described above, it is possible to realize the system of highly clean rooms 10 with a local exhaust system. For example, by using the system of highly clean rooms 10 when a local exhaust is desirable at the diaper-changing time at the nursing homes, it is possible to deal with the generation of the local nasty smell without sacrificing cleanliness inside. Also, the system of highly clean rooms 10 can make the painting process using solvent etc. safe, maintaining clean environment. The others are the same as the system of highly clean rooms 10 of any of the second to the eighteenth embodiments.

According to the eighth embodiment, the same advantages as the first to the seventh embodiments can be obtained and further the system of highly clean rooms 10 with the local exhaust system can be realized. For example, when a local exhaust is desirable at the diaper-changing time at the nursing homes, by using the system of highly clean rooms 10, it is possible to deal with the generation of the local nasty smell without sacrificing cleanliness inside. Also the system of highly clean rooms 10 can make the painting process using solvent etc. safe, maintaining clean environment.

9. The Ninth Embodiment

Figure 42:
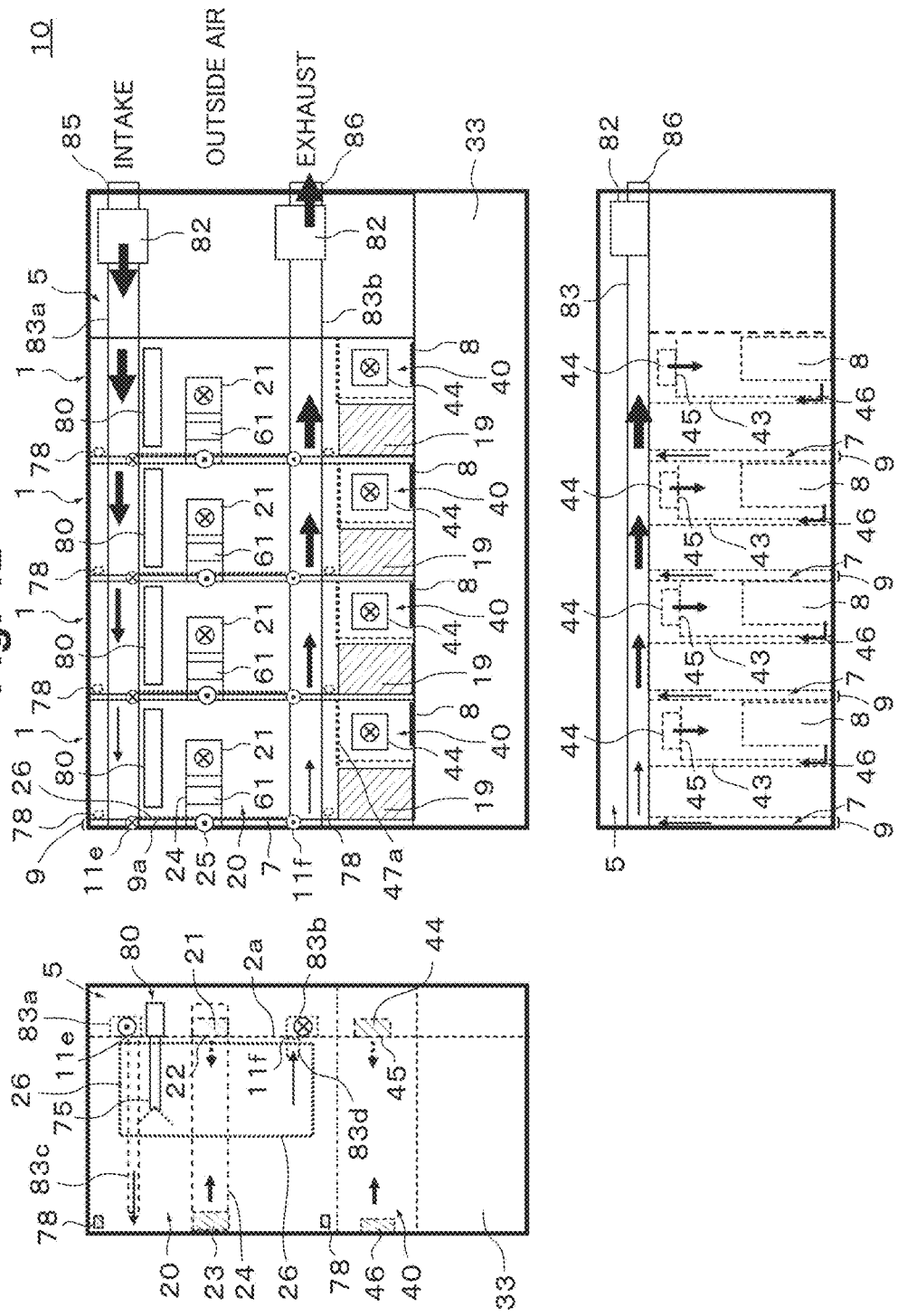
FIG. 42 A trihedral view showing an example of the sickroom and the nursing home (high grade type) including the system of highly clean rooms that is used in a sleeping state detection system according to a ninth embodiment.
Figure 43:
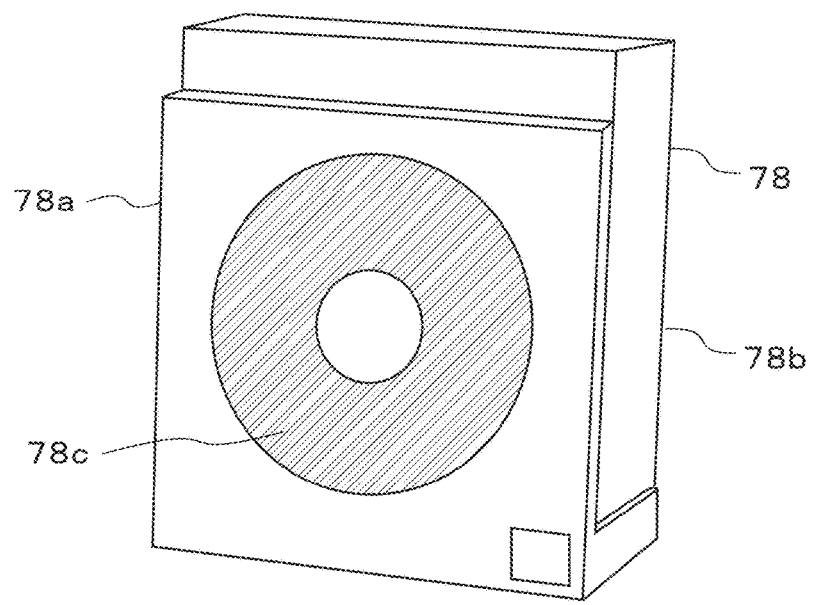
FIG. 43 A perspective view showing an example of the low flow rate fan filter unit.

FIG. 42 shows the system of highly clean rooms 10 used in a sleeping state detection system according to the ninth embodiment. The system of highly clean rooms 10 has a configuration in which plural rooms 1 are connected as the same as the system of highly clean rooms 10 shown in the fourth embodiment. As shown in FIG. 42, in the system of highly clean rooms 10, four rooms 1 having the main room 20 and the anteroom 40 are connected along the hallway 33, but the coupling number is not limited to four, can be selected appropriately. The lateral wall of the left side of the room 1 is the wall 9 having the structure that encloses the internal space. Also, each room 1 is provided with the anteroom 40, so persons can move in the main room 20 without breaking cleanliness of the main room 20.

The room 1 has the anteroom 40 and the main room 20. The anteroom 40 has the doorway 8 at the lateral wall facing the hallway 33 and is in contact with the utility space 19 such as the prefabricated bath etc., and is formed by partitioning the inside of the room 1 by the shoji door 47a which is provided facing the doorway 8 each other. The lateral wall of the left side in FIG. 42 of each room 1 has the structure of the wall 9 shown in the first embodiment. Also, as understood from the structure shown in FIG. 42, the wall 9 used here is the type of FIG. 8B moving fresh air to the internal space 7 along the gravitation direction. And the outside air introduction opening 11e and the inside air exhaust opening 11f are provided at the top plane of the wall 9 and the top plane of the wall 9 is provided to be on the same plane with the ceiling wall of the 2a. As the constitution of the anteroom 40, it is possible to select the constitution of the anteroom 40 shown in the third embodiment appropriately. Because parts of the constitution of the inside of the room 1 other than the anteroom 40 constitute the main room 20, by providing the anteroom 40 inside the room 1, persons can move in the main room 20 without deteriorating cleanliness of the main room 20. The constitution of the main room 20 has the same constitution as the room 1 (the living space 6) according to the ninth embodiment shown in FIG. 44 and, for example, the photocatalyst 61 is further provided inside the gas flow path 24. Whether or not installing the photocatalyst can be selected appropriately according to the usage of the main room 20. With respect to the constitution of the main room 20 on the side of the room 1, specifically, the fan filter unit 21 is provided in the space 5 between the roof and the ceiling of the main room 20 so that air can be blown into the main room 20, a part of the wall 9a separating the main room 20 from the internal space 7 is constituted of the gas exchange membrane 26 and air inside the internal space 7 and air inside the main room 20 can be exchanged.

An outside air introduction duct 83a and an exhaust duct 83b are provided on the ceiling wall 2a on the side of the space 5 between the roof and the ceiling in the main room 20. The outside air introduction duct 83a is provided traversing the four connected rooms 1. An outside air absorption opening 85 which is the other end of the outside air introduction duct 83a has a ventilation mechanism 82 such as a sirocco fan etc. The exhaust duct 83b is provided as the same as the outside air introduction duct 83a and an exhaust opening 86 which is the end of the exhaust duct 83b on the side of the outside air absorption opening 85 has the ventilation mechanism 82 such as a sirocco fan etc. Also, the outside air introduction duct 83a and the exhaust duct 83b are provided in parallel a constant distance apart. The outside air introduction duct 83a is provided so as to connect together the outside air introduction opening 11a of each room 1 airtightly in order and the tube 83c for introducing outside air into the internal space 7 is connected with the outside air introduction opening 11e of each room 1. Also, the exhaust duct 83d is provided so as to connect together the inside air exhaust opening 11f of each room 1 airtightly in order and the tube 83d for exhausting gases from the internal space 7 is connected with the inside air exhaust opening 11f of each room 1. By constituting like this, outside air absorbed from the air absorption opening 85 passes through the outside air introduction duct 83a and is introduced into the internal space 7 of the wall 9 of each room 1 through the outside air introduction opening 11e in order. The inside air exhausted via the inside air exhaust opening 11f from the internal space 7 of the wall 9 of each room 1 is exhausted in order, and exhausted from the exhaust opening 86 through the exhaust duct 83b. Also, the tube 83c is constituted so that the end opening to be the outside air introduction opening is in the vicinity of the floor of the room 1, and the tube 83d is constituted so that the end opening to be the inside air exhaust opening is in the vicinity of the ceiling wall 2a. For example, when air introduced from the outside air absorption opening 85 is warm in summer etc., the constitution enhances the air circulation efficiency. In addition, for example, by reversing the length of the tube 83c and the length of the tube 83d, it is possible to obtain the structure capable of enhancing the air circulation efficiency when air introduced from the outside air absorption opening 85 is cold in winter etc. Specifically, the latter is the recommended arrangement because the parallel component of the velocity vector of the two air currents on both sides of the gas exchange membrane 26 becomes large. The outside air introduction part and the exhaust part inside the internal space 7 are selected at least a part from the region in which the gas flow path 24 is not formed inside the internal space 7.

The two fan filter units 78 are placed at the two places of the corner on the internal wall 9a inside the main room 20. The fan filter unit 78 is not essentially limited as far as its flow rate is smaller than at least a few of the flow rate of the fan filter unit 21, preferably less than a single digit and it has the dust removal ability and the ventilation ability. For example, denoting the volume of the main room 20 as V, it is preferably equal to or more than V/2 h [m³/h], and it is preferable to be a small flow fan filter unit of which air supply amount is 15 [m³/h] or more and 66 [m³/h] or less. As the small flow fan filter unit, for example, the Blue air Mini (the name of article) made by Blue air Ltd. is preferable. FIG. 53 is the perspective view showing the overview of the small flow fan filter unit. The small flow fan filter unit is constituted by combining the filter part 78b to the main part 78a and a ventilation mechanism is provided inside the main part 78a so that air absorbed from the back part of the filter part 78b is made to blow out from the front surface of the main part 78a. The small flow fan filter unit has the outer size 160 [mm] in width, 95 [mm] in depth, 190 [mm] in height, 0.7 kg (including a filter) in weight, the sound upon operation is 44 [dB], the supply amount of clean air is 29 [m³/h] and the rated consuming power is 5 [W]. Also, it is possible to change the installation position of the small flow fan filter unit inside the main room 20. Also, by installing the two fan filter units 78 on the border of the internal space 7 and the main room 20 and by installing one fan filter unit 78 so as to introduce outside air and the other fan filter unit 78 so as to exhaust inside air, it is possible to realize a ventilation mechanism between the main room and the outside. In this case, because one of the two fan filter units 78 absorbs the outside air and the other exhausts the inside air, it is possible to improve the lifetime and the efficiency of the fan filter unit 78 for inside air exhaust more than several hundred times compared with the case of using it in the open system. Also, the two fan filter units 78 may be installed between the main room 20 and a hallway, the outdoor, etc. By this, for example, "the rotary exchange" of the exchange of these small flow fan filter units after time has passed is possible. That is, it is recommended to replace the aged ventilation mechanism 82 of the outside air absorption opening 85 side with the fan filter unit 78 which is used for inside air exhaust until then and install the new fan filter unit 78 for the inside air exhaust. The others are the same as any of the first to the eighth embodiments.

According to the ninth embodiment, the same advantages as any of the first to the seventh embodiments can be obtained. In addition, because the plural rooms 1 are connected, the outside air introduction part of each room 1 is connected by a duct, the exhaust part of each room 1 is connected by another duct and a ventilation mechanism is provided to each duct, the air introduction to the connected plural rooms 1 and the inside air exhaust can be made collectively. Also, for the apartment houses, nursing homes, hospitals, or paint factories which have many rooms 1, as necessary, by selecting the constitution of the system of highly clean rooms 10 appropriately, further by installing the gas exchange device 80, it is possible not only to obtain a lower dust space easily, but also to obtain a super highly clean space that can exhaust and decompose chemical substance, bad-smelling organic solvent particles, etc. in a short time. By constituting the system of highly clean rooms 10 like this, it is possible to speed up the restoration of health of patients in hospitals, or to reduce the risk of getting cancer of the bile duct etc. of people who engage in painting works etc.

10. The Tenth Embodiment

Figure 44:
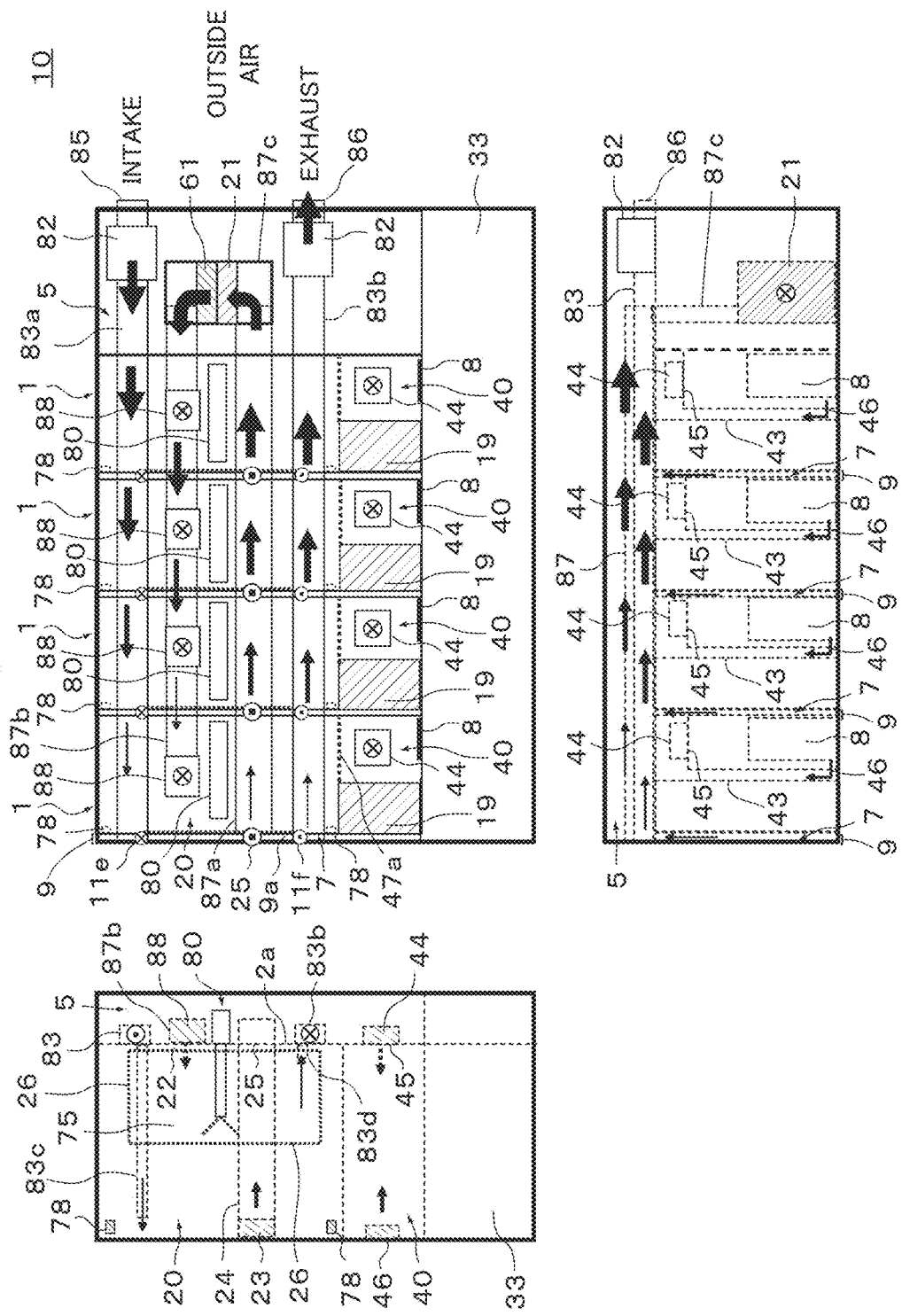
FIG. 44 A trihedral view showing an example of the sickroom and the nursing home (medium grade type) including the system of highly clean rooms that is used in a sleeping state detection system according to a tenth embodiment.

FIG. 44 shows the system of highly clean rooms 10 according to the tenth embodiment. The system of highly clean environment 10 is a central system in which the living spaces of the connected plural rooms 1 of the system of highly clean rooms 10 shown in the ninth embodiment communicate, and one or a few fan filter units 21 are arranged at the connected part.

As shown in FIG. 44, the system of highly clean environment 10 is constituted of the connected four rooms 1 each of which has the main room 20 and the anteroom 40, and has basically the same constitution as the system of highly clean environment 10 shown in FIG. 42. On the ceiling wall 2a on the side of the space 5 between the roof and the ceiling, a connection duct 87c which connects an absorption side duct 87a and a blow side duct 87b are further installed. The absorption side duct 87a and the blow side duct 87b are provided facing each other a constant distance apart, and provided in the region sandwiched between the outside air introduction duct 83a and the exhaust duct 83b. In this case, the absorption side duct 87a and the blow side duct 87b are preferably provided away from the outside air introduction duct 83a and the exhaust duct 83b, but it is not limited to this.

The blow opening 22 which is the opening provided in the ceiling wall 2a is provided inside the internal space 7 of the wall 9 of each room 1, and the absorption side duct 87a is provided so as to connect the blow opening 22 of each room 1 in order. Also, it is also possible to provide a ventilation part 88 every each room 1 in the upstream part of the blow opening 22 so as to send air to the room 1, and in that case, the absorption side duct 87a connects the ventilation part 88 of each room 1 airtightly in order. Also, in the top wall of the wall 9 constituting each room 1, in addition to the outside air introduction opening 11e and the inside air exhaust opening 11f, the opening 25 is provided. The opening 25 is provided between the outside air introduction opening 11e and the inside air exhaust opening 11f, and the opening 25 and the opening 23 provided in the inner wall 9a are connected by the gas flow path 24 airtightly. The absorption side duct 87a is provided so as to connect the opening 25 of each room 1 in order. The downstream side end of the absorption side duct 87a and the upstream side end of the blow side duct 87b are connected by the connection duct 87c provided outside the room 1, and the photocatalyst 61 and the fan filter unit 21 are provided inside the connection duct 87c. The fan filter unit 21 is constituted, for example, of a central air filtering device, a central air cleaning device, etc., however, for example, it is preferable to use the gas exchange device 80. With respect to the photocatalyst 61, for example, a filter using photocatalytic materials or an air cleaning device using the filter is preferable. Also, the fan filter unit 21 is preferably, for example, a large capacity fan filter unit, and for example, in the case of the main room 20 having the volume of 45 m$^3$, it is preferable that the air supply rate is 4 [m$^3$/min] or more and 22 [m$^3$/min] or less. Also, air is sent in order to the absorption side duct 87a through the gas flow path 24 stored in the wall 9 provided at the end of each room 1, then air is sent out inside the duct 87a from the all rooms 1 to join together, and therefore enters inside the connection duct 87c and changes its direction to 90 degrees. After entering inside the connection duct 87c, air passes through the fan filter unit 21 and the photocatalyst 61 in order, enters inside the blow side duct 87b, further changes its direction to 90 degrees, and gases are sent to each main room 20 from the blow opening 22 provided in each room 1. At this time, the gas flow path 24 to be connected to the upstream end of the absorption side duct 87a and the blow opening 22 to be connected with the downstream end of the blow side duct 87b are provided inside the same main room 20. And in each room 1, the opening 23 at the lower end of the gas flow path 24 for introducing the inside air of the room and the blow opening 22 for returning again all of the absorbed air after cleaning and subsequent processing by the fan filter unit 21 and the photocatalyst 61 as a pair and the room 1 as a whole is constructed to be closed. By constituting like this, the opening 23 at the lower end of the gas flow path 24 which is an absorption opening provided in each room 1 respectively and the blow opening 22 communicate with the fan filter unit 21 provided outside the room 1. From this, the 100% circulation feedback system can be provided to the four rooms 1 with one fan filter unit 21 at the same time, and the one fan filter unit 21 can supply clean air to the plural rooms 1.

Figure 45:
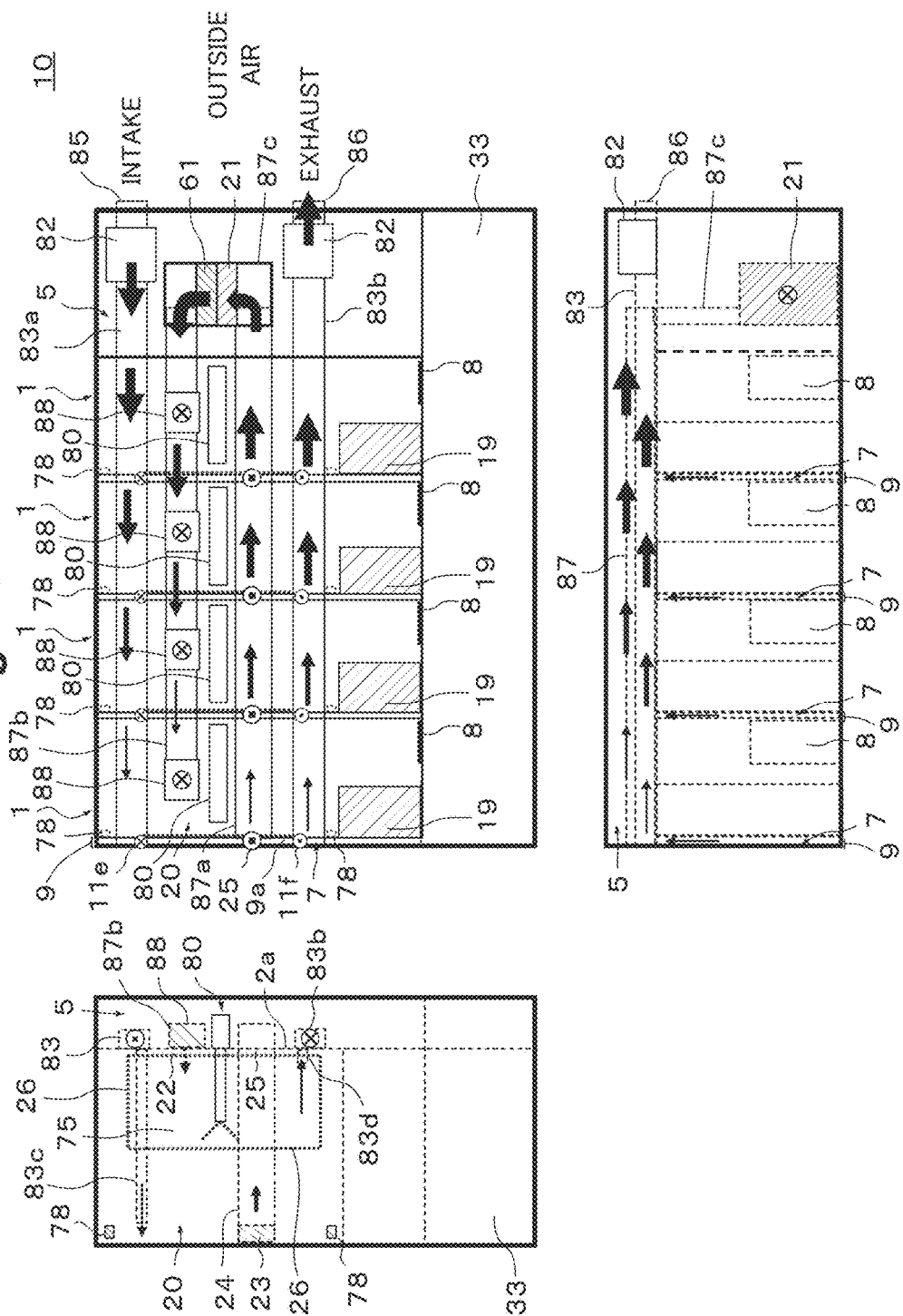
FIG. 45 A trihedral view showing an example of the sickroom and the nursing home (entry type) including a modification of the system of highly clean rooms that is used in the sleeping state detection system according to the tenth embodiment.

FIG. 45 shows a modification of the system of highly clean rooms 10 according to the tenth embodiment. The system of highly clean rooms 10 corresponds to the system of highly clean rooms 10 shown in FIG. 44 in which the constitution of the anteroom 40 is omitted. The other structure can be constituted as the same as the system of highly clean rooms 10. The configuration is a suitable system when the frequency of moving in the room 1 is small and the time of stay inside the living space is relatively long. The others are the same as any of the first to the ninth embodiments.

According to the tenth embodiment, the same advantages as any of the first to the ninth embodiments can be obtained. In addition, it is possible to provide the 100% circulation feedback system in the plural rooms 1 with one fan filter unit 21 at the same time and supply clean air to the plural rooms 1 by the one fan filter unit 21 and it is possible to make cleaning of the plural rooms 1 all together by the central system.

Example 1 of the Sleeping State Detection System

Figure 46A:
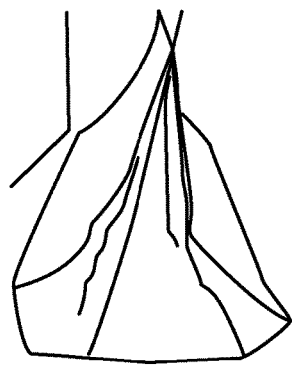
FIG. 46A A substitute picture for a drawing showing the tent-like structure made of the gas exchange membrane.
Figure 46B:
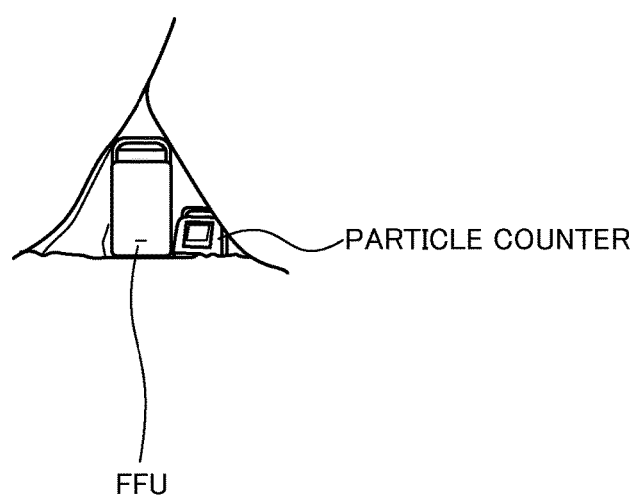
FIG. 46B A substitute picture for a drawing showing the tent-like structure made of the gas exchange membrane.
Figure 47:
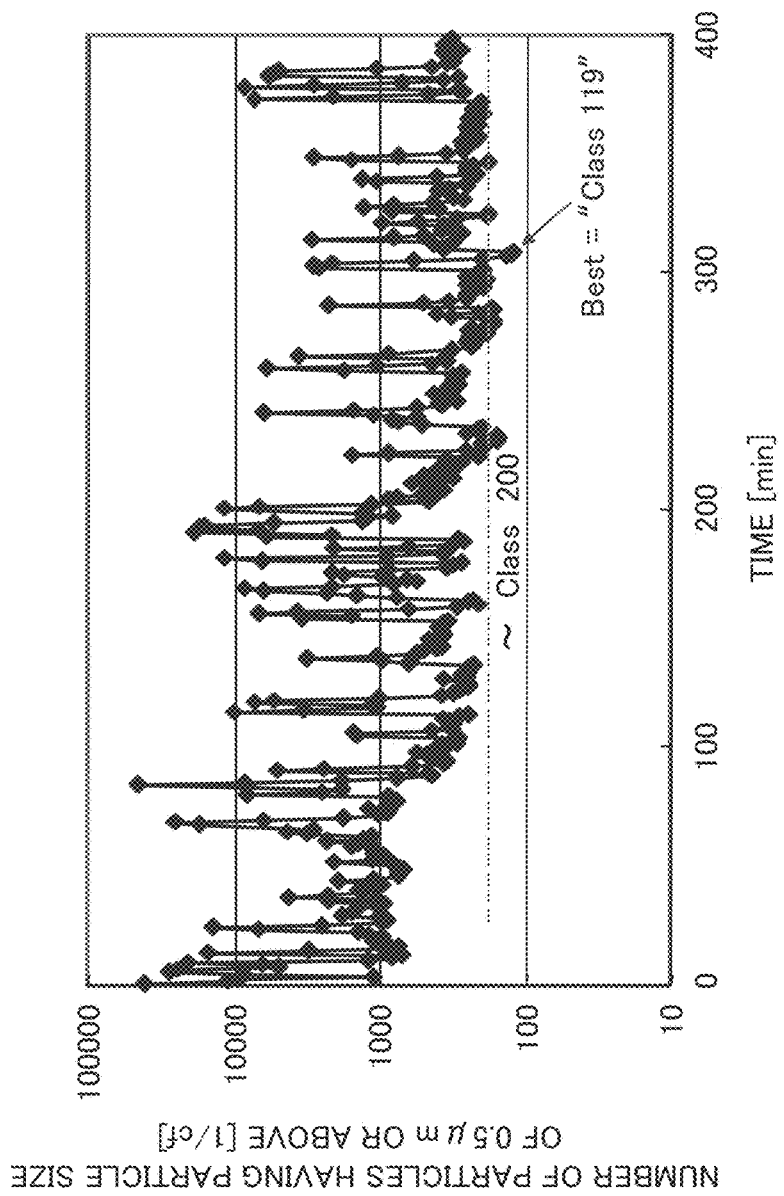
FIG. 47 A schematic view showing the result of measurement of the change over time in the total number of dust particles having the particle size of 0.5 μm or above inside the tent-like structure shown in FIG. 46A and FIG. 46B.

As shown in FIG. 46A and FIG. 46B, a tent-like structure, all of which consist of the gas exchange membrane 26, was made and placed on the floor of a bedroom of an apartment house. A subject slept on a futon spread on the floor. This case corresponds to a case where the area A of the tent-like structure becomes the maximum value in the equation (16), which is permitted structurally for the tent-like structure. Otherwise, in order to give equal gas exchange ability, the gas exchange box shown in FIG. 35 to FIG. 38 may be placed outside the closed space of the tent (as shown by an example of connection of the gas exchange box and the closed space and the room). In this case, the gas exchange ability of the tent itself is not necessary. This case is preferable when the tent-like structure is made of vinyl material (which is waterproof but not breathable) and the subject sleeps in it. The area A of the gas exchange membrane 26 has the value that satisfies the condition of the necessary area described before and obtain a suitable ability of supplying oxygen inside the tent. A fan filter unit (FFU) and a dust counter (particle counter) were placed on the floor inside the tent. As the fan filter unit, an air cleaning device (F-PDH35) made by Panasonic Corporation was used. The inside of the tent was cleaned by the fan filter unit and the number density of dust particles inside the tent was measured by the dust counter while the subject slept. The result is shown in FIG. 47. As shown in FIG. 47, while keeping a sufficient oxygen concentration by the good oxygen permeability, the subject can sleep comfortably in a good clean environment in which the number of dust particles decreased below the level of US 209D Class1000 on the average during about seven hours sleep (especially, when the subject sleeps soundly without tossing about, the number of dust particles decrease to the level of about US 209D Class100).

Spikes seen in FIG. 47 are caused by dusts whirled by tossing about etc. From the frequency spectrum of a series of spikes, it is possible to suppose the health state of the sleeping subject etc. When the system is used for a special nursing home for the aged etc., it is possible not only to confirm the safety of users of the system of highly clean rooms 10 but also to monitor persons under medical treatment with a high degree of accuracy from a remote place, including a deviation etc. from usual features during sleep (while taking privacy into consideration suitably because it is not an analysis based on image information etc.). As far as the present inventors know, it was found for the first time that it is possible to detect the sleeping state of the subject by measuring the density of dust particles during sleep.

Example 2 of the Sleeping State Detection System

Figure 48A:
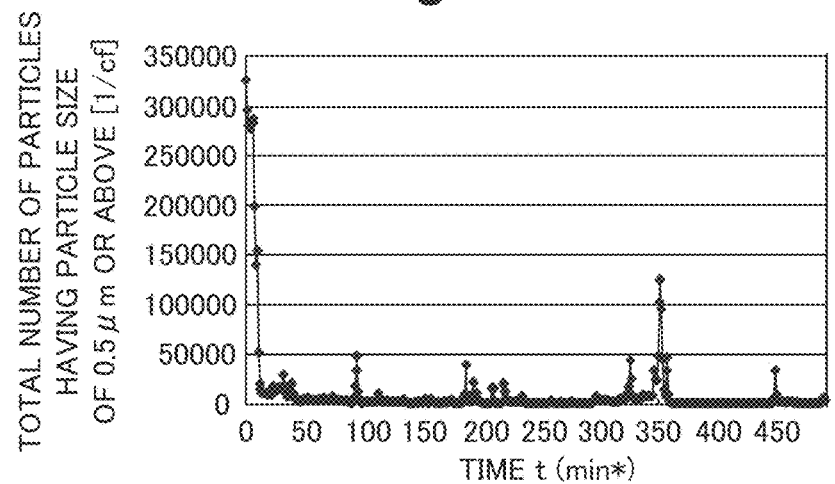
FIG. 48A A schematic view showing the result of measurement of the change over time in the total number of dust particles having the particle size of 0.5 μm or above inside the tent-like structure shown in FIG. 46A and FIG. 46B on the first day in the first continuous sleeping test while a subject sleeps inside the tent-like structure.
Figure 48B:
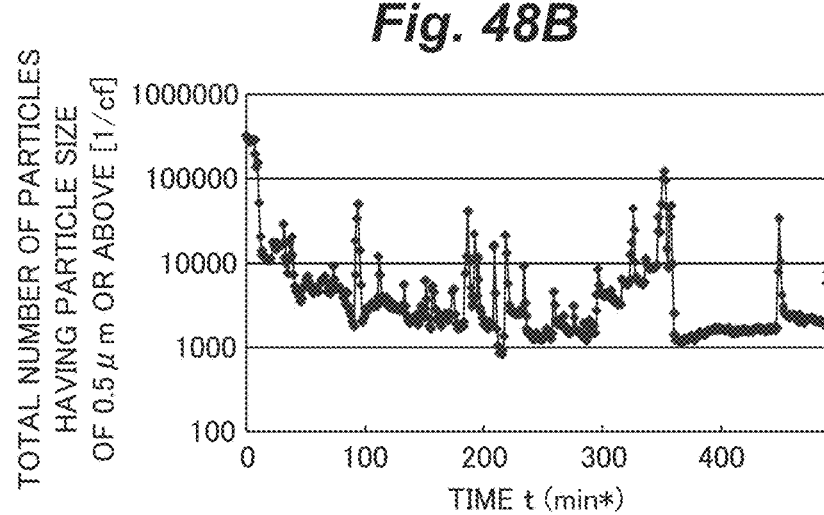
FIG. 48B A schematic view showing the result of measurement of the change over time in the total number of dust particles having the particle size of 0.5 μm or above inside the tent-like structure shown in FIG. 46A and FIG. 46B on the first day in the first continuous sleeping test while the subject sleeps inside the tent-like structure.
Figure 48C:
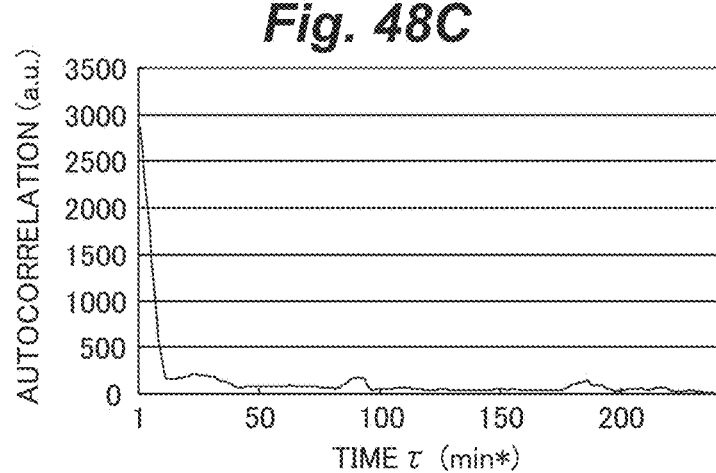
FIG. 48C A schematic view showing the autocorrelation calculated by using the autocorrelation function from the result of measurement shown in FIG. 48A.
Figure 49A:
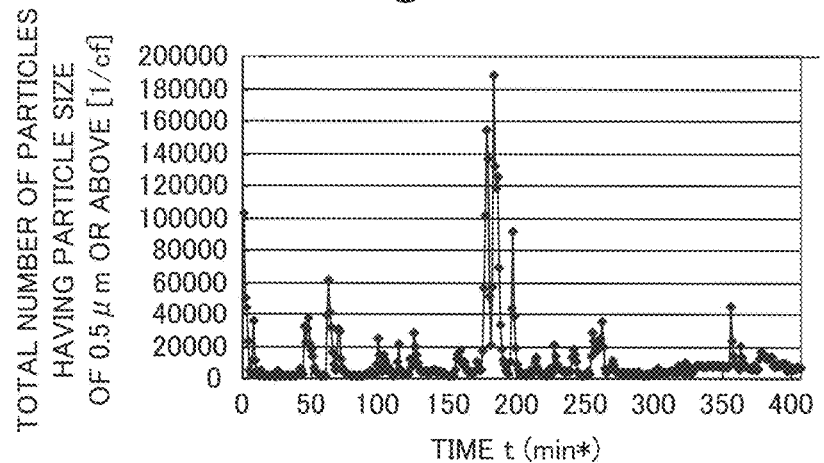
FIG. 49A A schematic view showing the result of measurement of the change over time in the total number of dust particles having the particle size of 0.5 μm or above inside the tent-like structure shown in FIG. 46A and FIG. 46B on the second day in the first continuous sleeping test while the subject sleeps inside the tent-like structure.
Figure 49B:
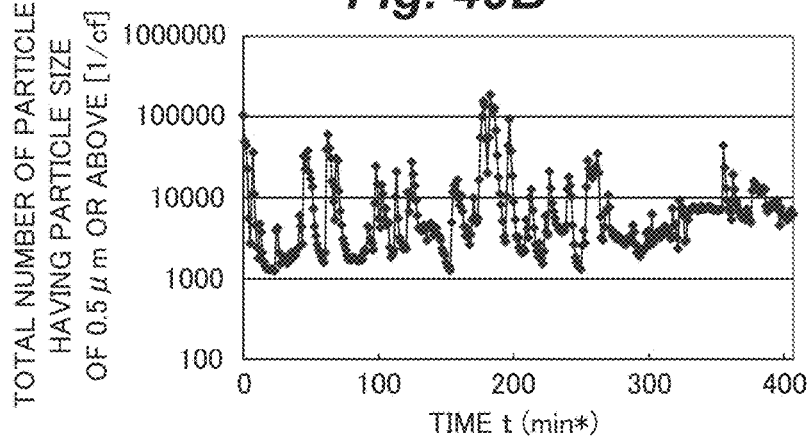
FIG. 49B A schematic view showing the result of measurement of the change over time in the total number of dust particles having the particle size of 0.5 μm or above inside the tent-like structure shown in FIG. 46A and FIG. 46B on the second day in the first continuous sleeping test while the subject sleeps inside the tent-like structure.
Figure 49C:
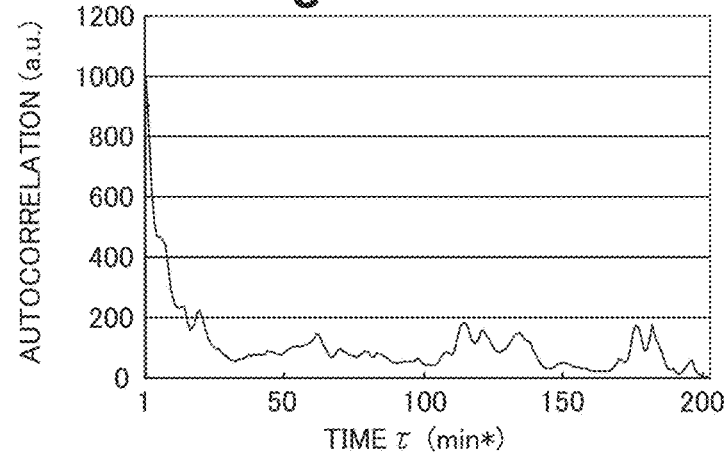
FIG. 49C A schematic view showing the autocorrelation calculated by using the autocorrelation function from the result of measurement shown in FIG. 49A.
Figure 50A:
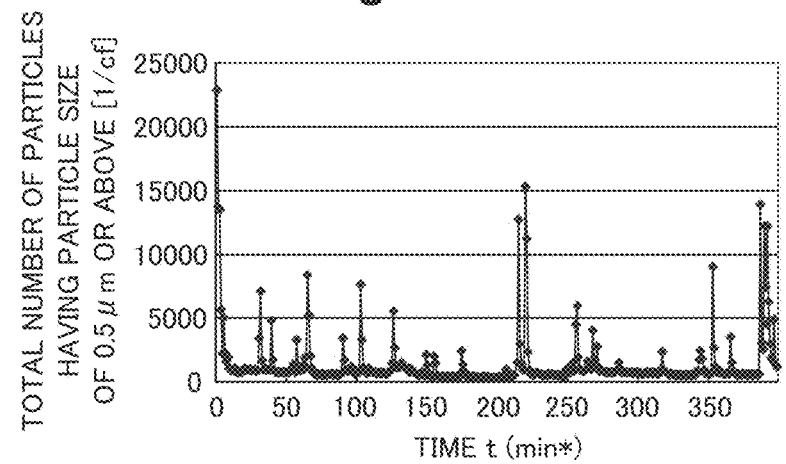
FIG. 50A A schematic view showing the result of measurement of the change over time in the total number of dust particles having the particle size of 0.5 μm or above inside the tent-like structure shown in FIG. 46A and FIG. 46B on the third day in the first continuous sleeping test while the subject sleeps inside the tent-like structure.
Figure 50B:
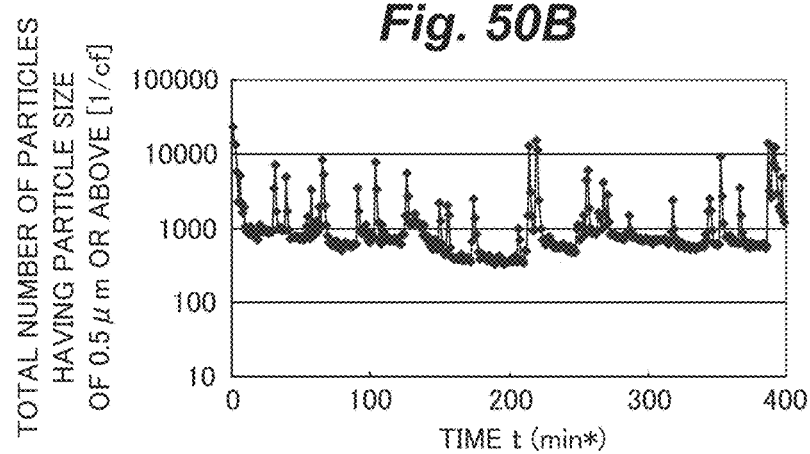
FIG. 50B A schematic view showing the result of measurement of the change over time in the total number of dust particles having the particle size of 0.5 μm or above inside the tent-like structure shown in FIG. 46A and FIG. 46B on the third day in the first continuous sleeping test while the subject sleeps inside the tent-like structure.
Figure 50C:
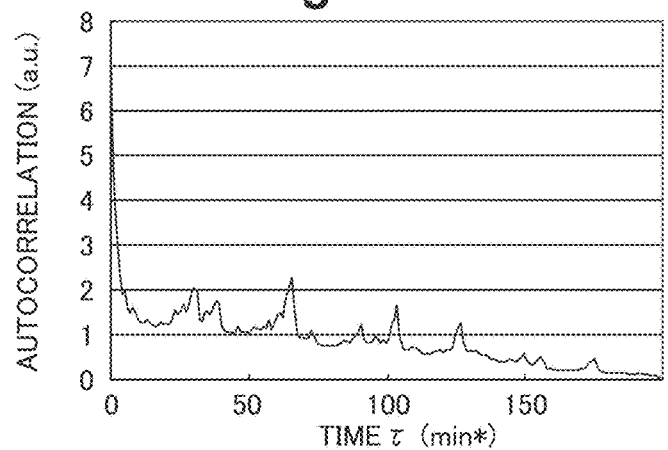
FIG. 50C A schematic view showing the autocorrelation calculated by using the autocorrelation function from the result of measurement shown in FIG. 50A.
Figure 51A:
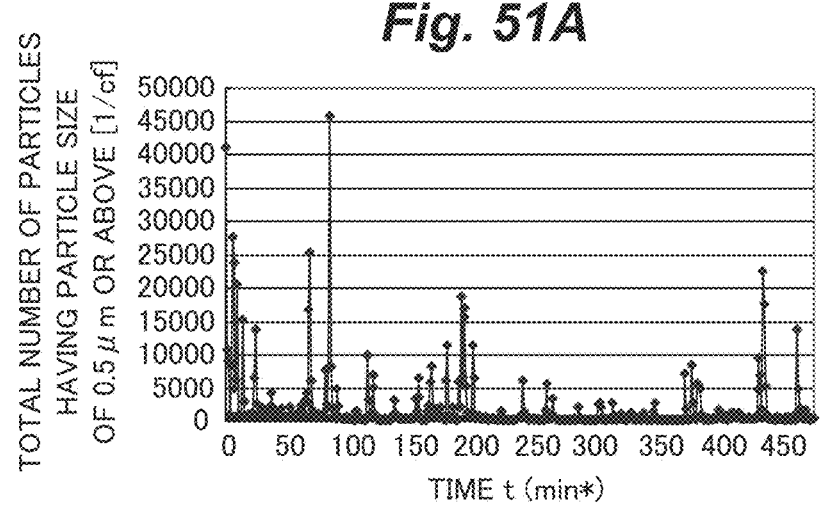
FIG. 51A A schematic view showing the result of measurement of the change over time in the total number of dust particles having the particle size of 0.5 μm or above inside the tent like structure shown in FIG. 46A and FIG. 46B on the fourth day in the first continuous sleeping test while the subject sleeps inside the tent-like structure.
Figure 51B:
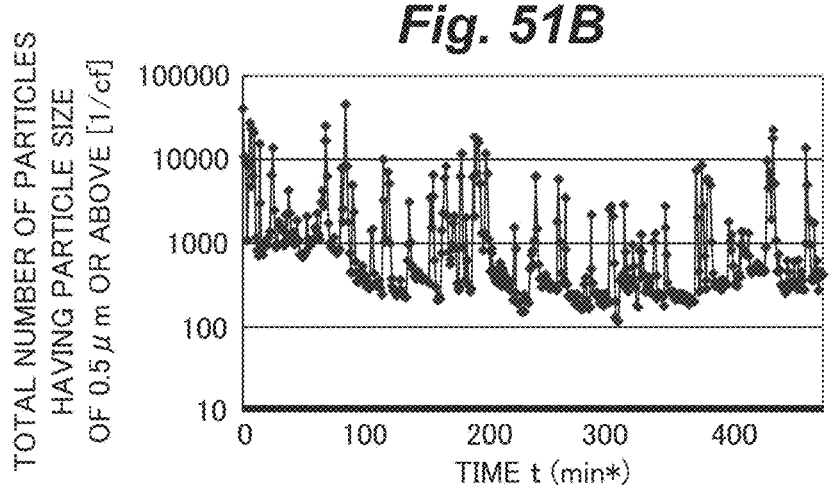
FIG. 51B A schematic view showing the result of measurement of the change over time in the total number of dust particles having the particle size of 0.5 μm or above inside the tent-like structure shown in FIG. 46A and FIG. 46B on the fourth day in the first continuous sleeping test while the subject sleeps inside the tent-like structure.
Figure 51C:
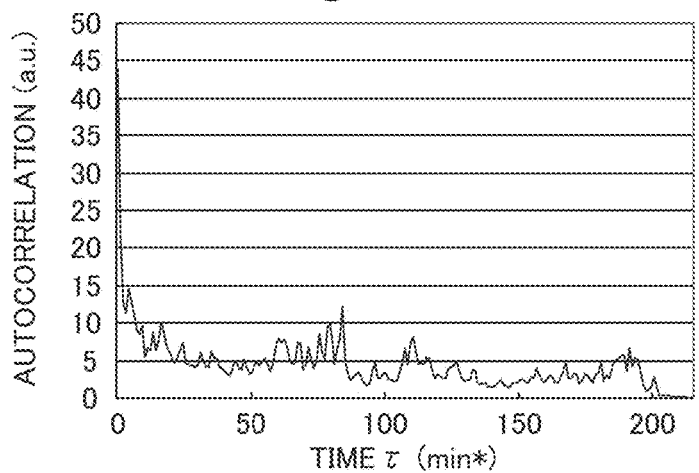
FIG. 51C A schematic view showing the autocorrelation calculated by using the autocorrelation function from the result of measurement shown in FIG. 51A.
Figure 52A:
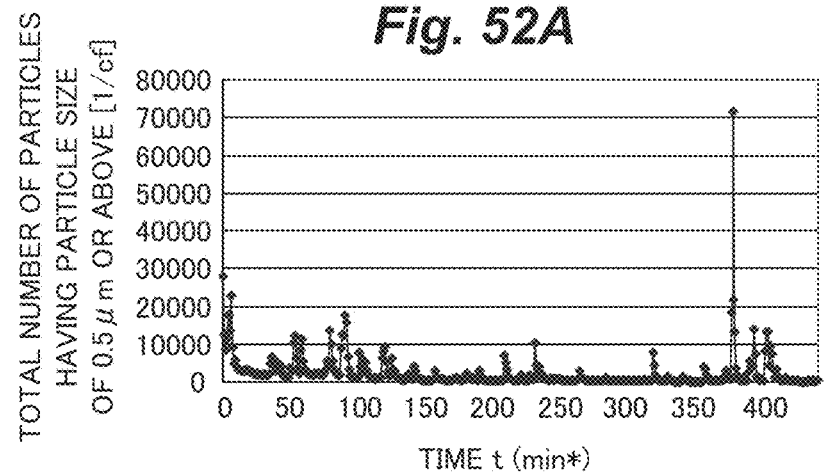
FIG. 52A A schematic view showing the result of measurement of the change over time in the total number of dust particles having the particle size of 0.5 μm or above inside the tent-like structure shown in FIG. 46A and FIG. 46B on the fifth day in the first continuous sleeping test while the subject sleeps inside the tent-like structure.
Figure 52B:
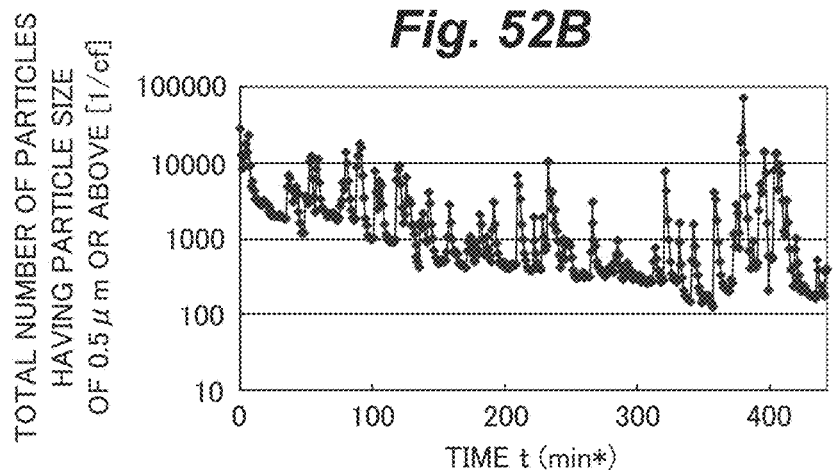
FIG. 52B A schematic view showing the result of measurement of the change over time in the total number of dust particles having the particle size of 0.5 μm or above inside the tent-like structure shown in FIG. 46A and FIG. 46B on the fifth day in the first continuous sleeping test while the subject sleeps inside the tent-like structure.
Figure 52C:
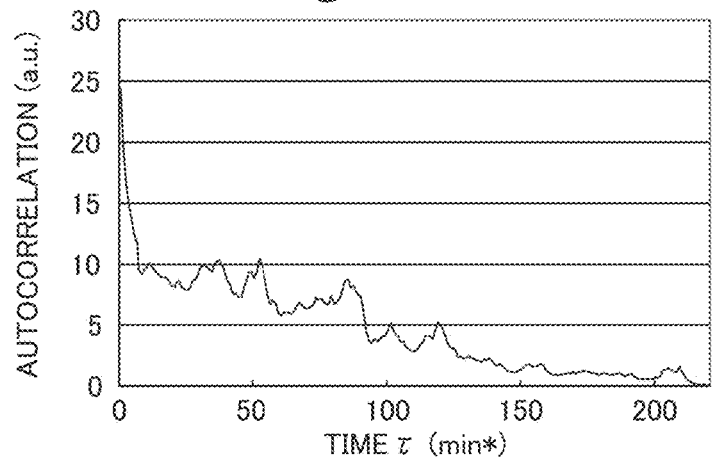
FIG. 52C A schematic view showing the autocorrelation calculated by using the autocorrelation function from the result of measurement shown in FIG. 52A.
Figure 53A:
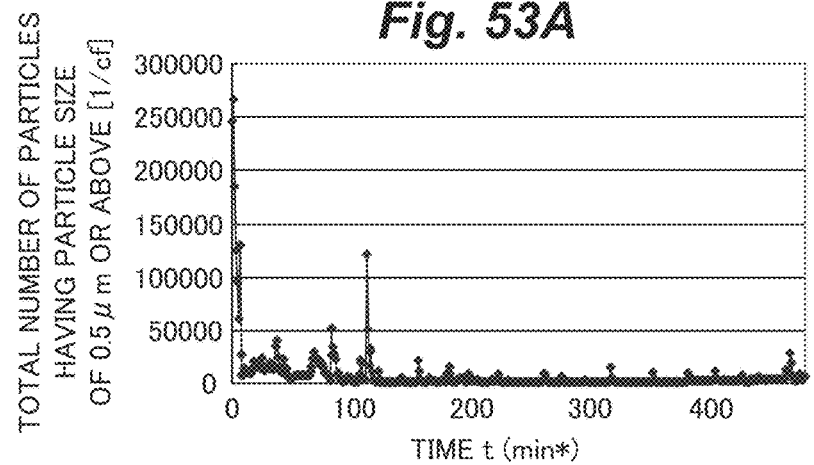
FIG. 53A A schematic view showing the result of measurement of the change over time in the total number of dust particles having the particle size of 0.5 μm or above inside the tent-like structure shown in FIG. 46A and FIG. 46B on the sixth day in the first continuous sleeping test while the subject sleeps inside the tent-like structure.
Figure 53B:
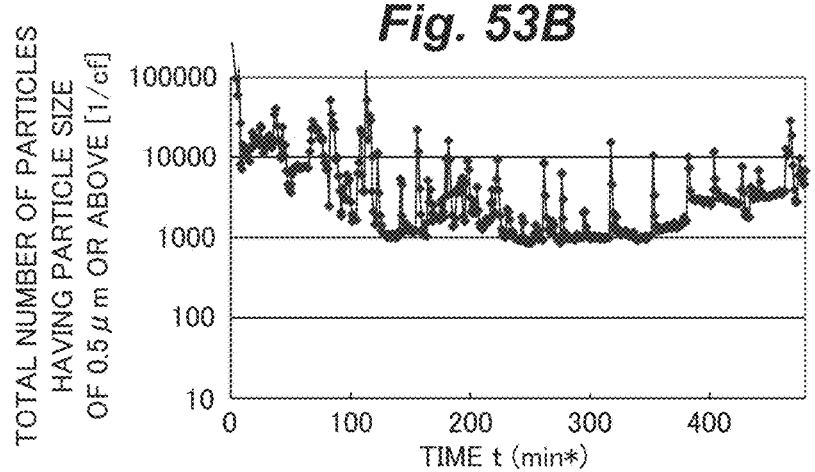
FIG. 53B A schematic view showing the result of measurement of the change over time in the total number of dust particles having the particle size of 0.5 μm or above inside the tent-like structure shown in FIG. 46A and FIG. 46B on the sixth day in the first continuous sleeping test while the subject sleeps inside the tent-like structure.
Figure 53C:
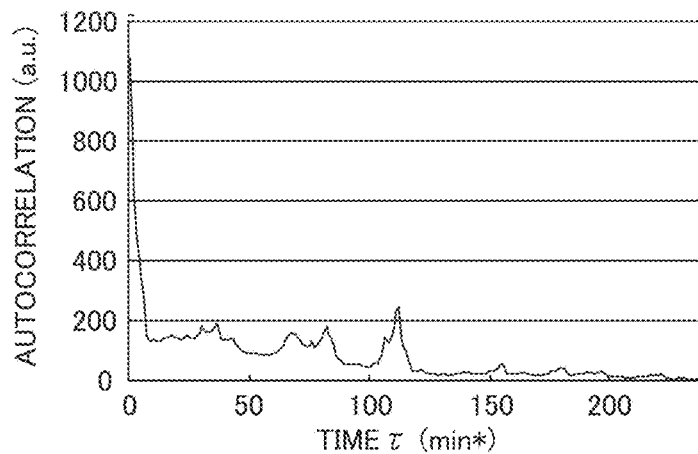
FIG. 53C A schematic view showing the autocorrelation calculated by using the autocorrelation function from the result of measurement shown in FIG. 53A.
Figure 54A:
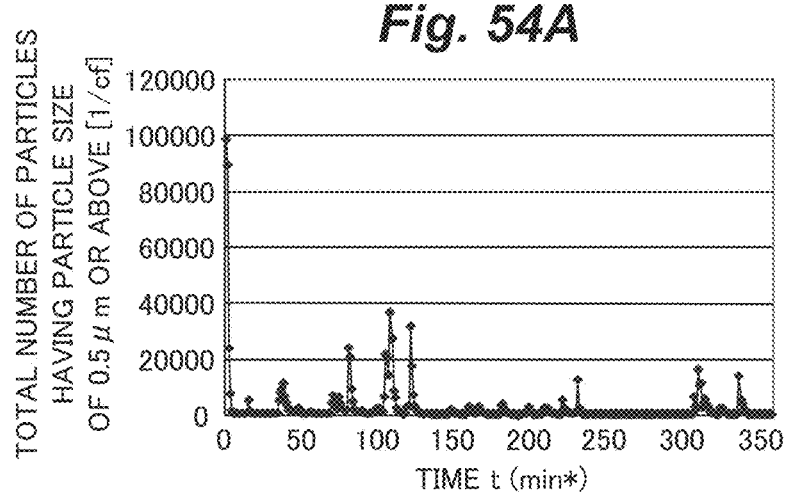
FIG. 54A A schematic view showing the result of measurement of the change over time in the total number of dust particles having the particle size of 0.5 μm or above inside the tent-like structure shown in FIG. 46A and FIG. 46B on the first day in the second continuous sleeping test while the subject sleeps inside the tent-like structure.
Figure 54B:
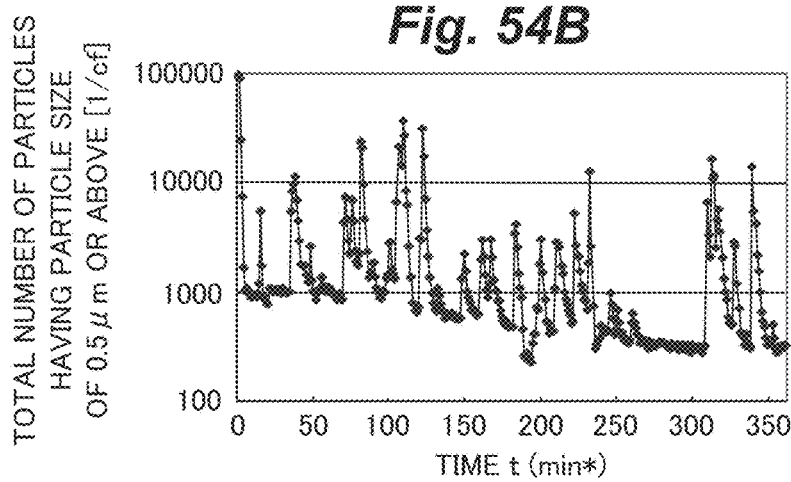
FIG. 54B A schematic view showing the result of measurement of the change over time in the total number of dust particles having the particle size of 0.5 μm or above inside the tent-like structure shown in FIG. 46A and FIG. 46B on the first day in the second continuous sleeping test while the subject sleeps inside the tent-like structure.
Figure 54C:
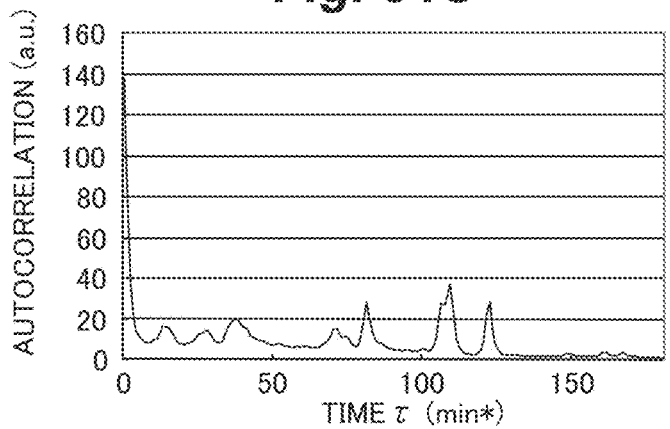
FIG. 54C A schematic view showing the autocorrelation calculated by using the autocorrelation function from the result of measurement shown in FIG. 54A.
Figure 55A:
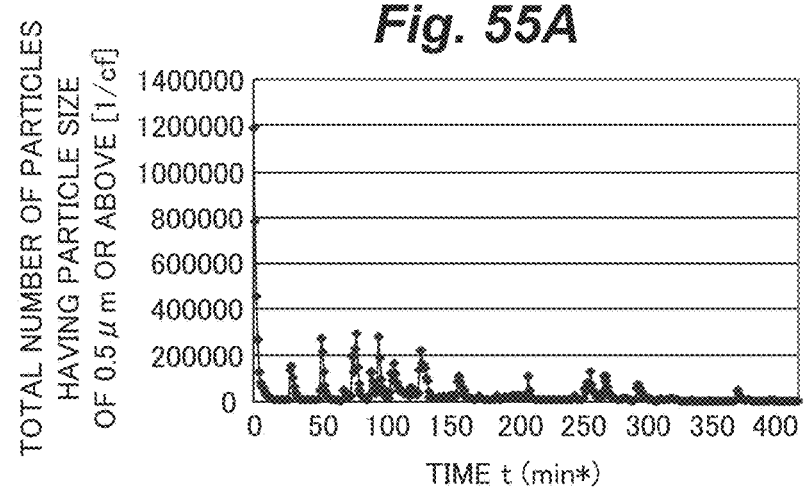
FIG. 55A A schematic view showing the result of measurement of the change over time in the total number of dust particles having the particle size of 0.5 μm or above inside the tent-like structure shown in FIG. 46A and FIG. 46B on the second day in the second continuous sleeping test while the subject sleeps inside the tent-like structure.
Figure 55B:
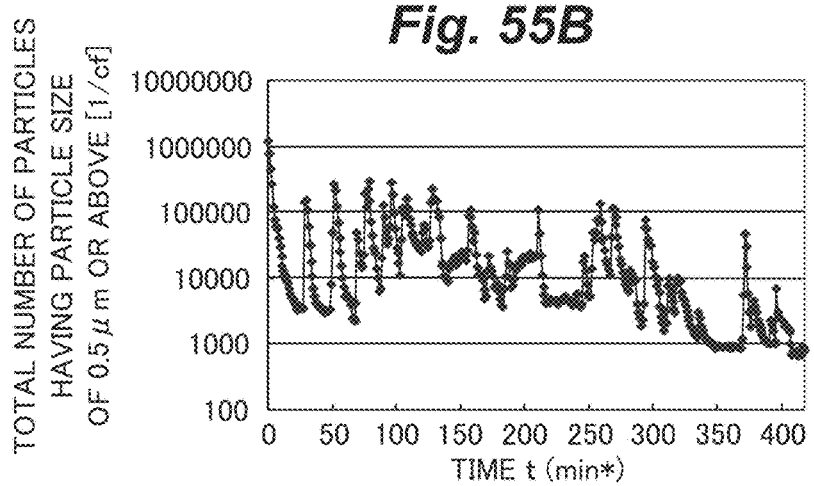
FIG. 55B A schematic view showing the result of measurement of the change over time in the total number of dust particles having the particle size of 0.5 μm or above inside the tent-like structure shown in FIG. 46A and FIG. 46B on the second day in the second continuous sleeping test while the subject sleeps inside the tent-like structure.
Figure 55C:
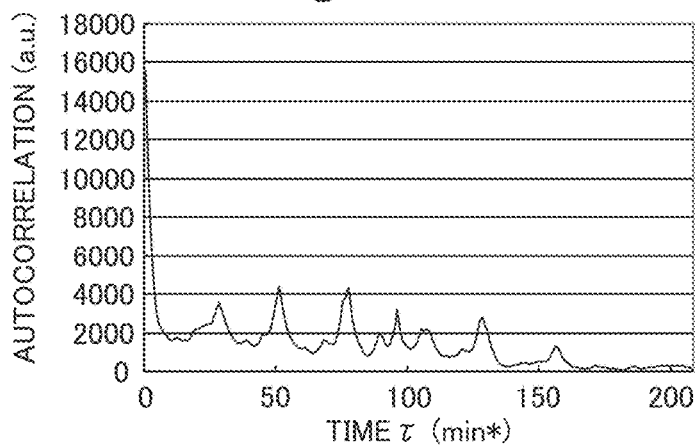
FIG. 55C A schematic view showing the autocorrelation calculated by using the autocorrelation function from the result of measurement shown in FIG. 55A.
Figure 56A:
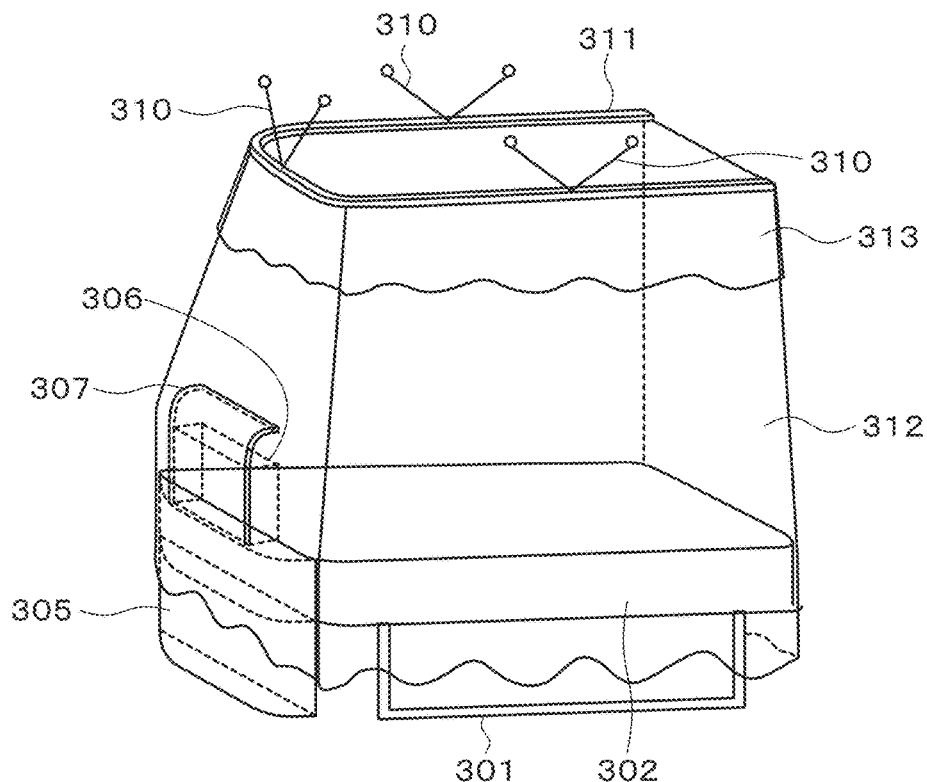
FIG. 56A A perspective view showing a highly clean simple bed system.
Figure 56B:
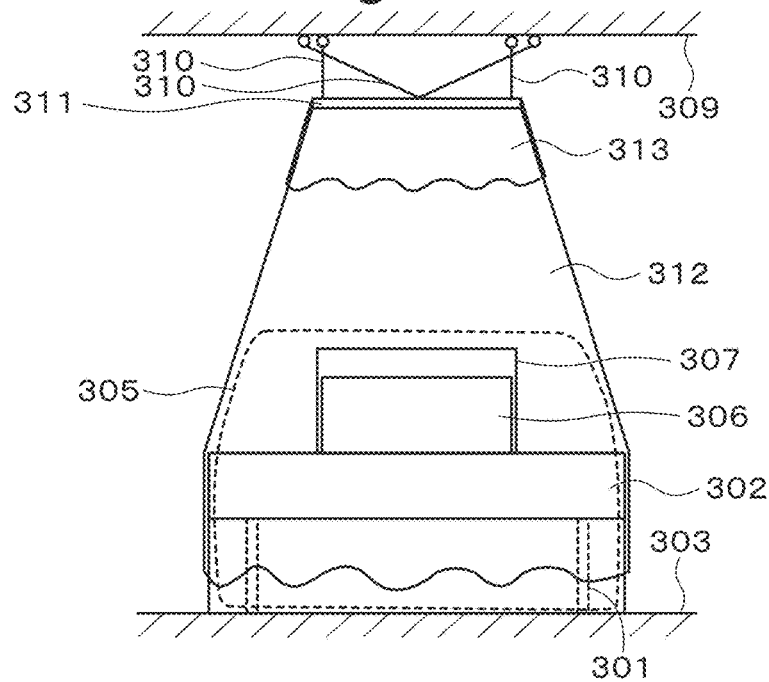
FIG. 56B A front view showing the highly clean simple bed system.
Figure 56C:
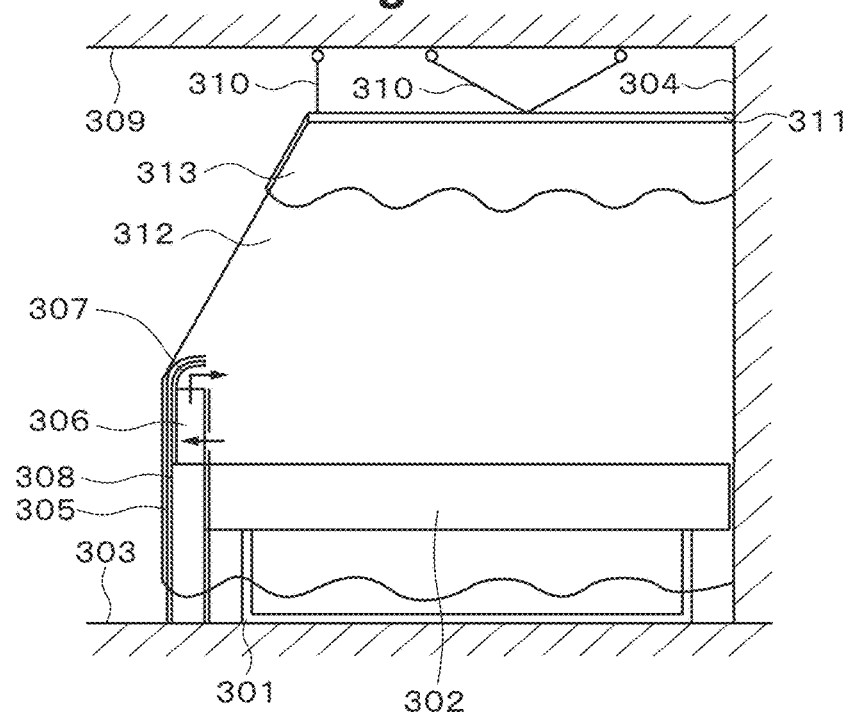
FIG. 56C A side view showing the highly clean simple bed system.
Figure 56D:
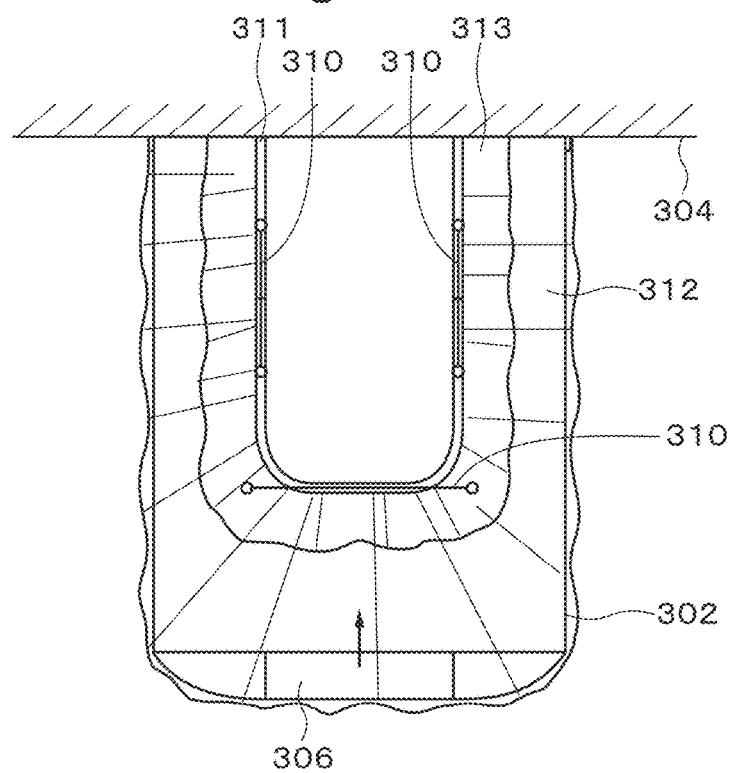
FIG. 56D A top view showing the highly clean simple bed system.

A sleeping test similar to the example 1 of the sleeping state detection system was carried out for a fixed period of time. The result is shown in FIG. 48A to FIG. 55C. FIG. 48A to FIG. 53C show the result of the first continuous sleeping test and FIG. 54A to FIG. 55C show the result of the second continuous sleeping test. The subject was the same as the example 1. Here, FIG. 48A, FIG. 49A, FIG. 50A, FIG. 51A, FIG. 52A, FIG. 53A, FIG. 54A and FIG. 55A show the change over time in the density of dust particles having particle size of 0.5 μm or above (1/cf) and FIG. 48B, FIG. 49B, FIG. 50B, FIG. 51B, FIG. 52B, FIG. 53B, FIG. 54B and FIG. 55B are enlarged views of areas with the low density of dust particles of FIG. 48A, FIG. 49A, FIG. 50A, FIG. 51A, FIG. 52A, FIG. 53A, FIG. 54A and FIG. 55A respectively. Horizontal axis of FIG. 48A, FIG. 49A, FIG. 50A, FIG. 51A, FIG. 52A, FIG. 53A, FIG. 54A, FIG. 55A, FIG. 48B, FIG. 49B, FIG. 50B, FIG. 51B, FIG. 52B, FIG. 53B, FIG. 54B and FIG. 55B show time t from the time of starting measurement (the time of starting sleeping, t=0). * of a unit min*of time t shows that though there is a 10-second internal for every 60-second measurement, data are plotted assuming that the horizontal axis shows the number of times of measurement (measurement time (minute)) for simplicity. FIG. 48A and FIG. 48B show data measured from May 31, 2013 to June 1 of the year. FIG. 49A and FIG. 49B show data measured from Jun. 1, 2013 to June 2 of the year. FIG. 50A and FIG. 50B show data measured from Jun. 2, 2013 to June 3 of the year. FIG. 51A and FIG. 51B show data measured from Jun. 3, 2013 to June 4 of the year. FIG. 52A and FIG. 52B show data measured from Jun. 4, 2013 to June 5 of the year. FIG. 53A and FIG. 53B show data measured from Jun. 5, 2013 to June 6 of the year. FIG. 54A and FIG. 54B show data measured from Apr. 29, 2014 to April 30 of the year. FIG. 55A and FIG. 55B show data measured from Apr. 30, 2014 to May 1 of the year, which were measured after the filter of fan filter unit was replaced with a new one. During about eleven months from the time when data of FIG. 53A~FIG. 53C were taken to the time when data of FIG. 54A~FIG. 54C were taken, the system was operated and the subject (the first inventor of the present invention) slept almost every day except an absent period for business trips. Comparing FIG. 48B, FIG. 49B, FIG. 50B, FIG. 51B, FIG. 52B and FIG. 53B with FIG. 54B, it is understood that the base line of cleanliness at rest keeps a level of US 209D Class100, showing that cleanliness does not drop at all for a long-term operation. Its reason is as follows. That is, the fan filter unit used operates in an environment isolated from the outside space, which is very different from usage of fan filter unit in conventional clean rooms. Therefore, the fan filter unit is free from the problem "choking with an intake of the outside air", which is unnecessary essentially. In fact, comparing FIG. 53B (cleanliness when the sleeping subject was at rest ~700), in which cleanliness was obtained after a new filter was used, with FIG. 54B, FIG. 54B shows rather good cleanliness ~400 (when the sleeping subject was at rest). FIG. 48C, FIG. 49C, FIG. 50C, FIG. 51C, FIG. 52C, FIG. 53C, FIG. 54C and FIG. 55C show the autocorrelation (the value of the autocorrelation function) that were calculated by using the autocorrelation function $$F(\tau)=\int_0^{t_{end}/2} n(t) \cdot n(t+\tau) dt$$

based on data of FIG. 48A, FIG. 49A, FIG. 50A, FIG. 51A, FIG. 52A, FIG. 53A, FIG. 54A and FIG. 55A respectively. Here, the lower limit of the integral is the time of starting measurement (the time of starting sleep, t=0) and the upper limit of the integral is taken as $t_{end}/2$ where $t_{end}$ is the time of completing measurement (or the latest time of measurement till the point in time when monitored at any time. n(t) and F(τ) are referred as t-Hypnokinetogram and τ-Hypnokinetogram respectively because they indicate involuntary body movement during sleep. With data accumulation (creation of big data) and its analysis of the waveform and the diagram, it is expected that it becomes possible to obtain new knowledge, realize new diagnosis and decide necessity of medical treatment like the analysis by an electrocardiogram and an electroencephalogram. Because probes etc. are not attached to the body, information obtained by reproduction of true usual life and sleeping state is considered to be valuable.

From FIG. 48a~FIG. 55C, with respect to the density of dust particles and the autocorrelation during sleep, an obvious tendency that reflects the sleeping state. More specifically, the density of dust particles is high just after starting sleep, then the density of dust particles decreases rapidly and thereafter cleanliness better than US 209D Class1000 is kept. However, it is understood that the density of dust particles rapidly increases like peaks about every 90 minutes. This time of about 90 minutes corresponds to one cycle of pattern of "non-REM sleep→REM sleep". This tendency is obviously appeared in FIG. 48C, FIG. 49C, FIG. 50C, FIG. 51C, FIG. 52C, FIG. 53C, FIG. 54C and FIG. 55C that show the change over time of the autocorrelation. From this, it is understood that the density of dust particles n(t) reflects the sleeping state and therefore the autocorrelation reflects the sleeping state. More specifically, for example, in FIG. 48A~FIG. 48C, which show data taken in a night when the subject slept relatively soundly, the long period structure is observed. Contrary to this, in FIG. 51A~FIG. 51C, which show data taken in a night when the subject slept relatively shallowly, the short period structure is observed. When carefully observing, it is seen that the short period structure in FIG. 51C is superposed on the long period structure in FIG. 48C. That is, the envelope of the spectrum of FIG. 52C is almost the same as FIG. 49C at τ~90 minutes and τ~180 minutes. This suggests that both of them share any same process. However, the presence of high frequency components and a peak around τ~110 minutes in FIG. 52C show that any difference also exists between both of them. By accumulating data and correlating with the situation of physical complaint on that day, it is expected that it becomes possible to analyze the health state and classify finely into cases in the condition of a person who has not become ill yet. During the time of about 90 minutes, one cycle of the pattern of "non-REM sleep→REM sleep" is observed and a higher order structure appears. This was made clear for the first time by noninvasive and noncontact measurement.

As described above, FIG. 48C, FIG. 49C, FIG. 50C, FIG. 51C, FIG. 52C, FIG. 53C, FIG. 54C and FIG. 55C show characteristic spectrum respectively. And it becomes possible to measure information of sleep and higher order (health) information with a noncontact and noninvasive method while the subject is in an unconscious state. It is to be noted that the density of dust particles rapidly increases like a peak from the time of end of REM sleep in the latter half of one cycle to the time of start of non-REM sleep in the next cycle. As seen in FIG. 48B, FIG. 49B, FIG. 50B, FIG. 51B, FIG. 52B, FIG. 53B, FIG. 54B and FIG. 55B, the base line at rest indicates cleanliness of about US 209D Class100~1000 depending on the situation of the tent type highly clean system shown in FIG. 46A and FIG. 46B, bedding and the opening between the tent and the floor. It was confirmed that when a weight such as a blanket made of toweling is put on the hem of the tent type highly clean system from the outside to improve adhesion of the hem to the floor (when a futon is used) and therefore improve airtightness of the internal space of the tent type highly clean system, high cleanliness of US 209D Class10~1 level equal to FIG. 10 and FIG. 11.

Example 3 of the Sleeping State Detection System

FIG. 56A, FIG. 56B, FIG. 56C and FIG. 56D are a perspective view, a front view, a side view and a top view showing a highly clean simple bed system in which a highly clean space is constituted on a simple bed. As shown in FIG. 56A, FIG. 56B, FIG. 56C and FIG. 56D, in the highly clean simple bed system, a simple bed in which a bed 302 is put on a frame 301 for support is placed on the floor 303 of the room. An edge of the bed 302 is in contact with or locates near a lateral wall 304 of the room. On the other end of the bed 302, a fan filter unit 306 is placed on a frame 305 placed on the floor 303. The fan filter unit 306 is placed on the center line in the longitudinal direction of the bed 302. The fan filter unit 306 absorbs air from an air absorbing opening provided in its lower part and exhausts clean air upwardly from an air exhausting opening provided in its upper part. A ventilation guide plate 307 is attached on the frame 305. The ventilation guide plate 307 extends vertically to a height a little higher than the height of the fan filter unit 306 and its upper part bends to the side of the bed 302. Air exhausted upwardly from the upper part of the fan filter unit 306 blows against a curved part of the upper part of the ventilation guide plate 307 and then flows over the bed 302 in the direction parallel to the bed 302. The frame 305, the fan filter unit 306 and the ventilation guide plate 307 are covered with an enclosure 308 except the air exhausting part. The enclosure 308 is made of material not passing through air. A curtain rail 311 is placed parallel to the bed 302 above the simple bed in a state where the curtain rail 311 is held by a hanging rod 310 fixed to the ceiling 309. The curtain rail 311 has a U-like planar shape a litter smaller than the bed 302. Both edges of the curtain rail 311 are fixed to the lateral wall 304. An inner gas exchange membrane 302 is hanged on the curtain rail 311. The inner gas exchange membrane 312 has a size that can cover the simple bed. The hem of the inner gas exchange membrane 312 locates at a height about, for example, 10 cm higher than the floor 303. The inner gas exchange membrane 312 can be moved along the curtain rail 311 and can open the space surrounded by the inner gas exchange membrane 312. One end of the inner gas exchange membrane 312 in its longitudinal direction is fixed to the lateral wall 304 by the seal and the other end can be attached or removed to or from the lateral wall 304 by a magic tape (registered trademark) etc. An outer gas exchange membrane 3213 is stuck on the side of the curtain rail 311. The outer gas exchange membrane 313 is provided to a height that it overlaps with the inner gas exchange membrane 312 over a fixed range of height. For example, the outer gas exchange membrane 313 overlaps with the inner gas exchange membrane 312 over a range of about, for example, about 30 cm from the curtain rail 311 downward. Because the inner gas exchange membrane 312 and the outer gas exchange membrane 313 overlaps, no opening is formed between the inner gas exchange membrane 312 and the outer gas exchange membrane 313 and therefore it is possible to prevent dust particles from the outside invading the space surrounded by the inner gas exchange membrane 312. Furthermore, because the inner gas exchange membrane 312 and the enclosure 308 overlaps over a fixed length, for example, about 30 cm in the height direction, no opening is formed between the inner gas exchange membrane 312 and the enclosure 308 and therefore it is possible to prevent dust particles from the outside invading the space surrounded by the inner gas exchange membrane 312.

Figure 57A:
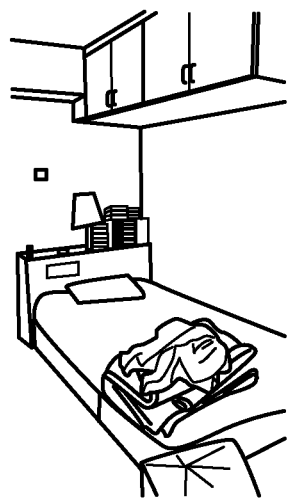
FIG. 57A A substitute picture showing a prototype of the highly clean simple bed system shown in FIG. 56A to FIG. 56D in an open state.
Figure 57B:
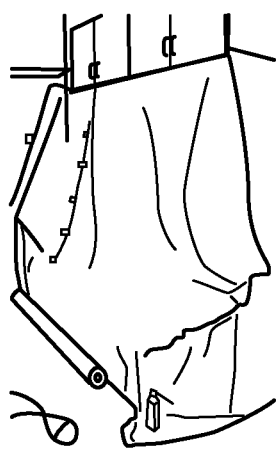
FIG. 57B A substitute picture showing the prototype of the highly clean simple bed system shown in FIG. 56A to FIG. 56D in a closed state (when using).

A prototype of the highly clean simple bed system was produced experimentally. FIG. 57A shows a bed (which corresponds to a simple bed) placed in a usual room. FIG. 57B shows that an inner gas exchange membrane was hung by using a closet placed on the lateral wall of the room and covered the bed entirely. The hem of the inner gas exchange membrane was in contact with the floor and a weight was put on the hem to prevent the inner gas exchange membrane turning over. A stand was put on the floor between the inner gas exchange membrane and the bed and a fan filter unit was put on the stand. In this case, no outer gas exchange membrane was placed. A dust counter was put between the inner gas exchange membrane and the bed.

Figure 58:
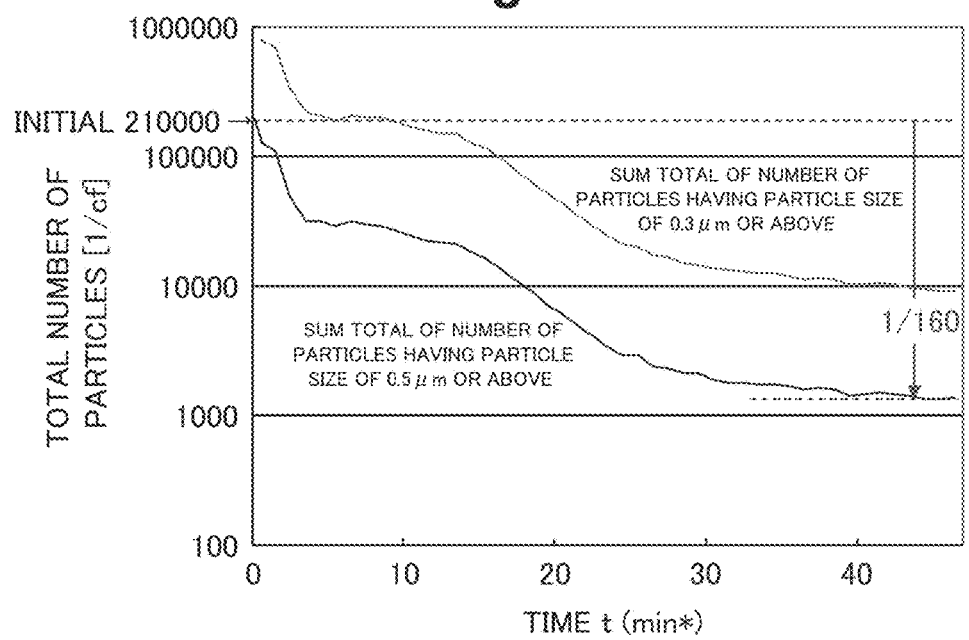
FIG. 58 A schematic view showing the change over time in cleanliness of the prototype of the highly clean simple bed system shown in FIG. 56A to FIG. 56D.

FIG. 58 shows the result of measurement of the number density of dust particles of the inside, which is covered by the inner gas exchange membrane, in the prototype of the highly clean simple bed system shown in FIG. 57B. As shown in FIG. 58, the number density of dust particles decreases to about 1300 [l/cf] after 40 minutes from the initial value 210,000 [l/cf]. It is understood that the number density of dust particles decreased about $\frac{1}{160}$ of the initial value. It is clearly understood from the result of FIG. 11 and FIG. 12 that it is possible to improve further cleanliness by improving airtightness by, for example, increasing the contact area of the bed and the inner gas exchange membrane.

Example 4 of the Sleeping State Detection System

Figure 59A:
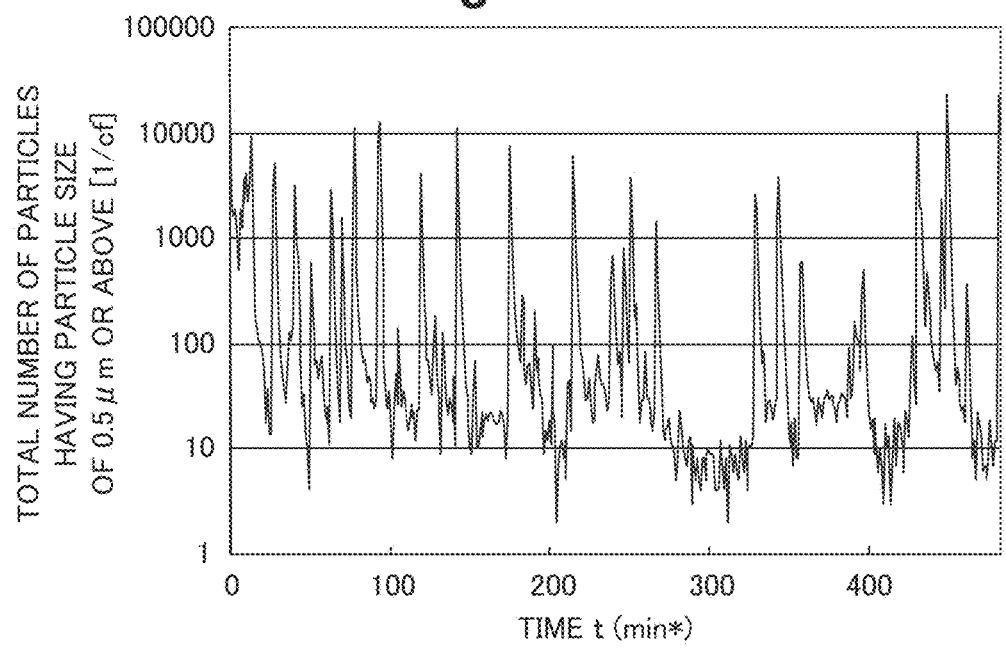
FIG. 59A A schematic view showing the result of measurement of the change over time in the total number of dust particles having the particle size of 0.5 μm or above inside the tent-like structure shown in FIG. 46A and FIG. 46B in the third continuous sleeping test while the subject sleeps inside the tent-like structure.
Figure 59B:
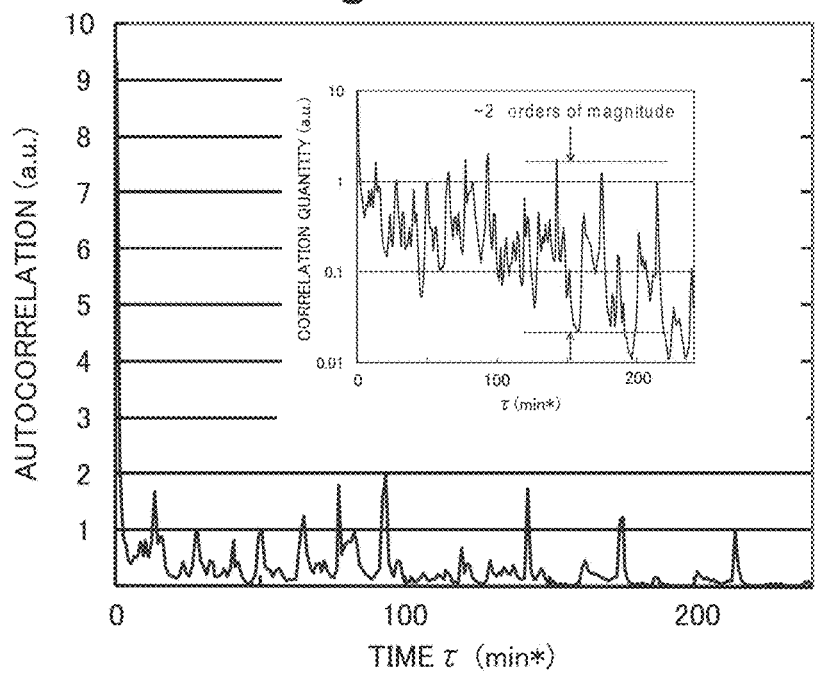
FIG. 59B A schematic view showing the autocorrelation calculated by using the autocorrelation function from the result of measurement shown in FIG. 59A.

As the same as the example 1 of the sleeping state detection system, the third sleeping test was carried out in the tent-like structure shown in FIG. 46A and FIG. 46B and the density of dust particles was measured. The third sleeping test was carried out from Oct. 23, 2014 after about six months from the second sleeping test to October 24 of the year. The result is shown in FIG. 59A. As shown in FIG. 59A, time slots in which the total number of particles having particle size of 0.5 μm or above is constant to be below 10 are observed (high cleanliness above US 209D Class10 was achieved and cleanliness one digit higher than an operating room of a hospital or a germ-free room was realized). It is understood that cleanliness was improved about a hundred fold compared with the example 1 of the sleeping state detection system. This was realized by three conditions, which are 1) 100% circulation feedback system, 2) a numerator S of $n = S\sigma/\gamma F$ thus obtained is determined to be the area of the inner surface of the closed space (if there are leak paths connecting the inside and the outside of the closed space, a component of the area of the inner surface of the space in which the tent is placed, so such situation is avoided.) and 3) σ is made to be small (the area of the surface of each part of the fan filter unit exposed in the closed space is included in the area of the inner surface of the closed space. Therefore, the dropping rate of dust per unit area and unit time is held down by cleaning each part). These conditions are important and effective. In order to eliminate leak paths, it is effective to put a weight on the hem of the tent-like structure and make the hem contact with the floor. However, it is difficult to put a weight on the hem in the closed space. Therefore, it is important to improve adhesion of the hem of the gas exchange membrane 26 constituting the tent-like structure and the closed space inside the tent-like structure. Adhesion is improved by inserting the hem of the gas exchange membrane 26 constituting the tent-like structure under the futon and press the hem by the weight of bedding (futon) and the sleeping subject, so that cleanliness higher than US 209D Class10 shown in FIG. 59A was realized (It is to be noted that this method can be used inside the closed space). Direction of an air flow by the fan filter unit is determined so that the air flow does not blow against the surface of the enclosure, that is, the tent-like structure and flows along the surface. FIG. 59B shows a linear plot of the autocorrelation calculated by using the autocorrelation function, relating to the time series data. Inserted figure in FIG. 59B shows a logarithmic plot. Because cleanliness was improved a hundred fold and the background number of dust became $1/100$, the peak to valley ratio of the autocorrelation function became about double figures and repetitive structures in characteristic τ-Hypnokinetogram at τ≥125 min. was also found, as shown in the inserted figure. In the future, by creating big data and analyzing accumulated data, it is expected that medical and nursing information equal to the electrocardiogram and the electroencephalogram can be extracted.

The embodiments and examples of the present invention have been explained specifically. However, the present invention is not limited to these embodiments and examples, but various changes and modifications based on the technical idea of the present invention are possible. For example, the wall 9 shown in the embodiments is not necessarily limited to the lateral wall of the room 1, but may be a part of the ceiling wall or the floor wall. Also, the wall 9 may constitute a part of the multiple structure of a gas exchange device.

Also, in the case where the area A of the gas exchange membrane 26 calculated like this has the value giving oxygen supply ability suitable for the main room 20, the gas exchange membrane 26 may be directly in contact with the outer space (for example, outdoors, space of a hallway, or a room itself in which a tent is placed in the case of the tent structure consisting of the gas exchange membrane shown in FIG. 46A and FIG. 46B [the areas of the gas exchange membrane occupying a corner or all of the side surface and the surface of the ceiling satisfies the condition of the above necessary area] the room itself to be placed the tent). In this case, maintaining the favorable oxygen concentration with the sufficient ability of oxygen penetration, at the time of about seven hours sleep as shown in FIG. 47, it is possible to obtain good sleep in a good clean environment better than class1000 on average (about class100 especially during sound sleep without tossing about). The spikes seen in FIG. 47 result from dust flying when turning over etc., but from the frequency spectrum of the spike sequence, a sleeper's health state etc. can be presumed. In the case where the system of highly clean rooms 10 is applied to a special nursing home for the aged etc., it is possible not only to confirm the safety of the user of the system of highly clean rooms 10, but also to monitor plural persons under medical treatment from a distant place with high accuracy with respect to the change from the characteristic during general sleep etc. (not analysis based on the image information etc., so covering appropriate consideration on the privacy).

It may be possible to introduce air after dust is removed by the fan filter unit with the HEPA filter etc. in advance inside the room 1 in a low flow rate capable of rotating air inside the room 1 one time in about two hours and blow the same volume from the room 1 outside by another fan filter unit of the same model.

It is also possible to obtain a gas exchange mechanism by connecting the outside air introduction opening 71 of the gas exchange device 80 shown in the above with, for example, the outside air absorption opening 85 of the system of highly clean rooms 10 shown in FIG. 42, FIG. 44 and FIG. 45 and by connecting the exhaust opening 73 of the gas exchange device 80 with the exhaust opening 86 of the system of highly clean rooms 10. In this case, it is preferable to set the flow rate of the inside air flowing in the gas exchange device 80 at least equal to or larger than the flow rate capable of rotating air inside the living space 6 one time in two hours. Also, the room 1 constituting the system of highly clean rooms 10 is provided inside with the circulation feedback mechanism in which the opening for absorbing air inside the room and the blow opening for returning again all of the absorbed air after cleaning inside the room are provided as a pair. Like this, it is effective that the system of highly clean rooms has at least one living space (highly clean room) characterizing in having two elements of the gas exchange mechanism and circulation feedback mechanism. This is understood that in the room 1, the trilaminar structure of the "outside air/membrane/inside air" in which the internal space 7 communicating with the outer space of the wall 9 is in contact with the living space 6 via the gas exchange membrane 26 is "cut" and "pasted" on another place such as the space between the roof and the ceiling through the absorption tube 75 and the gas flow path 83, etc. It is desirable to make the ratio of the area and the volume (the total area of the membrane/the volume of the device) of the trilaminar structure large as much as possible. Also, the position of "the pasting place" or "the destination" of the functional part relative to the living space 6 does not matter as far as the inside air feedback path (for example, the gas flow path 24) communicates with the living space 6 and the outside air absorption and exhaust opening (for example, the outside air absorption opening 85 and the exhaust opening 86). That is, unless otherwise existing the gas exchange ability, the existing place itself of the trilaminar structure of "outside air/membrane/inside air" does not need to be existed in contact with the living space 6 at the outer edges of the living space 6 and the place can be moved at any place and be set through the air flow tube (for example, the absorption tube 75, the gas flow path 83, etc.) as far as the gas exchange ability is ensured. The total area of the gas exchange membrane 26 in the gas exchange device 80 secures the enough oxygen concentration for persons to act inside by satisfying the equation (15) at the very least and further, by making the area as large as possible, in addition to the above, deodorizing and the harmful gas exhaust function can be enhanced. Also, with respect to the opening for absorbing air inside the living space 6 and the blow opening for returning again all of the absorbed air after cleaning inside the living space 6, for example, it is effective to have the structure of the absorption opening 23 and the blow opening 22 in the system of highly clean rooms 10 shown in FIG. 6~FIG. 8, or FIG. 42, FIG. 44 and FIG. 45, or, most simply, by installing the gas exchange device 80 communicating with the inside of the living space 6 and further placing an air conditioner fixed on the wall, a stand-alone air cleaning device or a photocatalyst deodorization device for filtering all of the absorbed air and blowing it again from the air flow emission opening inside the living space 6 and operating them.

Also, for example, it is possible to provide a first-class ventilation facility by installing an air supply device (machine) with a high cleanliness filter which is effective for ventilation and an exhaust device (machine) in a living space as a structure of full-time mechanical ventilation equipment. Also, in each system of highly clean rooms 10 shown in the above, a low flow rate fan filter unit with the HEPA filter having the exhaust flow rate that does not nearly affect the system in its flow rate, as shown in FIG. 42, FIG. 44 and FIG. 45 may be installed as a mechanical ventilation between the main room and the hallway or between the main room and the outside in pair at the absorption side (in) and the exhaust side (out).

Also, the internal space of the room 1 described as a living space assuming the daily life is not limited to mere living and it is needless to say that the internal space can be used as a high quality operation space such as a dust-free lacquering space or a high quality painting space including lacquering without worrying about low yield ratio by dust, etc. Especially, in the case of painting operation, when using especially harmful organic solvent etc., it is desirable to use a local exhaust system by the gas exchange device exchanging only gas constituent but not passing through dust for safety and health maintenance of workers.

Also, in order to pass all of gases flowing from the blow opening of the fan filter unit 21 through the opening 23 provided in a part of the inner wall 9a and return them to the fan filter unit 21 through the gas flow path 24 communicating the opening 23 and the gas flow opening airtightly, if the space of the room may be reduced, it may be possible to use the duct installed later such as bellows etc. fixed along the inner wall 9a. It is also possible to use the outside space adjacent to the main room 20 as an outside air introduction space. That is, by constituting the lateral wall 2 of the main room 20 by the gas exchange membrane 26, the main room 20 can be directly connected with an outdoor space (outside space) via the gas exchange membrane 26. In this case, the outside air introduction space is a semi-infinite open space.

Also, it is also possible to install the two fan filter units with the HEPA filter for the inlet and the outlet respectively in the main room 20 with the flow rate capable of circulating air inside the main room one time in two hours.

By constructing the room 1 with a partition wall that partially includes the gas exchange membrane 26, it is possible to make a complete closed space for the outer space and further build in a fail-safe mechanism regarding the maintenance of cleanliness and sterility at the time of loss of power because there is no pressure difference between the inside and the outside of the room 1.

The fan filter unit 21 is preferably used for the interface between the main room 20 or the living space 6 and the internal space 7, but if permitting to sacrifice attainable cleanliness a little, it is not necessary to apply this configuration. That is, if the structure that a part of the partition wall provided between the internal space 7 and the main room 20 or the living space 6 is constituted by the gas exchange membrane and fresh air is taken in the internal space 7, it is possible to use the existing air conditioner fixed on the wall as it is as the main fan filter unit 21.

And, the numerals, structures, constitutions, figures, materials, etc. described in the embodiments and examples are only examples, and as necessary, different numerals, structures, constitutions, figures, materials, etc. may be used.

Also, according to the present invention, by using the numerals, structures and constitutions described in the above embodiments and examples, it is possible to control the microbial environment of activity environment and living environment of people to the desired environment by making the airborne microbes once zero in a predetermined space (the "vacuum" equivalent state in the microbial environment is realized) in a similar way that the vacuum technology and vacuum chamber is used to make the inside of the vacuum chamber to vacuum once and set the inside gas environment freely, or make use the vacuum environment in thin-film growth and manufacturing the materials and devices. Under the conditions, by positively introducing better microbes, or introducing gas phase medicinal products, aroma, etc., it is possible not only to realize the new medical environment, techniques and the nursing environment, but also to create and develop the new medical treatment, medical treatment technique, services (for example, refer to safety confirmation methods and analysis method of health condition described before. Especially, in the case of dosing medicines for lungs, dosing can be done with high quality air under favorable "S/N ratio", that is, with no "noise" like dust, germs, etc. (the elements other than medicine is almost zero). Especially, by combining the control of the microbial environment or the environment free from airborne radioactive substances and the noncontact, noninvasive detection of the sleeping state in the involuntary state, it is possible to carryout a cross-correlation analysis concerning the positive change of users. This will become a base for taking effective measures in each field. As necessary, different numerals, structures, constitutions and methods may be used.

EXPLANATION OF REFERENCE NUMERALS 201 room or closed space
202 bed
203 subject
204 pillow
205 quilt
206 dust counter
207 computer
208 fan filter unit

The invention claimed is:

1. A system using information of involuntary body movement during sleep, comprising:
a room or closed space in which a subject sleeps, the room being provided inside with a living space as a closed space; and
a dust counter disposed inside the living space or closed space; and
a computer,
at least a part of at least one of walls of the room or closed space being constituted by a wall with an internal space capable of introducing outside air, comprising: airways communicating an outside of the room or closed space and the internal space, provided on the edge of the wall, at least one of major surfaces forming the internal space being made of a membrane not passing through dust particles but passing through gas molecules, the membrane having the area A set by scaling of {(V/A)/(D/L)} where V is the volume of the living space or closed space, A is the area of the membrane, L is the thickness of the membrane and D is the diffusion constant of oxygen in the membrane, the area A of the membrane being set so as to satisfy at least $$A \geqq \frac{BL}{D\left(\frac{V_{O_2}}{V} - \eta\right)} \quad (15)$$

where B is the oxygen consumption rate inside the living space or closed space, Vo2 is the volume of oxygen in equilibrium state with the outside and without oxygen consumption inside the living space or closed space and $\eta$ ($\eta > 0.18$) is the target oxygen concentration inside the living space or closed space, at least one fan filter unit being disposed in the room or closed space, the computer being configured to analyze the state of the subject being examined by measuring information of involuntary body movement during sleep of the subject by measuring changes in the dust particle counts inside of the living space or closed space by the dust counter with the inside of the living space or closed space being kept cleaner than the outside.

2. The system using information of involuntary body movement during sleep according to claim 1 wherein the room or closed space is constituted so that all of gases which are absorbed from an absorption opening of the fan filter unit and flow inside the living space or closed space from a blow opening of the fan filter unit are fed back to the absorption opening of the fan filter unit.

3. The system using information of involuntary body movement during sleep according to claim 1 wherein the room or closed space is a tent in which a part or all of the side and the ceiling is occupied by the membrane.

4. The system using information of involuntary body movement during sleep according to claim 1 wherein cleanliness of the inside of the living space or closed space is determined so that the number density of dust particles corresponding to attainable cleanliness of the living space or closed space when the subject is at rest is smaller than the number density of dust particles emitted inside the living space or closed space when the subject tosses about.

5. The system using information of involuntary body movement during sleep according to claim 1 wherein the inside of the living space or closed space is kept at a cleanliness of US 209D Class100 or better.

6. The system using information of involuntary body movement during sleep according to claim 1 wherein the state of the subject is examined by performing analysis of characteristic of the change over time in a parameter as the number of dust particles inside the living space or closed space.

7. The system using information of involuntary body movement during sleep according to claim 6 wherein the analysis of characteristic of the change over time is an autocorrelation function analysis.

8. The system using information of involuntary body movement during sleep according to claim 7, further comprising an arithmetic unit for obtaining the autocorrelation by calculating the autocorrelation function from the result of measurement of the change over time in the number of dust particles measured by the dust counter.

9. The system using information of involuntary body movement during sleep according to claim 1 wherein the system using information of involuntary body movement during sleep is a sleeping state detection system which detects the sleeping state of the subject by measuring the change over time in the number of dust particles inside the living space or closed space by the dust counter in a state where the inside of the living space or closed space is kept cleaner than the outside of the living space or closed space, while the subject sleeps.

10. The system using information of involuntary body movement during sleep according to claim 9 wherein the health state of the subject is ascertained by detecting the sleeping state of the subject.

11. The system using information of involuntary body movement during sleep according to claim 1 wherein the state of the subject is measured by contact measurement while the subject sleeps and the state of the subject is examined by combining data obtained by the contact measurement with data of information of involuntary body movement during sleep of the subject obtained by measuring the change over time in the number of dust particles inside the living space or closed space.

12. The system using information of involuntary body movement during sleep according to claim 1 wherein the state of the subject is examined by combining data of information of involuntary body movement during sleep of the subject obtained by measuring the change over time in the number of dust particles inside the living space or closed space, data of activity of the subject in the conscious state and IoT data.

13. A method using information of involuntary body movement during sleep, comprising:

analyzing the state of a subject by measuring information of involuntary body movement during sleep of the subject by measuring changes in the dust particle counts inside a room or closed space in which the subject sleeps, the room being provided inside a living space as a closed space, by a dust counter with the inside of the living space or closed space being kept cleaner than an outside of the living space or closed space, while the subject sleeps, at least a part of at least one of walls of the room or closed space being provided with a membrane not passing through dust particles but passing through gas molecules in contact with the living space or closed space, the surface of the membrane on the opposite side of the living space or closed space being in contact with outside air, the membrane having the area A set by scaling of {(V/A)/(D/L)} where V is the volume of the living space or closed space, A is the area of the membrane, L is the thickness of the membrane and D is the diffusion constant of oxygen in the membrane, the area A of the membrane being set so as to satisfy at least $$A \geqq \frac{BL}{D\left(\frac{V_{O_2}}{V} - \eta\right)} \quad (15)$$

where B is the oxygen consumption rate inside the living space or closed space, Vo2 is the volume of oxygen in equilibrium state with an outside of the room or closed space and without oxygen consumption inside the living space or closed space and η (η>0.18) is the target oxygen concentration inside the living space or closed space, at least one fan filter unit being disposed in the room or closed space.

14. The method using information of involuntary body movement during sleep according to claim 13 wherein cleanliness of the inside of the living space or closed space is determined so that the number density of dust particles corresponding to attainable cleanliness of the living space or closed space when the subject is at rest is smaller than the number density of dust particles emitted inside the living space or closed space when the subject tosses about.

15. The method using information of involuntary body movement during sleep according to claim 13 wherein the state of the subject is examined by performing analysis of characteristic of the change over time in a parameter as the number of dust particles inside the living space or closed space.

16. A system using information of involuntary body movement during sleep, comprising:
a room or closed space in which a subject sleeps, the room being provided inside with a living space as a closed space; and
a dust counter disposed inside the living space or closed space; and
a computer,
at least a part of at least one of walls of the room or closed space being provided with a membrane not passing through dust particles but passing through gas molecules in contact with the living space or closed space,
the surface of the membrane on the opposite side of the living space or closed space being in contact with outside air,
the membrane having the area A set by scaling of $\{(V/A)/(D/L)\}$ where V is the volume of the living space or closed space, A is the area of the membrane, L is the thickness of the membrane and D is the diffusion constant of oxygen in the membrane,
the area A of the membrane being set so as to satisfy at least $$A \geq \frac{BL}{D\left(\frac{V_{O_2}}{V} - \eta\right)} \quad (15)$$

where B is the oxygen consumption rate inside the living space or closed space, Vo2 is the volume of oxygen in equilibrium state with an outside of the room or closed space and without oxygen consumption inside the living space or closed space and η (η>0.18) is the target oxygen concentration inside the living space or closed space, at least one fan filter unit being disposed in the room or closed space, the computer being configured to analyze the state of the subject being examined by measuring information of involuntary body movement during sleep of the subject by measuring changes in the dust particle counts inside the living space or closed space by the dust counter with the inside of the living space or closed space being kept cleaner than the outside.

17. The system using information of involuntary body movement during sleep according to claim 16 wherein cleanliness of the inside of the living space or closed space is determined so that the number density of dust particles corresponding to attainable cleanliness of the living space or closed space when the subject is at rest is smaller than the number density of dust particles emitted inside the living space or closed space when the subject tosses about.

18. The system using information of involuntary body movement during sleep according to claim 16 wherein the state of the subject is examined by performing analysis of characteristic of the change over time in a parameter as the number of dust particles inside the living space or closed space.

19. The system using information of involuntary body movement during sleep according to claim 16 wherein the system using information of involuntary body movement during sleep is a sleeping state detection system which detects the sleeping state of the subject by measuring the change over time in the number of dust particles inside the living space or closed space by the dust counter in a state where the inside of the living space or closed space is kept cleaner than the outside of the living space or closed space, while the subject sleeps.

20. The system using information of involuntary body movement during sleep according to claim 16 wherein the state of the subject is examined by combining data of information of involuntary body movement during sleep of the subject obtained by measuring the change over time in the number of dust particles inside the living space or closed space, data of activity of the subject in the conscious state and IoT data.

\* \* \* \* \*